(12) United States Patent
Vetter et al.

(10) Patent No.: US 12,582,434 B1
(45) Date of Patent: Mar. 24, 2026

(54) EXCISIONAL DEVICES AND METHODS

(71) Applicant: TransMed7, LLC, Portola Valley, CA (US)

(72) Inventors: Paul A Vetter, Portola Valley, CA (US); James W Vetter, Portola Valley, CA (US); Robert D Sauchyn, Regina (CA)

(73) Assignee: TRANSMED7 LLC, Portola Valley, CA (US)

( * ) Notice: Subject to any disclaimer, the term of this patent is extended or adjusted under 35 U.S.C. 154(b) by 0 days.

(21) Appl. No.: 19/019,424

(22) Filed: Jan. 13, 2025

Related U.S. Application Data

(63) Continuation-in-part of application No. 18/822,319, filed on Sep. 2, 2024, which is a continuation of
(Continued)

(51) Int. Cl.
*A61B 17/32* (2006.01)
*A61B 5/00* (2006.01)
(Continued)

(52) U.S. Cl.
CPC ...... *A61B 17/32075* (2013.01); *A61B 5/0036* (2018.08); *A61B 5/0066* (2013.01);
(Continued)

(58) Field of Classification Search
CPC ............ A61B 17/32075; A61B 5/0036; A61B 5/0066; A61B 5/0084; A61B 8/12;
(Continued)

(56) References Cited

U.S. PATENT DOCUMENTS

| | | | |
|---|---|---|---|
| 5,174,300 A | 12/1992 | Bales et al. | |
| 5,251,641 A | 10/1993 | Xavier | |

(Continued)

FOREIGN PATENT DOCUMENTS

| | | | |
|---|---|---|---|
| EP | 2196155 A2 | 6/2010 | |
| EP | 3829450 B1 | 11/2023 | |

OTHER PUBLICATIONS

International Search Report and Written Opinion of the International Searching Authority in PCT/US2025/011469 dated Apr. 25, 2025 (8 pages).

(Continued)

*Primary Examiner* — Joel Lamprecht
(74) *Attorney, Agent, or Firm* — YOUNG LAW FIRM, P.C.

(57) ABSTRACT

A platform device for material excision or removal from vascular structures for either handheld or stereotactic table or robotics platform use may comprise a work element or elements configured to selectively open and close at least one articulable beak or scoopula configured to penetrate and remove intra-vascular materials or obstructions, or follow a central lumen of another device or over a wire in a longitudinal direction. A telescoping set of inner and outer tube axially actuated together and to actuate a beak set, axially actuated differentially, whether controlled mechanically or electronically may be combined with an outer tubular sheath, which may be full circumference or partial circumference along its length, to form a system for rotational non-sharp dissection, coring, severing off, transporting or in the reverse, depositing various fluids and solids for a variety of clinical uses.

3 Claims, 85 Drawing Sheets

Related U.S. Application Data application No. 18/081,298, filed on Dec. 14, 2022, now Pat. No. 12,178,468, which is a continuation of application No. 16/840,715, filed on Apr. 6, 2020, now Pat. No. 11,596,436.

(60) Provisional application No. 63/619,920, filed on Jan. 11, 2024.

(51) Int. Cl.
*A61B 8/12* (2006.01)
*A61B 17/22* (2006.01)
*A61B 17/3207* (2006.01)

(52) U.S. Cl.
CPC .............. *A61B 5/0084* (2013.01); *A61B 8/12* (2013.01); *A61B 17/22031* (2013.01); *A61B 17/320758* (2013.01); *A61B 2017/22038* (2013.01); *A61B 2017/22069* (2013.01)

(58) Field of Classification Search
CPC ...... A61B 17/22031; A61B 17/320758; A61B 2017/22038; A61B 2017/22069
See application file for complete search history.

(56) References Cited

U.S. PATENT DOCUMENTS

| | | | |
|---|---|---|---|
| 5,415,169 | A | 5/1995 | Siczek et al. |
| 5,526,822 | A | 6/1996 | Burbank |
| 5,873,886 | A | 2/1999 | Larsen et al. |
| 6,139,508 | A | 10/2000 | Simpson et al. |
| 9,226,733 | B2 | 1/2016 | Flatland et al. |
| 9,603,585 | B2 | 3/2017 | Polo |
| 10,835,312 | B2 * | 11/2020 | Vetter .................... A61B 34/20 |
| 2002/0165580 | A1 | 11/2002 | Zwiefel et al. |
| 2003/0032955 | A1 | 2/2003 | Mulier |
| 2003/0125639 | A1 | 7/2003 | Fisher et al. |
| 2004/0230157 | A1 | 11/2004 | Perry et al. |
| 2005/0070885 | A1 | 3/2005 | Nobis et al. |
| 2005/0209564 | A1 | 9/2005 | Bonner et al. |
| 2006/0004323 | A1 | 1/2006 | Chang et al. |
| 2006/0205992 | A1 | 9/2006 | Lubock et al. |
| 2007/0244507 | A1 | 10/2007 | Szweda et al. |
| 2007/0249999 | A1 | 10/2007 | Sklar et al. |
| 2007/0282197 | A1 | 12/2007 | Bill et al. |
| 2008/0015466 | A1 | 1/2008 | Lerman |
| 2008/0167524 | A1 | 7/2008 | Goldwasser et al. |
| 2009/0287114 | A1 | 11/2009 | Lee |
| 2010/0049162 | A1 | 2/2010 | Hameed |
| 2010/0121153 | A1 | 5/2010 | To |
| 2010/0168610 | A1 | 7/2010 | Lacombe et al. |
| 2011/0060188 | A1 | 3/2011 | Sharon et al. |
| 2011/0245725 | A1 | 10/2011 | Flatland et al. |
| 2013/0041256 | A1 | 2/2013 | Flebig |
| 2013/0096459 | A1 | 4/2013 | Vetter |
| 2014/0180079 | A1 | 6/2014 | Brown |
| 2014/0213932 | A1 | 7/2014 | Knoll et al. |
| 2016/0089208 | A1 | 3/2016 | Vetter |
| 2016/0287223 | A1 | 10/2016 | Hingston et al. |
| 2016/0367311 | A1 | 12/2016 | Gerrans |
| 2017/0020554 | A1 | 1/2017 | Vetter |
| 2019/0183466 | A1 | 6/2019 | Vetter et al. |
| 2019/0254649 | A1 | 8/2019 | Walters et al. |
| 2019/0365360 | A1 | 12/2019 | Vetter et al. |
| 2020/0214661 | A1 | 7/2020 | Tropello |
| 2021/0321976 | A1 | 10/2021 | De Beni et al. |
| 2022/0370051 | A1 | 11/2022 | Vetter et al. |
| 2023/0015315 | A1 | 1/2023 | Vetter et al. |
| 2023/0404613 | A1 | 12/2023 | Vetter et al. |

OTHER PUBLICATIONS

International Search Report and Written Opinion of the International Searching Authority in PCT/US2025/011468 dated Jun. 20, 2025 (12 pages).
BD EleVation Breast Biopsy System Quick Reference Guide © 2019 BD. All rights reserved. BD-10898 (6 pages).
BD EleVation Breast Biopsy Value Analysis Brief, © 2021 BD. All rights reserved. 0921/6110 BD-27449 2797 (8 pages).
Mammotome Breast Biopsy System ST EX MR, © 2012 Devicor Medical Products, Inc. MDM 12-0016 (11 pages).
Finesse Ultra Breast Biopsy System Ultrasound Guided Breast Biopsy Technical Guide.
© Copyright C. R. Bard, Inc., 2009. All Rights Reserved. S11704-0 (2 pages).
Boston Scientific Radial Jaw 4 Single Use Biopsy Forceps, © 2016 Boston Scientific Corporation or its affiliates. ENDO-392404-AA Jun. 2016 (2 pages).
Comprehensive Review Mammotome Elite tetherless Vacuum-Assisted Biopsy System, Kimberly C. Hutcherson, MD / North Metropolitan Radiology Associates, LLP Northside Gwinnett Breast Center / Northside Hospital Gwinnett / Lawrenceville, GA 30046, © 2023 Devicor Medical Products, Inc. MDM# 210526 Rev 10/23.
David S. Zimmon, MD et al., Endoscopic multiple biopsy and rapid diagnosis by in situ fixation and histopathologic processing, www.giejournal.org vol. 86, No. 2 : 2017 Gastrointestinal Endoscopy 333-342 (10 pages).
Anwarul Islam, A New Single-Use Bone Marrow Biopsy Needle with Core Retention Design, Sci & Tech Res| BJSTR. MS.ID. 003294, DOI: 10.26717/BJSTR.2019.19.003294 (7 pages).
Hologic, Breast Biopsy Solutions, PB-00884 Hologic Inc. © 2021 All rights reserved. Hologic (7 pages).
Diversatek Healthcare GIJaw Single Use Biopsy Forceps, © 2018 Diversatek, Inc. | All Rights Reserved. 080-0073 08/18 (2 pages).
International Search Report and Written Opinion of the International Searching Authority in PCT/US2025/011467 dated May 15, 2025 (10 pages).

* cited by examiner

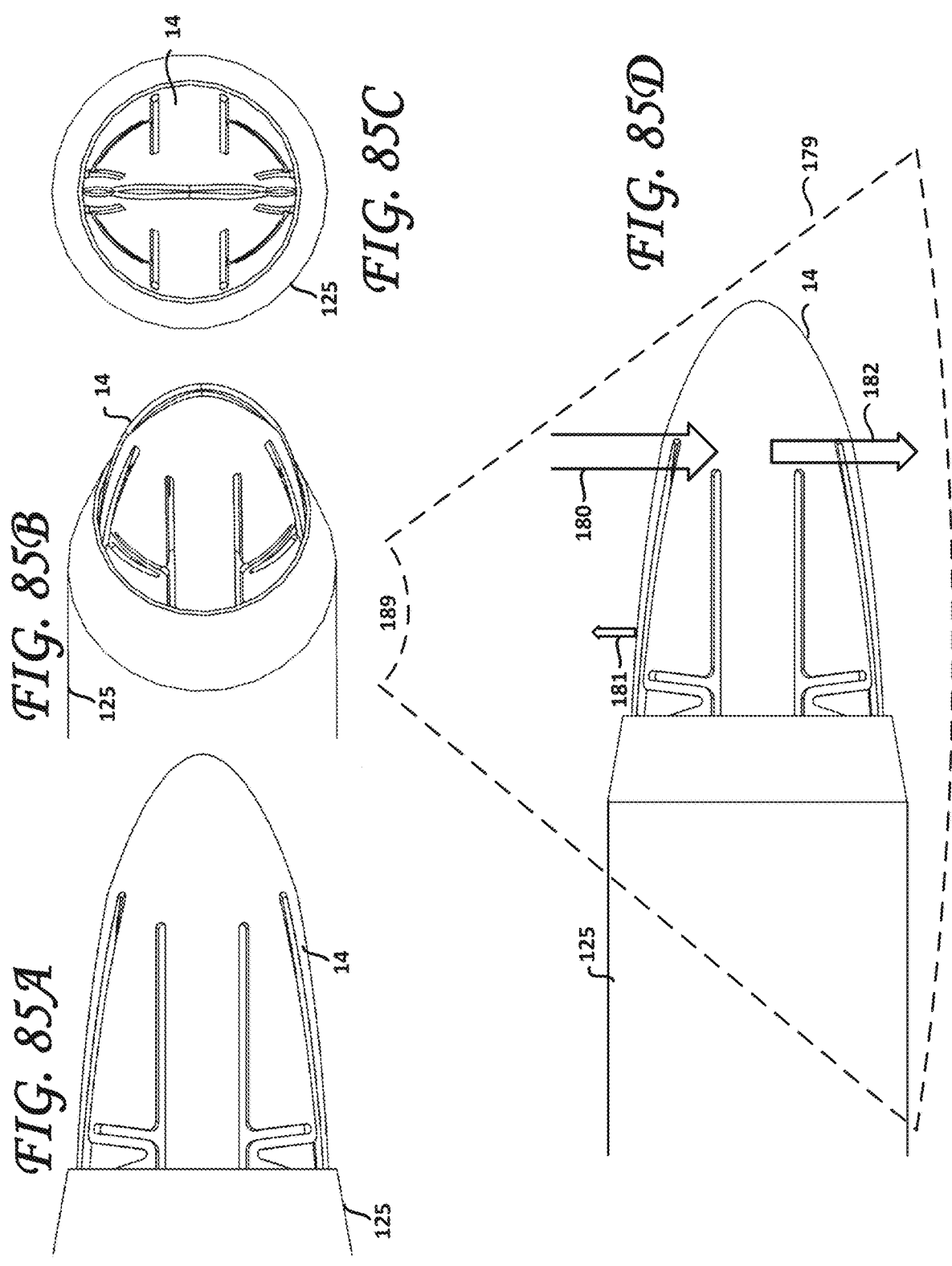

EXCISIONAL DEVICES AND METHODS

BACKGROUND

Embodiments relate to medical devices and methods. More particularly, embodiments relate to hand-held or mounted, manually or robotically guided, single, or multiple insertion, single or multiple excisional and interventional devices and corresponding methods for vascular imaging, evaluation, clearing, restoration, and regenerative applications. Embodiments further relate to improvements over currently used acute and chronic total and subtotal vessel occlusion removal or interventional systems, specifically in providing minimally invasive and more widely capable, reliable cardio-vascular excisional and interventional devices and methods.

SUMMARY

Embodiments are drawn to various medical devices and methods that may be used for intra-vascular interventional procedures and in any area of the body where tissue removal or therapeutic procedures are needed for diagnostic and therapeutic purposes. Many of the embodiments herein are drawn to vascular applications, however embodiments are likewise applicable to many other tubular areas including pulmonary, central and peripheral neural spaces, including the spinal canal, genitourinary spaces, bone marrow spaces and other areas of soft and hard tissue excisions or interventions throughout the body, including where the embodiments themselves create temporary or permanent spaces for access, restoration of channels that have been obliterated by diseases and other processes such as natural healing processes. An important aspect of embodiments is to include, in a portable way, chambers to aid imaging where they may be used in areas where, without such portability, clarity of imaging may be distorted or impeded altogether. Several embodiments combine excision and delivery with integrated imaging capabilities, which provides a means for bringing all needed capabilities to a site in some cases far removed from the manipulating mechanisms. According to one embodiment, an excisional device may be configured to remove liquids, solids, semi-solids and single or multiple material samples during a single insertion through the skin (percutaneous procedure) into any vascular area of the body where such a targeted interventional site may be found. Embodiments may comprise structures and functionality for different phases of a multi-phase vascular clearing or restoration or regenerative procedure, whose stages, though of necessarily altered steps, may equally apply to several other areas of the body, whether tubular or non-tubular in anatomic structure, and which may be performed by hand, by robotic manipulation or by device attachment to a specialized imaging table stage or Magnetic Resonance Imaging (MRI) stage whether manually controlled, fully automated or a combination of the two. Embodiments may also be partially or fully manipulated and operated remotely using robotic mechanisms that may be fully guided by an operator and may be enhanced by machine learning, interpretive imaging, post-processing and other adaptive intelligence enhancements or systems that may provide virtual structures from raw input data, which may further be refined as a result of multi-source shared inputs, data compression, data analysis and data logic techniques or processes. These refinements and information analyses may in turn be used to further refine which of the mechanical, imaging, and other features and components described herein may be subtracted as a result of information thus gained, paired, and further analyzed in the context of pathology and clinical outcomes results.

Embodiments may also comprise devices configured for insertion through the central lumen of another compatible excisional or interventional device. Embodiments of a device, along with associated related subcomponents described herein, may provide the capability to retrieve solid, contiguous, and/or fragmented materials as well as liquid and semi-solid tissues for analysis, diagnosis, and treatment, and to exhibit improvements in functionality and performance relative to present devices and methods for clearing chronic total occlusions and other vascular anomalies.

Although some embodiments find particular utility in cardio-vascular intervention procedures, other embodiments also find utility in, for instance, urologic and gynecologic applications, as well as various endoscopic (flexible scopes inserted into various hollow organs) interventions—and are not limited therefore to vascular applications described, shown, and claimed herein. Embodiments and elements thereof may be deployed in interventional procedures in coronaries, including bypass vessels (veins, internal mammary arteries, free radial grafts and in the case of peripheral vessels, synthetic grafts, native and bypass peripheral vessels including carotid arteries, renals, iliacs, femorals and distal vessels including venous and arterial vessels in various locations). Embodiments may include atherectomy and thrombectomy devices (those that remove plaque and other components of diseased vessel walls), which also contain a subset that may be used to treat both acute and chronic thromboembolic lesions and another subset that may be used to remove restenotic "scar" tissue obstructions (intimal hyperplasia); chronic total occlusion devices, which include a variety of devices some of which may be considered variants of atherectomy devices and finally, delivery devices to deliver medications, implants, stem cells, scaffolding or stents and devices such as other interventional devices performing functions listed above including use of laser energy, radiofrequency energy and others to ablate or otherwise alter pathophysiology of lesions that may contain calcific inclusions such as old plaque, areas of injury and healing as well as intimal and neo-intimal hyperplasia in native vessels, bypass vessels and implanted structures such as stents whether permanent or temporary, as well to be used, in various embodiments, as guiding elements including catheters and various types of guiding and interventional wires, imaging catheters and wires, contrast media, oxygenation elements, sensing instruments, radiation delivery elements, protective and shielding devices, downstream safety devices, high frequency ultrasound, high frequency pulsed lasers, and radiofrequency ablation devices among others. Embodiments may be configured to be fully or partially portable, disposable, or reusable and may be, for example, electrically/electronically-, mechanically-, hydraulically-, pneumatically-, magnetically-, remotely-, and/or manually-powered, controlled and operated.

According to another embodiment, a tissue excisional device may include a rigid distal work element formed from a single tube of material comprising cuts that define voids, the voids and remaining tube material defining a backbone portion, movable keystone portions, first and second articulable beaks and tendons extending between the movable keystone portions and the first and second beaks; an inner tube, the inner tube defining a longitudinal axis, a distal portion of the inner tube being attached to the backbone portion; an outer tube coaxially disposed over the inner tube, a distal portion of the outer tube being attached to the keystone portions, and a proximal driving and control assembly, coupled to a proximal portion of the inner tube and a proximal portion of the outer tube, and configured to drive the rigid distal work element in rotation and to selectively open and close the first and second beaks by differentially moving one of the inner and outer tubes relative to the other one of the inner and outer tubes along the longitudinal axis.

According to further embodiments, differentially moving may include differentially moving one of the inner and outer tubes relative to the other one of the inner and outer tubes along the longitudinal axis. Alternatively, differentially moving may include differentially rotating one of the inner and outer tubes relative to the other one of the inner and outer tubes. In one embodiment, the proximal driving and control assembly further may include a first dog element coupled to the proximal portion of the inner tube and a second dog element coupled to the proximal portion of the outer tube, each of the first and second dogs being configured to move independently of one another and enable the inner and outer tubes to move independently of one another. The proximal driving and control assembly further may include a motor and gear assembly coupled to the inner and outer tubes and to the first and second dogs to maintain both inner and outer tubes rotating together. One or more of the first and second dogs may be configured to axially slide relative to the other one of the first and second dogs.

In one embodiment, the first dog may be disposed non-coaxially with the second dog.

According to an embodiment, the distal portion of the inner tube may form a first inner tube flange connector and a facing second inner tube flange connector, each of the first and second inner tube flange connectors being connected to the respective backbone portions. The distal portion of the outer tube may form a first outer tube flange connector and a facing second outer tube flange connector, each of the first and second outer tube flange connectors being connected to the keystone portions and each of the first and second outer tube flange connectors may be at least partially located between the first and second inner tube flange connectors. Each of the first and second outer tube flange connectors may include a first portion having a radius of curvature that matches a radius of curvature of the outer tube and a second portion having a smaller radius of curvature that matches a radius of curvature of the rigid distal work element and a transition section between the first and second portions, thereby presenting a tapered profile. At least a portion of each of the inner tube flange connectors may be interdigitated with, disposed in close proximity to and substantially level with one of the outer tube flange connectors, such that differential tortional stresses on the rigid distal work element and on the first and second beaks are limited. The first and second inner tube flange connectors and the first and second outer tube flange connectors together present a tapered profile, to reduce frictional drag of tissue as the tissue excisional device may be forwarded through tissue to a target site.

Another embodiment is a tissue excisional device that may include a rigid distal work element formed from a single tube of material comprising cuts that define voids, the voids and remaining tube material defining a backbone portion, movable keystone portions, first and second articulable beaks and tendons extending between the movable keystone portions and the first and second beaks; an inner tube, the inner tube defining a longitudinal axis, a distal portion of the inner tube being attached to the backbone portion; an outer tube coaxially disposed over the inner tube, a distal portion of the outer tube being attached to the keystone portions, such that movement of the outer tube relative to the inner tube parallel to the longitudinal axis may be operative to open and to close the first and second articulable beaks. The distal portion of the inner tube may form a first inner tube flange connector and a facing second inner tube flange connector, each of the first and second inner tube flange connectors being connected to the respective backbone portions. The distal portion of the outer tube may form a first outer tube flange connector and a facing second outer tube flange connector, each of the first and second outer tube flange connectors being connected to the keystone portions. At least a portion of each of the first and second inner tube flange connectors may be interdigitated with, disposed in close proximity to and substantially level with one of the first and second outer tube flange connectors, such that differential tortional stresses on the rigid distal work element and on the first and second beaks are limited.

According to still further embodiments, each of the first and second outer tube flange connectors may include a first portion having a radius of curvature that matches a radius of curvature of the outer tube and a second portion having a radius of curvature that matches a radius of curvature of the rigid distal work element and a transition section between the first and second portions, thereby presenting a tapered profile. The first and second inner tube flange connectors and the first and second outer tube flange connectors together may present a tapered profile, to reduce frictional drag of tissue as the device may be forwarded through tissue to a target site.

A still further embodiment is a method of imaging and guiding a tissue excisional device during tissue excision. The method may include providing an ultrasound source and an excisional device comprising a rigid distal work element formed from a single tube of material comprising cuts that define voids, the voids and remaining tube material first and second beaks that are articulable between an open configuration and a closed configuration, the first and second beaks being configured to rotate and configured to alternatively present, along an ultrasound monitoring plane that intersects a target lesion within the tissue, a broad surface to the ultrasound source and a narrow, edge-on surface to the ultrasound source, and inserting at least the rigid distal work element into tissue while rotating and activating the ultrasound source to generate the ultrasound monitoring plane. When the monitoring plane drifts away from a target lesion: a tissue vibration may be detected whose frequency varies depending upon a distance away from the target lesion, and the ultrasound source may be re-positioned until a highest tissue vibration frequency may be detected and the target lesion re-acquired within the ultrasound monitoring plane.

According to further embodiments, the method may further include observing echogenic flashes on a display as the broad surface of each of the first and second beaks face the ultrasound source and reflect ultrasonic energy incident upon them, the flashes being interrupted by an interval during which the narrow, edge-on surface of each of the first and second beaks face the ultrasound source, during which interval less ultrasonic energy may be reflected, and guiding the rigid distal work element relative to the target lesion according to the observed echogenic flashes on the display. The rate of the echogenic flashes may be about twice a rate of rotation of the rigid distal work element.

Yet another embodiment is a method that may include providing an ultrasound source and an excisional device, the excisional device comprising a rigid distal work element formed from a single tube of material comprising cuts that define voids, the voids and remaining tube material defining first and second beaks comprising a thin and sharp inner edge and a non-sharp outer edge, the first and second beaks being articulable between an open configuration in which the thin and sharp inner edges are exposed and are oriented so as to cut tissue and a closed configuration in which, based on the resulting shape and angles of the circularly formed, closed apposition of the lips of the beaks, whether the inner, outer or both surfaces of the lips themselves are sharpened, the closed position of the beaks renders them non-cutting. The now non-sharp beak edges present a non-cutting, blunt surface to the tissues encountered, which when combined with rotation and gentle forward pressure, enable minimally traumatic separation of tissues without the need for cutting them; inserting at least the rigid distal work element into tissue while rotating and activating the ultrasound source; using the activated ultrasound source, advancing the rotating rigid distal work element to a target within the tissue with the first and second beaks in the closed configuration, such that the first and second beaks in the closed configuration present only the resulting non-sharp edges to the tissue, thereby effectuating a substantially non-traumatic tissue dissection to the target; transitioning the first and second beaks to the open configuration and coring through tissue using the exposed thin and sharp inner edges to cut and core through the tissue, and transitioning the first and second beaks back to the closed configuration to part off the cored tissue from surrounding tissue.

Each of the first and second beaks may be configured as first and second cutting blades when the first and second beaks are in the open configuration and may be configured as a singular blunt unit when the first and second beaks are in the closed configuration.

In further embodiments, while the rigid distal work element remains in the tissue: the parted off cored tissue may be transported proximally away from the rigid distal work element; a fluid may be loaded into the excisional device and into the rigid distal work element with the first and second beaks in the closed configuration, and at least a portion of the fluid may be delivered to the tissue by transitioning the first and second beaks to the open configuration, and the rigid distal work element may be retracted from the tissue while delivering the fluid with the first and second beaks in the open configuration or the rigid distal work element may be retracted from the tissue without delivering the fluid with the first and second beaks in the closed configuration.

A still further embodiment is a tissue excisional device that may include a proximal driving and control assembly; a distal work element formed from a single tube of material comprising cuts that define voids, the voids and remaining tube material defining a backbone portion, movable keystone portions; first and second beaks and tendons extending between the movable keystone portions and the first and second beaks; an inner tube, the inner tube defining a longitudinal axis, a proximal portion of the inner tube being coupled to the proximal driving and control assembly, a distal portion of the inner tube being attached to the backbone portion; an outer tube coaxially disposed over the inner tube, a proximal portion of the outer tube being coupled to the proximal driving and control assembly, a distal portion of the outer tube being attached to the keystone portions, such that axial movement of the outer tube relative to the inner tube may be operative to selectively open and close the first and second beaks; a portion of the inner tube may include one or more of changes in material thicknesses, density and laser cuts that form voids in a material of the inner tube over at least a portion of a length of the inner tube to vary one or more of a flexibility and an ability to transmit torque of at least the portion of the inner tube, and a portion of the outer tube may include one or more of changes in material thicknesses, density and laser cuts that form voids in a material of the outer tube over at least a portion of a length of the outer tube to vary one or more of a flexibility and an ability to transmit torque of at least the portion of the outer tube.

In further embodiments, the distal work element may be rigid. The portion of the inner tube may be configured such that the changes in material thicknesses, density or laser cuts result in the inner tube having a gradient of flexibility from a proximal end of the portion of the inner tube to a distal end of the portion of the inner tube. The portion of the outer tube may be configured such that the changes in material thicknesses, density or laser cuts result in the inner tube having a gradient of flexibility from a proximal end of the portion of the outer tube to a distal end of the portion of the inner tube.

In yet additional embodiments, a distal portion of the inner tube may form a first inner tube flange connector and a facing second inner tube flange connector, each of the first and second inner tube flange connectors being connected to the respective backbone portions. A distal portion of the outer tube may form a first outer tube flange connector and a facing second outer tube flange connector, each of the first and second outer tube flange connectors being connected to the keystone portions and each of the first and second outer tube flange connectors may be at least partially located between the first and second inner tube flange connectors. Each of the first and second outer tube flange connectors may include a first portion having a radius of curvature that matches a radius of curvature of the outer tube and a second portion having a radius of curvature that matches a radius of curvature of the rigid distal work element and a transition section between the first and second portions, thereby presenting a tapered profile. At least a portion of each of the inner tube flange connectors may be interdigitated with, disposed in close proximity to and substantially level with one of the outer tube flange connectors, such that differential tortional stresses on the rigid distal work element and on the first and second beaks are limited. The first and second inner tube flange connectors and the first and second outer tube flange connectors together may present a tapered profile, to reduce frictional drag of tissue as the device may be forwarded through tissue to a target site.

BRIEF DESCRIPTION OF THE DRAWINGS

FIGS. 85A, 85B, 85C and 85D show a work element as described above for FIGS. 84A-D with the work element now in stop action vertical position with respect to ultrasound waves showing the behaviors of ultrasound vectors when a work element is in this vertical position of normal rotations according to embodiments.

DETAILED DESCRIPTION

Figure 1:
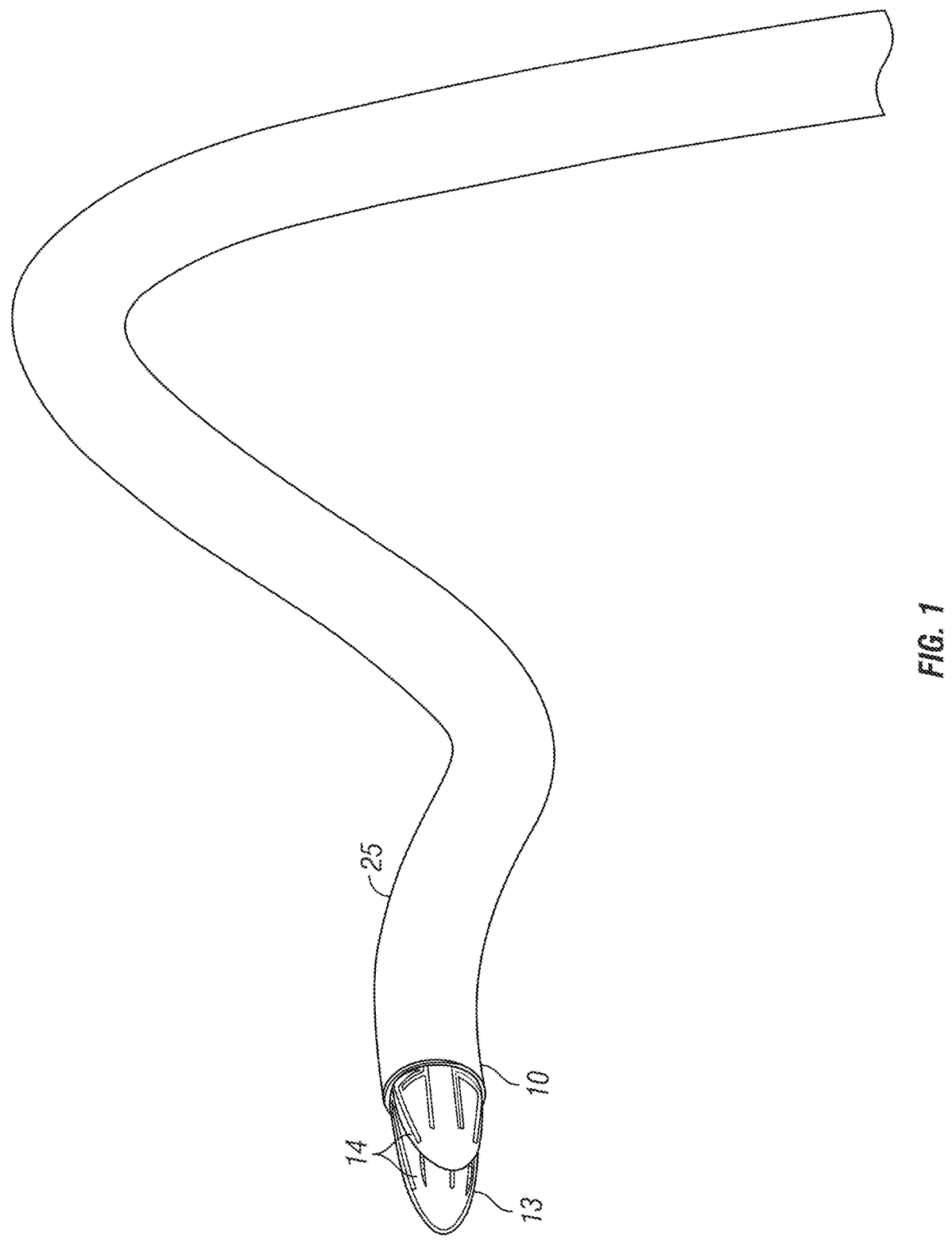
FIG. 1 is a perspective side view of a work element and its flexible shaft comprising an excisional device, according to one embodiment.

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations. Indeed, although the figures are variously described as showing "an embodiment" or characterized as being "according to embodiments," all of the structures and associated functionalities may be present in a single device or one or more of the structures and associated functionalities may be omitted from one device or present in another device. Alternatively, some of the structures and functionalities shown and described herein may be included in some devices according to one or more embodiments, while other structures and functionalities shown and described herein may be included in in or more other devices according to embodiments. Similarly, the acts or steps shown and described herein may form a single embodiment of a single method or some acts or steps may be added or omitted in other sequences to form one or more embodiments of one or more other disclosed methods.

According to embodiments, a device for material or tissue excision may be configured to remove intra-vascular materials, whether totally occluding a vessel or subtotally occluding vessels and may comprise a range of work element dimensions ranging from, for example, approximately 0.002" to 0.249" diameter (⅓ French to 19 French), or other appropriate dimensions both larger and smaller depending on applications and field of use requirements. According to embodiments, an excisional device may comprise a single tube or a single tube at least partially disposed within a coaxially-disposed or non-coaxially disposed outer tube or tubes, which outer tube or tubes may include other non- or coaxially disposed additional tubes attached to or co-extruded therewith and may comprise or include a fixed or removable distal scoopula(s) or beak(s). A work element may comprise one or more scoopulas and/or one or more beaks, as well as one or more blade elements. Such scoopula (s) and/or beak(s) may be fixed or articulable, sharpened, or unsharpened at their tips or along their side axes, and combinations of the two may be interchanged, according to embodiments. In the case of either articulable beaks or scoopulas, the principles of action as described herein and according to embodiments may be similar or different to that used for one relative to the other.

Herein, beaks may refer to that portion of a work element whose primary functions may comprise coring, shaving, penetrating with or without coring, dissecting, widening, isolating areas generally, articulating for purposes of positioning, shielding, isolating delivering agents or other components such as imaging equipment, guiding wires or tubes, inflatables or sensing equipment, or for retrieving liquids, solids or semi-solids and therefor may also be fixed, articulable, sharpened or unsharpened, and may have various features and shapes according to various embodiments. Beaks may comprise longitudinal living hinge elements such that the beaks may be expanded "out of round" to a more flattened shape, or alternatively to a different shape than when at rest. A beak driving assembly or assemblies in the device may have operating characteristics and features to enable rotational speeds advantageously to be chosen to optimize "sweep" ultrasound imaging using mechanical array or at a different speed to increase the information provided with phased array imaging, for example and may include longitudinal and "off angle" sweep capabilities as they are articulated to "shine" ultrasound or light energy at various structures of interest. These capabilities can also be used to receive signals in return and/or for reference signal processing. These capabilities can also be used together with "light out, sound in" systems that combine light and sound efferent and afferent signal processing to increase information available using a combination of these modalities. These rotational, longitudinal "pullback" and angular speeds may be generally in the same range as useful cutting, pullback/advancement and angular speeds associated with a desired interventional procedure, or they may be outside that normal range and activated separately for diagnostic or other therapeutic procedures (radiation delivery, medication "painting," injecting or other delivery).

A driving assembly or assemblies (hereafter, collectively "driving assembly" for ease of reference) for beaks may be controllable at the handle end of the device (e.g., proximally and outside the body) and can be quite sophisticated, reusable and electronically optimized for torque, rotational speed (rpm) and frequency (in the cases of translation, angular changes and oscillation motions). The driving assembly may also comprise variable control as needed and may also include the ability to halt work element motions at a part-off phase (a phase at which a cut or cored piece of tissue is separated from surrounding tissue), with automated rearward (proximal) translation for purposes of delivering excised materials (e.g., pieces of tissue) to a transport portion of the device where, according to one embodiment, vacuum along with fluid management flows and swirling action may complete the rearward delivery (for example, into a serial collection magazine or receptacle of the device). According to embodiments herein, driving mechanisms may also include delivery of electrical, mechanical, radiant, ultrasonic, electromagnetic, electron beam and simple magnetic, among other, energies distally to a work element in a desired target work area, whereby conversion or re-conversion to another energy form may be made in the work area. As examples, electrical energy may be delivered to a receiving electromagnetic device to mechanically actuate a distal element, or turbine power generated may be transmitted distally via inert gases or mechanical spinning of elements acting directly on a distal element or simply via fluids that may be present or introduced in the presence of spinning elements of a device according to embodiments, that may function to both create vacuum at the distal work element area while also creating mechanical motion in another or the same element, such as a high speed, low torque rotational element, such that simultaneous dissolution and sucking of debris such as clotted blood or particulate matter rearward and safely out of the work area may be accomplished. Yet another example is that an e-beam sent distally may be directionally guided or influenced by elements in the work area in which case energy may be precisely redirected and focused by embodiments herein, rather than merely converted to another form of energy per se. Multiple energies such as "light in, sound out" technologies among others, combining more than one modality to interrogate an area and supply more detailed information based on the modalities utilized in such a combination may be, at the same time, delivered, received and in some cases advantageously altered by elements of the present embodiments.

Energized excisional elements may refer to high energy, focused ultrasound, laser energies and other forms of energies capable of disrupting, dis-attaching, vaporizing, dissolution, or other modalities to remove from a site, or break down into small enough particles that may be easily cleared naturally, components of obstructing lesions, including, as shown in various figures that follow, the use of a plurality of such devices as may be required for specific applications of such energy delivery devices, according to embodiments herein.

In general, a scoopula may be a portion of the work element or elements of the device or may be a separate structure from the primary work element. A scoopula may be characterized by an elongated portion of its morphology and may have among its principal functions to define and/or isolate a work area within a vascular structure, and may for that purpose be fixed or articulable, with sharpened or unsharpened edges, and with a variety of shapes, according to various embodiments. Another principal function of a scoopula or multiple scoopulas may be to lead the way for following work elements, owing to the extreme streamlining of the structure such that areas to which access is difficult may be readily accessed due to the shape of the scoopula. Once in place, a scoopula may then be configured to deliver other work elements to perform their own functions, while the scoopula may continue to form a stable base from which to operate within a more defined space as a result. In that way, a scoopula structure may also be thought of as a protective element that may be cycled between closed-end or, in its more natural resting shape for example, as an open ended element, yet capable of functioning as a directing device. In one embodiment, the scoopula may for example, refer to a beak element in combination with an elongated half-round cutout section (not necessarily exactly "half" of the whole tubular section) where a portion of a tubular section proximal to a beak element has part of its wall removed, as described and shown herein, and according to various embodiments. Additionally, both scoopulas and beaks may be primarily designated for rotation at low speeds. In other embodiments, beaks may be configured for rotation at speeds varying, for example, from 1 revolution per minute (RPM) to several thousand RPM.

A scoopula may perform functions that are the same or similar to the functions discharged by the beak or beaks. Indeed, according to one embodiment, a first scoopula may isolate a portion of a work area while a second scoopula may isolate a part of a work area in concert with the first scoopula and either may be used to core or shave materials as though it or they were a beak or beaks. Another work element having articulable beaks, according to one embodiment, may be configured to capture and remove materials in the thus isolated work area. In this manner, an operator need not be limited to using a beak versus a scoopula at any stage of an intervention, based on the demands of the operation, including for example specific functions or vascular anatomic limitations for which one or the other may be better suited, to be performed and the objectives to be achieved with the present device and the elements of and accessories thereto. In the case of imaging equipment delivery, a scoopula may be used to adjust the scope, elevation, rotation, direction and distance to a target for the particular imaging modality, as well as for an excisional or other penetrating element, including guiding wires, micro-catheters, energy delivery devices, including ablative and dissolution devices and also imaging elements including imaging catheters and imaging guiding wires. This function could be quite useful particularly when imaging modalities utilizing higher frequencies and shorter penetration capabilities might otherwise be out of their range, according to embodiments. As shown herein, a transparent, expandable imaging element may serve by limiting absorption or distortion, to "transfer" or project a capability to image and visualize structures that may otherwise be beyond the reach of imaging frequencies or power specific to such a modality, a case in point being the enlargement of depth available to optical coherence tomography, by providing a near field that is relatively distortion and absorption free. Additionally, a chamber such as illustrated in the figures and described in the present disclosure, could exclude the unwanted absorption of light as a consequence of blood for example in a vascular structure, where such a chamber could be utilized together with a supporting element that would permit blood flow around such a supporting element and also around such an imaging chamber. In this way, downstream flow may be permitted while at the same time imaging fields between and imaging element and areas of interest can proceed without the absorption due to blood flow. Likewise, when certain imaging or sensing equipment may need to operate in a blood free environment, a fixed or an articulating scoopula with or without an additional sealing element such as an inflatable cuff, could function to lessen the need for flushing fluids, by fully or partially isolating an area of interest from contamination of the image by blood for example. This isolation capability could also provide for a stable volume from which to clear and aspirate intravascular disease materials such as clotted blood, both fresh and aged, as well as particulate material from intimal disease such as plaque materials or various combinations of several of these frequently encountered materials including debris that may form as a consequence of a clearing, shaving or other intervention. In the case of an expandable cuff element, as well as a plurality of expandable elevating elements, perfusion could be controlled to a minimum level to prevent downstream tissue damage or even minimal levels of temporary ischemia for example.

Embodiments of devices comprising variations of scoopula(s) may be configured to isolate the working surface(s) from the flow surfaces of a vessel. According to methods herein, in use in a vascular lumen, for example, this means that in the lumen and/or potential lumen (tight stenoses and complete occlusions, whether chronic or acute) a targeted work space will be established and protected before and additionally as soon as there is sufficient space to permit blood flow, immediately upon improvement in flow channels as a result of removal of obstructing materials. Such elements may likewise permit providing gently forced flow for the purposes of downstream oxygenation and nutrition, introduction of imaging equipment while minimizing ischemic time and also quickly enhancing natural flows based on driving pressures relieved by new or widened lumens. The lumen space may be isolated from the working space so that any elements that are released during removal actions may also be prevented from impairing flow in the protected flow lumen of the vessel being widened in caliber. This space may then be utilized such that vacuum may be maximized in the working side of the vessel as defined by the scoopula, and also in certain embodiments, while protecting the flow side. For example, according to methods, an embodiment may simultaneously press against the wall on the flow side (opposite to the working side) causing the working side of a catheter to be pressed against the lesion side of the vessel so that the elements on the working side of a device may be held precisely at the desired depth (for example for removing as much or little of a lesion as may be optimal for various considerations such as transport, degree of aggressiveness, rate of removal, particulate size of the material being removed, as the working beak element(s) are given purchase). Embodiments may also provide a stable, (geometrically) straight reference platform. This reference platform may be used to straighten a desired segment of a vessel such that a uniform depth of lesion material may be safely removed without the concern for asymmetrically removing deep-wall elements (for example in an otherwise naturally or as a result of disease, tortuous section of a vessel) that may lead to weakening, aneurism formation or even perforation during the procedure, according to methods and embodiments herein.

Thus, according to one embodiment, the scoopula may serve as an isolating element, as a reference platform, as a delivery platform permitting downstream element introduction, as a stabilizing element and as a preventer of distal embolization. A living hinge or hinges may be defined in one or more portions of the scoopula. These living hinges or locally elastically deformable regions may include straight longitudinal (axial) curved longitudinal (spirals, complex diagonals, etc.,) and crossways configurations, as defined by kerfs cut into the tube from which the scoopula may be constructed. Embodiments may utilize any of these for example, depending on particular function, desired radius and degree of flexion and/or deflection, for use in specific vascular anatomic considerations among other considerations (whether or not more than one scoopula is used for example), according to methods. Such configurations may enable expansion, variable, controllable rigidity, and geometry changes that enable tailored cuts that function as tip deflections, as well as for the purpose of temporary or permanent vessel expansion, the resultant forces of which may advantageously be directed in a radial direction, and scaffolding prior to stenting implant procedures or as standalone therapeutic procedures such as angioplasty of vessels, advantageously without the inherent strength limitations and non-directional expansion (radially) of typical balloon angioplasty technologies.

Advantageously, distal flow around and/or through such structures may be less restrictive than balloon-based technologies that occupy the entire cross-section of a vessel such as an artery, according to embodiments. Even when, in certain cases, very narrow spaces for distal flows are provided in specialized balloon devices, these are significantly limited in practical application and make these devices necessarily bulkier and harder to maneuver as a consequence. In contrast, according to embodiments and methods herein, flow rates can be significantly higher based on expansion elements free of such relatively thicker material and inflation materials. These configurations may also be used to enhance isolation and flow control on the proximal and distal ends of the isolation (working, non- or restricted-flow) chamber. The sides of a scoopula may also be controllable with these living hinges to enhance working chamber isolation control. The back side of a scoopula may be configured to enable pressing the working side against the obstructive material. Such urging may be carried out with, for example, incorporated elements of the scoopula such as pontoon-type inflatables, struts that are themselves living hinge elements, and/or may be a portion of the existing beak-actuating tendons or may be separate elements, and/or may include structural living hinge portions that change the effective caliber and or geometrical configuration(s) of the device work element or distal tip such that pressure may be applied in the direction opposite the obstructive material direction within a vascular structure. Cuts for spiral(s), lateral expansions (longitudinal scoopula living hinge(s)), and combinations of the above may all be incorporated into the scoopula or scoopulas, according to embodiments.

One embodiment is a device comprising two co-axially-disposed work elements. Whether a work element comprises one or more scoopulas or beaks, or combinations thereof, two or more co-axially placed work elements (referred to herein as a complex work element) may have particular advantages with regard to cutting or coring efficiencies in certain tissue types or with certain obstruction matrices. For example, a first work element or portion thereof, may be configured as a tubular structure ending in a fixed or articulable scoopula. A second work element may be co-axially placed inside or outside of the first work element and may comprise one or more articulable beaks. According to one embodiment, the beak driving assembly and the scoopula driving assembly (which may be one and the same) may differentially rotate the first and second work elements such that the beak or beaks of the first work element may be driven in rotation at a first speed and/or direction and the scoopula or scoopulas of the second work element may be driven in rotation at a second rotational speed and/or direction that may be different from the first rotational speed and/or direction. In such an embodiment, open beaks may be extended distally along the length of the scoopula, and the beaks rotating differentially (at different speeds or in different directions, relatively) may create a shearing action between edges of the beak(s) and the sides of the scoopula(s), for example. Additionally, as the beaks are extended distally up to and even beyond the end of the extended portion of the scoopula(s), the scoopula(s) may serve as a tissue or obstruction anchoring mechanism, and cutting efficiency of the beak tips may be enhanced as a result.

According to one embodiment, a complex work element may be composed of work elements comprising two or more beaks. The ability to fine tune the length or degree of beak tip exposure of one work element versus the other, and the ability to fine tune the differential rim speeds (rim in this case referring to rotating beak tips as tissue or obstructions are penetrated and severed) enables a clean coring action accompanied by a gentle attack on materials to be cored. If oppositely-rotating work elements are used, the tissue or obstruction to be cored may be presented with, for example, sabre-shaped cutting surfaces that minimally expose the tissue to the cutting blades and vice versa for maximum coring efficiency. Additionally, precisely opposed cutting action may advantageously prevent twisting of underlying deeper wall components, which is a known risk factor for tearing, dissection and other unfavorable tissue disruptions with resulting complete occlusion and flow obstruction, as well as frank vessel wall perforation, often requiring emergency open surgical intervention. Even without discernable acute events, deeper subclinical tissue disruption may lead to more aggressive healing responses in time leading to thrombus formation during the initial recovery period and restenosis due to intimal or deeper, hyperplasia of a vessel during the more extended recovery period. A stable scoopula edge in combination with a rotating inner or outer cutting element, according to embodiments, achieves this favorable effect (non-twisting cutting action) as may two or more oppositely rotating, separate beaks or scoopulas with their crossing distal edges, according to other embodiments. The above-described element may be included in various embodiments herein as may other elements that further stabilize complex work elements, for example, backside struts among others (asymmetry of expansion forces as another example).

Several of the embodiments described herein include luminal access channels arranged in various locations designed to take advantage of a particular type of imaging modality and to likewise minimize their limitations. For example, when an access lumen is expected to image structures that require a longer depth of penetration, then typically an ultrasound element may be utilized. Likewise, if an access lumen is expected to be located in an area where blood is flowing, then again, ultrasound imaging catheters may be the imaging modality of choice in that location. On the other hand, given its higher resolution, optical coherence tomography (OCT) may be the imaging modality of choice where closer examination and more accurate guidance would be desirable, particularly when its limitations such as reduced depth of penetration can be overcome by positioning in close approximation of the desired field of study. This accounts for the variety of locations illustrated throughout many of the configurations. An additional issue for the higher resolution optical coherence tomography imaging modality is that there is absorption and scattering caused by certain tissues that impede its ability to image effectively. Such issues are encountered within vascular structures in particular, where blood flow is needed for delivering nutrients and oxygen to prevent ischemia and cell death and so in certain embodiments, blood flow is reduced or even stopped for a short period of time during OCT imaging.

Other methods and devices are shown in various illustrations and descriptions including the use of imaging chambers that can be used without interrupting blood flow to downstream locations, such as the several embodiments of imaging chambers described herein, many of which have other capabilities incorporated within the imaging chambers, such as cutting ribbons, parting off functions and supporting functions. Being transparent, expandable structures that can be filled with saline or other transparent fluids and being constructed so as not to distort or impede optical transmission and reception, these may also function to extend the reach of OCT for example and thereby increase the capabilities of OCT by overcoming or partially overcoming some of its inherent characteristics, including distortion, scattering and obstruction of the optical signals and receptions sent and received for the purpose of analysis and precise guidance, according to embodiments herein. Additionally, such imaging chambers often include, in the various embodiments herein, internal channels permitting the introduction, positioning, and supporting of various excisional modalities such as those utilizing physically sharp blade elements, flush and vacuum to excise, entrap, collect, and transport disease elements partially or completely occluding vessels such as arteries, veins and other tubular structures. Other therapeutic elements may likewise be introduced and optimally positioned via these internal channels, which themselves may be elevated, positioned, and otherwise supported with various structures including scoopula elements, inflatables, other types of expandable elements as well as simple tubular elements as shown and described in various embodiments herein. Such therapeutic elements may include ablative modalities such as high frequency, focused ultrasound, lasers, radiofrequency delivery elements whether unipolar or bipolar, as well as high energy spark impulses among others for example when encountering a particularly hard proximal cap in a chronically totally occluded vascular channel. Likewise, channels may be optimized for specific delivery of other modalities, including for example, delivering high speed jets of liquid to break up, dissolve or ablate offending materials such as thrombus and other debris, according to embodiments. Additionally, in certain embodiments, delivery of fluids, agents or locally activated physical disruptive solutions, while simultaneously applying vacuum to transport and remove such offending materials are shown and described, in some assemblies as described and illustrated, in concert with other elements that help isolate, trap and augment in other ways, the effectiveness of the mobilization and removal of these abnormal materials, according to methods and embodiments.

According to one embodiment, fluids, anesthetic or therapeutic agents or radioactive materials, to cite a few non-limiting examples, may be delivered through the inner tube and out of the beaks 14 to a precisely characterized locus within the tissue, under ultrasound guidance. The opening and closing of the beaks 14 may be controlled such that the fluids or substances within the inner tube to which the work element is coupled are contained and constrained to within the contained cylindrical space until the distal end of the device reaches the intended target within the tissue, whereupon the beaks 14 may be opened and the fluid and/or substances delivered through the open beaks to the target lesion. Such may be carried out, for example, after an excisional operation to deliver therapeutic agents to and around the target lesion and, if desired along the retraction path as the device is removed from the body.

The luminal channels are also available for flushing to help clear debris, dilute the effects of blood to obstruct optical imaging, and for such methods as comparative flow, such as Fractional Flow Reserve or other techniques and processes, and pressure measuring for diagnostic flow reserve assessment as well as for before and after treatment comparisons as endpoint determinates.

The role of the basic excisional structures described herein, particularly with or without a scoopula, is likewise multifunctional, according to embodiments. Their roles include excision and removal of offending obstructing materials. In the process of doing so, however, such devices may be often called upon for delivery of other elements specialized for dealing with chronic total occlusions and other stepwise therapeutic maneuvers. For example, several embodiments demonstrate how smaller working elements may be strongly supported by the larger working assembly, positioned proximal to the either subtotally or totally occluded segments of a vessel, the larger element temporarily serving as a platform for imaging using various modalities. The larger primary assembly or work element(s) may also be called upon to strongly, precisely elevate, provide back support to, angle and otherwise optimally position smaller elements, while providing a robust, precise, and stable platform from which the smaller elements can image, guide and operate together with other elements delivered to the site of activity. The larger device may also provide a stable reference point and may also ensure adequate flow beyond the area upon which the smaller elements are engaged. The larger elements may provide directionality, shielding and isolation to the smaller elements to optimize safety and ensure that an area of interventional activity is completely cleared of materials while protecting against clearances that proceed too deeply into normal vascular layers and structures, in some cases based upon optimal positioning of guidance modalities either leading the way, or directly adjacent to a cutting, coring or ablating element. Another method described and illustrated herein makes use of depth limiting elements, which are described in several of the embodiments herein and that may be used together with or independently of imaging as desired.

Another significant aspect of the various embodiments disclosed herein includes the use of staged introduction of elements. In simple cases, where all that would be required is the use of the primary excisional device, then other elements need not be introduced at the beginning of a procedure, but may thereafter be introduced at will through available channels. For example, one embodiment of the excisional device may be used in a standalone manner for penetrating through or around, excising, parting off, collecting, and transporting out of the body, offending obstructive materials. The same instrument, however, can be utilized with imaging for more precise interventions. In a like manner, a standalone excising embodiment may utilize a distally-delivered parting off chamber, whether equipped with inherent parting off capabilities or not. In certain use cases, where a scoopula may not be needed or even desirable, the one simpler embodiment is fully capable of all the functionalities with or without the scoopula, except for the directionality it provides as well as the inherent protection of a vessel wall that has obstructive disease on one side but other sides are not affected. In that instance, therefore, it may be desirable to shield it from the cutting effects of blades or other cutting and excising modalities.

A significant aspect of the staged introduction capabilities disclosed herein is that when dealing with obstructive materials, there may be multiple acceptable options. For example, in the case of a mixed obstructive lesion where thrombus may be anticipated, a first phase clearing of thrombus may involve certain elements to be combined to clear the clot(s), which after accomplishment of that phase, the firmer plaque material may then be precisely excised without as much risk of downstream embolization. Throughout the illustrations and descriptions herein, there are provisions for a multitude of combinations of elements and embodiments as are shown. Moreover, there are other combinations that are not shown but are clearly optional and may be favorable, and all such combinations are considered to be encompassed by the disclosure of embodiments herein. One such combination involves certain elements providing elevation while others may then by utilizing that platform positioning, angle an excisional or imaging element to permit penetration or excision. Once penetration is achieved, a small channel may be enlarged or an expandable element may simply be utilized to provide powerful backup support in certain embodiments. Likewise, an elevation platform may be optimally utilized with a centering expandable element that may then create an opportunity for clearing an off-center obstruction.

A significant capability that is illustrated and described in several embodiments herein is the overall commonality of access and imaging enhancements that is provided by devices and methods described herein that is enabled by carrying certain structures far distally to a site by introducing needed elements in a tailored approach for a given area in the body, with the uniquely different requirements specific to the anatomy and composition. The elements of an interventional or excisional device that may contribute to an overall assembly specific for a region of interest, according to embodiments herein, may include various cannula channels and other chambers whose functions are optimized by shared capabilities with other elements for enabling image optimization and for providing directionality including rotation, angulation and other coordinates manipulations in a platform described and illustrated herein that provides stability and support. Such elements demonstrate that the devices described and illustrated herein are equally suited to, for example, bronchial passageways as they are for vascular spaces, one example being the portability of elements that are utilized for recreating an optimized ultrasound or optical guidance pathway in an area that may be lacking a natural medium through which to transmit and receive minimally obstructive, minimally distorted signals. In order to take advantage of the in-situ and precision imaging available in this manner, further embodiments include elements designed to enhance local control of parameters such as precision directionality and depth of excision, imaging, and sampling according to embodiments and methods herein.

Several embodiments are shown that may be more or less effective on their own depending on the nature of the material being excised, ablated, or otherwise disrupted for removal or clearing and in order to maximize effectiveness, elements are described and illustrated that work together with other elements in assemblies that overcome limitations that would otherwise exist.

The terms "imaging" or "imaging element," or "excising and imaging" refer to elements that can have multiple capabilities. For example, tubular lumens, expandable chambers and the imaging elements themselves may be referred to with such terms indicating that the designs of the embodiments can be presumed to be optimized for the option of including imaging modalities of various types in these elements or may refer to the imaging elements themselves in which case it can be presumed that the various modalities are generally interchangeable. It should also be noted that the dimensions of the illustrated structures may change as newer iterations of modalities as well as the types and sizes of excisional elements that may also be forthcoming due to advances in construction, materials, methods, and manufacturing, as these can be presumed to enhance the capabilities of the embodiments herein. All such variations are within the scope of the embodiments disclosed herein.

Many of the illustrations herein reference use of the disclosed devices and methods in vascular structures. However, these devices and methods may be used in a variety of tissues and organ systems, including lymphatic channels, nerve conduits, urinary channels, and other closed and open living structures such as gynecologic and other ductal, hollow spaces such as airways, spinal cord channels, central nervous system spaces and any of many more potential spaces. The specific application likewise may require dimensions other than those suggested by the illustrated proportions and scale. However, it is presumed that the same principles of action and function would be preserved and that such other use cases and variations are well within the scope of the present disclosure.

As used throughout this disclosure, the term "work element" or "work elements" may comprise one or more tubes, and the terms "inner" and "outer" tubes may be used with reference to a single work element, or in reference to two or more co-axially located work elements (or "complex work elements", as used herein), which may comprise one or more tubes to enable their specific function. Generally speaking, the terms "distal" and 'forward" refer to downstream positions (e.g., away from the surgeon or practitioner), whereas "proximal to" or "back end" refer to positions more upstream in a flowing vessel (e.g., closer to surgeon or practitioner). Likewise, "inferior to" or "underside" refers to a location that appears at or near the bottom in an illustration, opposite a "top" or "upper" area, although it must be understood that where working in blood vessels is concerned, these are relative terms that may be inferior in an illustration for example but may actually be at the top depending on the rotation of the vessel as well as the rotation of the elements of an embodiment or embodiments. A coaxially-disposed outer tube, according to one embodiment, may also comprise one or more coatings. According to one embodiment, an outer tube may comprise a stainless steel hypodermic tubing ("hypo tube"). Such a stainless hypo tube, according to one embodiment, may be provided with (e.g., laser) cuts to selectively remove tube material to define a monolithic distal assembly that defines beaks, a living hinge that attaches the beak(s) to the generally tubular body of the device or that homogeneously spans between the beak(s) and the generally tubular body of the device. According to one embodiment, cuts in the hypo tube may define one or more tendons configured to actuate the beak(s). The cuts in the hypo tube may also define one or more tendon actuation tabs or body portion actuation tabs that enable actuation (e.g., opening and closing) the beak(s) through the tendons or body portion, according to embodiments, and limit the travel thereof. The tendon actuator tab(s) or body portion tab(s) may be located at any location along the length of the hypo tube. According to one embodiment, portions of the tube may be rigid. According to another embodiment, laser cuts along the proximally extended body portion of the tube may enable flexibility over its entire length or one or more portions thereof. The device may also comprise materials other than stainless steel, such as plastics or other suitable materials, which may incorporate the features of the beak(s), tendon(s), and, according to embodiments, tendon actuation tab(s) or an internal tube actuator element. Aspects of the devices and methods disclosed herein are related to the devices and methods disclosed in co-pending and/or commonly assigned U.S. Pat. No. 9,463,001 entitled "SOFT TISSUE CORING BIOPSY DEVICES AND METHODS"; U.S. Pat. No. 10,070,884 entitled "SOFT TISSUE CORING BIOPSY DEVICES AND METHODS"; U.S. Pat. No. 9,155,527 entitled "SOFT TISSUE CORING BIOPSY DEVICES AND METHODS"; U.S. Pat. No. 8,992,441 entitled "AUTOMATED, SELECTABLE, SOFT TISSUE EXCISION BIOPSY DEVICES AND METHODS"; U.S. Pat. No. 9,039,633 entitled "AUTOMATED SELECTABLE SOFT TISSUE EXCISION BIOPSY DEVICES AND METHODS"; U.S. Pat. No. 10,076,315 entitled "SOFT TISSUE BIOPSY OR EXCISIONAL DEVICES AND METHODS"; U.S. Pat. No. 9,999,758 entitled "IN SITU MATERIAL DELIVERY DEVICES AND METHODS"; and U.S. Pat. No. 10,231,750 entitled "EXCISIONAL DEVICE DISTAL WORKING END ACTUATION MECHANISM AND METHOD"; the entire disclosures of which are hereby incorporated herein in their entirety.

Reference will now be made in detail to the construction and operation of implementations of the embodiments illustrated in the accompanying drawings. The following description is only exemplary of the embodiments and methods described and shown herein. The embodiments, therefore, are not limited to these implementations, but may be realized by other implementations.

FIG. 1 is a perspective view of a flexible excisional and imaging device 10 according to an embodiment. As shown, the imaging device 10 may include a work element 13 constructed of and from, in one embodiment, a monolithic tube with an articulated beak set 14 and a flexible outer sleeve 25.

Figure 2:
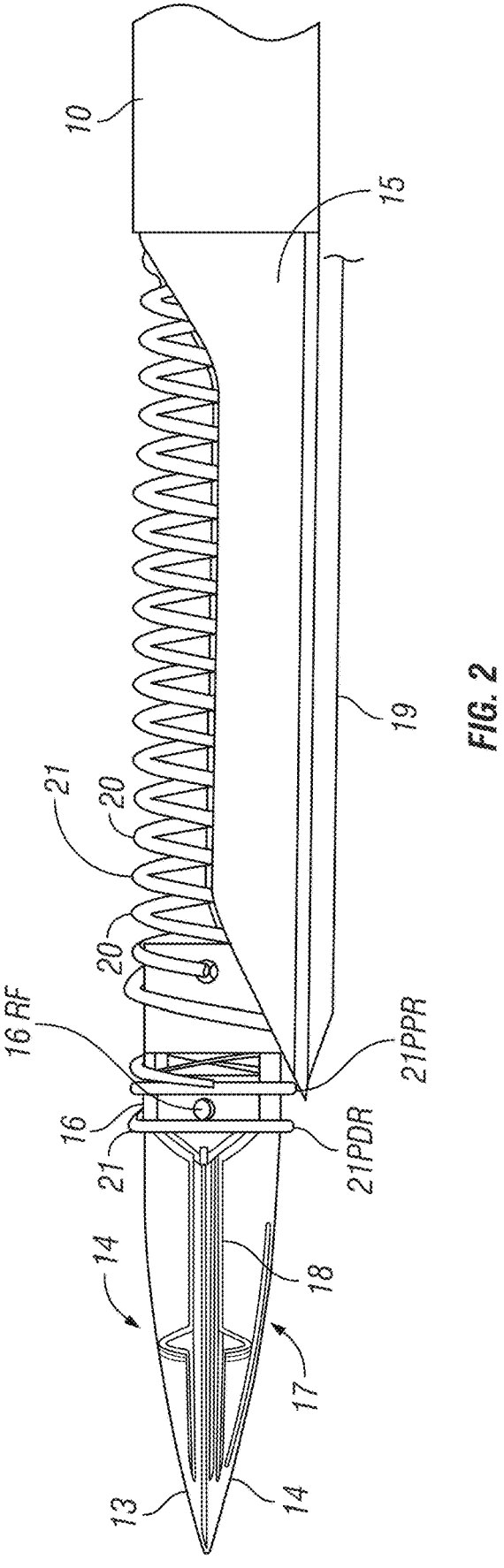
FIG. 2 is a side view of an excisional device in a closed configuration, according to one embodiment.

FIG. 2 is a side view of an excisional device in a closed configuration, according to one embodiment. As previously described, the features of the work element may be cut from a single tube. Such a work element enables matching lips or tips only, with scissors mating at lateral lips overlap during, and at closure, and includes living hinge element 17, living tendons 18, travel limiting structures such as keystone-shaped, or tendon actuation element 16 (hereinafter referred to as the "keystone" element), and a movable scoopula 15. According to embodiments, travel limiting element 16 may include a race follower element 16RF that may circulate around the work element 13's inner diameter, within an area defined axially by the forward termination of the coil of helical actuator 21 including roughly parallel over a portion of its flight, distal race limiter 21PDR and roughly parallel over a portion of its flight, proximal race limiter 21PPR. According to embodiments, helical actuator element 20 may be a helical tubular element whose flights or windings of revolution may nest between flights or turns of helical actuator 21, whose revolutions may be of similar pitch for example, so that when two such helical elements thus configured rotate together at the same speed, no relative axial motion between the two occurs. However, were one of the elements 20, 21 to be rotated at a different pace or rotational speed from the other, then a relative or differential axial motion between the two would necessarily occur. Referring to FIG. 2 then, were proximal actuator element 20 made to spin faster in, for instance, a clockwise direction (rotational direction referenced to looking from proximal vantage point to distal) than distal actuator 21, the relative axial motion between the two would cause actuator 21 to crawl forward along actuator element 20's windings until their rotational speeds were equalized at which point axial motion would cease. To return actuator 21 to its original axial starting position relative to actuator element 20, its rotational speed would simply need to speed up higher relative to actuator element 20's rotational speed until such original starting point were again reached. Thereafter, maintaining equal rotational speeds for actuator 21 and actuator element 20 would ensure that further axial changes between the two would cease and stabilize-to the extent relative rotational speeds of the two actuator elements were held stable, according to embodiments. Alternatively, actuator element 20's speed could be slowed to match that of actuator 21, with the same result of synchronous rotational speed. Referring again to FIG. 2, actuator 21's termination in parallel distal and proximal race elements, enables continuous equal pace rotation of actuators 21 and 20, resulting in axial stability as well as permits advanced and retarded rotation of work element 13 brought about as a result of its solid attachment to actuator element 20, relative to actuator 21, whenever rotational speeds of actuator element 20 and 21 are different. In the event rotational speeds of actuator 21 and 20 are different, not only would work element 13 progress or regress in rotation, with keystone (i.e., travel limiter) or tendon actuation element race follower 16RF progressing and regressing rotationally together with the rest of work element 13, within the axial area defined by edge limiters 211 and 212, but race follower 16RF together with its attached travel limiter (keystone) 16, and living tendons 18 would move axially distally or proximally relative to the rest of work element 13 including its living hinge backbones 17, the direction of axial motion depending on whether actuator element 21 were rotating faster in a clockwise direction (direction of rotation referenced looking from a vantage point proximally to distally). In that case, the travel limiter 16, its race follower 16RF and attached tendons 18 would all retract axially in a proximal direction relative to the backbones 17 of work element 13 as a result of work element 13's attachment to actuator element 20, as actuator element 21's flights crawled back between actuator element 20's similar flights, all of which would cause the beak elements 14 to progressively close to a tightly apposed position for rotational dissection and penetration purposes or other purposes such as for severing off tissue cut by beak elements 14, according to embodiments.

Also illustrated in FIG. 2 is scoopula 15, which though shown straight, may be flexible along with outer flexible tube 10, according to embodiments and as shown in FIG. 1. The scoopula or trough 15 may be entirely or partially transparent over its entire extent or in key areas where optical transmission may be desirable. An additional, optional non-rotating flexible sheath may be provided to cover over actuator elements 20 and 21, is not shown in FIG. 2 but such an optional element is shown in subsequent figures. Additional tubular element 19, similar in function but different in location to, elements 23 and 24 shown in subsequent illustrations, may also be provided and may enable independent movement of guiding elements for example, with proximal entry point(s) (purposely undefined in this figure, since various choices of entry point(s) may satisfy specific indications, according to embodiments).

Figure 3:
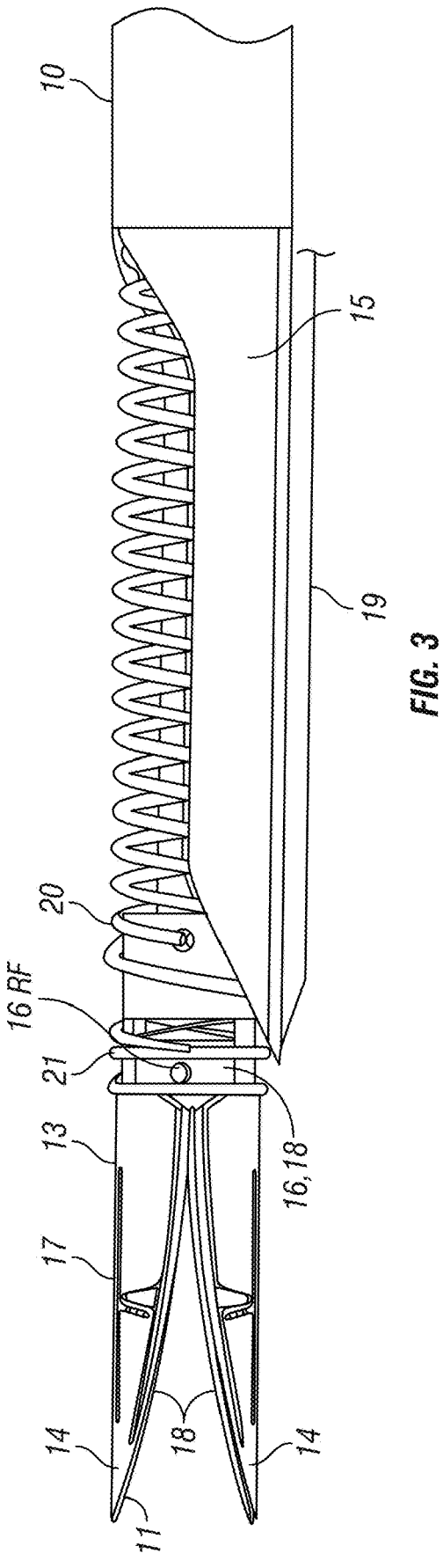
FIG. 3 is a side view of an excisional device in an open configuration, according to one embodiment.

FIG. 3 is a side view of an excisional device in an open configuration, according to one embodiment and illustrates another state of the work element 13 of FIG. 2, this time with the beak elements 14 widely open and extending beyond scoopula 15 (noting that keystone 16 and its race follower element 16RF are now in an axially advanced position, forcing tendons 18 also distally, while actuator element 20 is holding back living hinge backbones 17, as may be compared to keystone 16's position shown in FIG. 2. It is these relative changes that actuate beak elements 14, which themselves are enabled to be rotating during the entirety of the transitions from closed to open and back to closed as may be clinically desired, as often as may be useful, during a diagnostic and a therapeutic procedure)). The position of the keystone element shows additional space for "diving" or overdrive closure of the beak elements 14 as well as for overdriving opening (i.e., beak tips 14 will be extended to an expanded diameter that may be greater than the diameter of the tube from which they were formed). Another embodiment utilizing the same mechanism of converting differential angular motion into axial excursion for the purpose of actuating beaks is directly attaching a spiral element or a plurality of elements spaced between a number of one or more additional spiral elements, directly to the keystones (or a keystone or keystone equivalent) in embodiments, while the one or more spiral elements are (is) attached directly to the tubular base (backbone) structure(s) of the beak element(s) which, according to the illustrated embodiments, are of a single monolithic structure-that is, formed from a single tube of material from which material is selectively removed such that the remaining material forms the desired structures.

According to embodiments, a multi-strand much more linearly oriented than illustrated in this figure and FIG. 2 would impart little twist on the backbone structure nor on the keystones, which could then, with any additional side clearance that may be required, function in exactly the same manner, that is, that by twisting multiple, even only slightly angulated in some cases, (mostly co-linear with the longitudinal axis, but with a small degree of twist, for example in a multi-strand winding, every other strand or group of strands could be independently rotated relative to others in the winding assembly) elements differentially, one or one group to another, a small angular degree of rotation—one group being attached to the backbone slightly more or less than another group (keystone group) would achieve the same result as shown in FIG. 3 and other figures, and according to embodiments. Likewise, a minimally-twisted set of bands attached to or an extension of keystones themselves could nest between another one or more similar bands and again, with differential (slight) rotation could activate the beaks for opening and closing. Such bands, multiple strands or flexible tubes could also in addition to causing beak opening and closing, provide rotational motion and control according to embodiments.

Therefore, an embodiment may include a flexible tube, braids, windings, bands, or any combination thereof to provide a mechanisms for differentially causing keystones and backbones to open and close during spinning or reciprocating rotation, and also during non-rotation of the beaks for penetration, excision, and parting off purposes. Additionally, the scoopula portion is in a slightly more proximal or slid back position (relative to the flexible beak element(s) 14) to show the relative independence of scoopula 15 and work element 13 with its flexible actuators and other components, to project forward while being rotated, as well as optionally utilizing beaks open and closed to penetrate a total vascular occlusion for example. The degree of extension of the scoopula portion beyond the beak elements 14beak elements 14 could be used to limit exposure of vascular walls to the bulk of working assembly 13 as well as to its extremely sharp elements such as beak tips of beak elements 14 particularly when these are in the open position for example, until such time as using the working elements of 13's full capabilities may be deemed useful. It should be noted that the inclusion of a scoopula element enables beaks to excise effectively without the need for a non-rotating sheath (NRS) to cover the majority of the beaks for maximum efficiency of excision. Several illustrations in which the scoopula is included purposely indicate the relative independence of the beak elements 14 of a an NRS element 22 covering according to embodiments. The scoopula 15 shown and described in several illustrations may be fully transparent, or specific sections of a scoopula may be transparent to optical signals and others along the electromagnetic spectrum for purposes of optimal, direct local imaging, according to embodiments. The scoopula 15 may also be constructed with non- or minimally ferromagnetic materials such that it may be pre-placed in precise position, for use during magnetic resonance imaging where magnetic elements cannot be used. Once a stable position is established, other elements may be introduced and manipulated manually directly or robotically, or utilizing an automated, robotically controlled series of steps.

The side tubular element 19 may have numerous uses, particularly since the scoopula 15 of which it is a part, may be independently rotatable from other elements of the device, such that the access provided by tubular element 19 may be used for a variety of additional elements, such as a flexible (non-rigid) "flap" or one-way distal valve element(s) (not shown) which may be introduced to prevent distal embolization or to further isolate certain areas for pressure augmentation via channels in this and other embodiments. Additional lumens or channels similar to tubular element 19 may be added and used for contrast injection, flow augmentation, guide wire passage, imaging element passage such as phased-array "ultrasound on a wire" intravascular ultrasound (IVUS), fractional flow reserve (FFR) and instant wave-free ratio (iFR) devices among others, which are available on flexible wires ranging from about 0.009"-0.018" for example. The scoopula 15 itself or the beak elements 14 can be a mounting point for imaging technologies such as optical coherence tomography (OCT), IVUS, near infrared and other imaging modalities and combinations to assess such factors as plaque vulnerability, among others. Channels may be provided for fluid management including delivery and vacuum. A channel could be used for example, to over-pressurize a proximal segment while measuring iFR or FFR distally, to augment functional gradient measurement to gauge functional significance of stenotic segments before, during and after interventions, particularly in cases where it may be helpful to overcome limitations of abnormally decreased ambient intraluminal pressure as a result of impaired left ventricular function or sequential stenoses, and in cases where there may be a desire to avoid use of pharmaco-dynamic agents such as adenosine when performing functional studies. Such elements are shown in subsequent illustrations, along with additional tubular access channels associated with various elements of embodiments of the present device.

Figure 4:
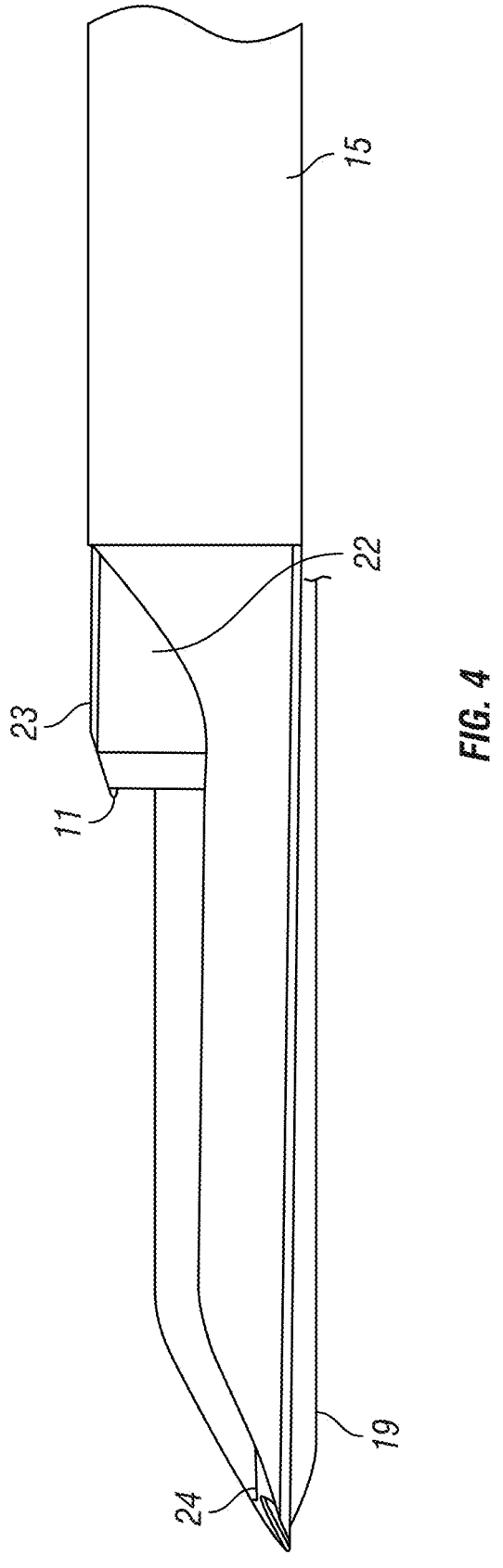
FIG. 4 is a side view of an excisional device, according to an additional configuration in one embodiment.

FIG. 4 is a side view of an excisional device, according to an additional configuration of one embodiment comprising a scoopula 15 with two additional access tubular elements 19, located on the outer surface; and reference 24, coaxially co-extruded with the scoopula's wall, which may provide an additional lumen or lumens for example for a guide wire or other working element close to a tubular lumen that can provide an access path along access tubular element 19 for an imaging catheter or wire in close proximity to coaxial tubular element 24 according to embodiments. Additionally, FIG. 4 shows an outer non- or differentially rotating sheath 22 covering the beak elements of beak elements 14beak elements 14, exposing, as may be desired, only the forward lateral and distal-most portions of beak edges 11 and their distal tips to any desired depth. The non- or differentially rotating sheath element 22 is shown equipped with an additional tubular lumen element 23 that may provide access as desired for an imaging catheter or wire and may be rotated by machine or by hand to sweep by rotation as well as axially in a distal and proximal direction to interrogate an area with close up views, particularly if the vessel being treated happened to be of large caliber, potentially beyond the range of an imaging modality that otherwise might be positioned less closely to the subject matter of interest, when utilizing a modality such as optical coherence tomography (OCT).

An additional feature of the use of element 23 lumen, whether collapsible and then expanded by filling its internal lumen with another element such as an imaging wire or catheter, is that when it is placed between the cutting elements and the tissue being excised, its position being so close to the cutting elements' edges 11, coupled to the depth limiting effect of beak edges 11 being so minimally exposed, then together or separately these may be utilized to more precisely control depth of cutting into the vascular disease, to avoid traumatizing deeper, normal (e.g., non-diseased or stenosed) wall components, for example, or for the purpose of enabling several, increasing diameter excisional passes for purposes of positively controlling the removal of lesion material and, therefore, limiting potential embolic material release into the bloodstream. Also, given that imaging elements can be placed in various locations often with the scoopula in the field of view, and that the entire or partial distal area of the scoopula 15 beginning in the trough section may include or may be formed of transparent material such as clear polymer or other such material, full sweep interrogation is enabled by certain imaging modalities that provide great detail such as optical coherence tomography (OCT) according to embodiments. Likewise, marking elements may be incorporated in the scoopula, or actually delivered to a vascular wall by device 10 to indicate which parts are facing away from the protective faces of the scoopula, for imaging reference purposes. The choices of access locations for imaging elements may thus be coupled with aggressive penetrating elements such as stiffer, more controllable guide wires and catheters among others as will be shown in further illustrations to follow, according to embodiments.

Figure 5:
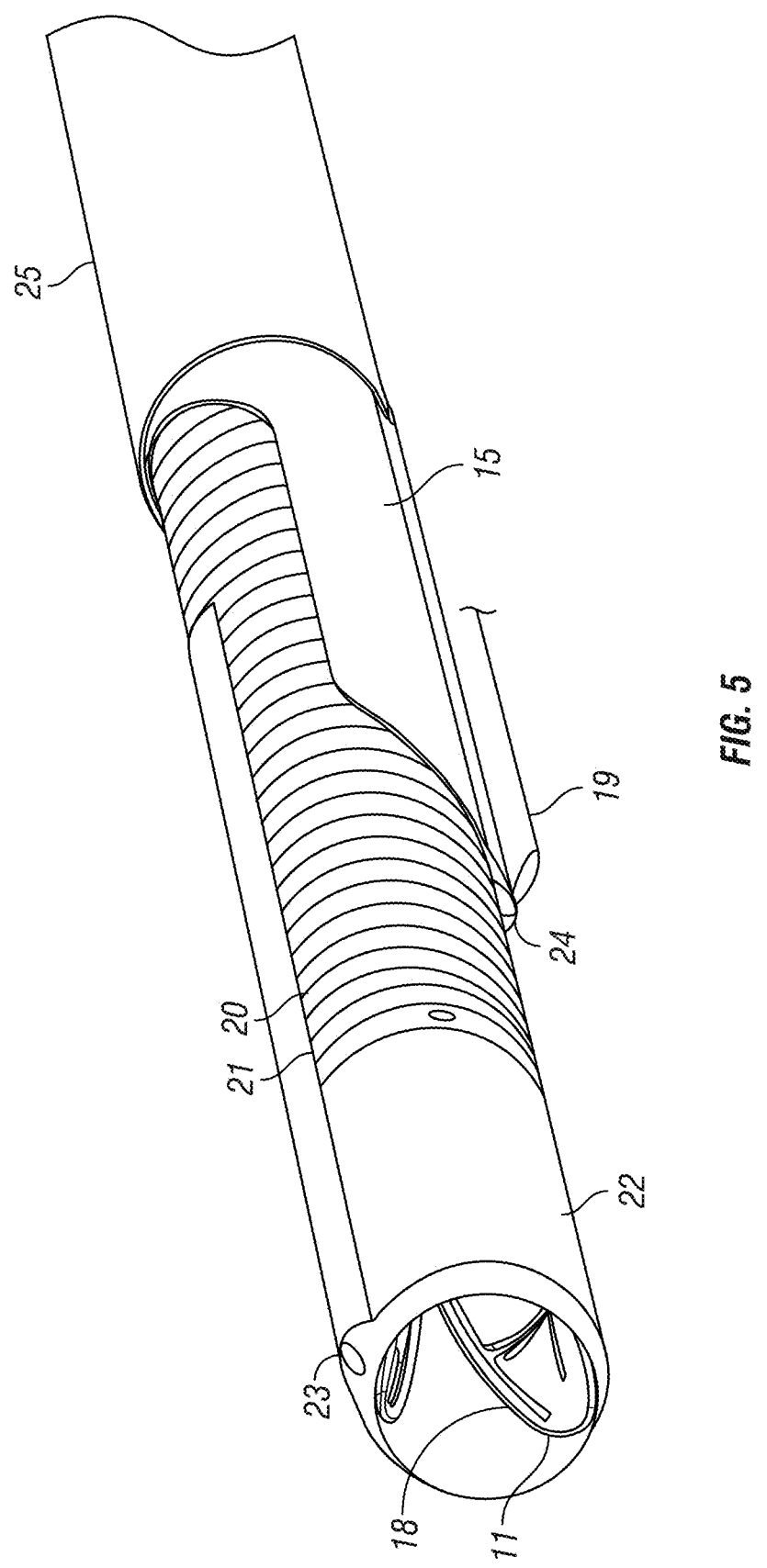
FIG. 5 is a perspective view of an excisional device in an open coring mode, according to one embodiment.

FIG. 5 is a perspective view of an excisional device in an open coring mode, according to one embodiment that is similar to that of FIG. 4 but now depicts a cut-away view of the non- or differentially rotating sheath 22 and its, partially shown in cutaway, collapsible tubular access element 23 for clarity and to reveal inner actuator elements 20 and 21, all of which may be flexible. Also highlighted by the clearances (cutaways) is the extremely thin wall nature of non- or differentially rotating element 22 including its access tubular lumen element 23, which may be partially or entirely made of a transparent material such as polyimide or other materials including a variety of transparent polymers. Note that non- or differentially rotating sheath 22 may continue all the way back proximally within over-tube element 25 or it may terminate at any point therein. Likewise, tubular access element 23 may also extend all the way proximal within over-tube element 25 or it may terminate at a different point within over-tube element 25. Note also that element 24 may also be a collapsible tubular lumen. Revealed as well in FIG. 5 are more of the details of the cutting, opening, and closing elements of the work element, including beak edges 11, tendons 18 and various other construction details. Also shown to further clarify the function of scoopula 15 as independently also rotatable and extendable, is a separate over-tube 25, which may cover over tubular element 19 or its wall may lie between element 19 and scoopula 15, in which case tubular element 19 may only be attached to scoopula 15 near the distal tip of scoopula 15, according to embodiments. A thin-walled sheath 22 has been removed to expose the flexible actuator elements 20 and 21, the latter forming a distal parallel race within which race follower 16RF freely rotates as elements 20 and 21 are rotated differentially. It should be noted that race follower element 16RF need not move far within its race boundaries in order to fully close and open beak edges 11 via differential motions of living hinge element 17 and tendons 18, resulting from the axial actions of elements 20 and 21 as outlined in detail previously. Also illustrated is separately extendable, optionally of polymeric and transparent material, scoopula 15, including its access tubular element 19 from within flexible over-tube 25 according to embodiments.

Figure 6:
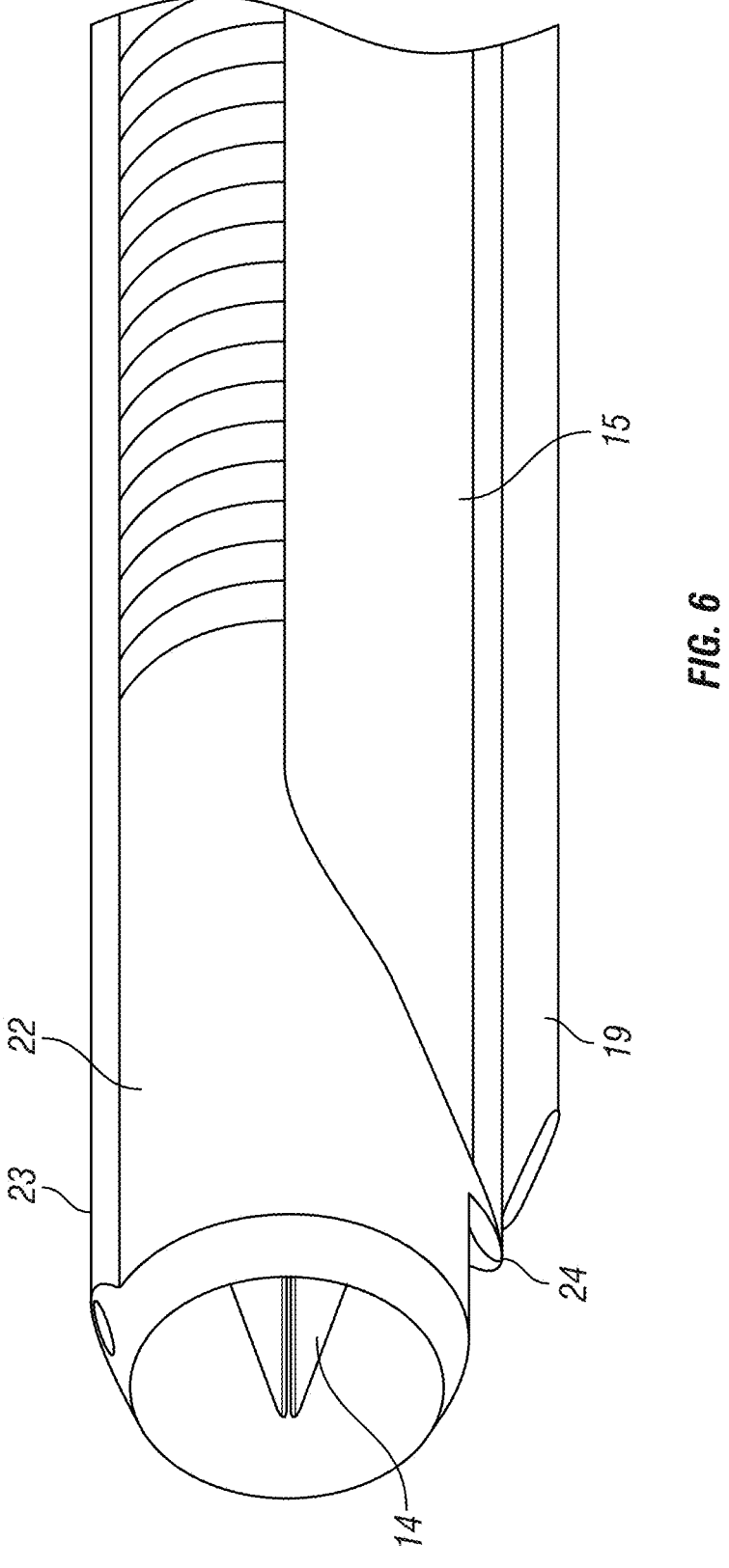
FIG. 6 is a perspective view of an excisional device of FIG. 5 in an additional closed configuration according to one embodiment.

FIG. 6 is a side view of the excisional device of FIG. 5, with work element 13 and its components now in extended, closed, configuration for severing off tissue and for rotational dissection with closed beak elements 14beak elements 14. As shown, the beak edges 11 are opposed to one another, partially or fully hiding their sharp edges for minimally traumatic blunt, rotational dissection of tissues. The non- or differentially rotating sheath 22 is now shown in non-cut-away view with lumen access port 23 partially rotated towards the viewer to demonstrate its positional capabilities for viewing proximity to a vascular wall, area of interest. Also shown is a scoopula 15 with its auxiliary tubular lumens 19 and 24.

Figure 7:
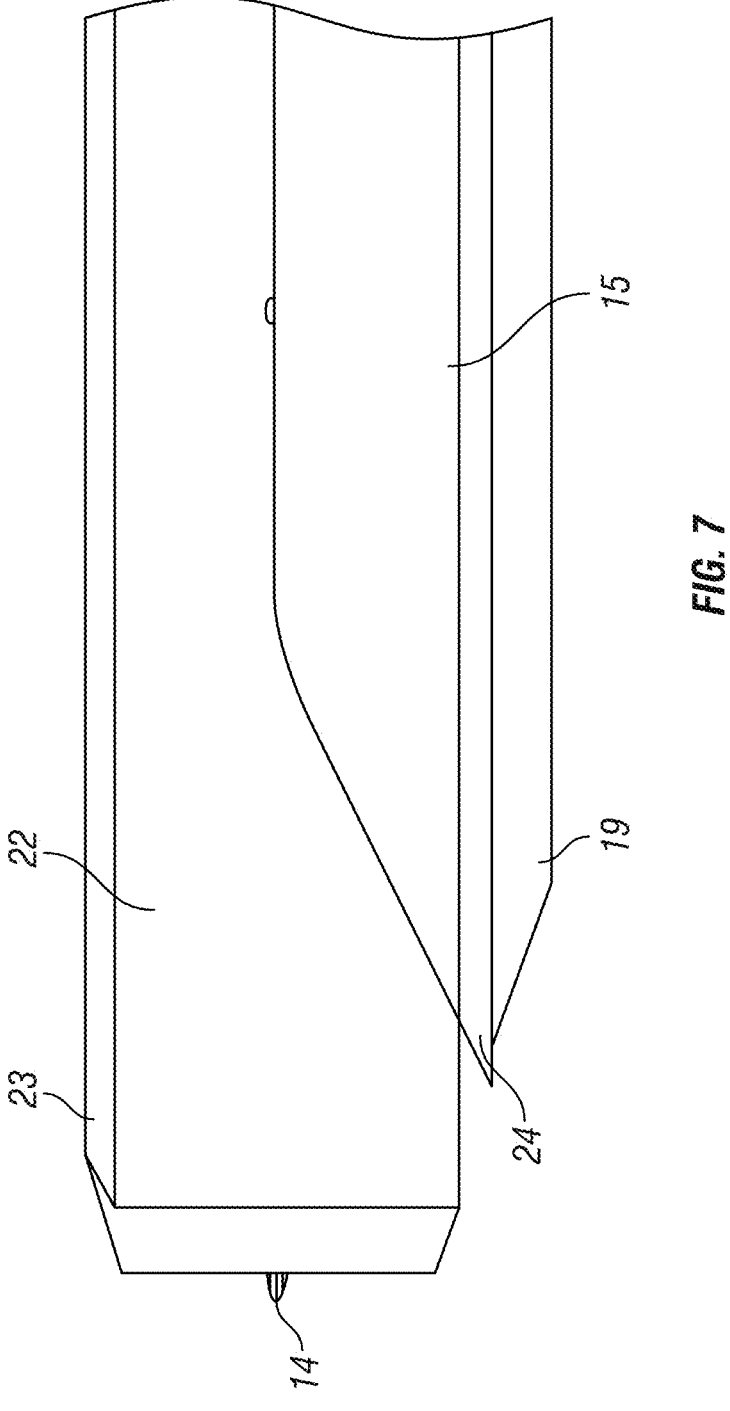
FIG. 7 is a side view of an excisional device of FIG. 6 in extended, closed configuration according to one embodiment.

FIG. 7 is a side view of an excisional imaging device or assembly of FIG. 6 to show that beak elements 14 closure and parting off can occur in a recessed position within a non- or differentially rotating sheath 22 as well as the various positions of the scoopula 15 and access channels 19, 23 and 24 according to embodiments.

Figure 8:
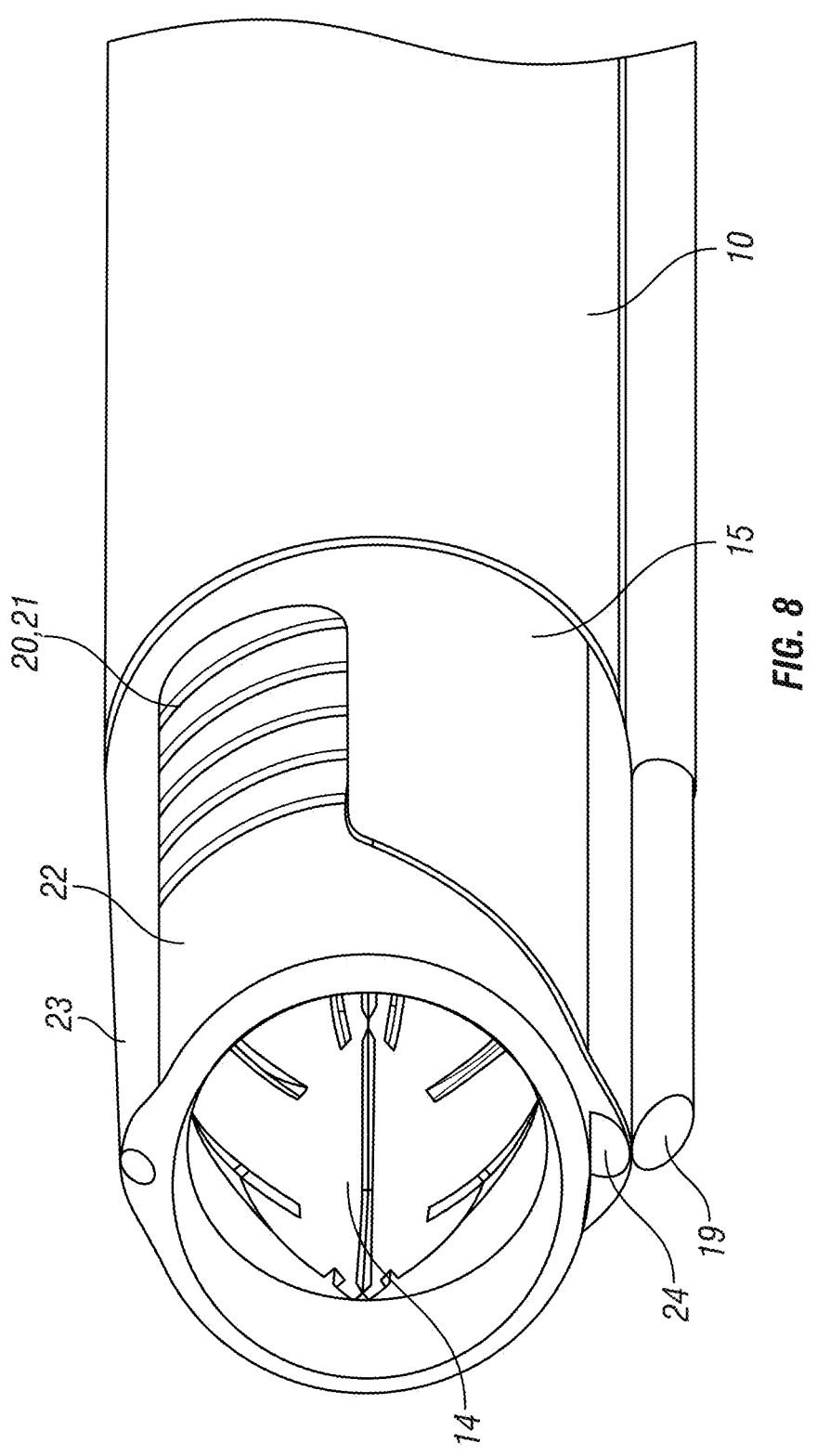
FIG. 8 is a perspective, closer-up view of an excisional device, revealing a working element in closed configuration according to one embodiment.

FIG. 8 is a more head-on view showing the same elements as in FIGS. 6 and 7 and clearly shows the coaxial nature of beak elements 14, with non- or differentially rotating sheath 22, disposed coaxially with scoopula 15 and outer housing 10, according to one embodiment.

Figure 9:
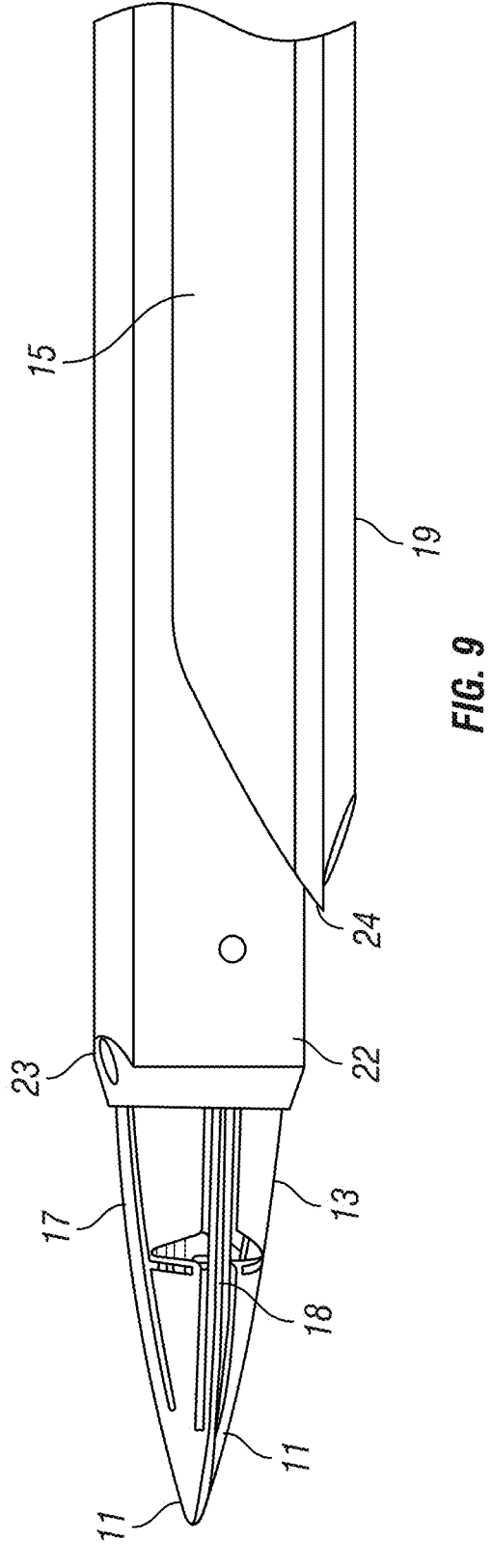
FIG. 9 is a side view of an assembly with a work element and other components of an excisional device, according to one embodiment.

FIG. 9 is a side view of an excisional imaging device or assembly (hereinafter "device" and "assembly" will generally be used interchangeably) in an extended, closed beak elements 14 configuration which allows for streamlined, minimally disruptive advancement, whether through a constricted luminal space, with or without a guiding element such as a guide wire or micro catheter for example and may also be used to penetrate a completely occluded vessel, using rotation to minimally dissect its way through potential spaces it creates or existing spaces it takes advantage of in the case of a small or even non-apparent channel in the tissue and according to embodiments.

Figure 10:
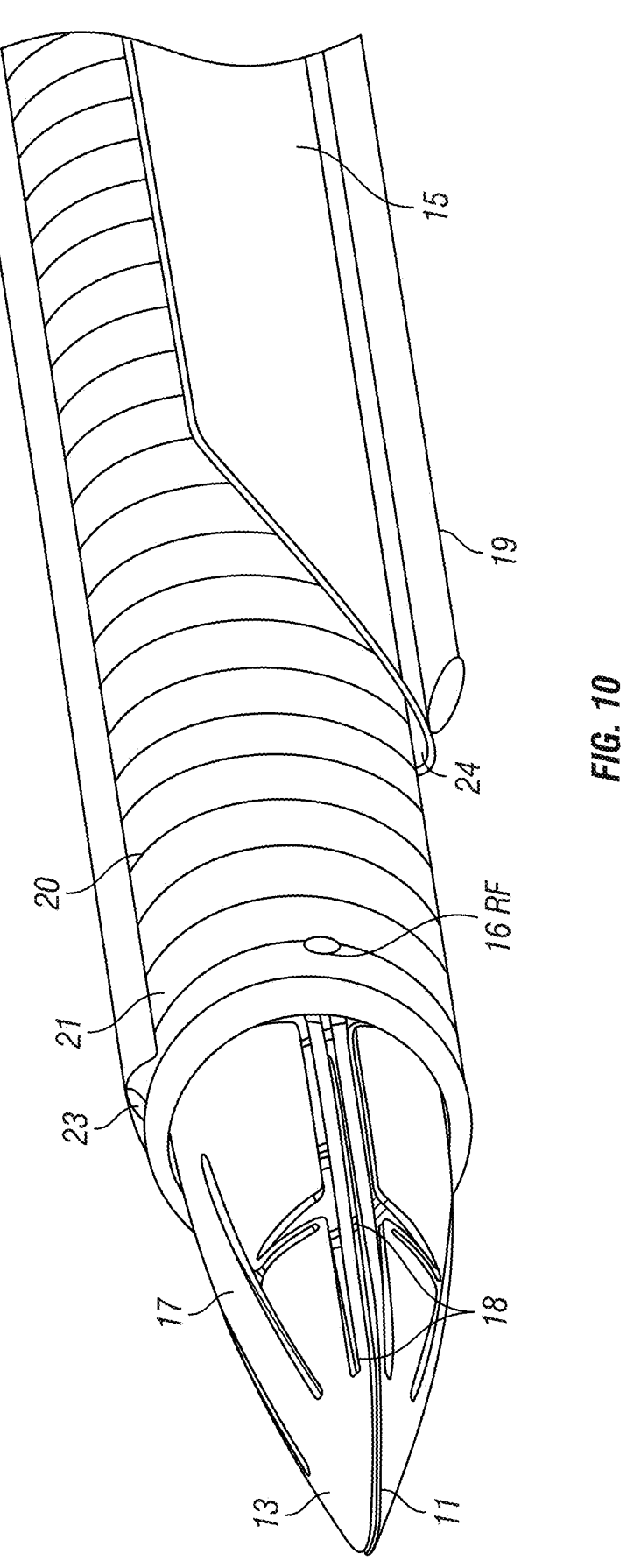
FIG. 10 is a perspective view rotated slightly to reveal forward and sideways rotation functionality of a work element of an excisional device with its working element in extended, closed position, according to one embodiment.

FIG. 10 is a side view rotated to demonstrate independent rotation capabilities of work element 13 for coring, rotational dissection and parting off, non- or differentially rotating sheath 22 with its tubular luminal channel in tandem aimed away from scoopula 15 as if 23 were directed towards and adjacent to a vascular wall to permit imaging elements introduced therein to gain close-up details of vascular wall structures and abnormalities, while other more global interrogations at longer range may be performed via one or more of the tubular access channels such as element 19 for example. Coring can be carried out both forward and sideways by exposing work element 13 to tissues in front of and along a vascular wall according to embodiments.

Figure 11:
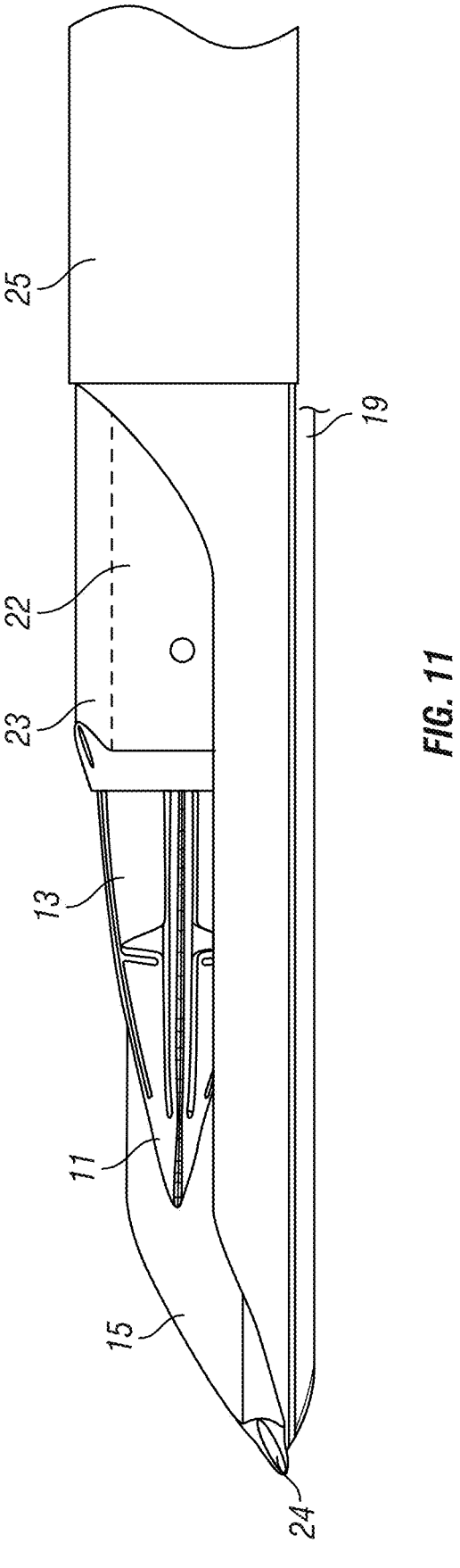
FIG. 11 is a side view of a device of FIG. 10 with its working element in closed configuration but in a different position relative to additional components, according to embodiments.

FIG. 11 shows a slightly tipped side view of an excisional device, revealing the working element in its closed configuration, according to one embodiment. In this illustration, the work element 13 is shown in closed configuration, depicting a clinical situation where the scoopula 15 defines and encompasses an entire area of interest for vascular disease de-bulking, all of which may be mainly guided by incorporated imaging instruments, introduced according to the preference of an operator, via the one or more access channels 19, 23 and 24 as desired. Each or all of these may travel along and slightly ahead of the cutting edges 11 of beaks 14 of working element 13 according to embodiments. Also shown in FIG. 11 is that the scoopula 15 may be extendable. In this case, a small space between the outer wall of scoopula 15 and outer wall of tubular access element 19 may permit outer flexible tube 25 to fit closely around scoopula 15 without the need for covering element 19 with a separate housing. In this case, the only attachment point for tubular access element 19 may be near the tip of scoopula 15 at or near its distal most point, according to one embodiment.

Figure 12:
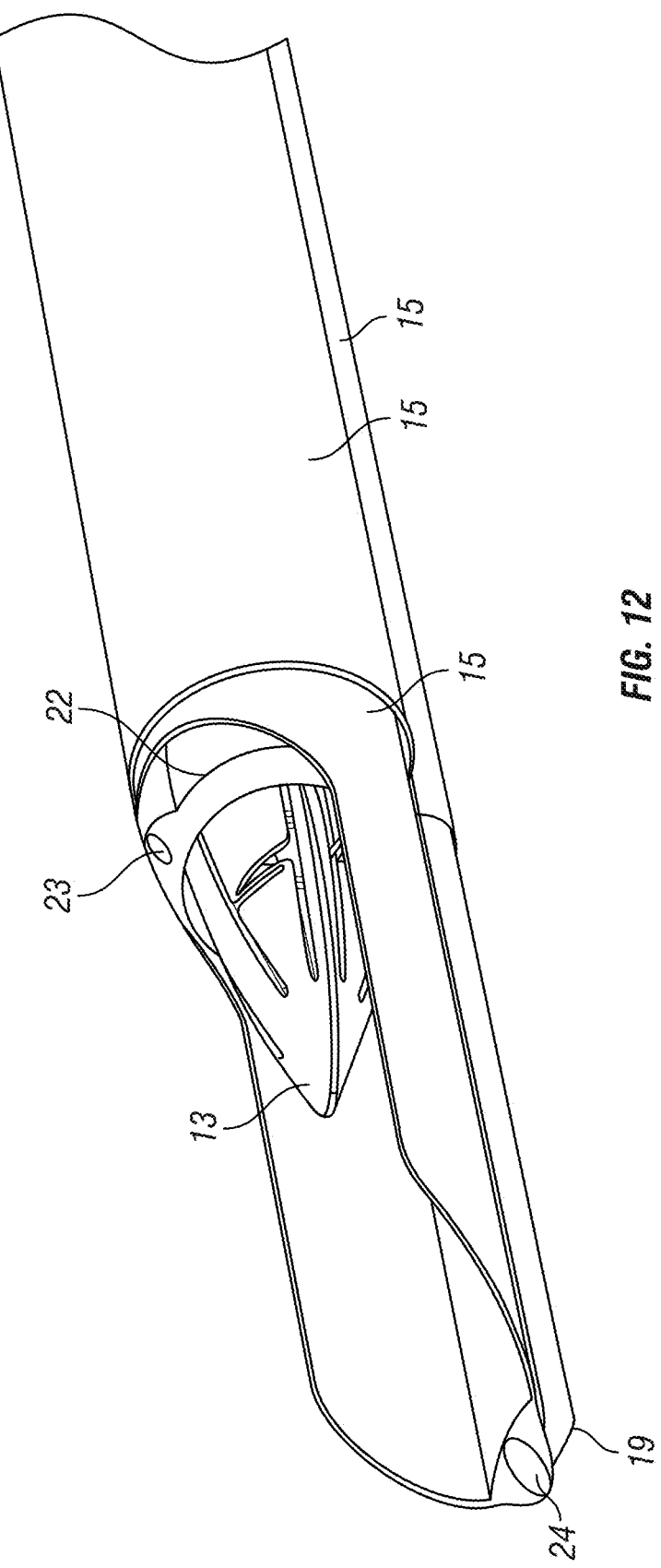
FIG. 12 is perspective view of a device of FIG. 11 of an excisional device, according to embodiments.

FIG. 12 is a perspective view of a work element 13 and other components of an excisional device, according to one embodiment, demonstrating a scoopula 15 constructed with a transparent distal section (forward of its junction with a highly torque-able proximal flexible tubular housing) including its auxiliary tubular access channels 19 and 24 such that non- or differentially rotatable element 22 may, with its own tubular access channel 23 may have full 360 degree viewing capability for full circle vascular wall, according to embodiments.

Figure 13:
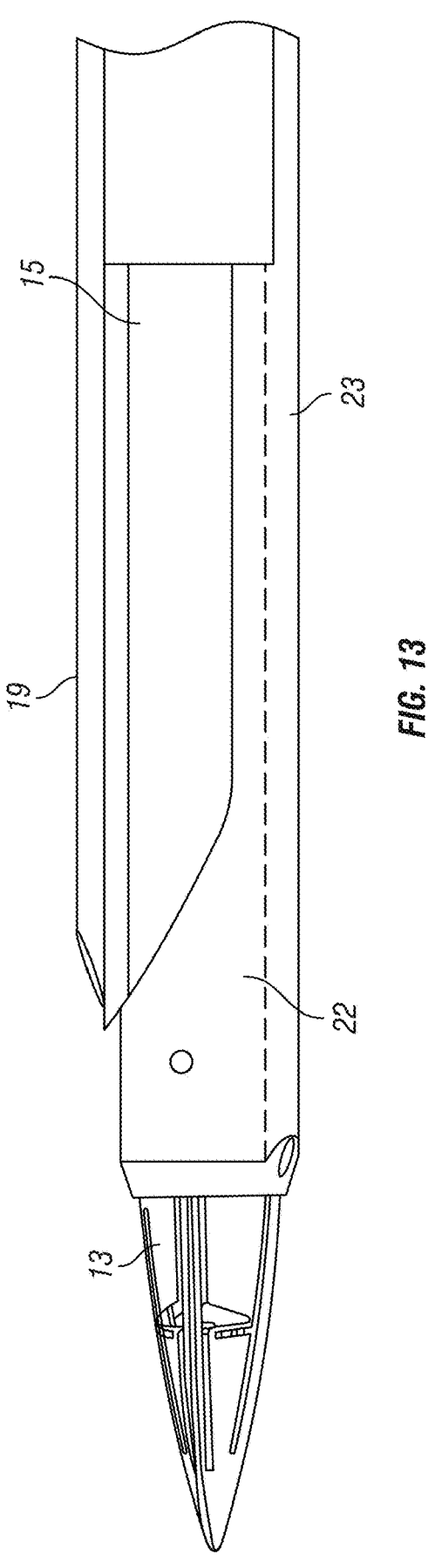
FIG. 13 is a side view of an excisional device of FIG. 10 with one of its components rotated to reveal additional positioning capabilities according to embodiments.

FIG. 13 shows the excisional imaging device of FIG. 1 with its beak elements 13 extended in a streamlined or parting off configuration while in this case scoopula 15 is rotated independently to an upper location where for example a branching vessel may be located and thus protected by the rotated scoopula 15. Similarly, a normal wall of a vessel may also be protected by the shielding effects of the scoopula wall. This location could also be selected to permit closer examination of structures in the wall or in obstructive disease lesions utilizing for example, access lumen or channel 19 through which to introduce imaging devices according to embodiments.

Figure 14:
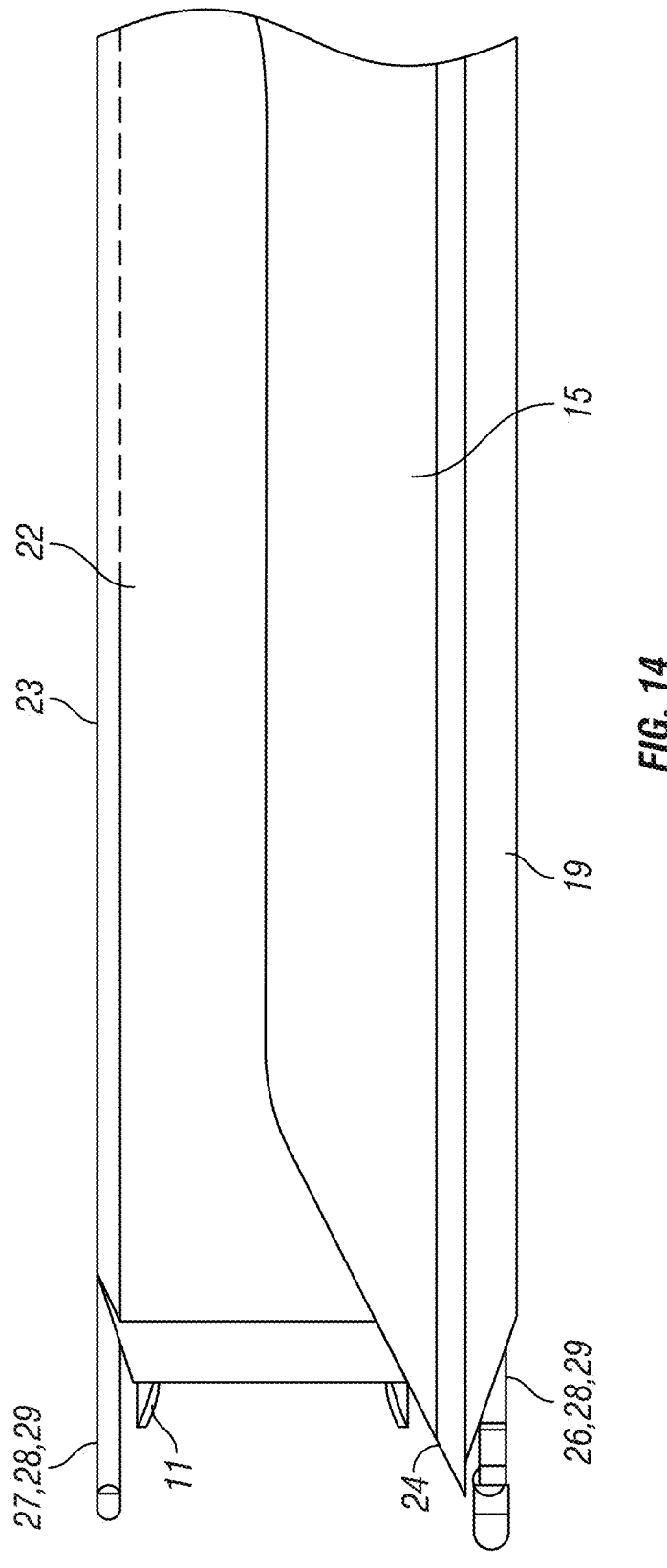
FIG. 14 shows side views of various imaging components of an imaging and excisional device revealing various configurations and positions of these components relative to a working excisional element, according to embodiments.

FIG. 14 shows additional components including various working elements of a device according to embodiments. In this illustration, beaks forward, cutting lips or edges 11 are wide open in an excising or coring position, and covered to a point where minimal exposure of the beak tips by a non- or differentially rotating sheath 22 may enable precise depth control as well as effective coring extending well past scoopula 15 if desired. Also shown are examples of imaging assemblies such as optical coherence tomography 26 as depicted in channel 19, while an intravascular ultrasound imaging catheter or wire is depicted emerging from within access channel 23. Both imaging elements may travel along and just forward of cutting beak tips 11 as shown and according to embodiments. Of note, again channels and imaging components are shown to scale according to devices available commercially, as is scoopula 15 and work element beak lip tips 11 and including materials capable of image transmission for such components as scoopula 15. Also, imaging assemblies may be introduced in any of the various available access channels according to the proximity of structures of interest within the body and according to the range and resolution capabilities for imaging catheters. Likewise, flow and pressure sensors 28 or other imaging components and/or associated catheters may be provided and advanced to permit assessment of minimal necessary flow through to sustain tissue viability or reflow after recanalization in cases of totally occluded vessels whether acutely occluded or chronically, as well as for diagnostic purposes in cases of subtotal occlusions and equally, to assess when adequacy of therapeutic interventions has been reached, may be introduced in any of the available channels as may be useful in a diagnostic and therapeutic procedure. Additional components 28 for sensing and ablating aberrant electrical pathways may also be utilized via access channels in the various locations, according to embodiments.

Figure 15:
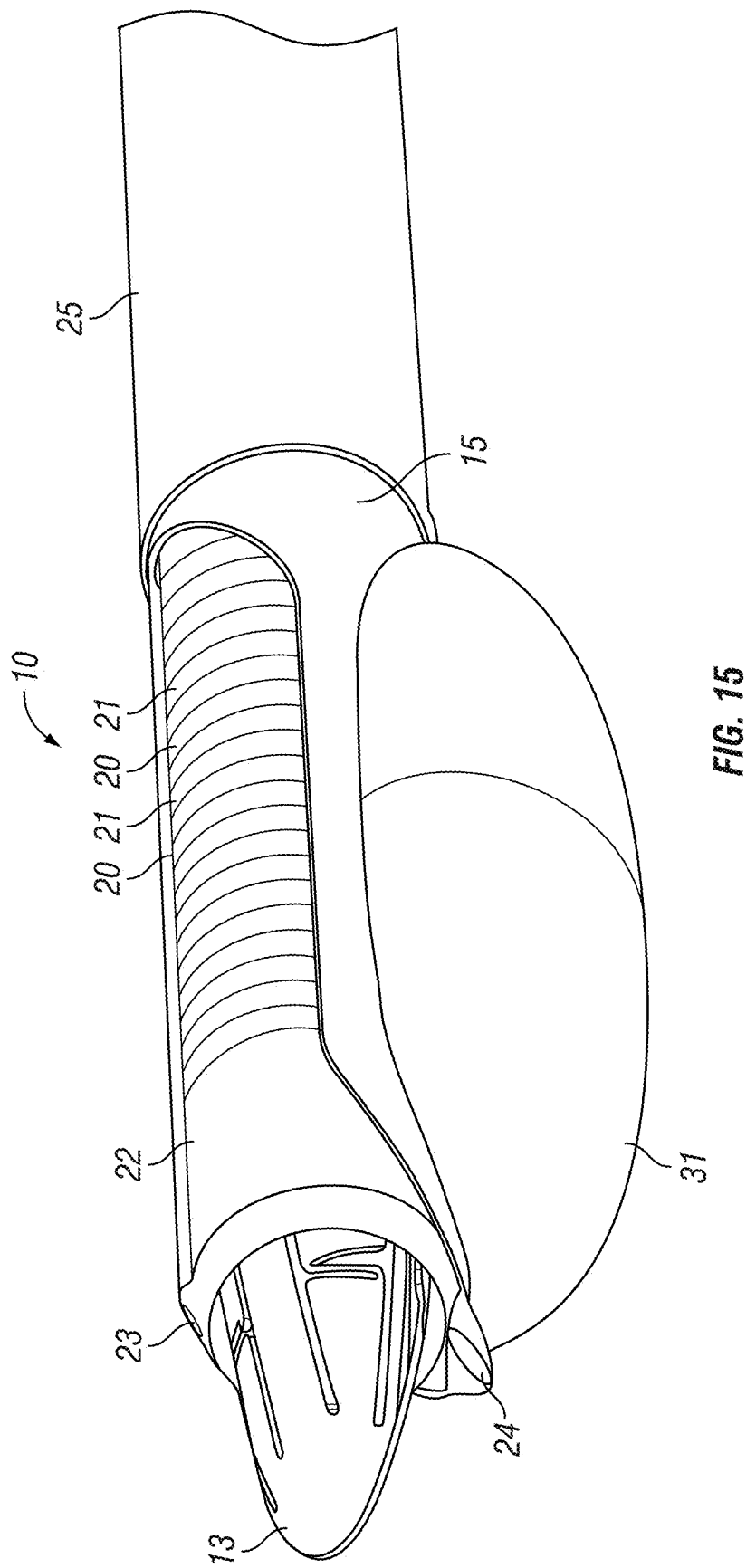
FIG. 15 is a perspective view of an excisional device of FIG. 1 showing an additional expandable element positioned on one side of the device according to embodiments.

FIG. 15 is a perspective view of an excisional device 10 equipped with an expandable element, according to embodiments. In this illustration, the device 10 is equipped with an expandable element 31 such as a balloon along the floor of scoopula 15. Such an expandable element 31 may be operative to urge the scoopula 15 and work element 13 against a diseased vascular wall or to aim work element 13 into an ostium of a branching vessel or both, according to embodiments, while utilizing any of the imaging modalities as may be useful for a specific vascular or other structural tubes or potential spaces, clearing therapeutic and diagnostic assessment, including endpoint determination, procedure. The degree of expansion of such an element 31 may be controllable automatically based on feedback information provided by imaging analysis and safety algorithms, including electrocardiographic information if in coronary vessels, or arterial oxygen saturation if in a pulmonary setting, according to embodiments. Similarly, cycling expansion back down and controlling rotational and degree of extension of, rotatable, extendable scoopula 15 from within and in reference to torque-able outer tube 25 along with rotation for cutting and cycling of work elements 13 during rotation between open and closed beaks, functions to core and part-off tissue for de-bulking and evacuation via a central lumen of the excisional imaging catheter, which may be automated via feedback and control algorithms, for the sake of precision, ease of use and to lessen radiation exposure for interventionists and patients according to embodiments.

Figure 16:
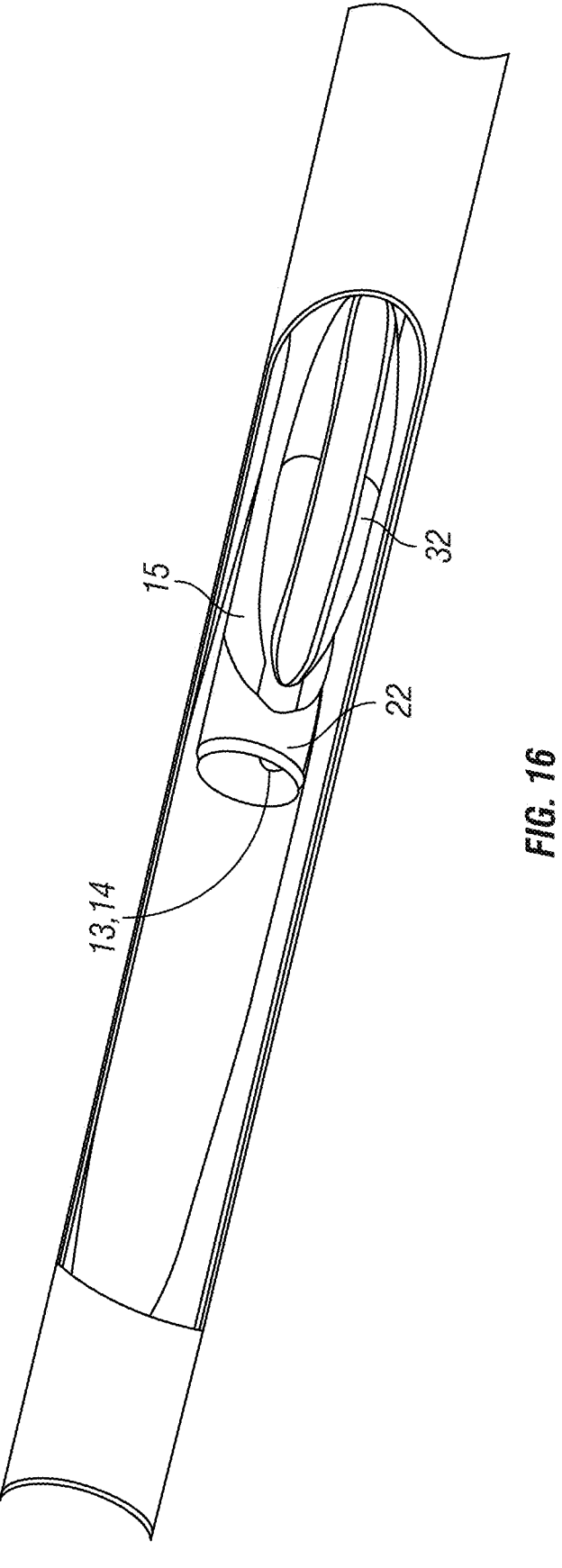
FIG. 16 is a view of a device of FIG. 15 within a cutaway model of a partially obstructed tube such as a blood vessel, further revealing the structure of the expandable element of FIG. 15 according to embodiments.

FIG. 16 shows an excisional imaging device within a cutaway view of a vascular structure with an obstructive partial occlusion being excised by work elements 13 with an additional supporting expandable pontoon shaped structure comprising a central passageway to permit continuous downstream flow during the working phase of obstructive disease removal according to embodiments. Note that each of the expandable elements may be differentially expanded as may be desired and that varying levels of expansion can be used to widen or narrow the flow channel located between the expandable elements for the purposes of optimizing flows according to downstream needs during ongoing perfusion or, in the case of restoring flow, to optimize reperfusion levels of flow according to embodiments.

Figure 17:
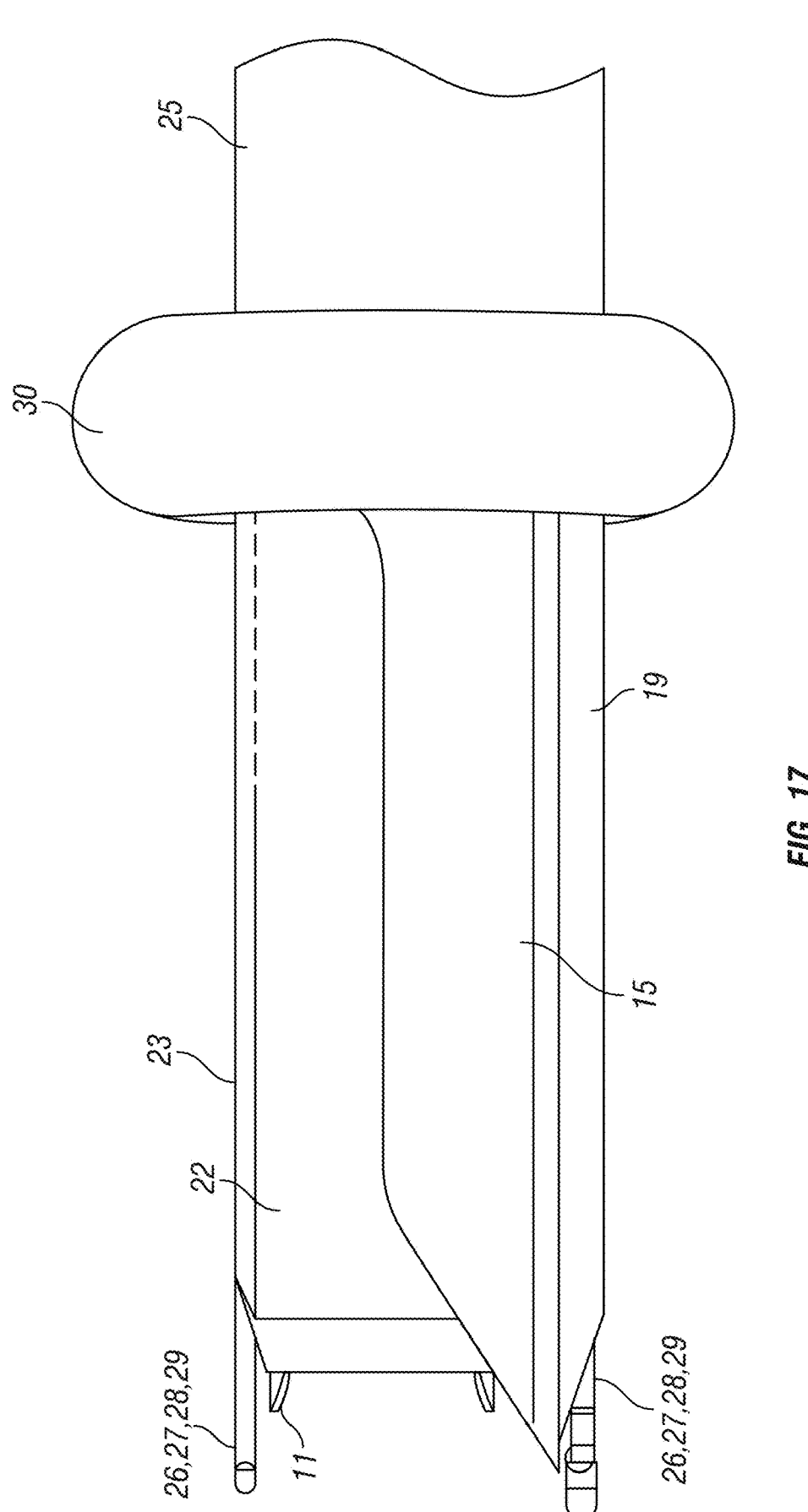
FIG. 17 is a side view of an excisional device of FIG. 1 with additional imaging catheters presented emerging from various forward channels ahead of excisional elements as shown and also including an expandable cuff near the proximal portion of the working end of a device according to embodiments.

FIG. 17 shows an excisional imaging assembly comprising an additional expandable cuff 30 located on flexible tube element 25. The expandable cuff 30 may be configured, according to one embodiment, to gently seal off flows distally (proximal to the work element 13 in this view) for a brief period during imaging and or excision procedures. According to one embodiment, the expandable cuff 30 may be expanded up to a point where flows are at a minimum level to prevent ischemia in distal organs while imaging and excisional work is proceeding in the working areas distal to its location. Expandable cuff 30 can be used to vary the downstream flows (by selectively inflating and deflating as needed) such that flushing blood out of the field of certain imaging systems most negatively affected by blood flows such as optimized coherence tomography ("OCT") can easily keep up with the flows permitted by the upstream expandable cuff 30, and furthermore the level of permissible reduction of flows to keep distal tissues well enough supplied, can be balanced according to physiologic monitoring, which may be controlled automatically to minimize operator work load and improve patient safety, according to embodiments.

Figure 18:
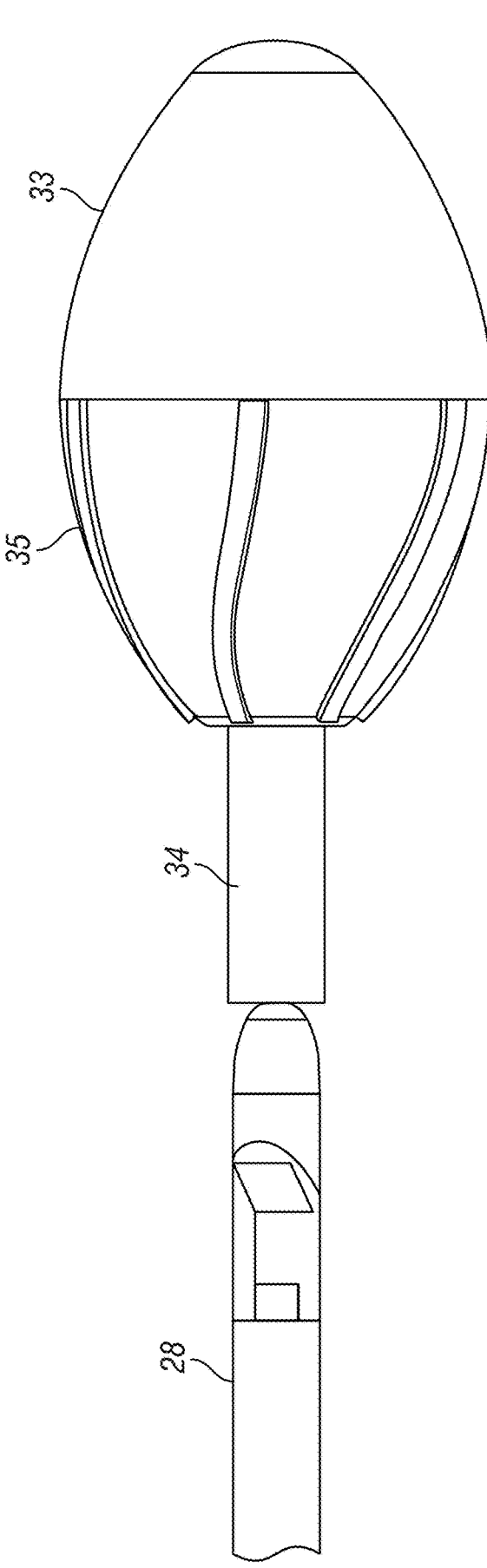
FIG. 18 is a side view of an expandable imaging chamber into which an imaging device may be introduced as shown lined up for entry via an integrated lumen according to embodiments.

FIG. 18 illustrates an expandable, transparent imaging chamber 33 that may be filled with gas or liquids to optimize imaging using, for example, OCT instruments by excluding distorting fluids such as blood, without necessarily limiting downstream flows given that the chamber may remain smaller than the available lumen of the vessel in which it is being deployed, and as is further described in various illustrations herein, may be positioned against an area of interest, leaving nothing between the tissues being studied and the imaging catheter other than the imaging chamber. This view serves to show various components of such a chamber including a central lumen 34 through which various imaging catheters or imaging wires and the like, represented in this case by an OCT catheter 28, may be advanced and deployed as desired. Also shown are blades 35 that may be expanded along with the chamber, which may serve as parting-off structures when used in concert with excisional elements (e.g., beaks) 14 (not shown in this illustration), according to embodiments.

Figure 19:
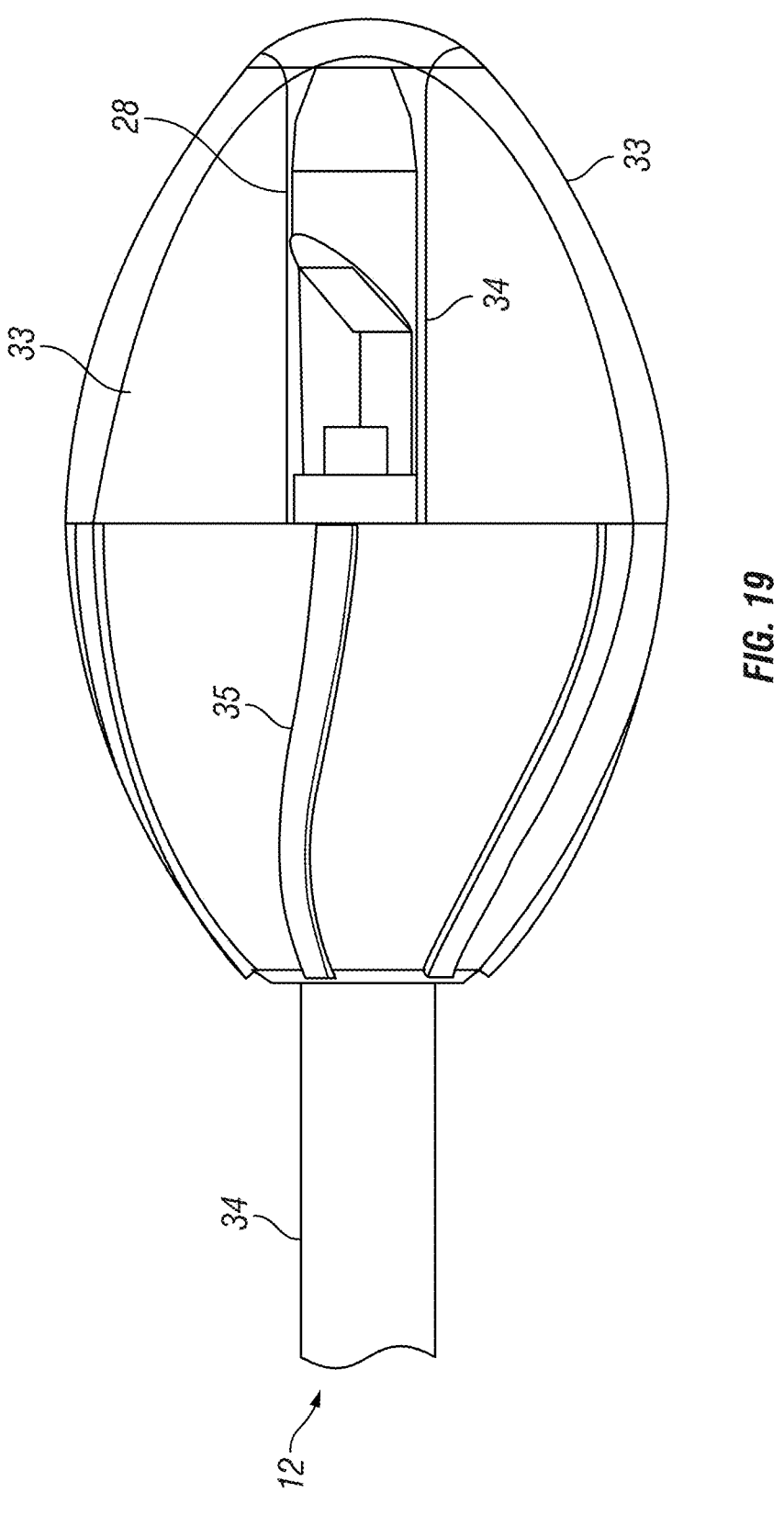
FIG. 19 is a side view of an expanded transparent imaging chamber with a forward portion of the chamber cut away to reveal an imaging element located internal to the chamber within an additional, likewise transparent lumen as shown according to embodiments.

FIG. 19 shows a closer view from the side of the same elements of FIG. 18, with in this case, imaging element 28 already advanced all the way to the forward surface of expandable, imaging/parting off transparent (to the selected imaging modality) chamber 33 with its blades 35 providing a sharp edge against which a spinning work element or elements such as beak cutting element edges 14 may completely sever diseased tissue from its attachments to a vascular wall without needing to bend for parting off, according to embodiments.

Figure 20:
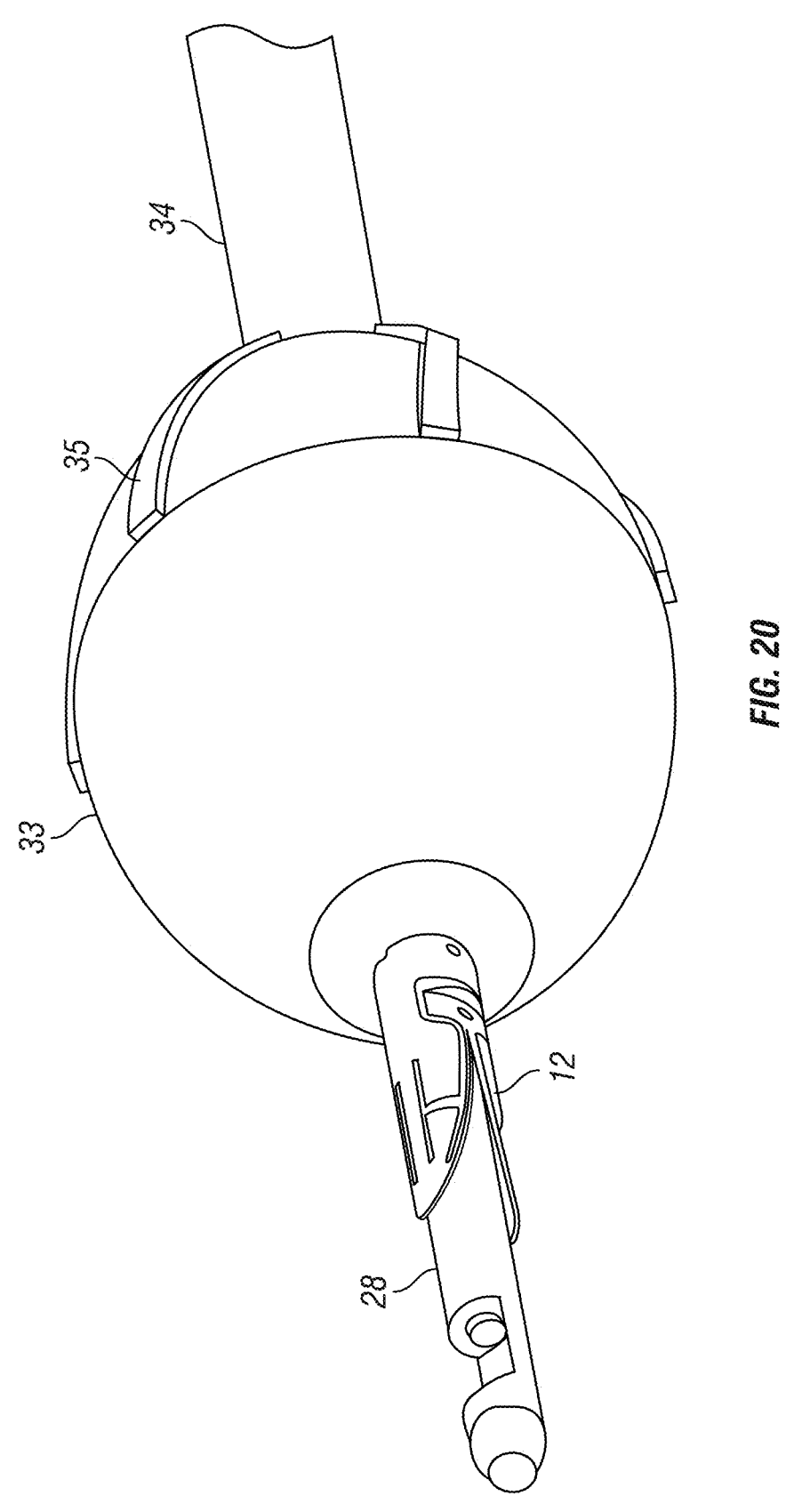
FIG. 20 is a perspective view showing an expandable, imaging, parting off, focusing, transparent lenticular chamber or tandem chambers, emerging through and from within which is an excisional work element of a device, itself within which excisional device an additional example of an imaging device is shown, according to embodiments.

FIG. 20 shows the elements and assemblies of FIGS. 18 and 19, configured with imaging, focusing, isolating, centering (in this case) chamber 33 with an imaging catheter 28 extended forward distally ahead of a smaller excisional working element, similar in structure and function to work element 13 discussed previously, but now in a larger gauge size (smaller diameter) and delineated as work element 12 for purposes of distinguishing it from a relatively larger work element 13, as may be the case when imaging a total occlusion within a vascular structure, utilizing expandable cutting and imaging chamber 33 for its stabilizing platform effects, along with imaging capabilities to enable smaller excisional dissecting work element 12 to advance through the center cap or soft thrombus occluding a vascular structure, while avoiding going off track and causing unwanted vascular wall injury in the process, according to embodiments. Such a smaller work element 12 may be seen extending through the central lumen of a larger work element 13 in FIGS. 31, 32, 38 and 39. The advantages of being able to precede a larger coring work element with a smaller coring work element 12 include the ability to provide a pilot hole as a means of creating an initial pathway through an occlusion (for introduction, for example, of guidewires or imaging catheters); centering or anchoring the larger work element 13 for subsequent coring of a larger diameter core; the creation of a small blood flow pathway through an occlusion; and the ability to efficiently core a very hard occlusion cap, which may be highly calcified, It should be noted that the distinguishing nature of work element 12 is that it is smaller than work element 13, and work element 12 may be of any size relative to work element 13 as long as it is able to be introduced to a target work site within the central lumen of work element 13. In such a manner, an occlusion may be initially cored with a very small work element 12 (which may be left in place through the cored occlusion), followed by a second pass with a larger work element 12 over the smaller work element 12 but still being placed within the central lumen of work element 13, and so on, up to the point of a final coring pass through the occlusion using work element 13, as may be desired. It should be noted that this method of crossing an occlusion or thrombus results in a safe and effective procedure for removal of stenotic tissue with a corresponding reduction in potential embolic material being released into the bloodstream, since work elements 12 and 13 represent the distal tip(s) of both coring and transport mechanisms as described herein, and according to embodiments. It should also be noted that work element 12 may indeed be the distal work element of an independent coring device introduced through the central lumen of an excisional device 10 and may be referred to herein as work element 12 or excisional device 12.

Figure 21:
FIG. 21 is a side view of an expandable chamber of FIG. 20 with additional cutting elements located along the forward hemisphere according to embodiments.

FIG. 21 illustrates an expandable transparent imaging, parting off cutting and excisional element 33 equipped with blades 35 on the forward area as well as the rearward area thereof. Such a device may be used in concert with a variety of assemblies illustrated in several figures such as FIGS. 11, 12, 16 and others, in a variety of positions relative to obstructive lesions in a vessel. The device may be used for forward excisions or rearward excisions as desired and may also utilize its included cutting blades 35 for parting off purposes in conjunction with a coring work element 13 through which it may be inserted, (i.e., the coring beaks of work element 13 could core up against the proximal side of an inflated element 33's blades 35 to part off cored tissue without the need to close work element 13's beaks for parting off cored tissue, as shown if FIG. 27) as well as for trapping and transporting abnormal and excised tissues according to embodiments, while also including imaging instruments within its transparent chamber, according to embodiments. Additionally, element 33 may be introduced to the far side of a lesion through a path bored or cored through the lesion (occlusion or thrombus) by a work element 12 or larger work element 13, as an example, and thus element 33 may be used to additionally ablate specific regions of a cored path through the lesion on a backward or forward path through a portion of the cored lesion.

Figure 22:
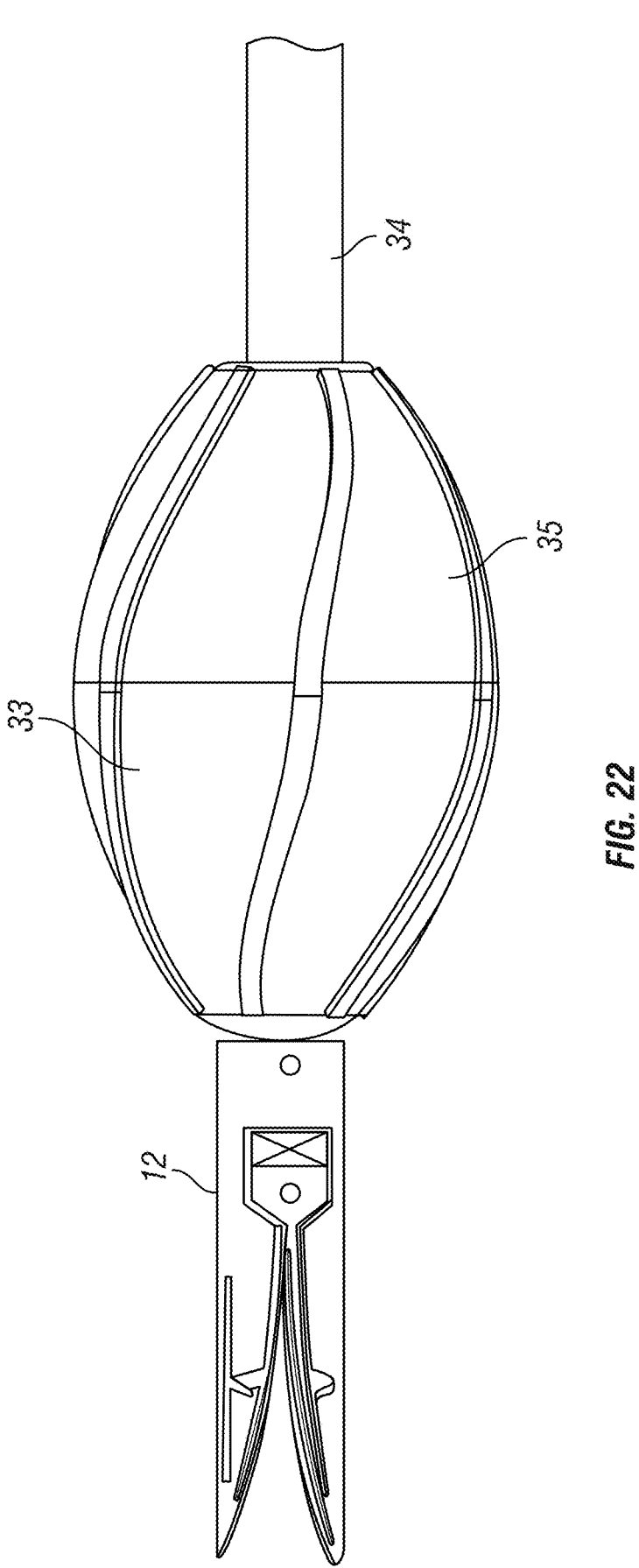
FIG. 22 is a side view of a device of FIG. 21 with an additional excisional device at the forward end of a more proximal expandable device according to embodiments.

FIG. 22 shows the same components and work elements of FIG. 21, shown here with the introduction of smaller excisional element 12 via central lumen 34 which, though not shown here, may be separate from an inflation/deflation tube that may be attached to the transparent, expandable imaging, cutting chamber 33 with its cutting blades 35, according to embodiments.

Figure 23:
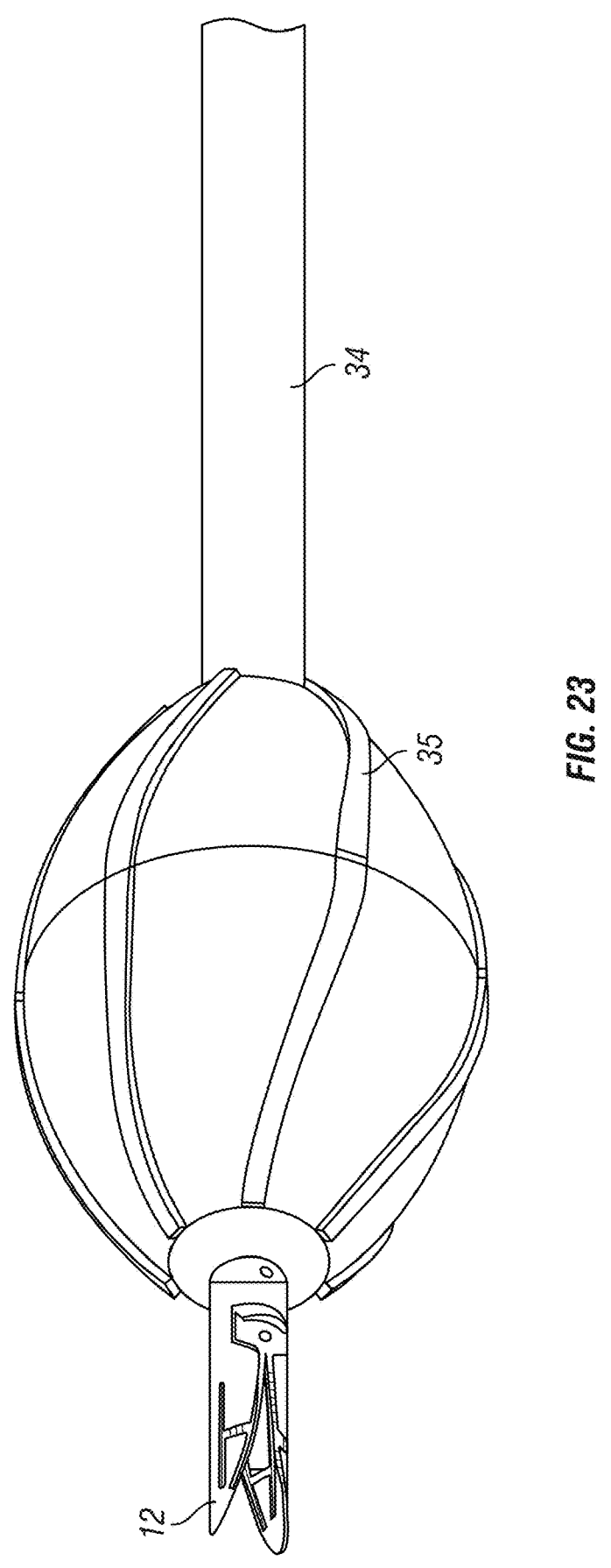
FIG. 23 is a perspective view of an expandable chamber of FIG. 22 with an excisional device at the forward end according to embodiments.

FIG. 23 shows, in perspective view, the elements previously illustrated in FIG. 22 and others, in detail, and again demonstrating parting off elements or blades 35 of expandable imaging chamber 33, according to embodiments.

Figure 24:
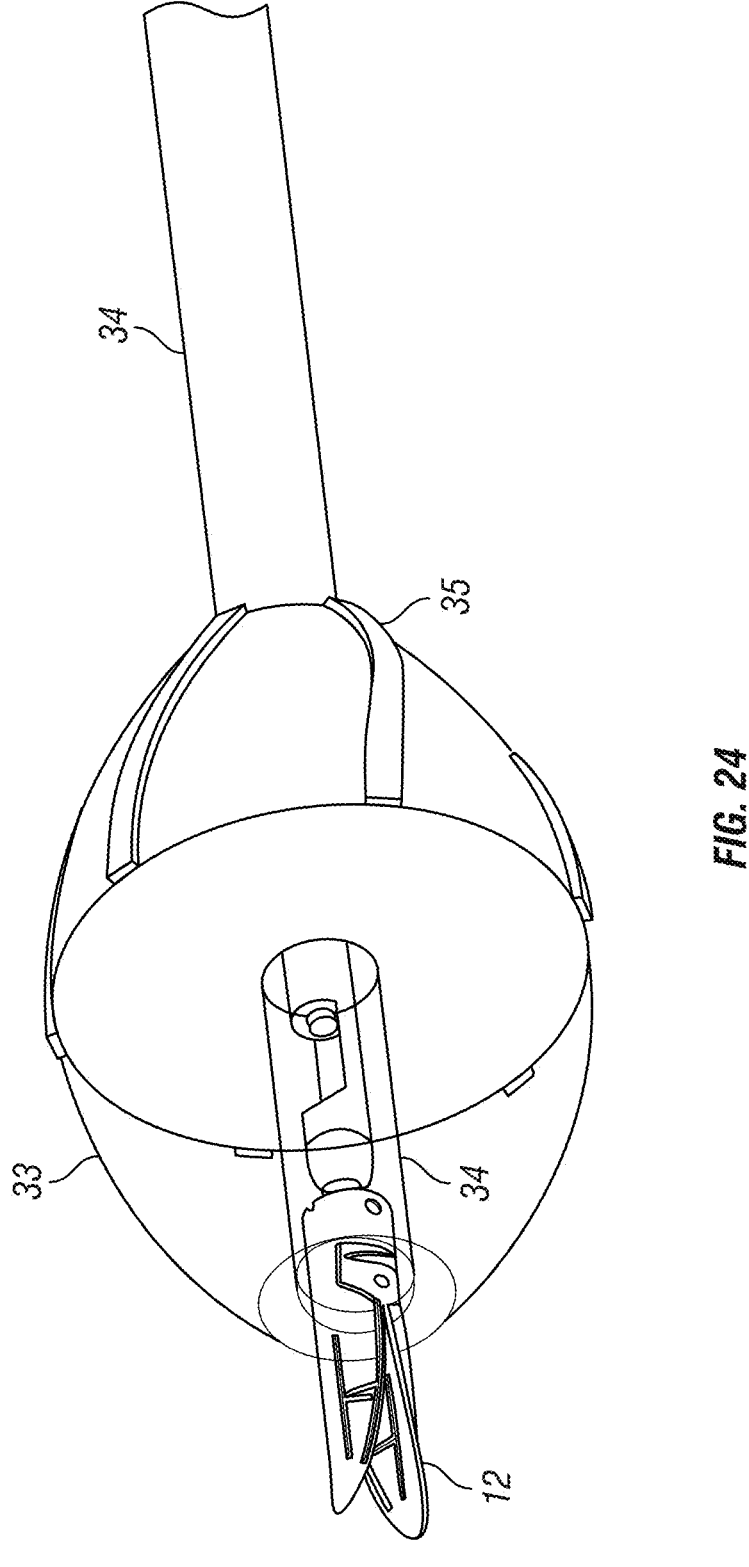
FIG. 24 is a perspective view of an assembly of FIGS. 20 and 21 with the forward portion of a transparent chamber shown as a transparency revealing an imaging element not yet advanced fully through the excisional work element of FIG. 20, all of which may be utilized in an excisional device of FIG. 1 according to embodiments.

FIG. 24 shows in perspective view, further details of transparent imaging, expandable, cutting and chamber 33, provided with a distally-disposed small excisional element 12. Close behind the small excisional element 12, is an imaging element showing that the two may be used sequentially or in concert initially and at various stages of a procedure such as to penetrate a hard cap of a chronic totally occluding plaque for example in an arterial structure, according to embodiments.

Figure 25:
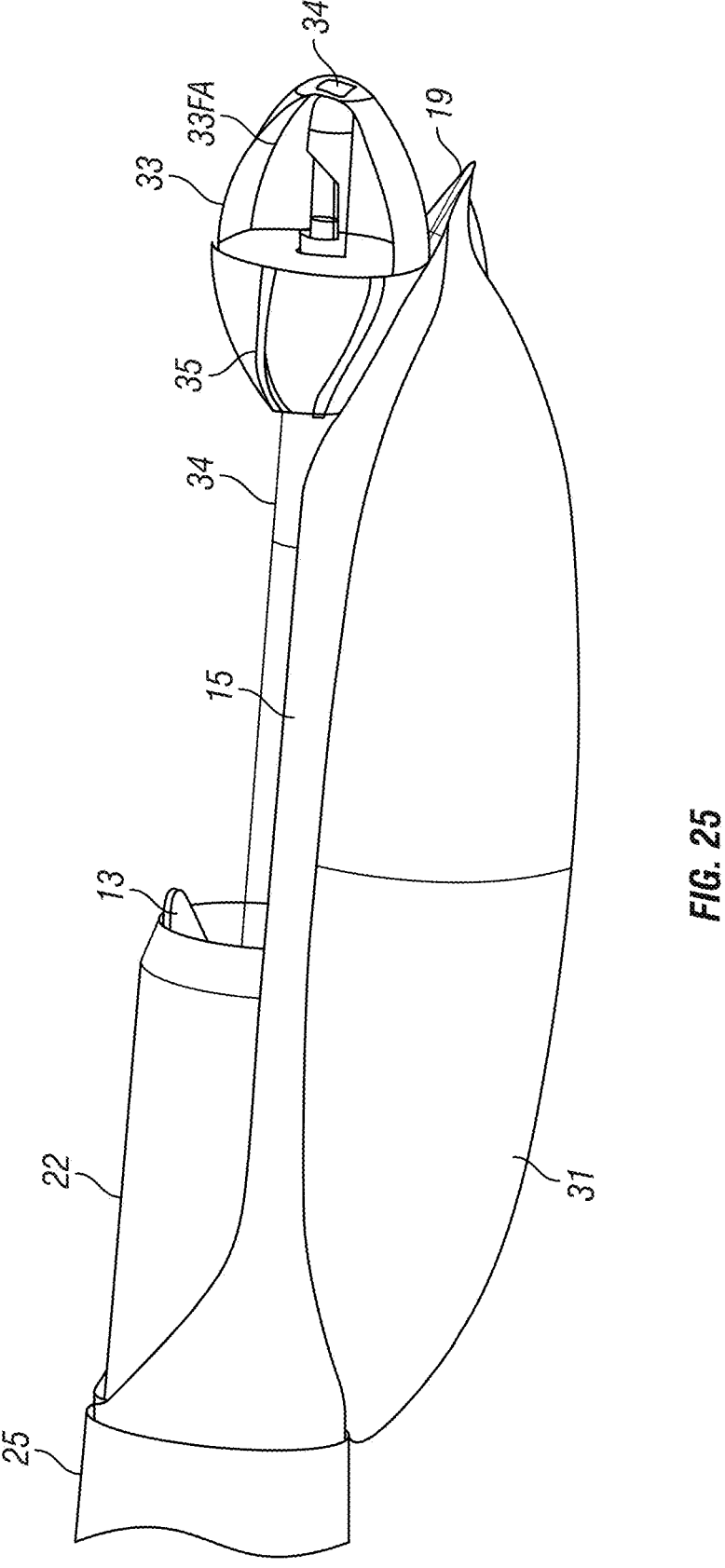
FIG. 25 is a perspective view of an assembly including an excisional device of FIG. 15 and an imaging chamber of FIG. 24 in position according to embodiments where these are used together as shown according to embodiments.

FIG. 25 is an illustration of elements of a combined imaging, excisional and disease evacuating device 10 according to an embodiment. Shown therein are a working dissecting and excisional work element 13, a non- or differentially rotating flexible sheath 22, an extendable, rotatable scoopula 15, with one example of a variety of access channels 19, an expandable imaging chamber 33 with its controlling central lumen 34, a side supporting expandable single lobe balloon element 31, a flexible proximal outer tube 25, according to one embodiment.

Figure 26:
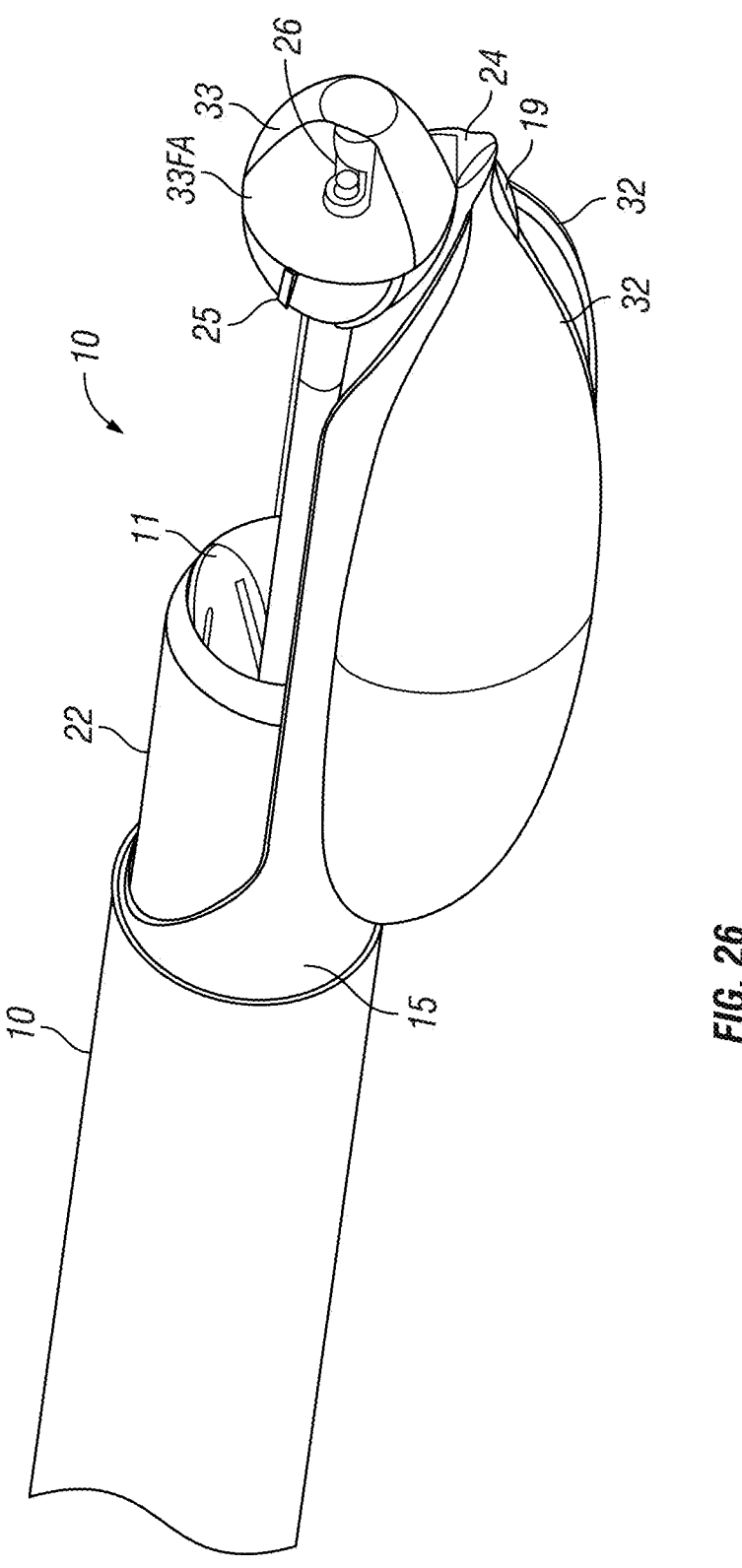
FIG. 26 is a perspective view of an assembly of FIG. 25 again showing an excisional element in partial forward excursion with beaks open in coring mode, according to embodiments.

FIG. 26 is a view of an excisional imaging assembly 10 with scoopula 15 supported by a double, flow-permitting expandable pressing structure 32, various access channels and lumens such as 19 and 24 as well as a beak lip or cutting edge 11 seen protruding slightly from the forward edge of non- or differentially rotating sheath 22. Also deployed is an expandable, transparent imaging, chamber 33 with its forward focusing area 33 FA indicated with an internally placed OCT imaging device in the distal portion of imaging chamber 33, which is itself located distally in the forward portion of scoopula 15. In this case, parting off could be carried out by the blade edge(s) against parting off blades 35 as may be desired according to embodiments. Also, although in-situ imaging capabilities are emphasized throughout for precision control of depth and positioning of excision passes, as shown in this illustration, the simple act of expanding element 33 in the trough of scoopula 15, enables automatic depth limitation of excisional elements 14 between NRS 22 and imaging chamber 33, according to embodiments. A simplifying mechanism of depth control is enabled by balancing forces of expansion between expandable structure 32 and expandable imaging chamber 33, while referencing imaging landmarks. For example, when the desire is to core only diseased tissues while leaving deeper vascular wall layers intact, without removal, invasion, or any other type of damage, then a virtual on-screen line could illustrate the imaging chamber's nominal expansion circumference, regardless of its current state of expansion. When the imaging chamber 33 and opposing pressing structure(s) 32 are expanded to set the virtual nominal line on the desired depth of tissue removal, the blades 11 could then automatically core to that depth and no further, because the tissue that is blocking or partially occluding a vessel generally projects into the vessel lumen and the endpoint is most favorably reached, when the obstructing tissue is removed, while leaving deeper vessel wall layers unharmed by overly aggressive tissue removal. If the chosen in-situ imaging modality happens to be OCT (optical coherence tomography), then viewing chamber 33, with its transparent medium, also automatically provides a downstream vessel, non-flow limiting, yet OCT transmissible, pathway to the vascular wall disease areas of interest. The aperture angle for imaging (given blood obscures OCT imaging), can also be controlled by the degree of chamber 33 flattening against the diseased vascular wall. The other components needed for this type of exercise include the control and imaging structures in FIG. 26 along with imaging displays (not shown in this figure) that enable reference designations to match up with physical depths of tissue removal, including the margin of standoff provided by the opposing balance of forces between elements 32 and 33, which in turn are enabled by the nature of the specific construction of the open ended, yet side coring and thus depth controllable, elements shown in this and subsequent figures, which as opposed to side-only cutting or forward-only cutting, have the inherent ability to directionally core beyond the diameter of the proximal housing (the limitation of side-cutting only devices whose forward end is not open, i.e. does not incorporate an open ended scoopula), yet remain capable of depth limitation and directionality not afforded to forward-only coring devices according to embodiments. As written in other areas, this capability is highly adaptable to automatic depth and directional control according to machine learning algorithms that can speedily cycle through a sequence of cuts that could clear a vessel of obstructive disease that may be (almost always is) asymmetrically distributed along vessel walls, always referencing deeper layers (may be readily identified and automatically referenced with machine learning algorithms) to avoid cutting, according to embodiments. This concept appears again in FIG. 54 where in-stent regrowth of obstructing tissue may be systematically, safely (referencing the metallic struts to avoid damaging in this case) and efficiently removed according to further embodiments.

Figure 27:
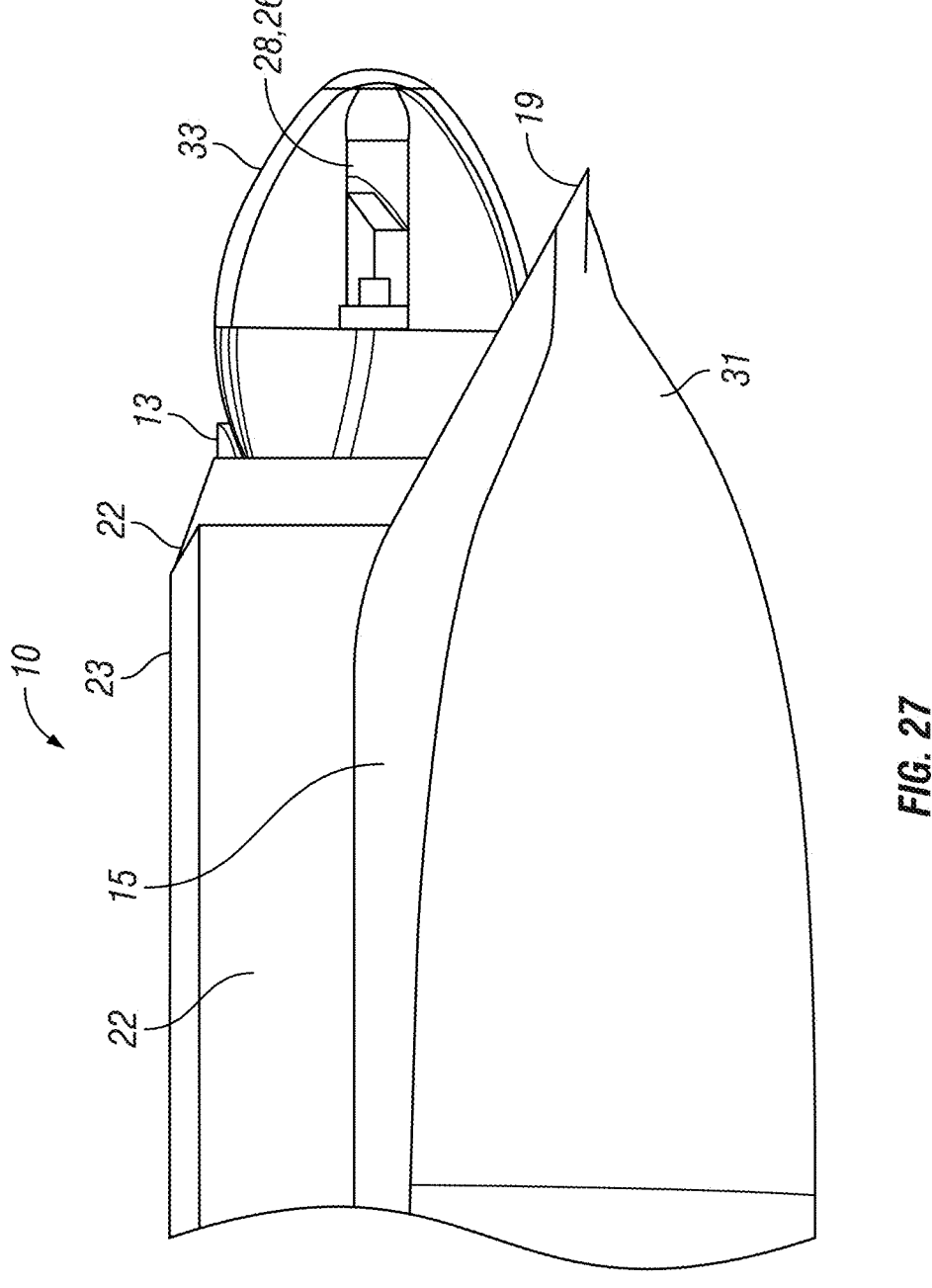
FIG. 27 is a side view of an assembly of FIG. 26 with the excisional element in full forward excursion as limited by imaging parting off chamber of FIG. 24 according to embodiments.

FIG. 27 is a side view of the excisional imaging assembly 10, showing the cutting elements of work element 13 fully open pressed and rotating against the rear edge of an expandable, transparent, imaging chamber 33 in order to part off cored tissue without having to close the beaks of work element 13. Chamber 33 is also shown with an inner OCT device inside its central lumen, the entire apparatus being supported by expandable element 31, according to embodiments.

Figure 28:
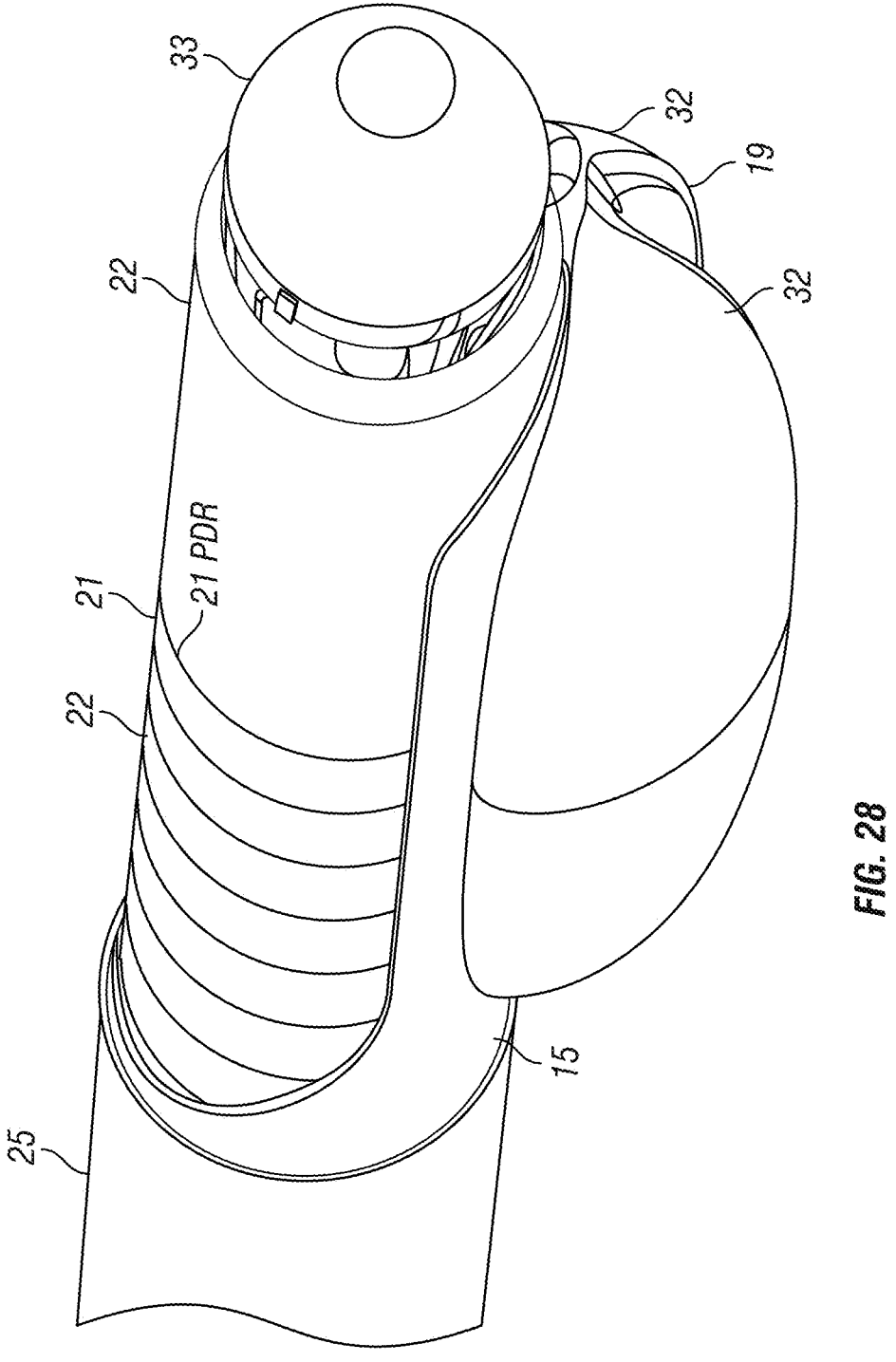
FIG. 28 is a perspective view of a device of FIG. 27 according to embodiments.

FIG. 28 is a head-on view of an excisional imaging, collecting and transporting device 10, each element which may be introduced and rotated into proper position within a vessel with a highly torque-capable outer flexible tube element 25, in this view, showing a position of cutting elements from an excisional assembly for example, as previously described and illustrated, against the rear portion of an expandable imaging, transparent chamber 33 according to embodiments. In this view, a variably open channel between the double, expandable supporting element 32 is also visible and according to embodiments, when this space is completely closed off, tubular access channel 19 may also be utilized to provide downstream flow.

Figure 29:
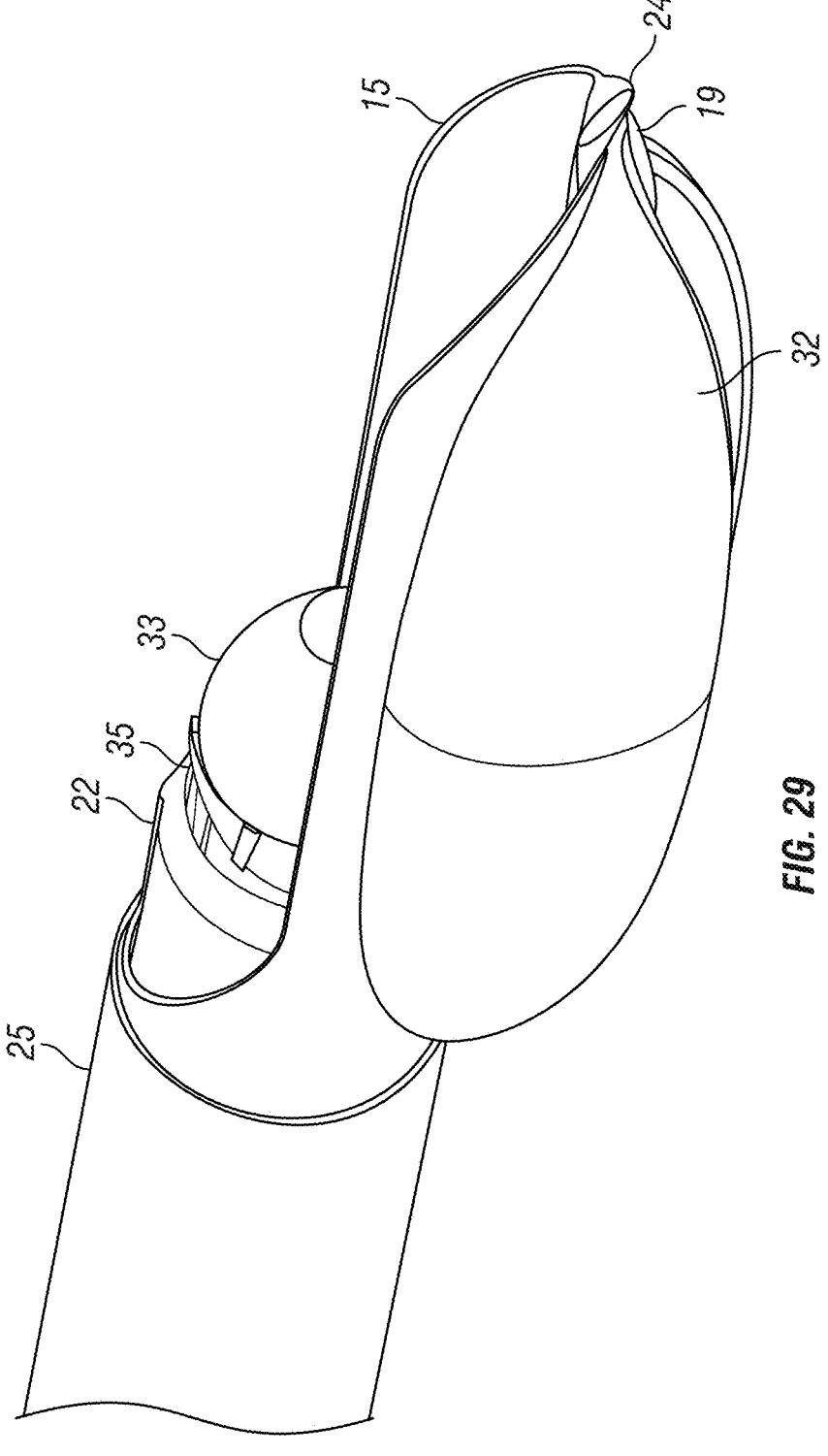
FIG. 29 is a perspective view of an assembly of FIG. 25 now illustrating retraction of imaging or parting off chamber of FIG. 24 in concert with excisional element of FIG. 15 to a proximal position that may be retracted further according to embodiments.

FIG. 29 shows the same elements in an imaging and excisional device 10, however in this case expandable, element 33, which may also function as an imaging chamber, is shown retracted back along scoopula 15 together with excisional elements that would have excised and parted off abnormal obstructing tissues using the rear side of element 33 with its cutting blades (not shown in this view). In this rearward position, tissue parted off and closed off from escape would then be in position for rearward storage within outer tube catheter element 25 or drawn fully rearward (proximally-directed) to transport obstructing tissues out of the entire assembly through the central lumen of the supporting flexible outer catheter 25, according to methods and embodiments.

Figure 30:
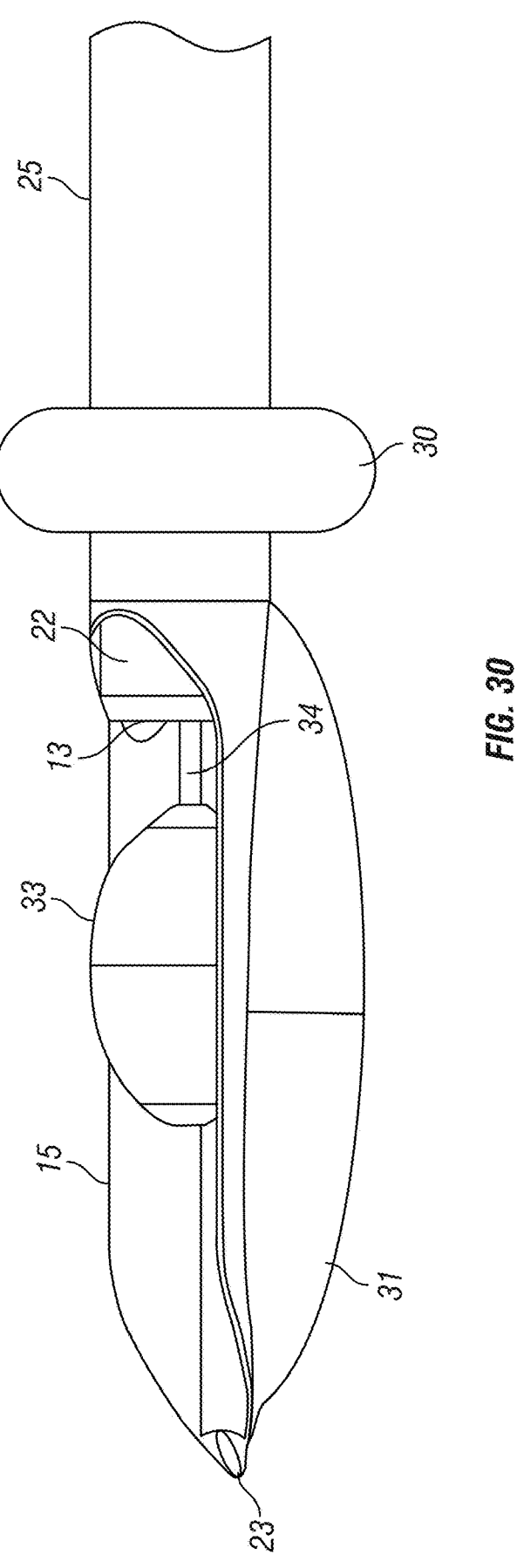
FIG. 30 is a perspective view of an excisional assembly of FIG. 29 with an additional expandable cuff element mounted proximal to the excisional area on a device of FIG. 1 according to embodiments.

FIG. 30 shows an embodiment in which an expandable transparent imaging chamber 33 is shown disposed halfway along scoopula 15, supported by its central lumen 34 and clear of main excisional blades of work element 13 In this illustration, excisional elements 14 are shown with a variant of sharp edges with a tip shape that enables parting off of excised tissue even when a tube such as tube 34 is in place where the edges of excisional blades and tips 11 would meet as well as being of a shape that is efficient for excision. As in FIG. 17, on outer tube element 25 is a proximal expandable cuff 30 that may be selectively inflated and deflated to modulate flow beyond its borders, optionally automatically and based on physiologic safety information sources including in a coronary example, electrocardiographic evidence of ischemia, for a variety of purposes already previously described herein including that it may be used as a torque input locker for the outer tube element 25. Moreover, when expanded, the expandable cuff 30 may provide backup support, in its position so close to distal working element(s) 13, such that distal elements may be advanced against any resistance they may encounter, relying at least partially on expandable cuff 30 for backup support and stability. Another use of expandable element 30 may be to limit reflow shock tissue damage by gradually allowing blood to re-enter tissues that may have been subjected to deeper levels of ischemia, again, referencing physiologic indicators manually or automatically, such as electrocardiographic or, indicators according to embodiments. Also shown is independently movable non- or differentially rotating sheath 22.

Figure 31:
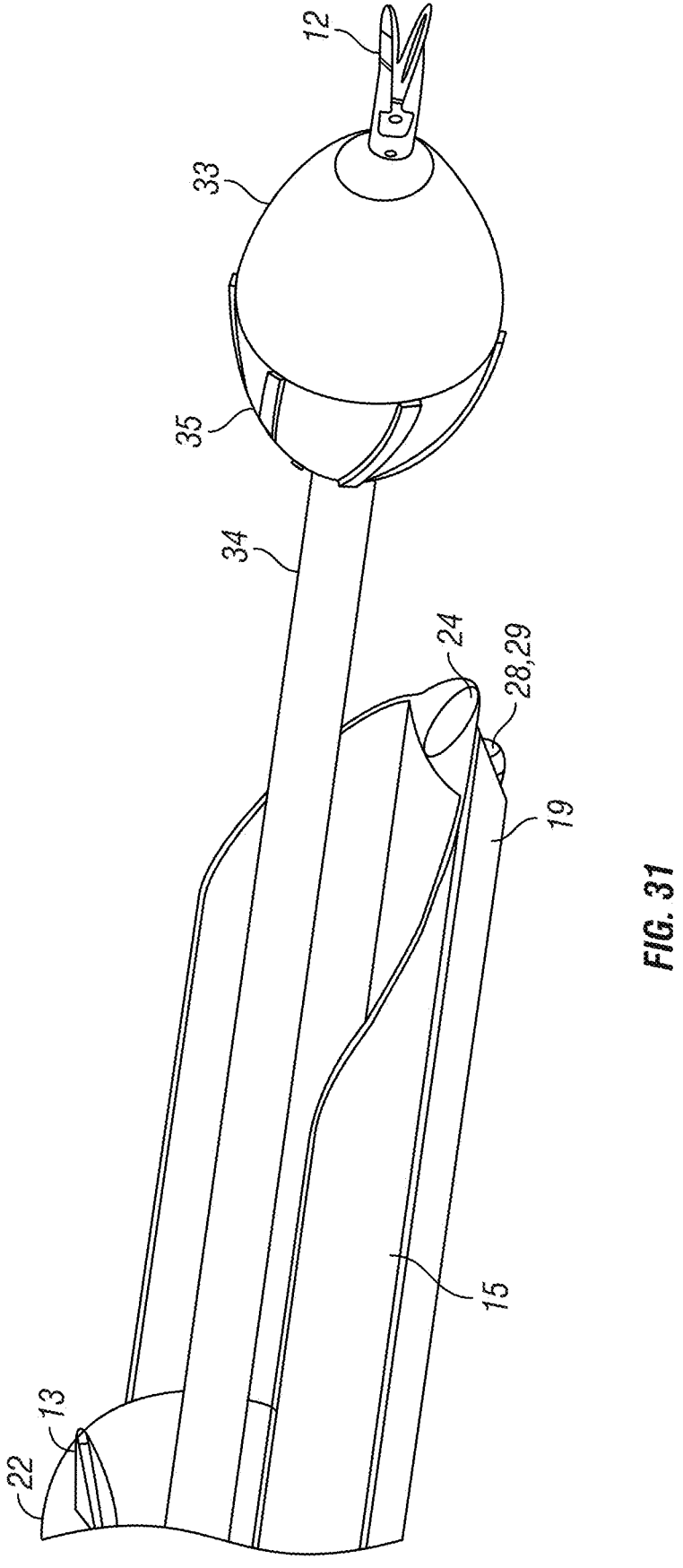
FIG. 31 is a perspective view of an excisional, expandable imaging device of FIG. 29 with one of its excisional elements along with its expandable chamber in an extended position according to embodiments.

FIG. 31 shows that the expandable, transparent imaging, parting off and supporting chamber 33 may be advanced far forward (distally) of scoopula 15 utilizing its controlling hollow shaft 34 through which it was been introduced. A smaller excisional device 12 may be guided in such a distal-most position by its platform 33 from which it emerged if, as in this illustration and according to an embodiment, the smaller excisional device is independently movable. Alternatively, the smaller excisional device 12 may be a fixed component (with respect to axial movement) of chamber 33, notwithstanding (an) actuation connection(s) according to embodiments that allow the smaller excisional device 12 to selectively assume an open, coring configuration or a closed, streamlined, dissection and parting-off configuration. Additionally, in this illustration, beak tips are shown in parting off position around a tube such as element 34. When the beaks are closed in this position, they may also function as a type of carrier bearing that may help provide support and stabilization for shaft 34 and its imaging chamber, which are far forward beyond support from an underlying scoopula. In this case beak tips may compensate for the loss of support that would have been provided by a scoopula 15, when an imaging chamber is advanced beyond its forward edge. Also, tube 34 is capable of rotating as it powers imaging chamber 33. Whether tube 34 is rotating or stationary, surface features such as slots or vanes may be utilized to augment transport of excised materials back through the catheter of FIG. 1's interior. If stationary, the differential rotation of cutting elements 14's inner tube compared with rotation or non-rotation of a tube or shaft 34, given helical element shapes on opposing surfaces of either or both of tube 34 (outer surface) and helical excisional elements rotational tube (inner surface), when rotated in a direction to exert a backwards force on excised tissues, would cause or help cause, backwards transport of excised tissues all the way out the back end of the excisional device of FIG. 1 according to embodiments.

Figure 32:
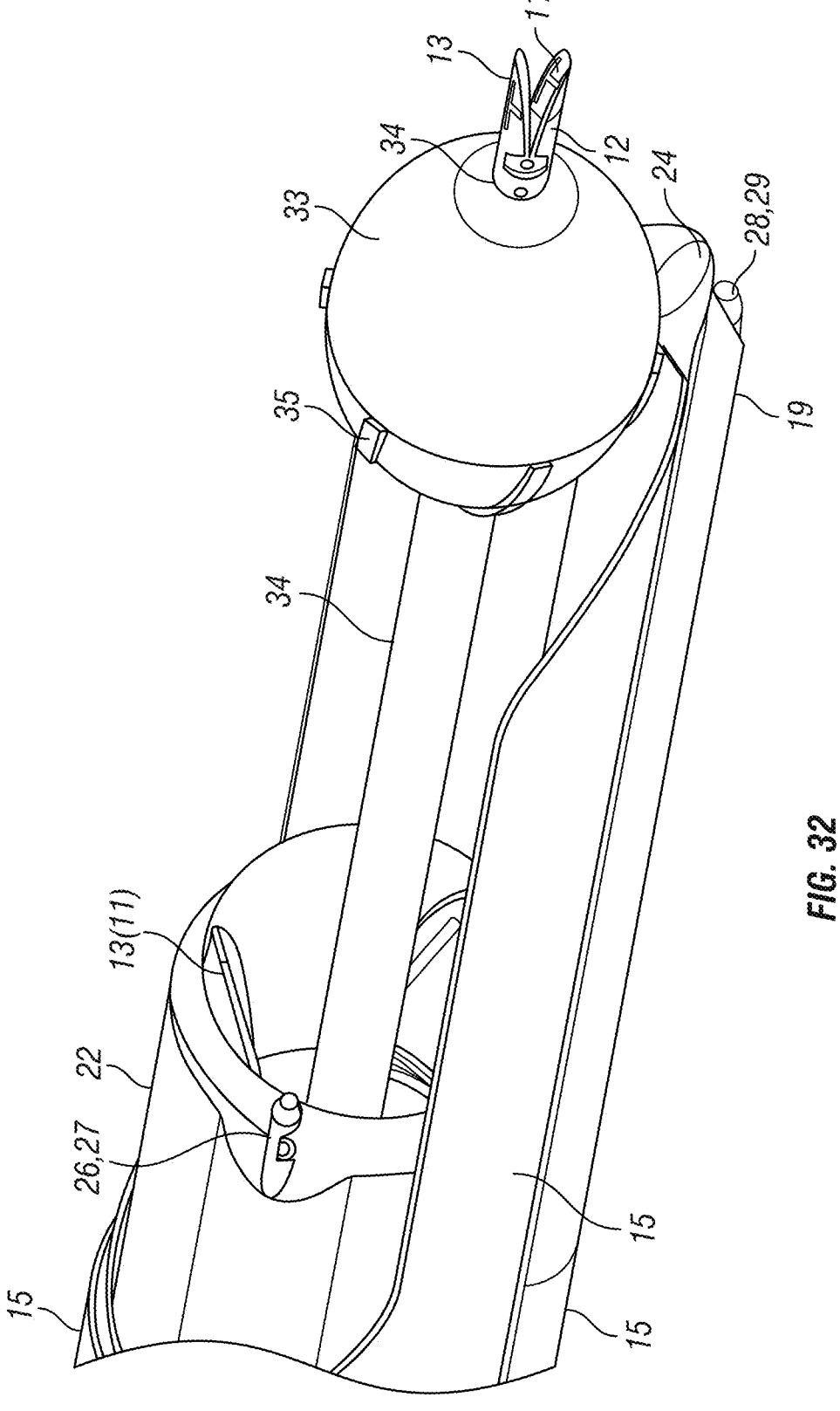
FIG. 32 is a perspective view of an excisional imaging assembly as in FIG. 29 revealing an additional imaging element in approximate alignment with its major excisional element and its expandable parting off chamber with an additional excisional element as well as showing an additional imaging element in an access channel in an approximate plane with its additional excisional element according to embodiments.

FIG. 32 shows the same elements as in 30 and 31, with beaks open and although imaging chamber 33 now has parting off ribbons mounted on its back surface, given the tip shapes 11 of FIGS. 30 and 31, enabling parting off either in the conventional beaks closed manner or against parting off ribbons, an operator has the choice of leaving imaging chamber 33 in any position desired, without needing to move it into a position for parting off excised tissues according to embodiments., Also, FIG. 31 includes, with the addition of examples of a variety of imaging elements 26, 27, 28, 29 and optionally imaging elements inside imaging chamber 33, noting that the positioning of such elements would optimally take advantage of their specific inherent capabilities and physical requirements. Note in this illustration, optional supporting expandable element 32 (not shown in FIG. 32 but present in FIG. 33) may be in non-expanded configuration or, optionally, may not be included in this version of an excisional imaging assembly according to embodiments.

Figure 33:
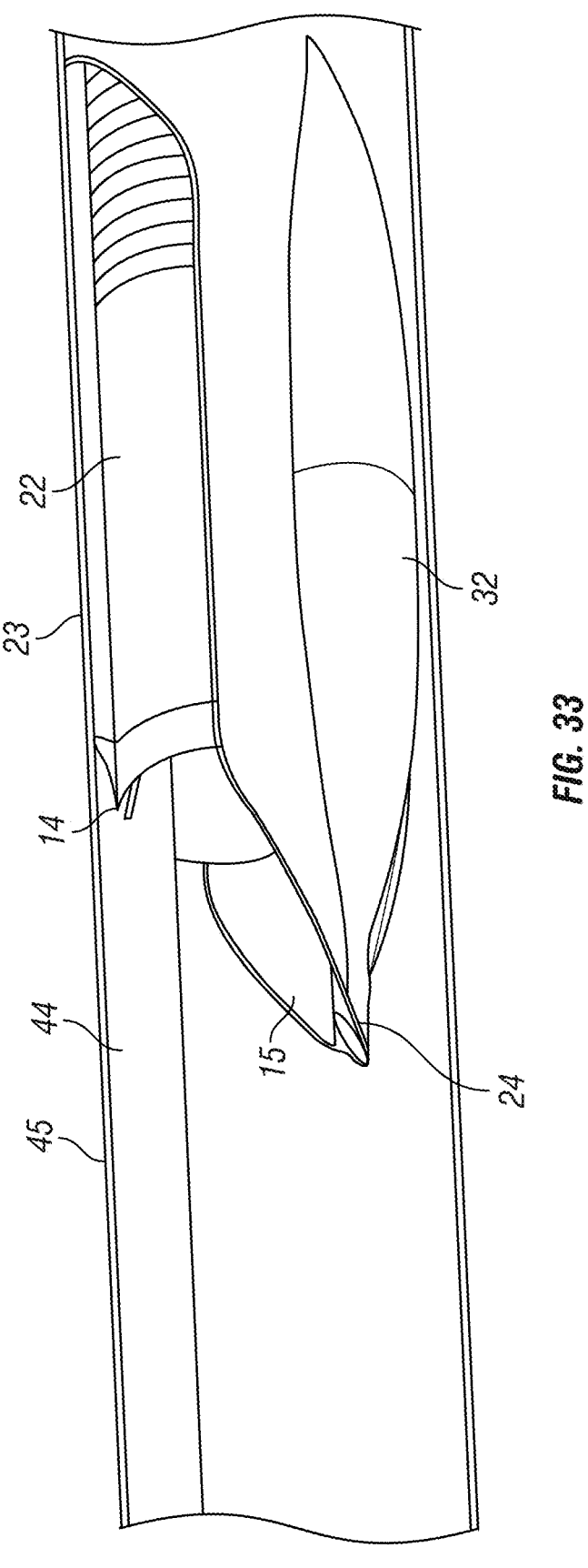
FIG. 33 is a perspective view of an excisional device of FIG. 1 within a vascular structure in the process of excising materials from the wall of a vascular structure according to embodiments.

FIG. 33 and several of the following illustrations show elements of an excisional imaging assembly in action phases within a diseased vessel such as an artery partially obstructed and in some cases totally occluded by obstructing materials 44 that are often located asymmetrically about the internal walls and in most cases form a part of an internal layer of an affected vessel 45. In this illustration, an excisional procedure according to one embodiment involves supporting element 32 of device 10 elevating its scoopula 15 such that excisional elements 13 of working element 14 are able to engage and excise obstructing materials 44 from the vessel 45. Lumen 24 may be utilized with imaging elements to guide the process with a modality such as ultrasound while another imaging modality such as OCT may be utilized at closer range via channel 23 in a non- or differentially rotating sheath (NRS) 22. Note also that NRS 22 may be utilized as a depth limiter depending upon exposure levels of work element 13's articulated beak elements 14s (longitudinal positioning of an NRS near the beak tips 11 or fully back to allow complete exposure of beak elements with the resultant intimate contact between cutting edges and tissues, with no other structure in between) as well as independent rotation of NRS 22 when in position near the cutting edge tips 11 of beak elements 14, such that thicker or thinner areas of an NRS 22 are to a lesser or greater level, between cutting edges and tissues being excised, according to embodiments. Note that both NRS 22 and scoopula 15 may be fully transparent or may have transparent areas according to embodiments.

Figure 34:
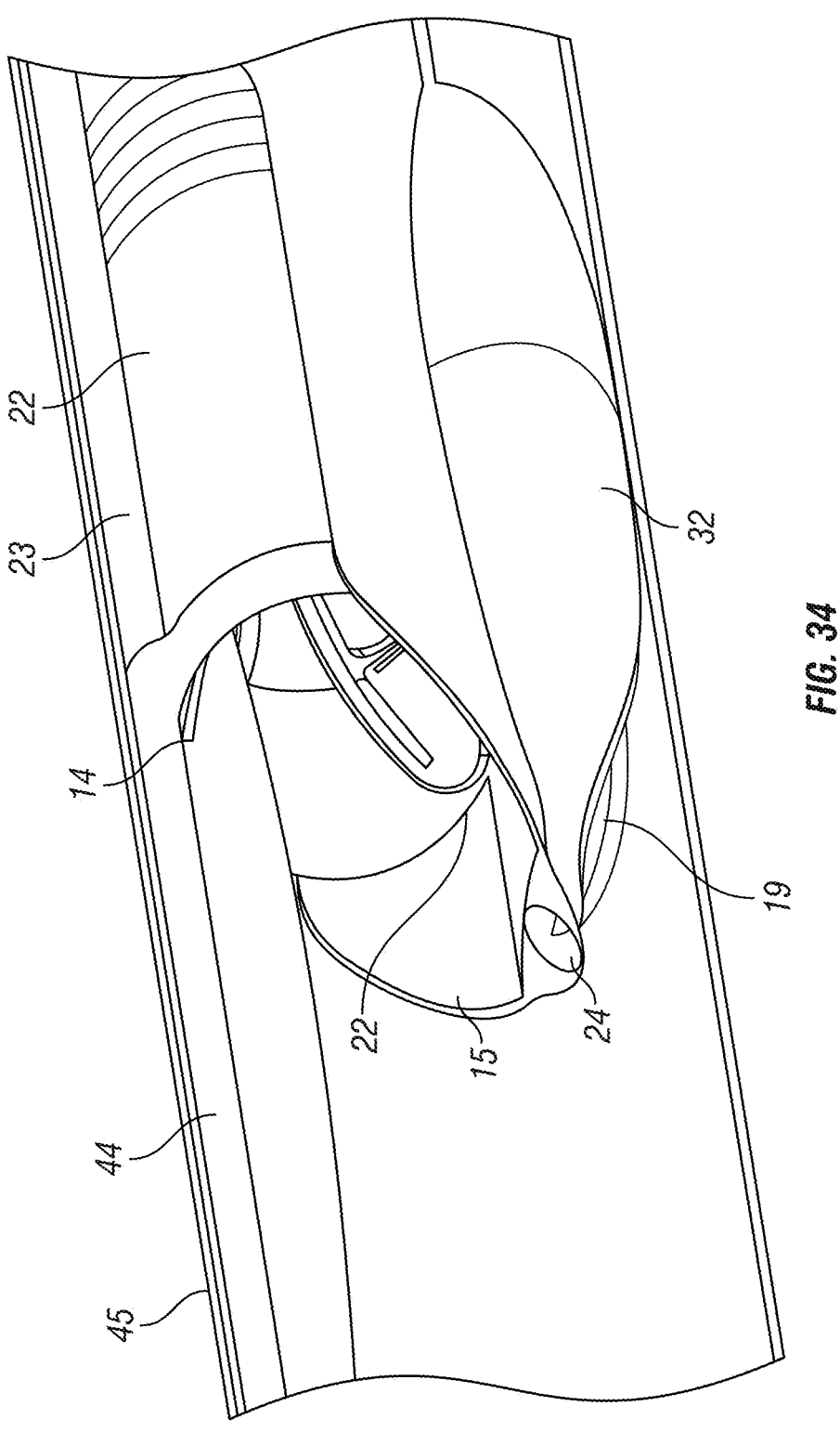
FIG. 34 is a more frontal perspective view of an excisional imaging device of FIG. 33 shown within a vascular space excising obstructive materials and also revealing a double expandable element with a variably opening, longitudinal channel between the individual halves, each half optionally expandable to a different degree one versus the other, located on the underside of a device according to embodiments.

FIG. 34 shows the present device 10, using the same elements as in FIG. 33, is shown from the front to more clearly show elements as the central channel and access or flow lumens 19 and 24 along with lumen 23 as well as the ability to utilize their positions for introducing imaging elements according to each imaging modality's capabilities and limitations. These channels are collapsible, representing potential spaces, or they may be rigid according to embodiments and are considered interchangeable, even within a single procedure and may be utilized by a single modality such as ultrasound, or in combination with physiologic measurers of flow restriction, fractional reserve and fractional flow gain following luminal improvements for such purposes as endpoint analysis, or in combination with other imaging modalities such as OCT. Also shown are the beak elements 14 involved in clearing disease material 44 from a vessel 45, according to embodiments.

Figure 35:
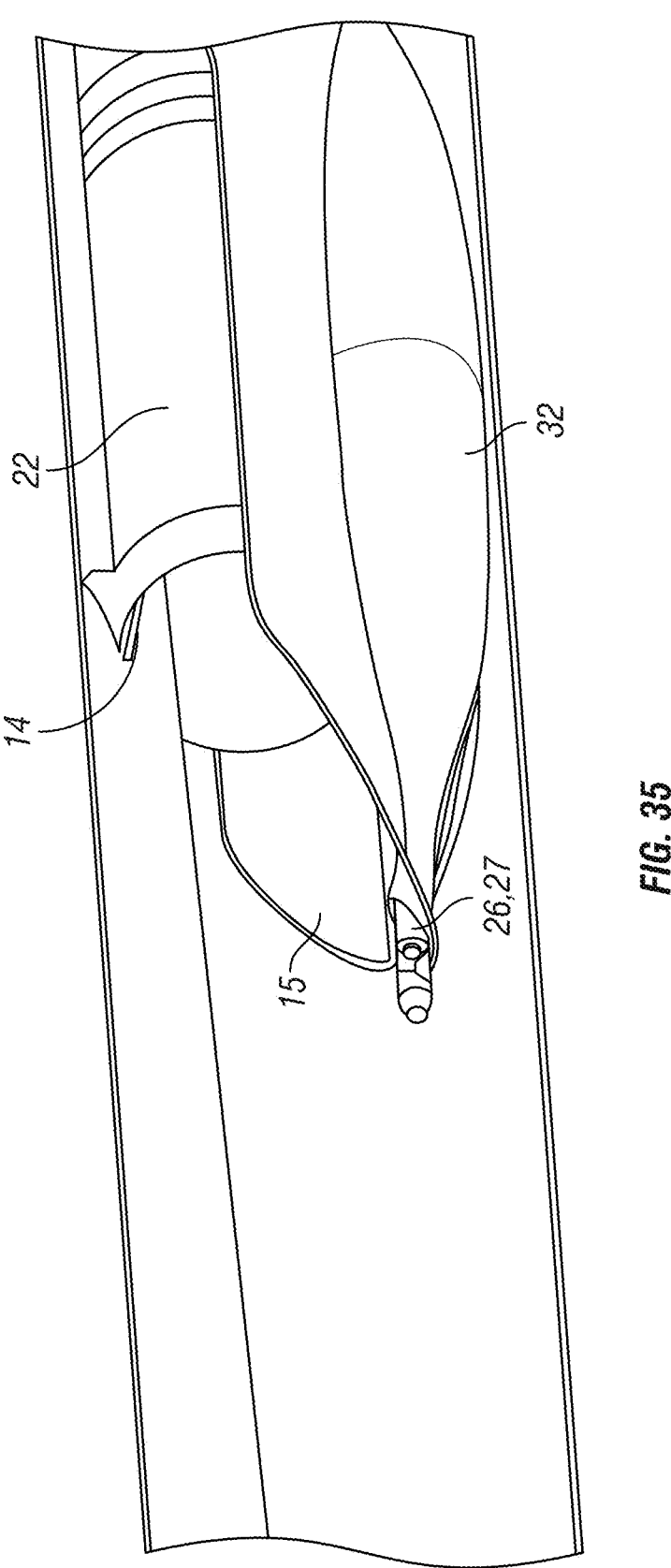
FIG. 35 is a perspective view of a device of FIG. 34 shown in a vascular space revealing one of the placements of an imaging element ahead of the element shown excising obstructive materials according to embodiments.

FIG. 35 is another perspective view of a working imaging, excisional, capture and transporting assembly 10 of FIG. 1, showing slight rotation of scoopula 15 supported by expandable element 32. In later illustrations, independent rotation of scoopula 15 from expandable supporting structure 32 will be shown such that automated disease material removal may be accomplished automatically and remotely, according to embodiments. Such automated disease material removal may include, according to embodiments, all needed motions such as expansion of element 32, control of rotation of scoopula 15, longitudinal positioning of and advancement of excisional elements 14 along with the same positioning choices for NRS 22 taking advantage of its thinner and thicker sections in contact with tissues creating a lesser or greater standoff between cutting blade(s) 14 and edges 11 and tissues being excised. This positioning of NRS 22 may also, according to embodiments, incorporate feedback and guidance from imaging elements such as ultrasound or OCT 27 (emanating from scoopula 15) to show overall and longitudinal extent of obstructive materials and ultrasound or OCT 27 (shown more distally in FIG. 35 and emanating from an additional, more inferior tandem lumen) for nearer-to-cutter, depth of removal guidance.

Figure 36:
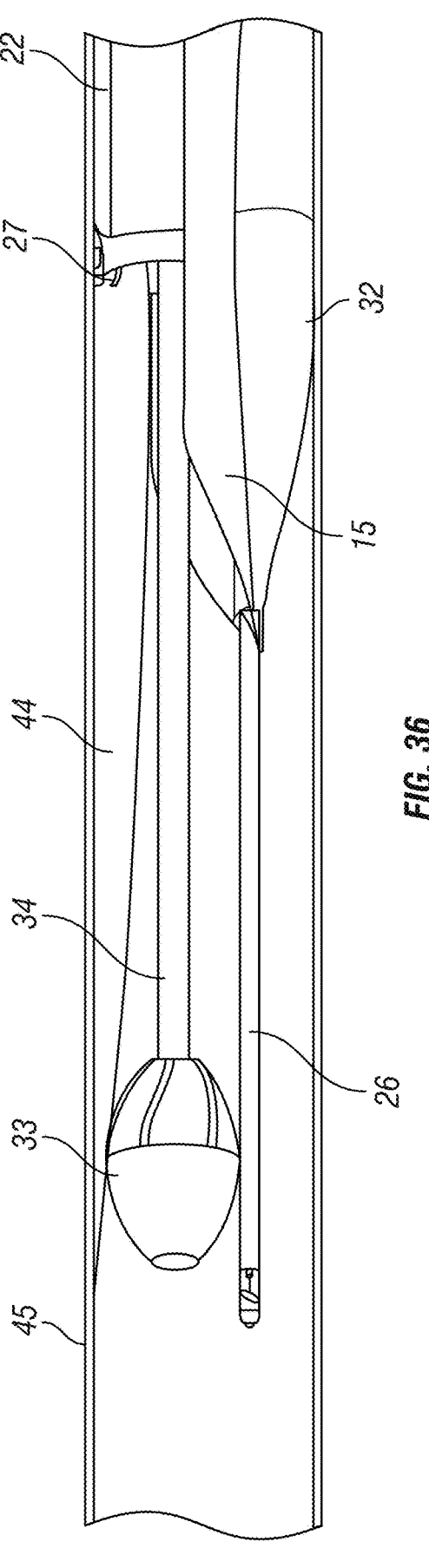
FIG. 36 is a perspective view of an excisional and imaging assembly shown in the process of excising obstructive materials from a vascular structure, with an expandable imaging parting off element extended to the distal edge of an asymmetric obstruction, as well as an additional imaging element extended out ahead of the expandable imaging parting off element according to embodiments.

FIG. 36 and subsequent figures re-introduce elements from previous illustrations, shown in several available positions within a diseased vessel 45. In this case, imaging modality ultrasound 26 with its longer range but lower resolution, is shown in a position in the bloodstream (blood does not block its imaging capabilities) to guide the longitudinal extent of disease material 44 while higher resolution OCT 27 (lower range but higher resolution) is positioned within imaging chamber 33 and up against a wall. In such a position, an OCT imager element can be in close proximity to both plaque (if this is the obstructing element) and excising elements shown farther back in this figure, and kept slightly ahead of NRS 22, such that OCT 27 may guide depth of excision in real time, in close coordination with the advancement of the cutting elements, for example. Given OCT 27's position inside transparent chamber 33, blood that is illustrated as still flowing due to the open channel provided in double balloon 32, does not interfere with the local OCT imaging through the blood-excluding transparent imaging chamber 33 and into the tissues to which imaging chamber 33 is in close proximity. Regulation of expansion pressure in element 32 both regulates flow and also by acting against supporting scoopula 15, regulates depth. Depth control may be a combination of several elements such as exposure levels of excisional elements controlled by NRS 22, to provide maximum precision of excision according to embodiments.

Figure 37:
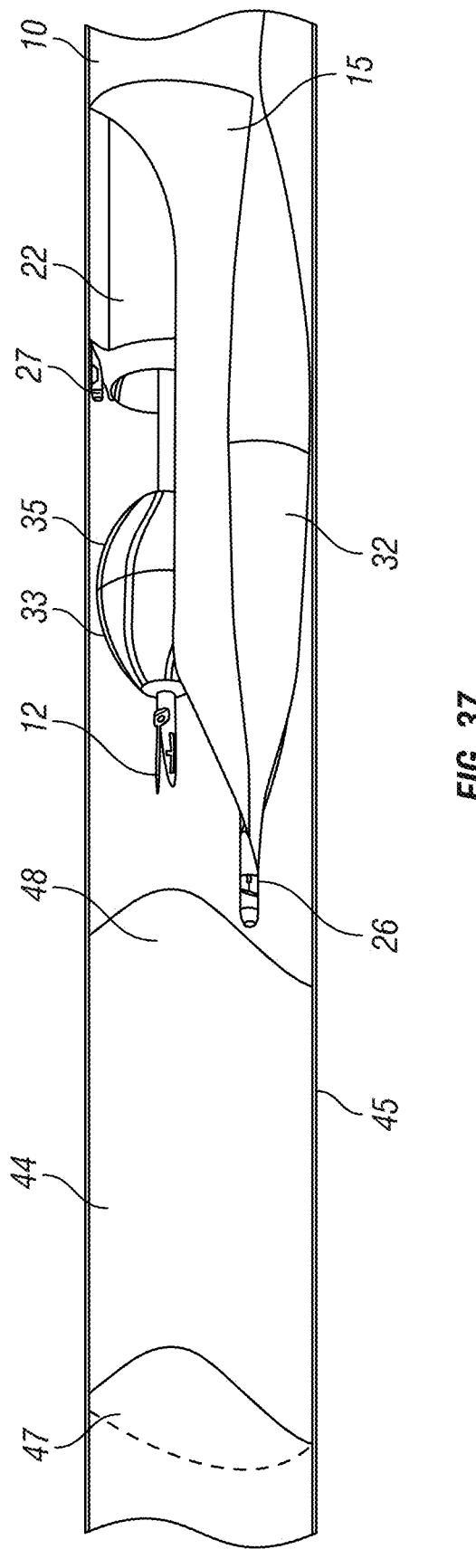
FIG. 37 is a perspective view of an excisional and imaging assembly of FIG. 32 shown approaching a totally occluded tubular structure such as a blood vessel, with one of the assembly's imaging elements poised at the near end of the total occlusion, while an inflatable supporting element is shown elevating the assembly to a point where a smaller additional excisional element is shown aimed at the nearest surface of the totally occluding material, as well as the larger excisional element slightly advanced within a scoopula portion of the assembly, while an expandable imaging, cutting and parting off element is shown supporting the smaller excisional element that is located at the forward edge of the expandable imaging, cutting and parting off element according to embodiments.

FIG. 37 provides an example of a totally occluded vessel 45 by mixed materials 44, which may include a hard, calcified proximal cap 48 and an often softer distal cap 47, as well as thrombus, plaque, and calcium deposits in various areas throughout the obstructing material. This situation helps illustrate some of the capabilities of various elements of the present device 10 according to embodiments, such as the elevation positioning contribution of expandable pressure-applying element 32, directional and rotational positioning and stabilizing capabilities contributed by supporting scoopula 15, centering-capable, expandable, transparent imaging and cutting or ablating element 33 with its cutting blades 35 (which may function as a part off mechanism in conjunction with work element 13 beaks, as previously described for FIG. 21 above) on both its forward and aft surfaces and smaller excisional element 12 poised to engage a proximal cap 48 of, for instance, a chronic total occlusion lesion. When an imaging ultrasound element 26 is inserted there through, it may also supply lay of the land geographic and composition information while OCT imaging element 27 may subsequently replace an ultrasound imaging element 26 in this location and be utilized later in the intervention for final, depth controlled clearing of any remaining disease material 44 that may still be present along a wall of vessel 45. Given the overlapping nature of OCT and IVUS (intravascular ultrasound), it becomes apparent that interchanging these modalities can be useful and also enabled by the capabilities of placing them in different locations by rotation of elements such as an NRS, by itself or in combination with expandable elements, can dial in the correct focal lengths of the various modalities, while deciding whether or not to occlude blood flow, with for example cuff 30, may also inform the decision as to which modality is best suited for a particular imaging task.

Figure 38:
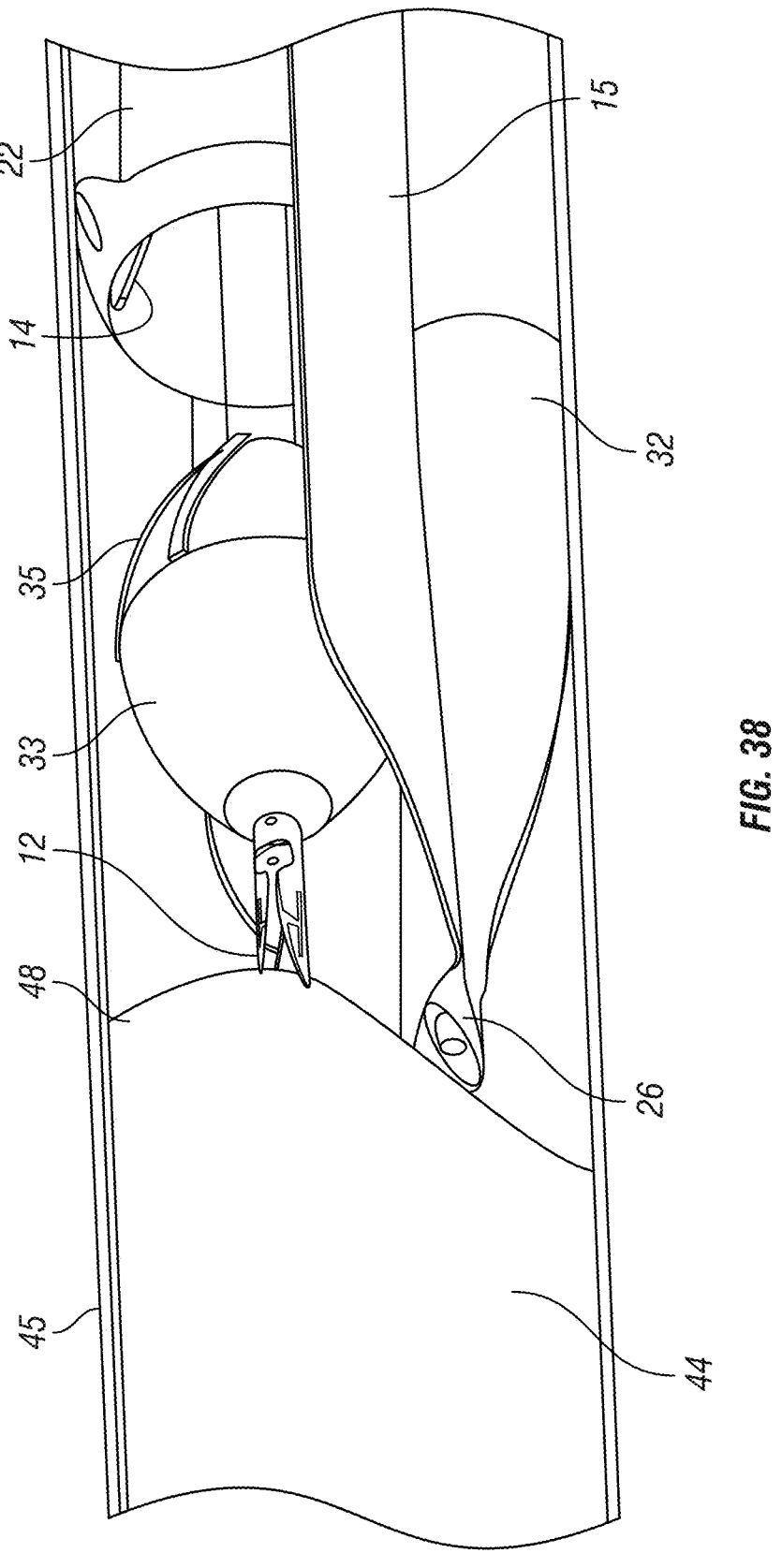
FIG. 38 is a closer up perspective view of an assembly described in FIG. 37, now shown with the smaller excisional element engaging the nearest portion of the totally obstructing material, in this case the expandable imaging parting off structure does not include the forward edge cutting blades, according to embodiments.

FIG. 38 provides a closer up view of the illustration described in FIG. 37, showing engagement by smaller excisional element 12 of the proximal cap 48 while scoopula 15 has been advanced up forward and elevated to provide, together with expandable imaging, supporting and centering chamber 33 and expanding supporting element 32, a maximally stable platform from which to operate excisional element 12 according to embodiments to selectively core through and part-off material from the proximal cap 48, the distal cap 47 and the intervening diseased obstructing material there between.

Figure 39:
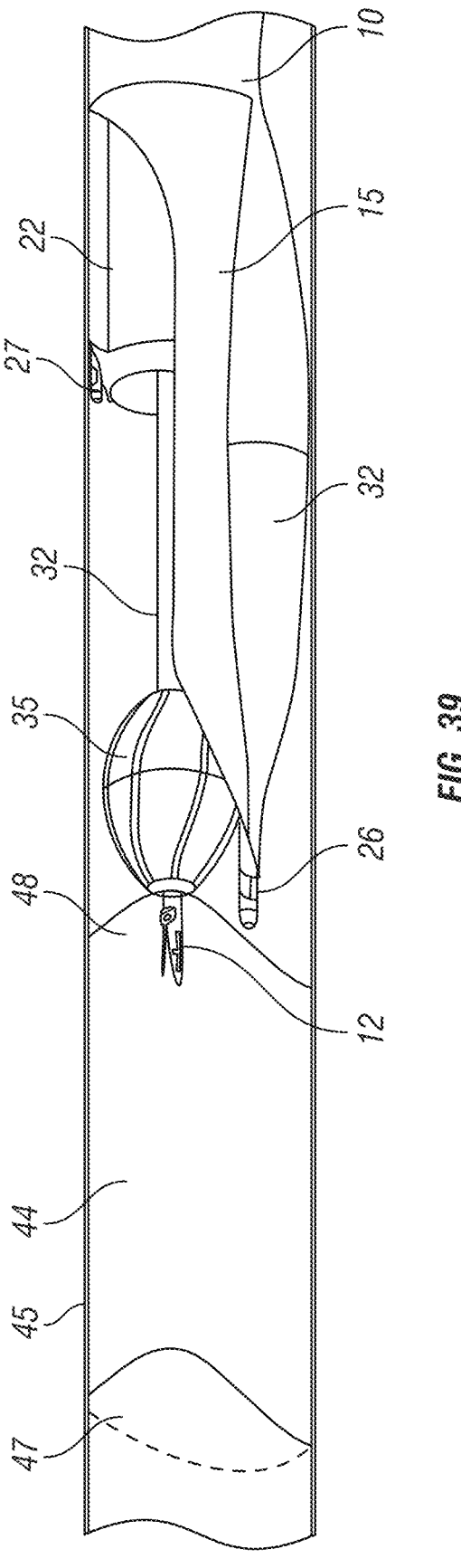
FIG. 39 is a perspective view of a tubular structure that is totally occluded as in FIGS. 37 and 38 with the exception that the expandable imaging, cutting, and parting off structure now is shown with the included forward cutting blades according to embodiments.

FIG. 39 illustrates the capabilities of the elements of an imaging, excisional assembly 10 and the various components arranged to support and control the smaller excisional element 12 as it bores through the hard proximal cap 48 of the totally occluding obstructive disease material 44 along with imaging guidance and maximal support as described above along with precise placement at the very proximal most edge of the proximal cap 48, while an OCT imaging element may be introduced within smaller excisional element 12 once any tissue still in the lumen proximal to it, has been removed, according to embodiments. It is to be noted here that the OCT imaging element and/or other imaging of treatment devices may be introduced within and past the smaller excisional element 12 as such is constructed from a tube of material from which material has been removed to define the functional structures that enable the smaller excisional element 12 to selectively open and close. A consequence of forming the small excisional device 12 out of a hollow tube of material (as may be the work element 13) is that there are no structures protruding within the central lumen of the smaller excisional element 12 that are closer to the rotational axis thereof than the inside wall surface of the hypo tube from which the small excisional element was formed.

Figure 40:
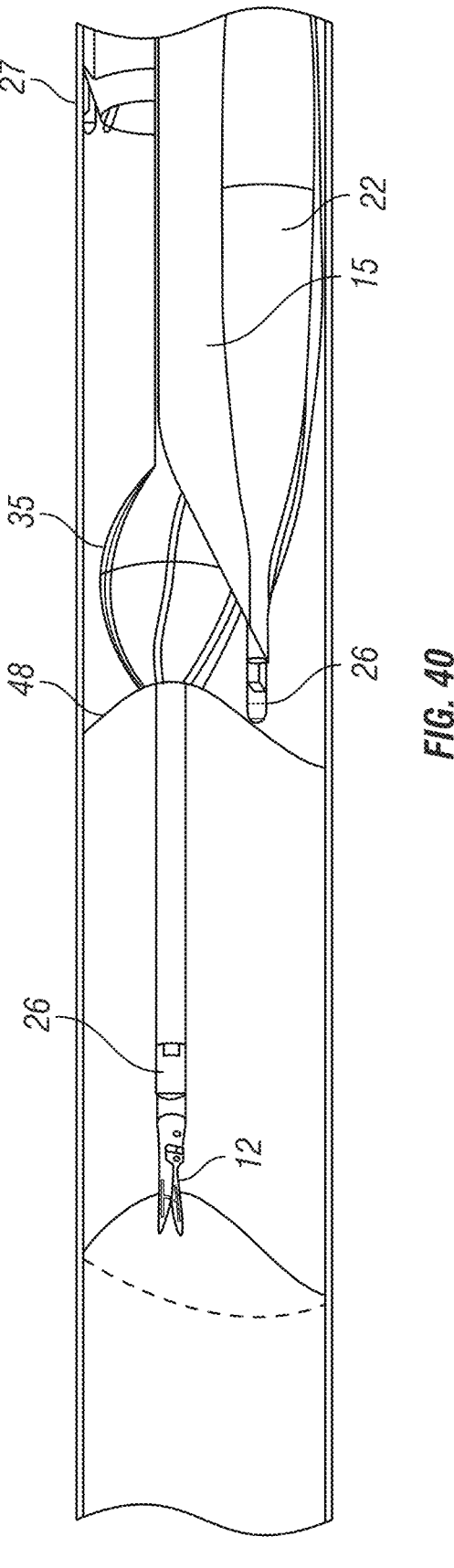
FIG. 40 is a perspective view of an excisional imaging assembly of FIG. 39 showing the smaller excisional element having cored all the way to the far end of the occluding obstruction as well as revealing an additional imaging element now advanced within the hollow tubular portion of the shaft of the smaller excisional element according to embodiments.

FIG. 40 illustrates further aspects of a device 10 in action, whereby after penetrating the proximal cap 48 and excising, parting off and transporting back obstructing materials, an imaging element such as OCT or other such guiding modality may be introduced within the central lumen of the smaller excisional element 12 to confirm proper placement and any extent of further penetration needed for complete progress through a total occlusion, particularly given that fluoroscopic guidance imaging may be of little use, due to the total occlusion nature of the vessel not permitting contrast agents to be injected beyond or even to the distal cap area (depending on collateral circulation availability). Even if collateral circulation were available, it may not reach the distal cap 48, in which case, guidance extension via the central open channel may be of desirable use, whether by OCT or ultrasound, or with microinjections of contrast through imaging element 33's (and also through the smaller excisional element 12's) central open lumen, as illustrated here and according to embodiments.

Figure 41:
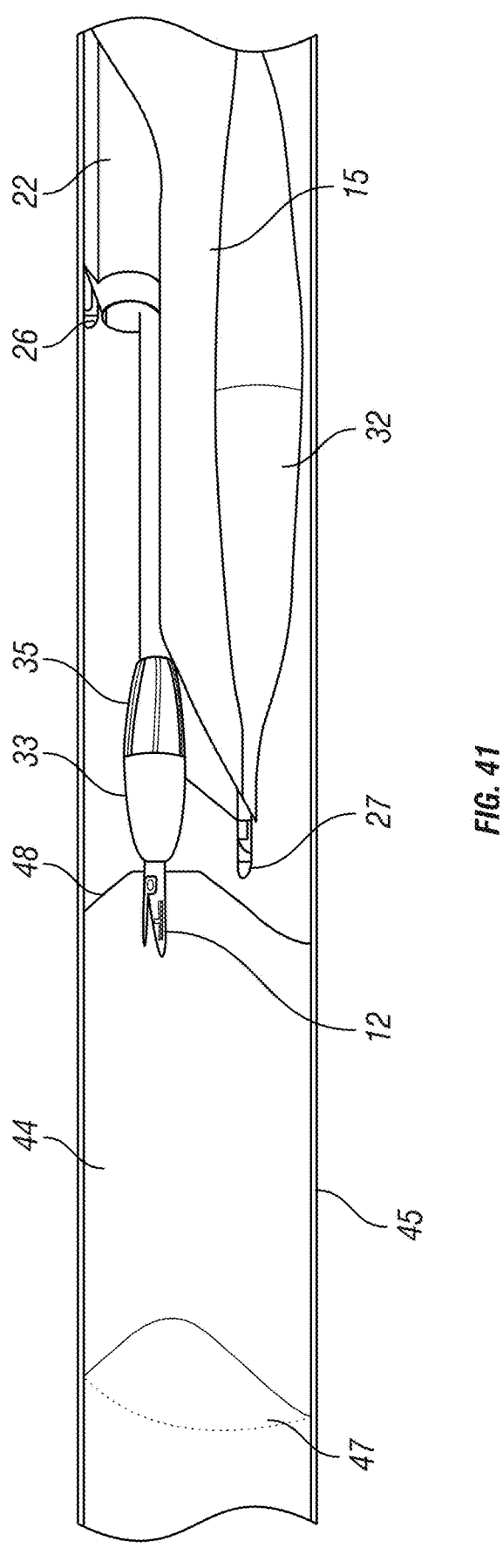
FIG. 41 is a perspective view of an excisional imaging assembly of FIG. 38 with the expandable imaging, parting off chamber in a mostly non-expanded state in a position just in front of an occluding obstruction according to embodiments.

FIG. 41 shows a potential next phase of an intervention in a case involving a complete occlusion of a vessel, whereby expandable, transparent, imaging chamber 33 is shown in a less expanded state to follow the smaller excisional element 12 more closely, as it penetrates deeper into and beyond a potentially hard proximal cap 48 of totally occlusive obstructing disease materials, after which advancement in the wake of smaller excisional element 12, expandable, transparent imaging chamber may be used for guidance as well as for further widening of a channel thus bored by the smaller excisional element 12, according to embodiments.

Figure 42:
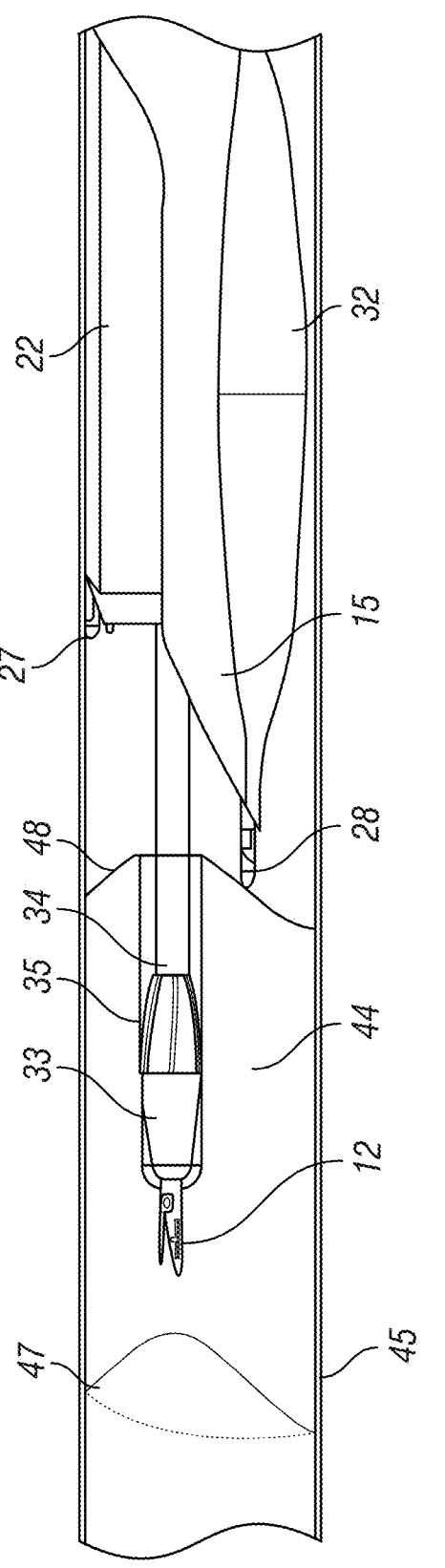
FIG. 42 is a side view of the excisional imaging assembly of FIG. 41 showing the expandable imaging, parting off chamber following the smaller excisional element partially through the occluding obstruction according to embodiments.

FIG. 42 shows that the progression described above as smaller excisional element 12 tunnels through obstructing material 44, it may be aided in its progress by backup support from partially expanded element 33, which element can also provide up close, even in-situ microscopic information about the nature of the occlusive materials along the way, according to embodiments.

Figure 43:
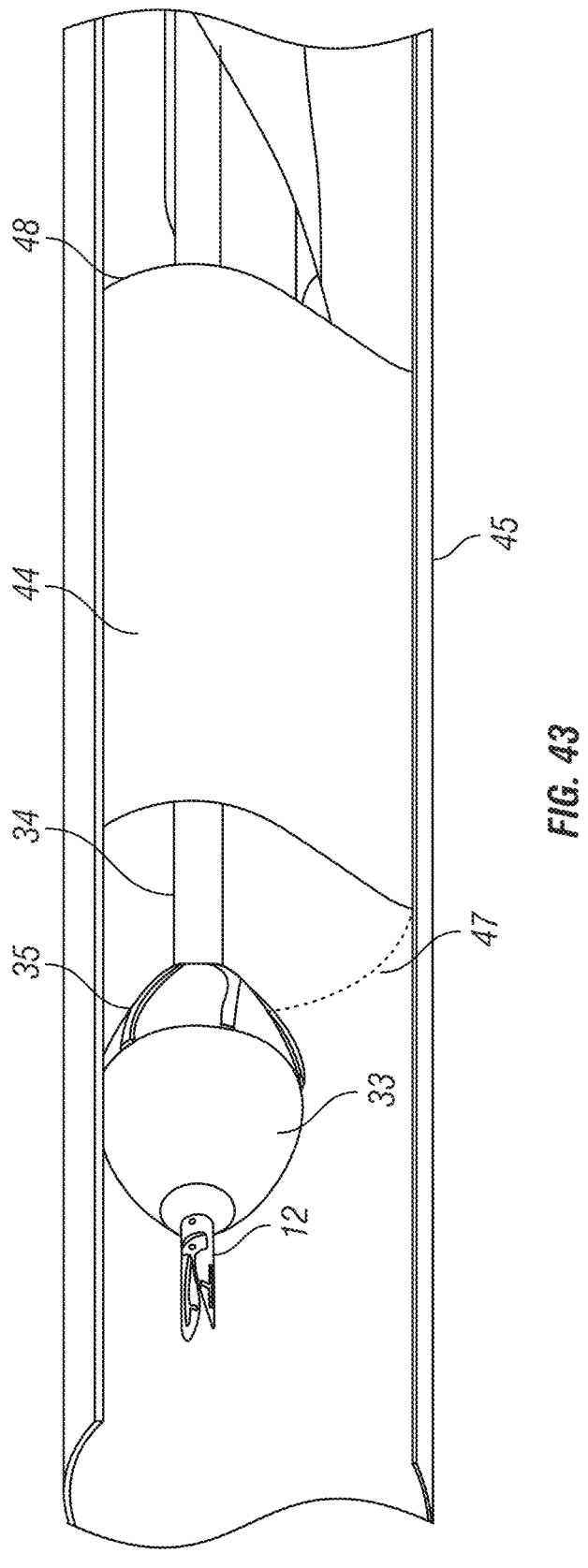
FIG. 43 is a perspective view of an imaging excisional assembly of FIG. 42 now showing the expandable imaging, parting off supporting chamber in expanded state at the far end of the occluding obstruction according to embodiments.

FIG. 43 shows still further progress as both smaller excisional element 12 and its supporting, trailing expandable, imaging, cutting and conjunctive parting off chamber 33 has also advanced beyond the distal cap 48 of totally occluding obstructive disease material, and which imaging, parting off chamber 33 is now poised for imaging and several additional options. The imaging chamber element 33 may serve as a rearward cutting instrument, using its cutting blades 35 on its rear surface and ultimately meeting up with an excisional assembly of device 10 with work element 13 located proximal to the proximal cap 48, or the imaging chamber 33 may remain in position to provide tow to help move a proximal excisional assembly forward, given its establishment in an anchoring position beyond the distal cap 47, or it may participate in a combination of the two movements. Another option is to leave a scoopula in position initially, and then as an NRS with its internal excising elements is advanced to excise and to meet up with imaging chamber 33 the material may be excised using this method. Another option is that a scoopula may also advance together with an NRS and including its excising cutters 14, through the remaining disease, excising and transporting materials back in the process while optionally using any of the choices for closely coordinated and closely approximated, precise imaging guidance all along the way according to embodiments.

Figure 44:
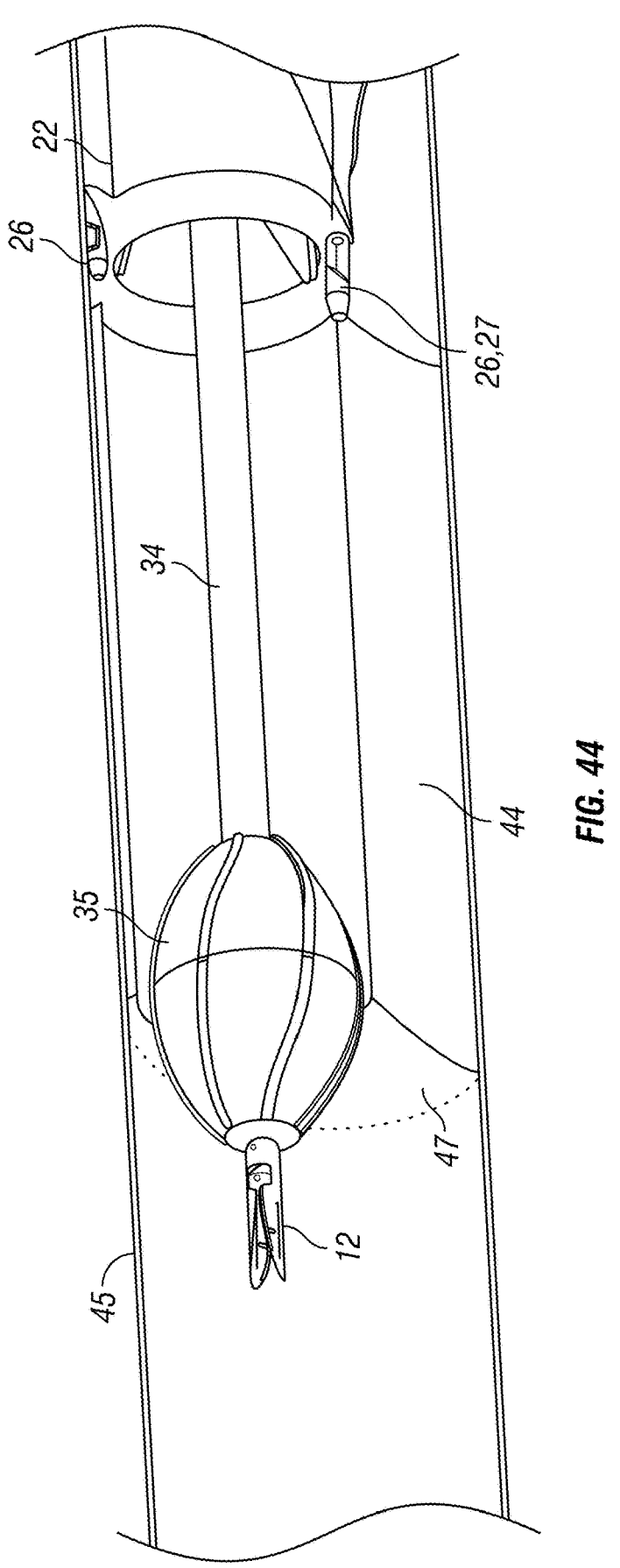
FIG. 44 is a perspective view of an excisional imaging assembly of FIG. 40 showing the expandable imaging, parting off, supporting, and cutting chamber in expanded state at the far end of a previously totally occluding obstruction according to embodiments.

FIG. 44 illustrates just such a partial relief of a total occlusion with removal of some of the materials of disease material 44, 47 by one of the methods described above. Next steps may involve a combination of some of the described methods or may proceed with next steps as would be the case with a subtotal occlusion, including the use of any of the elements previously described including guidance, as well as others still to be described in the following illustrations and according to embodiments.

Figure 45:
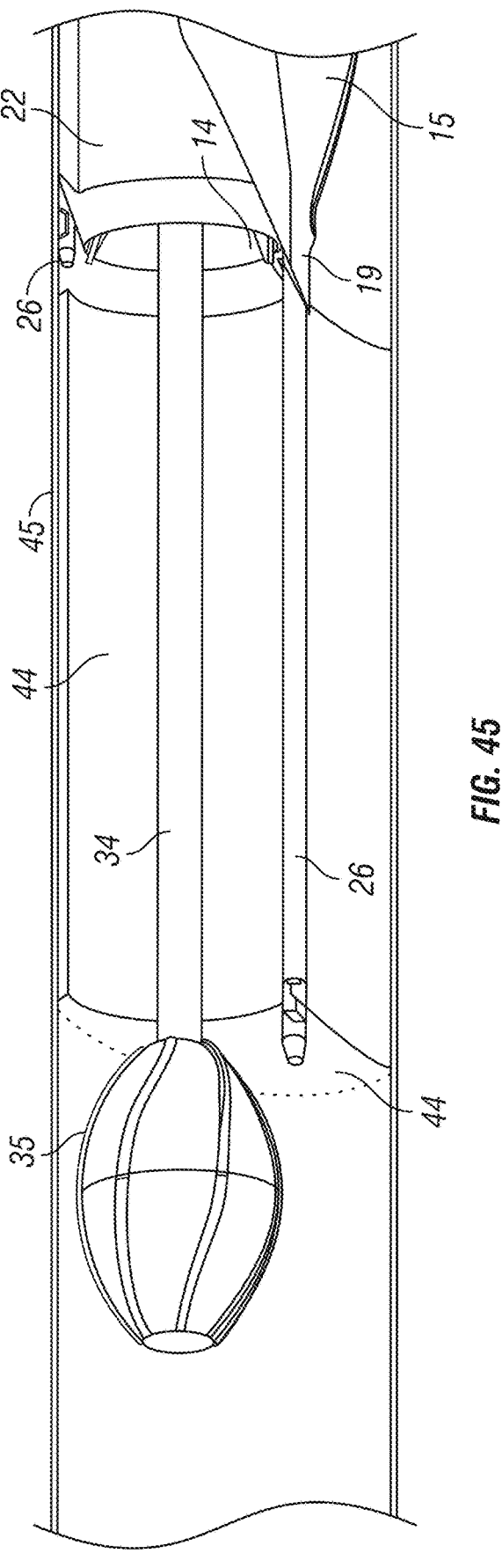
FIG. 45 is a perspective view of an excisional imaging assembly of FIG. 44 in a previously occluded tubular structure, with the expandable imaging, parting off, supporting and cutting chamber, in this case without the smaller excisional element and with an imaging element extended out from a tubular channel in the scoopula, to the far end of the obstructing material according to embodiments.

FIG. 45 illustrates some of the placement options for guidance modalities once the chronic or acute total occlusion has been converted into a subtotal obstruction, here showing in this example, the advancement of an October 26 element, which before downstream blood flow is fully restored, or allowed to proceed, may be simpler to use while less affected by blood interference, according to methods and embodiments.

Figure 46:
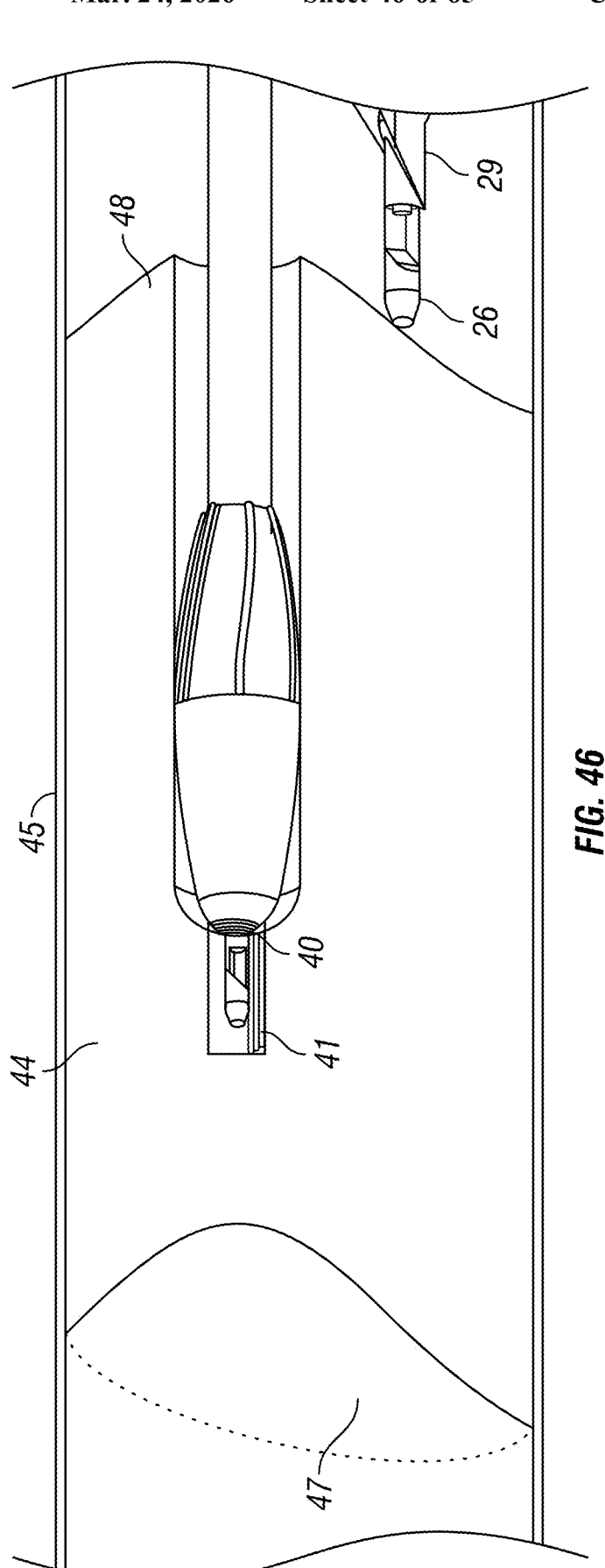
FIG. 46 is a close up perspective view of a smaller, in this case energized excisional element shown in partial cutaway view, to reveal an integrated imaging element in its central lumen followed closely by an expandable supporting chamber of FIG. 42 all within a totally occluding obstruction that exists within a tubular structure such as a blood vessel, as well as revealing a small portion of a supporting scoopula of a device of FIG. 40 and an additional imaging element protruding within there from according to embodiments.

FIG. 46 illustrates in a partial cutaway view, another excisional and ablative element 40, in this case a coaxially located laser energy beam delivery element 40 with multiple laser energy delivery fiber optic tip elements indicated as 41, and also in this case, a coaxially located imaging element, supported by the various elements already described in detail above, including in this illustration, an imaging chamber in partial expansion as in prior examples and according to embodiments.

Figure 47:
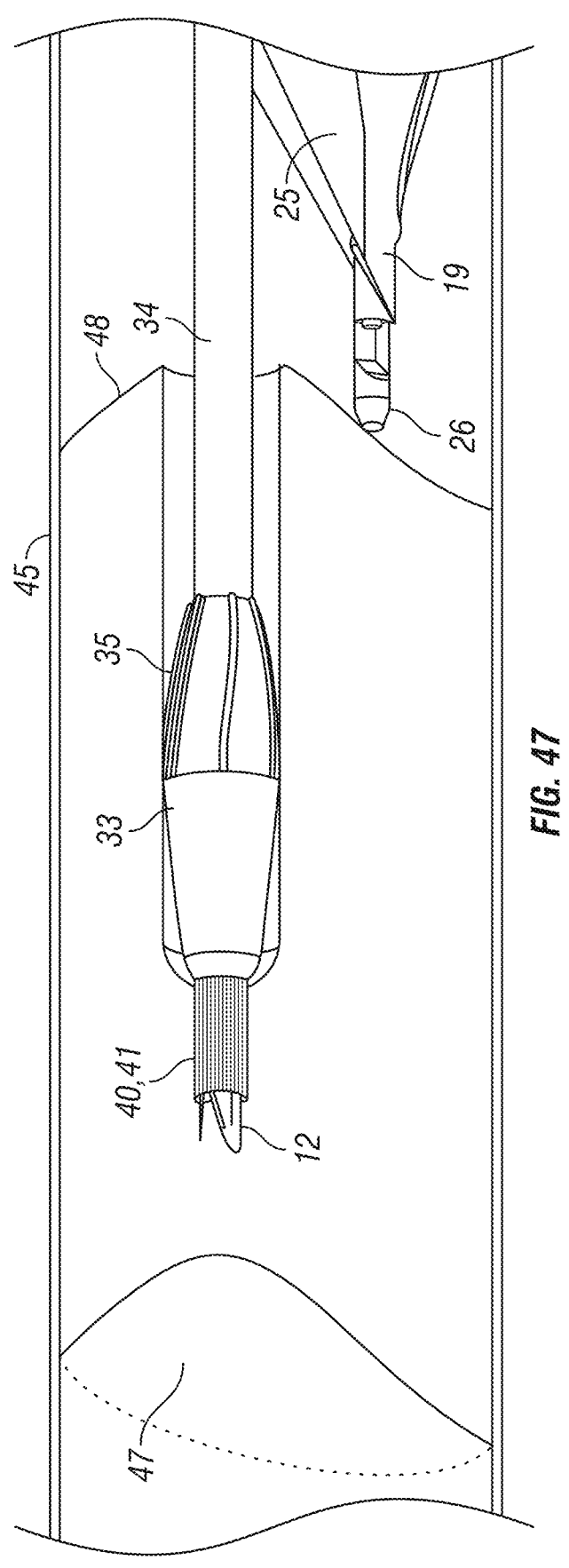
FIG. 47 is a side view of an imaging excisional assembly of FIG. 46 with in this case its smaller, energized excisional element shown in non-cutaway view, along with an additional smaller excisional element of FIG. 44 coaxially located with the energized excisional element and again closely followed by a supporting, expandable, imaging, parting off element shown in partially expanded state according to embodiments.

FIG. 47 introduces the concept of augmented, combined excisional and ablative elements 12, 40, 41 coaxially located relative to each other and extending through an expandable, transparent imaging and cutting chamber element 33 according to embodiments. However it should be noted that, while represented by a laser element in this case, any number of energy sources may be substituted and considered within the scope of the present invention, including high energy, focused ultrasound, inert gas augmented or simple monopolar or bipolar radiofrequency or other shock wave producing modalities, hydro-dissection modalities or any other source of energy transmission that may utilize these methods and devices for placement, access, guidance, support and control according to embodiments. It should also be noted that while illustrated in this figure with laser element 40 with its multiple tip elements 41 wrapped coaxially around work element 12, that laser element 40 may also be coaxially located relative to work element 12 inside the central lumen of work element 12.

Figure 48:
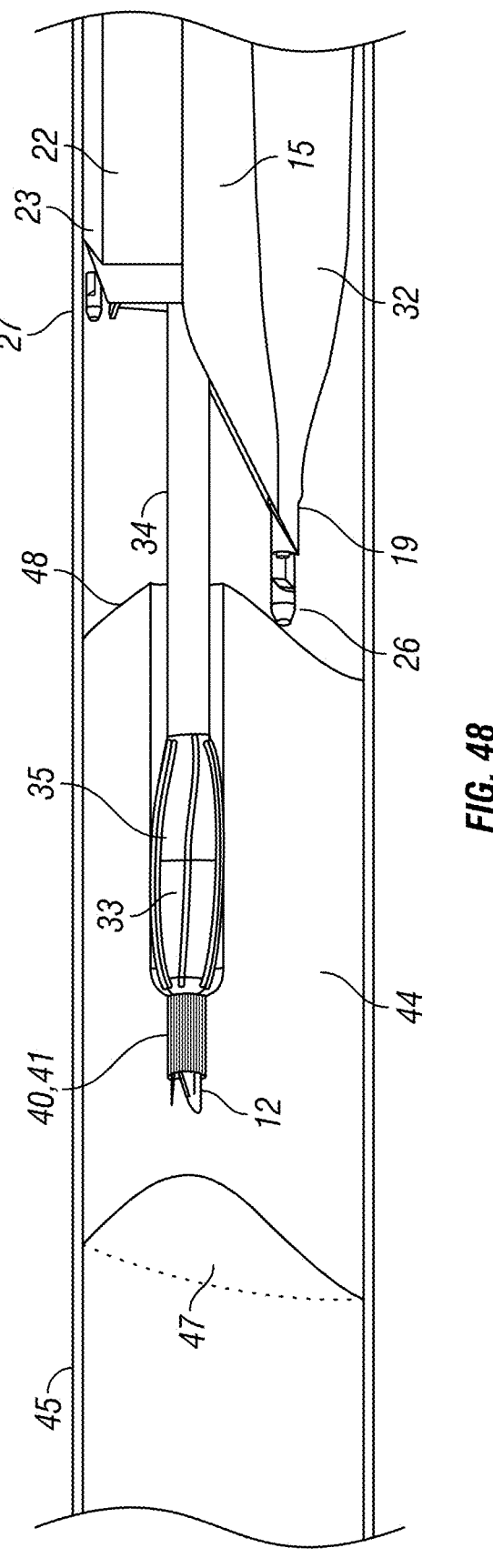
FIG. 48 is a side view of an imaging excisional assembly of FIG. 47 with its smaller energized excisional element and additional coaxial excisional element of FIG. 44, closely followed in this case with the alternative version of an expandable imaging, parting off, supporting and cutting element shown more than half way through a totally occluding obstruction that exists within a tubular structure, such as a blood vessel, all of which working elements are supported in an elevated position by a scoopula and its expandable element attached to its inferior portion, and also visible are two imaging elements each in one of several locations provided according to embodiments. Furthermore, the shape of the imaging chamber, though shown with curved sides in various states of expansion, may equally be shown to have sides, which are constructed to expand in a parallel manner according to embodiments.

FIG. 48 adds further to the disclosure of combined excisional modalities including rotational cutting augmenting channel widening following the pilot bore established by other modalities, using chamber 33 with its cutting blades 35 on both forward and rear areas. Indeed, as shown, the smaller excisional device 12 and its ablative elements 40, 41 may create the pilot bore ahead of the imaging and cutting chamber 33 which, by virtue of its girth and blades fore and aft, cuts through material in its path, following the pilot bore, thereby widening the channel through which it advances through the diseased material. During rotation under the power transmission via shaft 34, for example, a wider channel may be progressively produced with expansion and cutting of the elements of chamber 33 in preparation for complete removal of remaining materials using other elements of an excisional imaging assembly according to embodiments.

Figure 49:
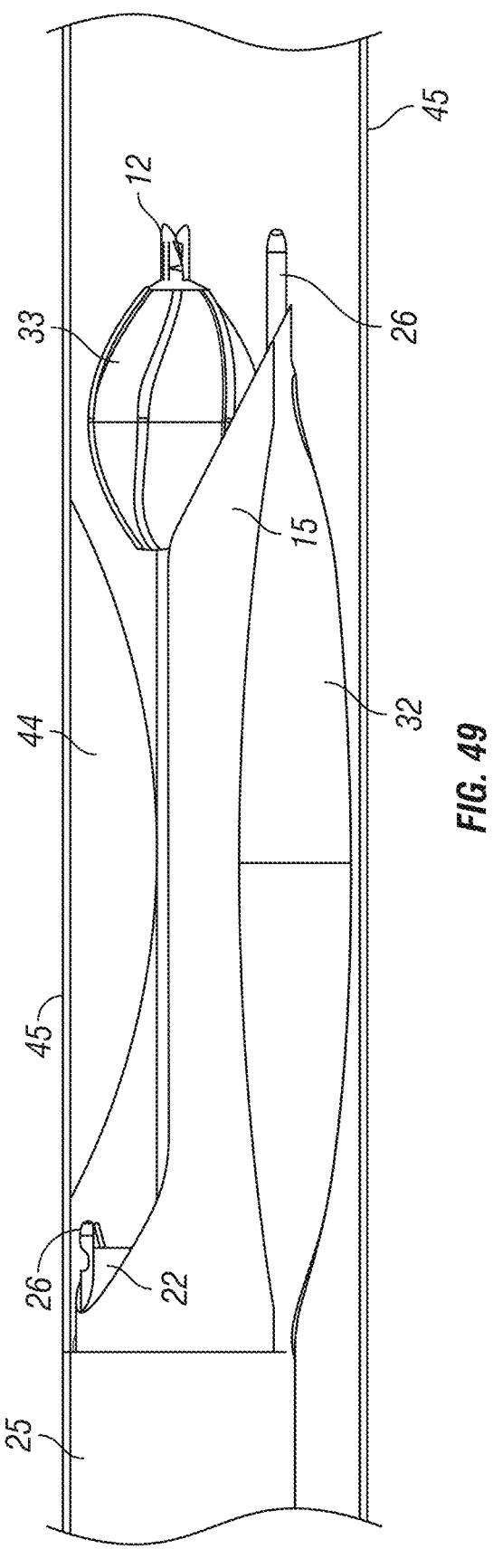
FIG. 49 is a side view of an excisional imaging assembly in this case with various elements of the assembly straddling an obstructive lesion within a tubular structure such as a blood vessel with a larger excisional element and an imaging element near the cutting surfaces on the near side of the obstruction and an imaging, parting off cutting chamber on the far side along with an additional imaging element emerging from a supporting scoopula with its underside expandable elevating element, which is shown supporting elements of the assembly according to embodiments.

FIG. 49 illustrates advantages of a stepwise utilization method of various elements described and illustrated herein, showing a previously total occlusion, now converted into a subtotal lesion 44 of a vessel 45, being addressed with guidance elements such as OCT element 26, shown here below the imaging chamber element 33, along with a combination of depth control using expandable support balloon element 32 to center and/or position imaging chamber 33, with an additional optional guidance element, similar to or equal to OCT element 26, shown in location adjacent to excisional blades of work element 13, and with its imaging tip shown just ahead of the distal end of the non-rotating sheath element 22 according to embodiments.

Figure 50:
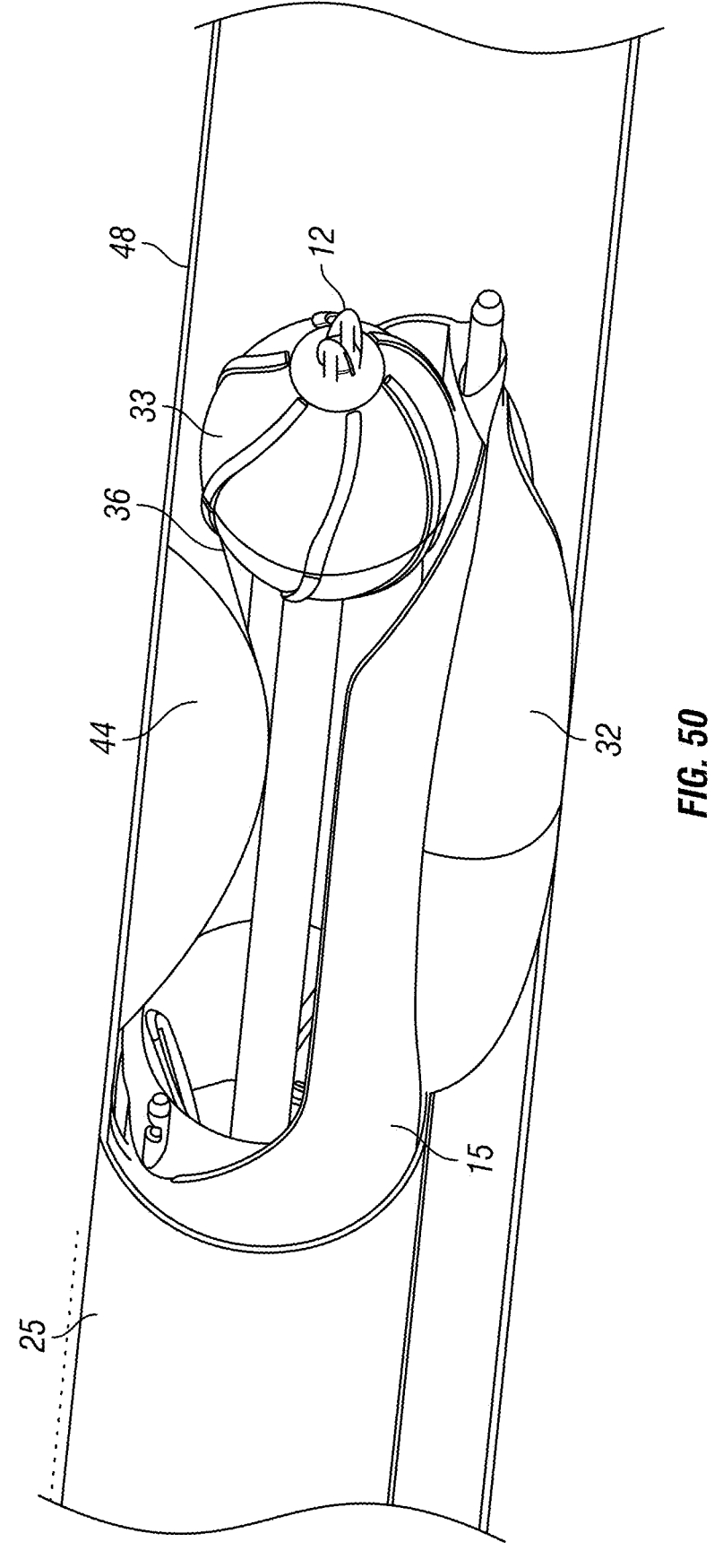
FIG. 50 is a side view of an expandable, transparent, imaging, projecting, focusing and directing chamber showing additional tethering elements attached thereto, with an interventional channel internal to the expandable, transparent, imaging, projecting, focusing and directing chamber and a tandem imaging channel invaginated into or internal to, the expandable transparent chamber in a straight position within an excisional assembly and according to embodiments.

FIG. 50 illustrates another configuration of an expandable, transparent imaging and in this embodiment, angleable, captured chamber 33 with its additional restraining tether(s) 36 (see FIG. 51) showing imaging and cutting chamber 33 in straight line position and over and under tandem lumens of scoopula element 15 to enable imaging elements such as October 26 (shown in an invaginated lumen within chamber 33 in the following FIG. 51) to continuously monitor and guide progress without the need to clear tissue from the lumen of an excisional device such as smaller excisional work element 12, again seen here ready to engage and bore through a proximal cap 48 of a totally occluding obstructing disease material 44 in a vessel 45. Also, any element, such as that shown as OCT catheter 26 in the following FIG. 51, can exert forward pressure on chamber 33 to augment bending of such a chamber in a direction opposite to placement of a tandem-placed lumen of scoopula 15 as shown and according to embodiments.

Figure 51:
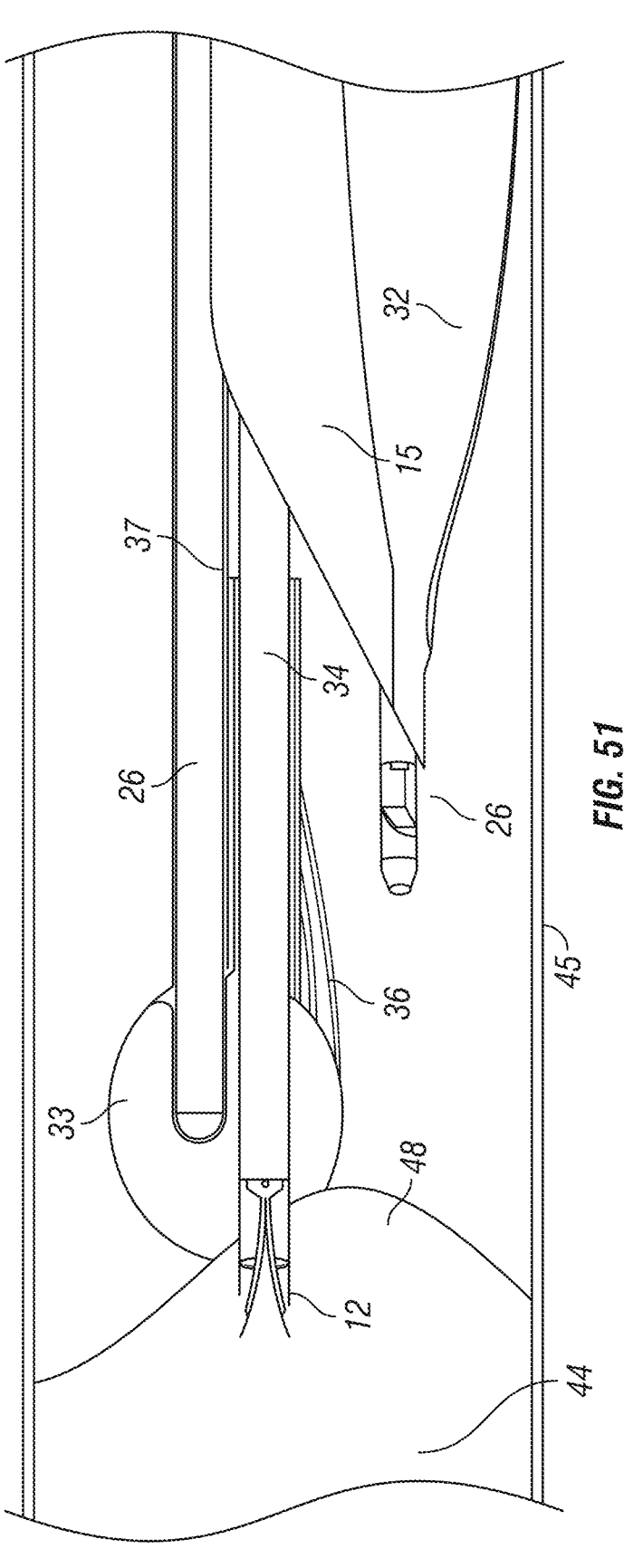
FIG. 51 is a side view of the assembly shown in FIG. 50, in this case in an angled position according to embodiments.

FIG. 51 shows the assembly as in FIG. 50. In this illustration, however, the angling and simultaneous imaging, guidance and boring capabilities are shown in FIG. 50 and as before, utilizing any of the additional ports, such as the dual incorporated over/under lumens of scoopula element 15, for guidance is shown with an additional, optional imaging (such as OCT) element 26 located in a lumen channel of scoopula 15, which element is stably supported by expandable support element 32. In this illustration, elevation, and stability as well as guidance is provided to imaging chamber 33 as well as its incorporated imaging element 26 and significantly, stability for the angle of attack provided by tandem, tethered imaging chamber 33, such that smaller excisional element 12 is properly elevated and directed for optimum penetration. Expandable element 33 may be selectively angled as desired. One such method for doing so is simple inflation given the differential placement of tandem lumens where a central directable lumen is affixed to a forward and rear wall of captured (within the scoopula 15 bed) imaging chamber 33, while lumen for imaging element 26 is only affixed to the rear wall. Thus, advancement of imaging element 26 while holding back central lumen 34 would cause angulation of lumen 34 as shown. An additional angling method comprises differentially expanding upper and lower portions of cutting and imaging chamber 33. Yet another method may include advancing the inner lumen relative to the outer wall would, due to the asymmetry of forward restraint provided by tether(s) 36 would result in angulation in the direction of restraint, in this case shown as downwards, which in combination with a highly torque-capable shaft 34/37 would result in angle and rotation control of cutting and imaging chamber 33, in turn and which, in combination with elevation and platform stability provided by scoopula 15, which may itself be articulable, and its supporting expandable elements 32 as guided by imaging elements, provides precise control of excisional direction, position, support and progress, according to embodiments. Likewise, placing interventional elements in an upper space and, for example, an OCT imaging element in the flexing lumen 34, OCT imaging direction could be aimed forwards, backwards or at any combination of angles for more options without needing to change the basic configuration of an OCT element, according to embodiments.

Figure 52:
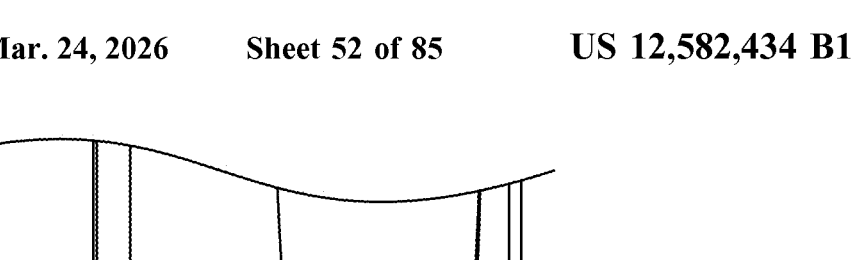
FIG. 52 is another side view of the assembly shown in FIG. 51 in angled position with a different excisional element according to embodiments

FIG. 52 illustrates the utility of the angle-capable imaging chamber 33 of FIGS. 50 and 51, where an energy-based, touchless excisional element may be introduced in the angled segment of imaging chamber 33, using the same capabilities as described in FIG. 51, to direct energy in the proper direction and at the desired intensity. In order to properly place imaging chamber 33, again, the mechanisms of excisional imaging device of FIG. 51 may be utilized for elevation and stabilization control.

Figure 53:
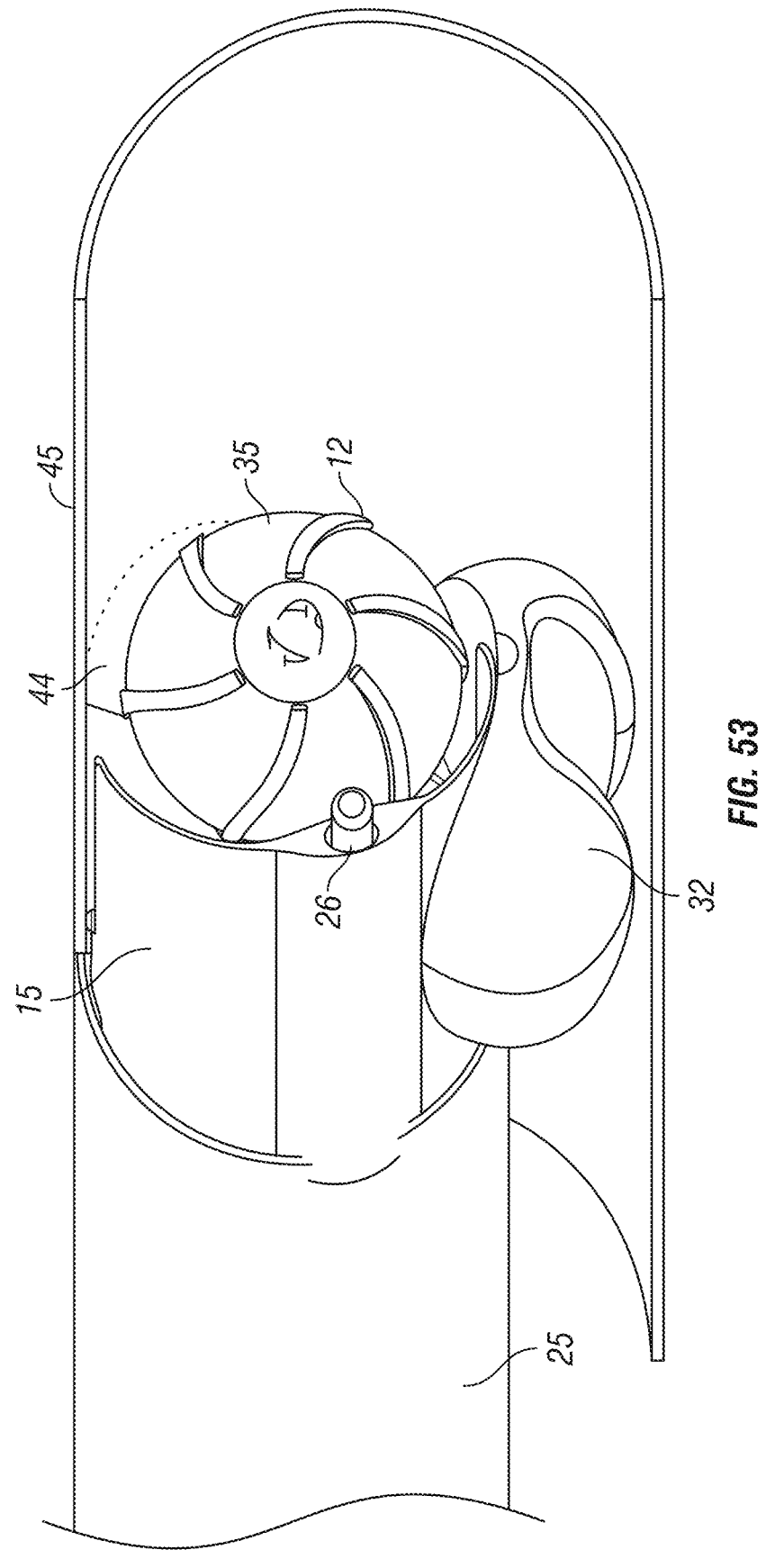
FIG. 53 is a perspective view of an excisional imaging assembly of FIG. 50 in a tubular structure that has a partially occluding obstruction, in this case showing independent, in this case clockwise, rotation of a scoopula component and an expandable supporting element on its underside, shown here as a flow providing double element as illustrated in FIG. 34, which reveals a flow channel space between the double expandable support element according to embodiments.

FIG. 53 shows a device of previous figures where scoopula 15 is rotatable independently of supporting element 32, which such a device may also have beak elements 14 replaced by other excisional or ablative modalities such as excisional laser energy emitters for example. Such an element is shown here with an excisional laser, which may be optionally guided sequentially or simultaneously with other imaging elements disclosed herein. Imaging and energized excision and ablation may likewise be accomplished in rapid sequence over shared light guide tubes or shafts or may be accomplished with coaxial rows ("coliseum seating") of dedicated light guide tubes, or columns among rows, as well as alternating guides within rows or columns according to embodiments, and these may be utilized to provide real-time feedback control and guidance. Similarly, one of the lumens of tandem, expandable, flexing-capable imaging chamber may be equipped with an inner surface that may be used to guide light pulses in the event that an imaging and excisional light source catheter may be too stiff to itself accommodate to a curve desired and achievable by such a lumen within imaging chamber 33, according to embodiments. In this manner, extremely short-wavelength electromagnetic energies may be utilized to limit the depth of excision and ablation, modulating distances and intensity of penetration by positioning within an expandable, flexible, shape changing imaging chamber 33, which may be thought of as a focusing, "shading" device, in addition to its role in providing directionality and positioning, according to embodiments.

Figure 54:
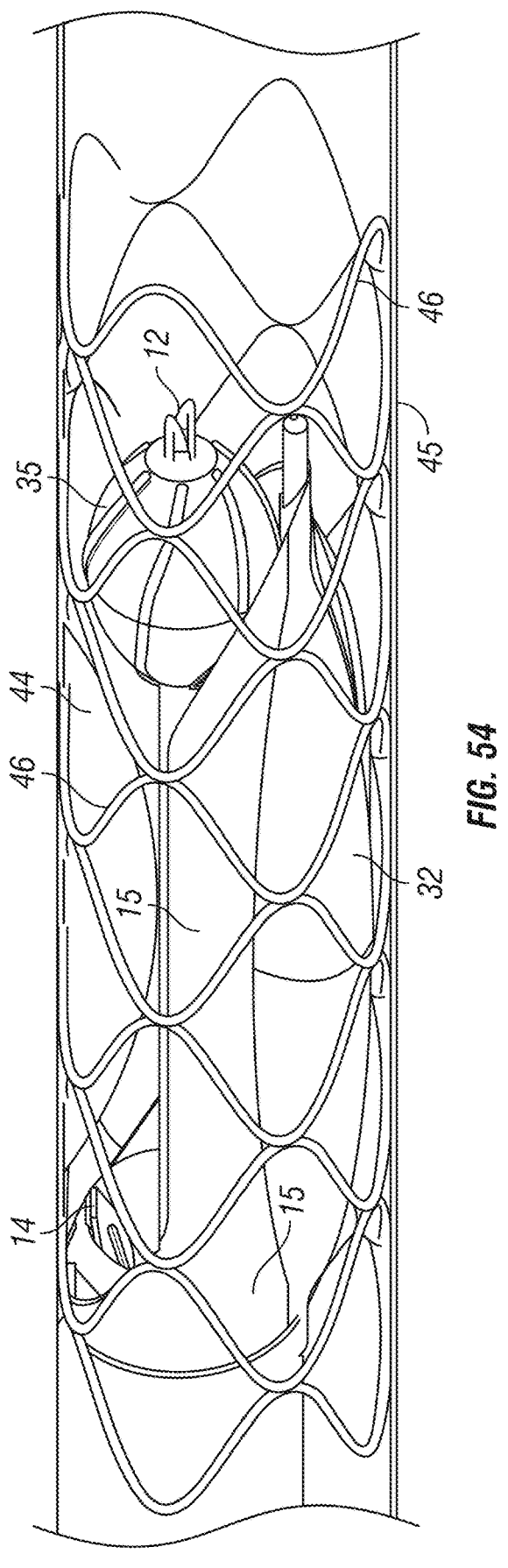
FIG. 54 is a perspective view of an excisional imaging device shown inside a stent that has obstructive material partially occluding a vessel such as a vascular structure, and as in FIG. 53 again showing independent rotation of a scoopula and its expandable flow channel providing supporting element on its underside according to embodiments.

FIG. 54 shows an application of the methods and devices described and shown herein, in the context of restenosis within an implantable device such as a stent 46. When intimal hyperplasia ("scar") occurs in response to a stented segment of a vessel, it is often difficult and potentially tedious to remove all tissue while minimizing damage effectively and optimally to stent struts. However, automated, robotically controlled complete de-bulking with excisional assemblies as shown and described herein could be carried out without the need for excess fluoroscopic guidance, thereby minimizing the health concerns for operators and patients alike. Once strut locations are established by imaging, particularly utilizing expandable, imaging, depth controlling imaging chamber 33, precise and stable positioning can proceed followed by the rapid succession of steps including longitudinal location, initial rotation, supporting elevation and pressure, flushing and aspiration, excision, parting off and transport, excisional element retraction. These steps may be repeated as needed under imaging feedback until all traces of obstruction to flow are removed and full lumen cross section is once again made available for optimal flow, according to embodiments.

Figure 55:
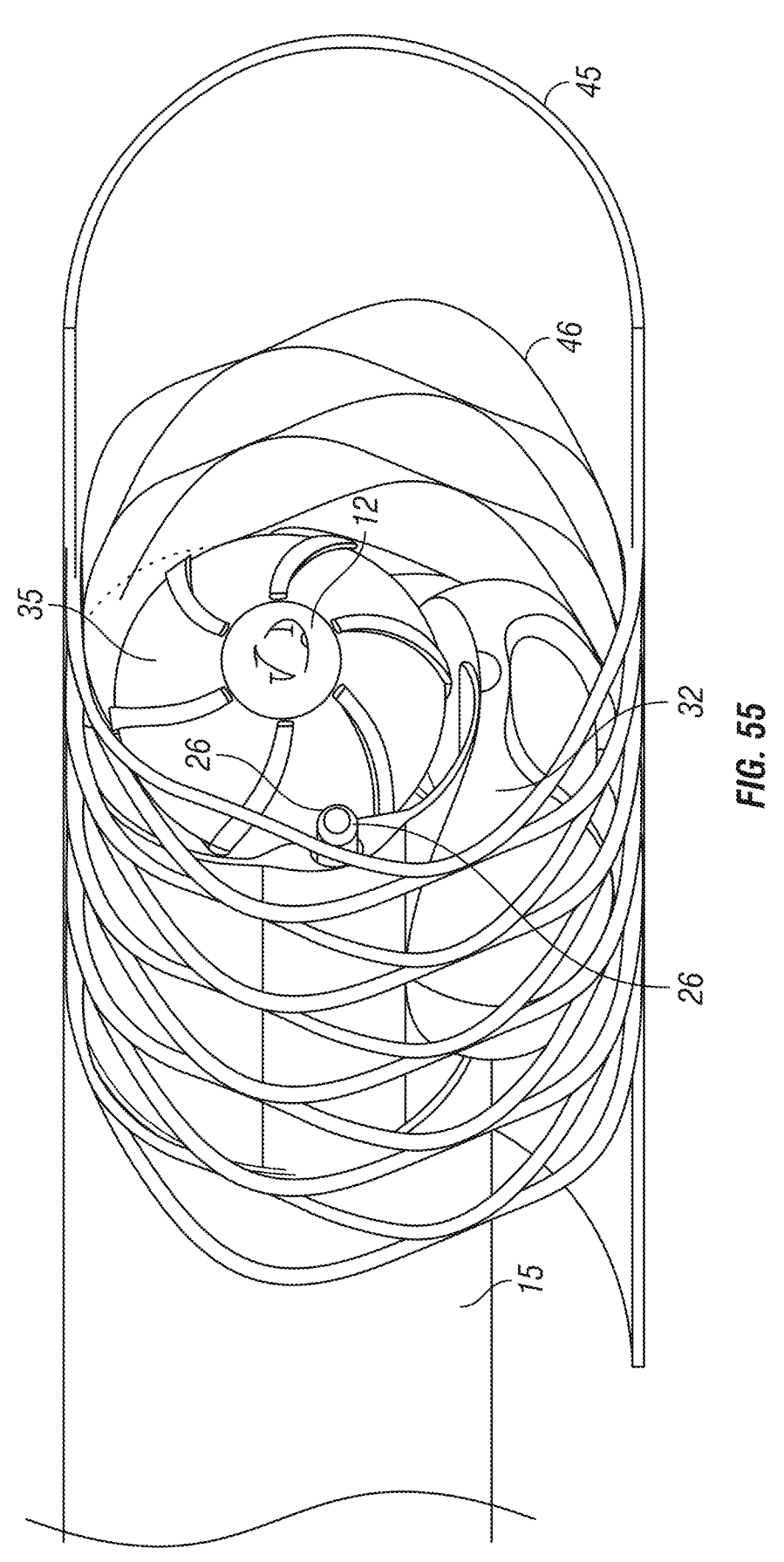
FIG. 55 is a more head-on perspective view of an excisional imaging device of FIG. 56 showing slightly more clockwise, in this case, rotation of a scoopula with respect to its inferiorly placed expandable supporting, flow providing and stabilizing element within a stented segment, again partially filled with obstructive material, of a vascular structure, also again showing an expandable imaging, parting off, cutting chamber with a smaller excisional element located at the imaging chamber's forward end according to embodiments.

FIG. 55 further illustrates the use of longitudinal and rotational positioning, stability and support, guidance and depth control provided by the various elements described and shown herein. In FIG. 55, stability and flow enabling and control provided by expandable element 32 are enhanced by the expandable element 32 being able to remain in place-both axially and rotationally-due to its attachment, including expansion controls, to the outer tube element 25 rather than to the scoopula 15. This attachment and control arrangement enables expandable element 32 to provide a stable platform upon which scoopula 15 may be moved in rotation and axial position, which may be particularly useful during automatic cycling steps. In this manner, certain steps may remain unchanged for several cycles while others can occur quickly and efficiently according to robotic manipulations driven by algorithms, which themselves can be modulated automatically with imaging and physiologic feedback according to embodiments. Manual override may be made available for safety but automated steps may limit procedure times, radiation exposure and ischemia in the case of this intervention occurring in a vascular structure. Another limiting factor is often simply fatigue among operators and patients alike, which can be reduced with efficiencies provided by automation. A sequence could then be longitudinal placement followed by expansion with flow control and support by expandable element 32, followed by a series of rotational positioning(s) of scoopula 15 with automatic excision steps carried out at each rotational position until either or all obstructing materials are cleared. In some instances, depending on the distribution radially of obstructive materials, a relocation of supporting expandable element 32 may be necessary, but generally not as frequently as would be the case were scoopula 15 not independently movable with respect to element 32. Independent relative movements combined with imaging from the surface (such as fluoroscopic), imaging in-situ via ports as illustrated herein, and physiologic parameters feedback (comparative proximal and distal pressures and flows, as measured via the various lumens available as illustrated and described), can all be utilized to maximize patient safety while enabling a maximally efficient procedure, according to embodiments.

Figure 56:
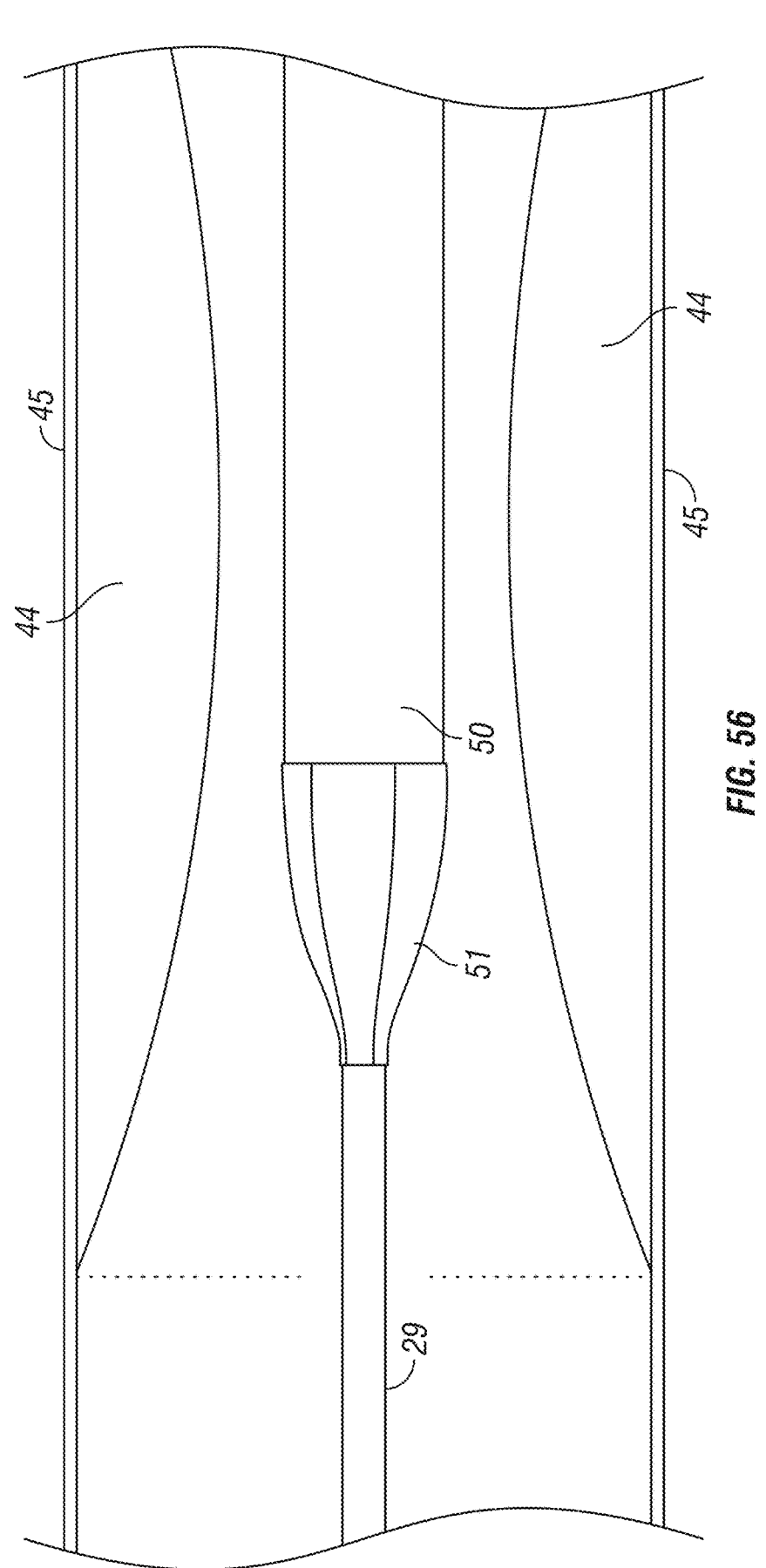
FIG. 56 is a side view of a protection element shown for clarity in isolation and in a streamlined closed configuration, within a partially obstructed tubular vessel such as a vascular structure, according to embodiments.

FIG. 56 introduces another device that may be used in combination with the imaging, excision and ablative elements described herein intended to isolate an area being treated that may (as is common in several clinical presentations including diseased segments that may be chronic, subtotally obstructing disease complicated with acute thromboembolic materials that may worsen or completely obstruct flow) contain a mixture of old and new materials of varying composition. In addition to isolating an area, the elements in this and following descriptions and illustrations may also be used to direct flows of various media emanating from other elements that form an assembly for the purpose of removing debris and loose materials, in particular those that may cause the presentation of paroxysmal symptoms related to intermittent obstruction. In this case, an assembly comprising cannula 50 and flush, aspiration, and protection element 51 is shown inside a symmetrically obstructed vessel 45 by obstructing materials 44, which in this instance may be soft plaque or thrombus or a combination thereof. The assembly comprising cannula 50 and flush, aspiration and protection cover 51, which may be constructed of a mesh, fabric, or thin flexible membrane material, for example, is shown having been advanced into position over a guiding wire 29, while in a streamlined, non-expanded configuration according to embodiments. The following figures will illustrate the use of cannula element 50 and cover element 51.

Figure 57:
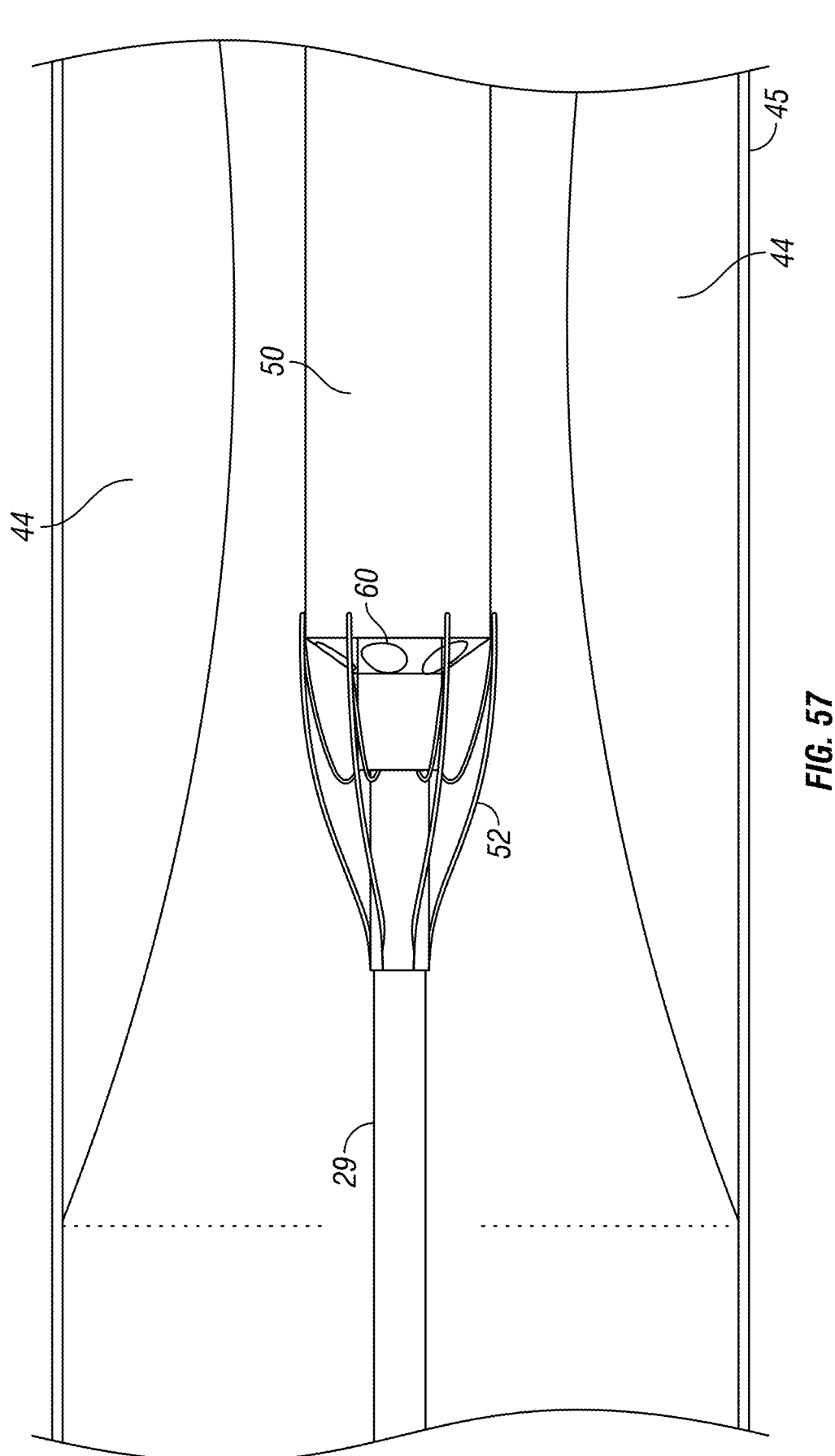
FIG. 57 is a side view of a device of FIG. 56 where an outer covering is transparent, revealing inner supporting and actuating elements in streamlined, collapsed configuration according to embodiments.

FIG. 57 shows a transparent outer covering, revealing additional deployment control elements (e.g., struts) 52 and orifices 60 of cannula element 50 and cover 51 (material between the control elements (e.g., struts 52)), again within a diseased vessel 45. Illustrated here are elements for controlling both placement of cover element 51 and tube with expandable struts elements 52 relative to orifices 60 of cannula 50 as well as degree of opening of flush, aspiration and protection cover element 51. An inner extension of cannula 50 is shown coaxial and surrounding a tubular portion of element 52, such that its axial position relative to axial position of its surrounded tubular element of 52 causes struts to withdraw inwards, closing flush, aspiration and protection cover 51 (transparent in this illustration) also inwards to close off space between flush, aspiration and protection cover 51, which is connected to struts of element 52, and the larger diameter area of cannula 50 near orifices 60 as shown and according to embodiments. It should be noted that struts of element 52 may each be made of two parts, one part of which may be connected to cover element 51 at the surface of cover element 51, with a second part connected to the central shaft 50 and also contain flexible material between the central shaft 50 and the first part of each strut 52, as further illustrated in FIG. 62 below, and in order to create segmented spaces within an expanded cover element 51.

Figure 58:
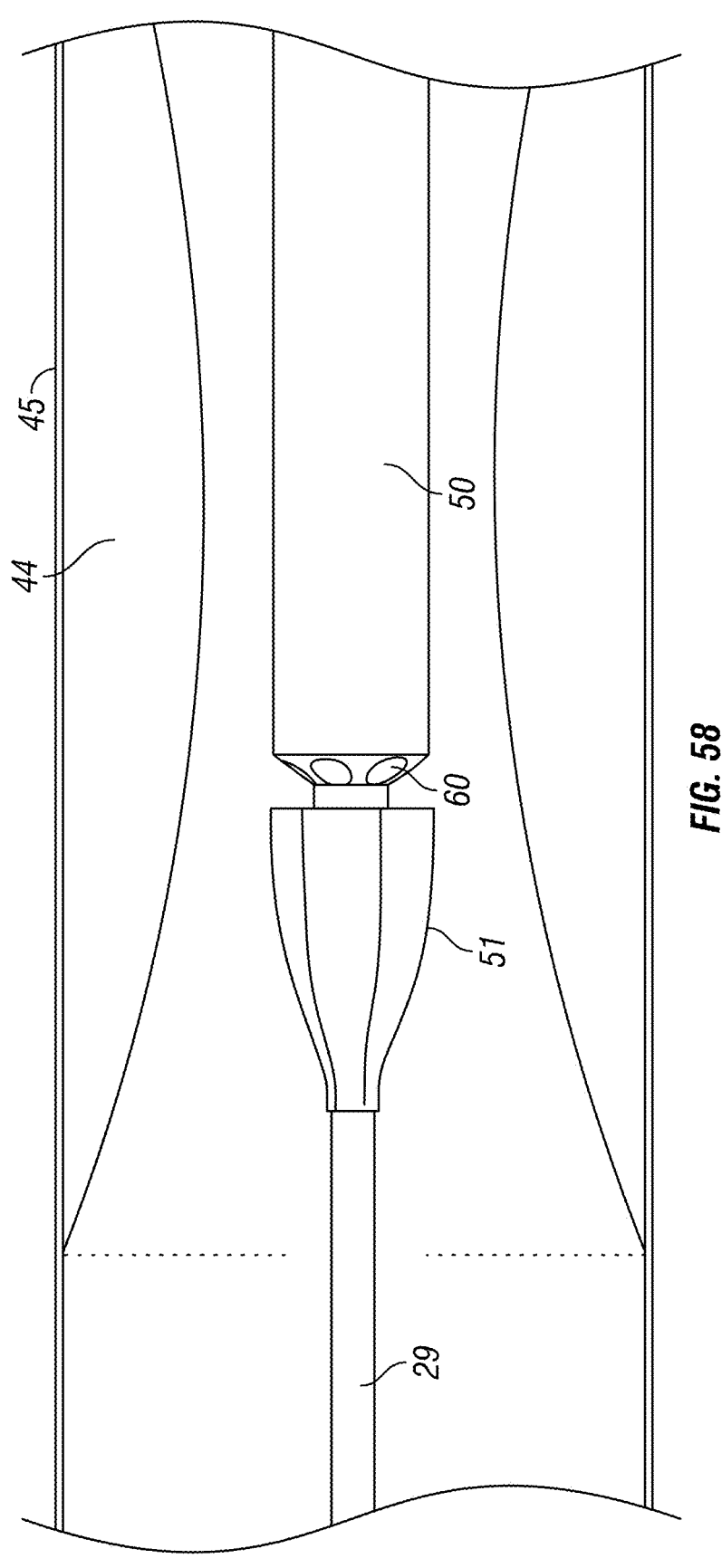
FIG. 58 is a side view of an assembly including elements of FIGS. 56 and 57 which are in a partially extended position further revealing additional elements shown as orifices in a face of a tubular element of the assembly, proximal to a protection element of FIGS. 56 and 57 according to embodiments.

FIG. 58 shows extension away from cannula 50 of flush, aspiration and protection cover 51 revealing orifices 60 to be located farther from the proximal edge of flush, aspiration and protection cover 51 according to embodiments. In this position, flush flows, which may be of relatively powerful forward jet-like in nature, and may also include other media, including simple microbubbles of carbon dioxide gas in solution and also may include other agents such as thrombolytic and antiplatelet medications for example, may be controllable both in direction and intensity by controlling the degree of separation between the two according to embodiments.

Figure 59:
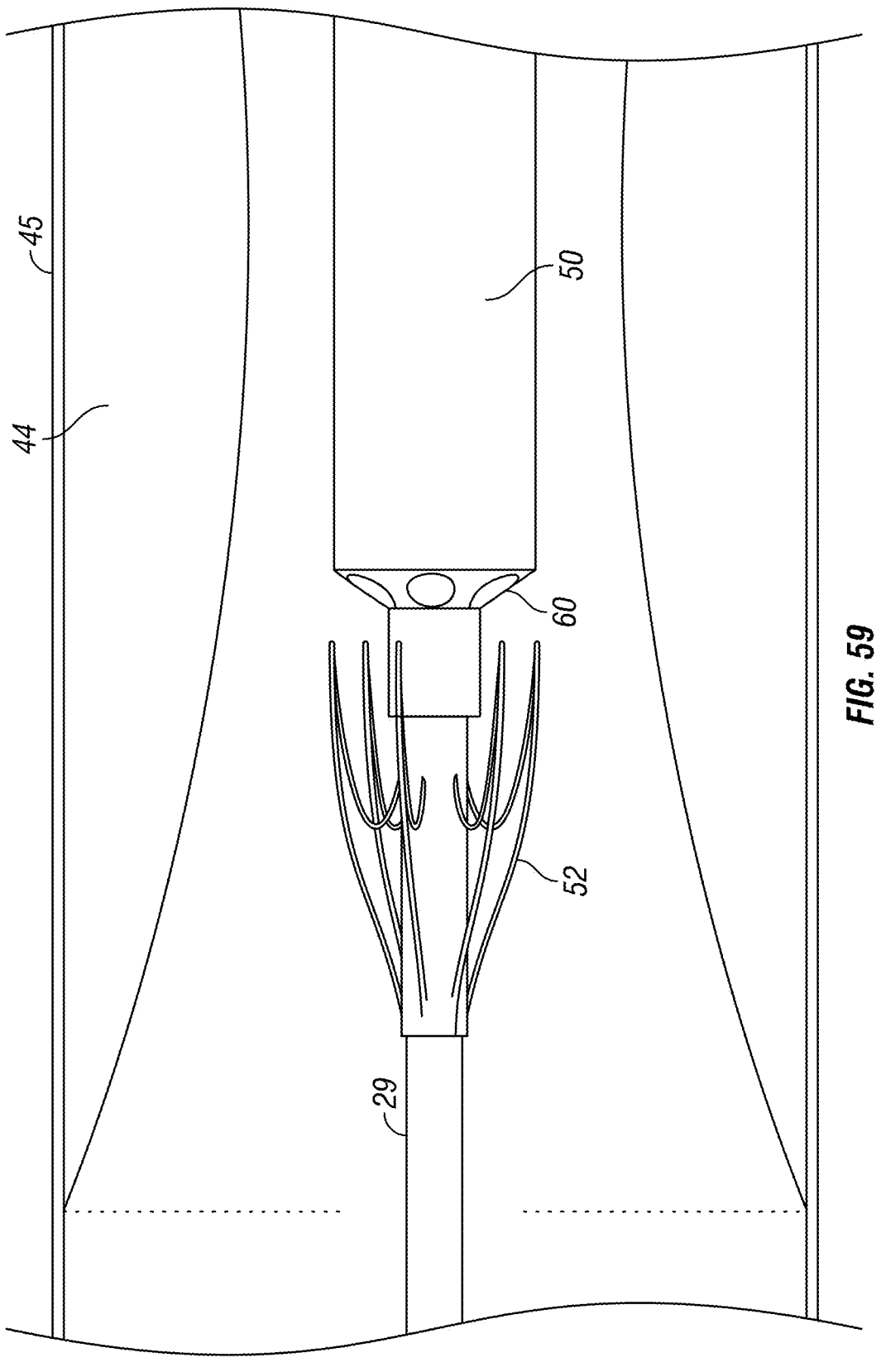
FIG. 59 is a side view of an assembly of FIG. 58 with an outer covering transparent revealing the separation of the protection element from the orifices located more proximally according to embodiments.

FIG. 59 illustrates the relationship further with a transparent outer cover 51 over struts 52, revealing flow directing elements to direct and isolate injected and activated agents that may act physically with high mechanical index impulses for thrombolysis, dissolution and clearing or chemical agents for the same purpose, that using this mechanism may act directly on a local segment of a tubular structure affected by the process, while isolating, trapping and aspirating the resulting materials removing them from the area completely to prevent escape into regions proximal or distal to the isolated area where their effects may be harmful and difficult to reverse once escaped, according to embodiments. Also revealed in this illustration is the control of addition of fluids into the area isolated by elements in this illustration relative to that aspirated, including any debris included as a result of flows of fluids against diseased areas within a vessel 45. Controlling the flow rates, aspiration forces and gap between flush, aspiration and protection cover 51 for example and orifices 60 together modulate relative flow and aspiration rates according to embodiments.

Figure 60:
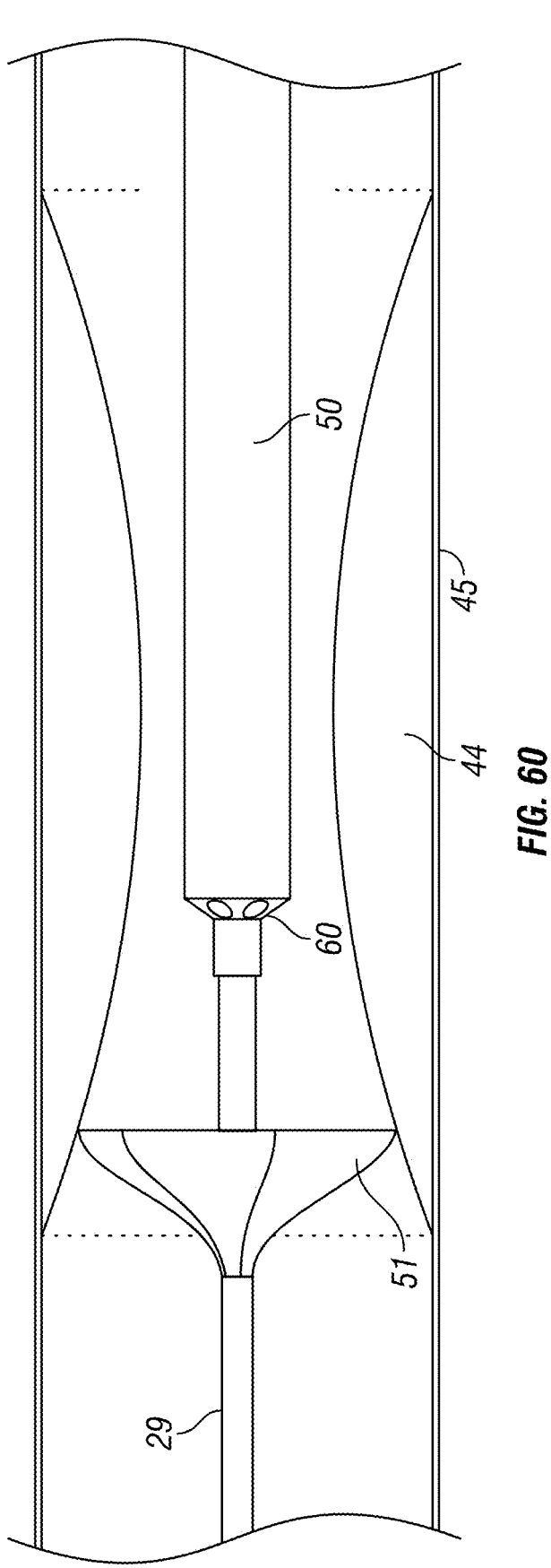
FIG. 60 is a side view of an assembly of FIG. 58 with its covering deployed and extended shown within a partially obstructed tubular structure such as a blood vessel, with its other element and its orifices also visible in an embodiment.

FIG. 60 illustrates the capability to deploy flush, aspiration and protection cover 51 into a shape that promotes a recirculation pattern within the space between the orifices of 60, which will be shown subsequently. The flush, aspiration and protection cover 51 may also generate aspiration forces, which are controllable by varying the position and degree of deployment of flush, aspiration and protection cover 51, which flows are further manipulated and controlled with deployment control strut elements 52. In the case of thrombus or other loosely attached debris, it is desirable to clear any such materials by flushing and aspirating with powerful streams of fluids, while protecting downstream, smaller caliber vessels from being plugged up with such debris, and according to embodiments.

Figure 61:
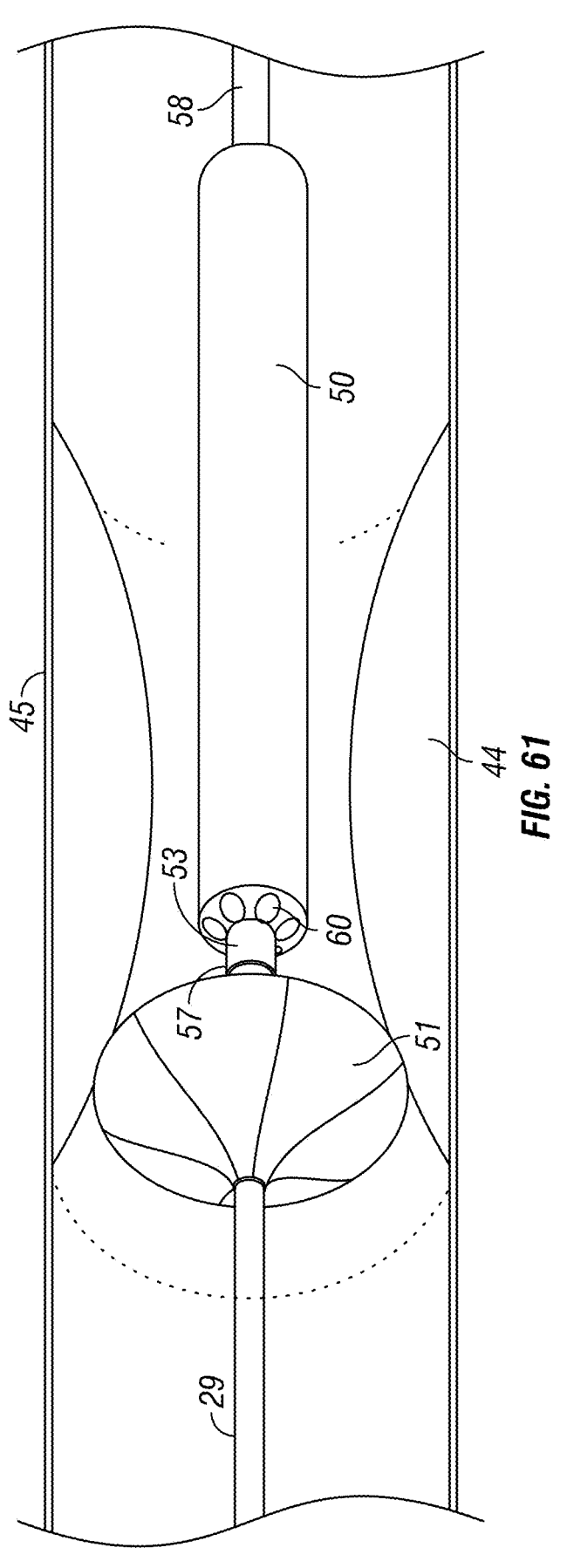
FIG. 61 is a profile view from the front of an assembly of FIG. 60 revealing the elements of the orifices arranged radially projecting towards an extended element according to embodiments.

FIG. 61 is a perspective view from the front looking back to further illustrate the mechanisms as well as to point out that space 57 between cannula 58 and larger cannula 53 is available for flush fluids and any agents desired especially where these agents may be able to be used in higher concentrations given the local isolation of a segment of interest, while as will be seen subsequently, orifices 60 have the capability for high speed flow and aspiration according to embodiments, to remove such agents when they are no longer needed, along with any harmful obstructing materials responsible for an acute occlusion, in this case in a vascular space. Additionally, in the case of utilizing high mechanical index impulses, laser energies and others that may disrupt and help remove such offending materials from the area, the open central lumen is also available for delivery of activating instruments, for example in the case of microbubble collapse to create sheer forces, (sonothrombolysis) a surface high frequency ultrasound transducer to create such integrity-disrupting forces may be sufficient for the dissolution of micro-thrombi, however in the case where a more local source of energy may be required, a transducer may be introduced (not shown here) more closely to the area via the central lumen of cannula 58 for the purpose according to embodiments.

Figure 62:
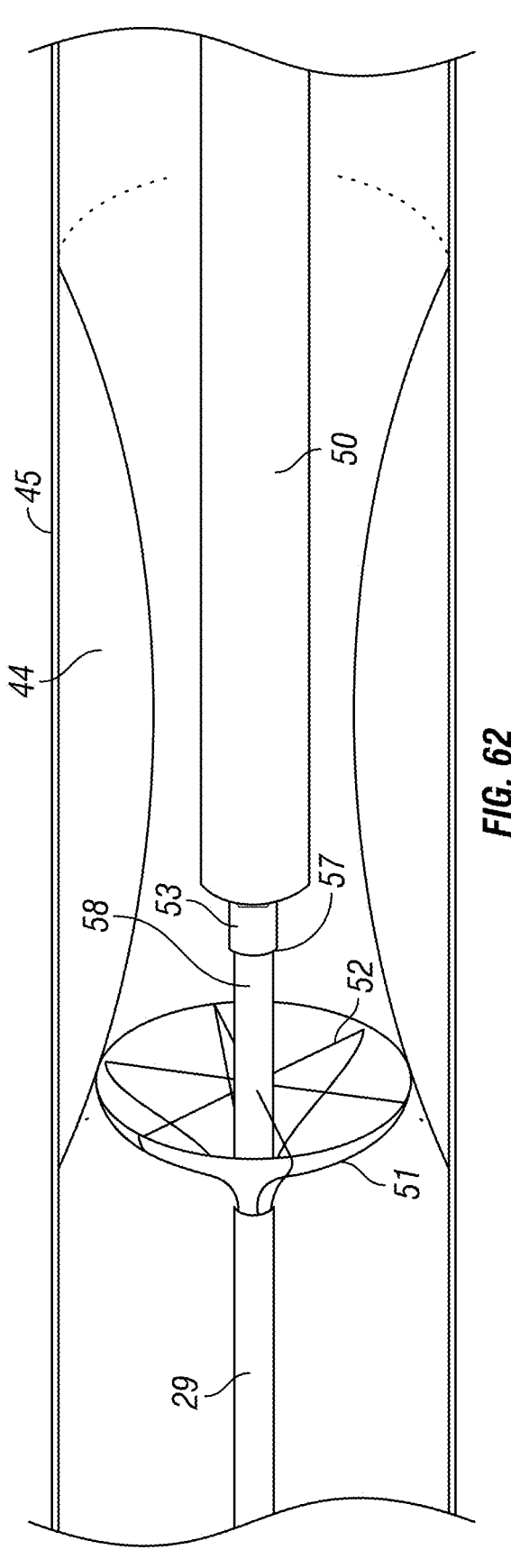
FIG. 62 is a profile view from the rear revealing strut deployment elements of an assembly of FIG. 61 according to embodiments.

FIG. 62 shows the same assembly as in FIG. 62 from the rear illustrating the septation spaces created by elements 52 that may serve to stabilize, vector, and concentrate flows outwards while optimizing isolation and augmenting flows in the return path for aspiration, according to embodiments.

Figure 63:
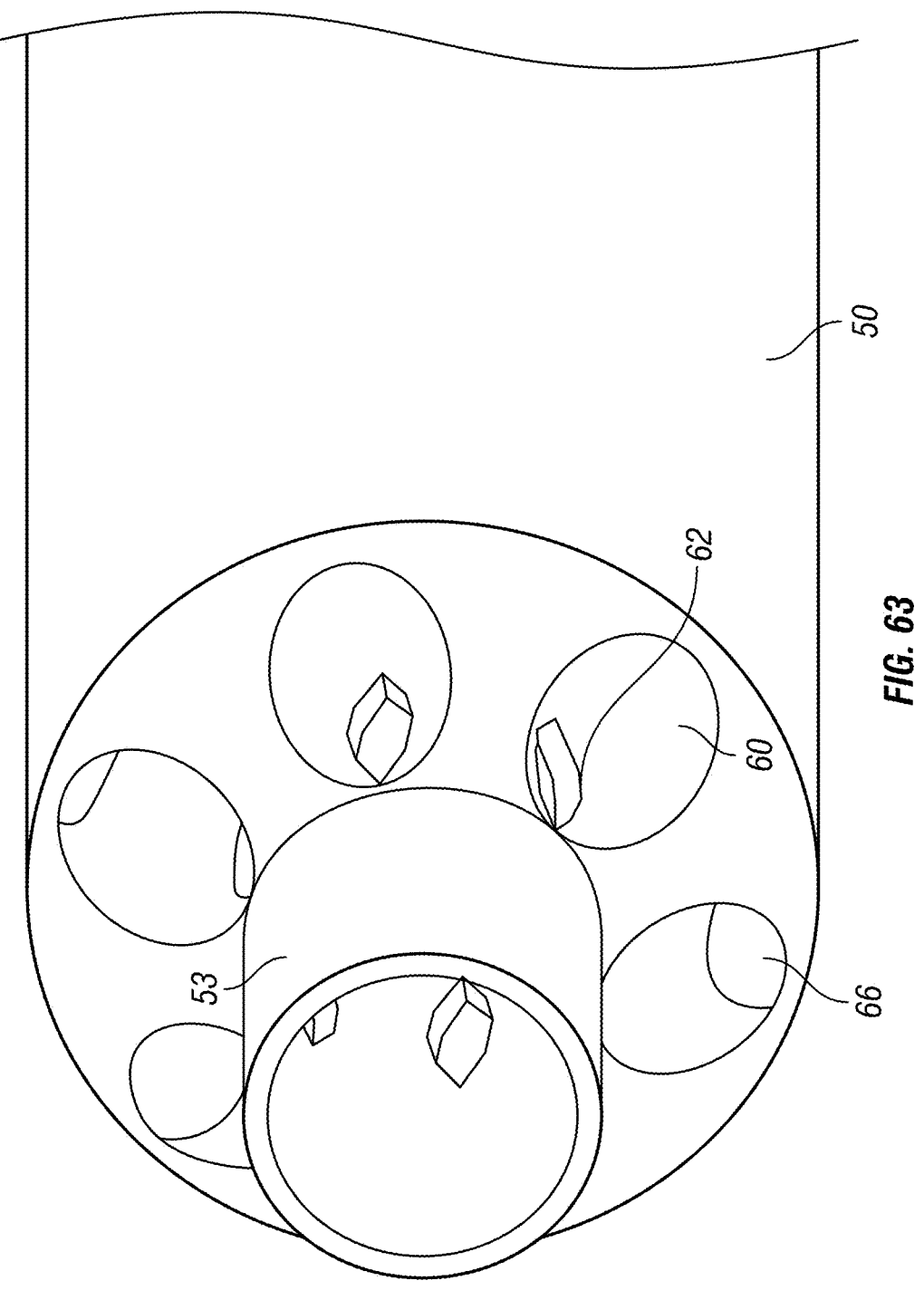
FIG. 63 is a close up perspective view from the front of an element of an assembly of FIG. 61 with other elements removed to reveal the internal structures of the element according to embodiments.

FIG. 63 reveals inner details of catheter 50 including orifices 60 as well as internally placed hydrodynamic shapes 66 that, by directing flows over such shapes, create low pressure areas through low pressure orifices 62 for aspiration according to embodiments.

Figure 64:
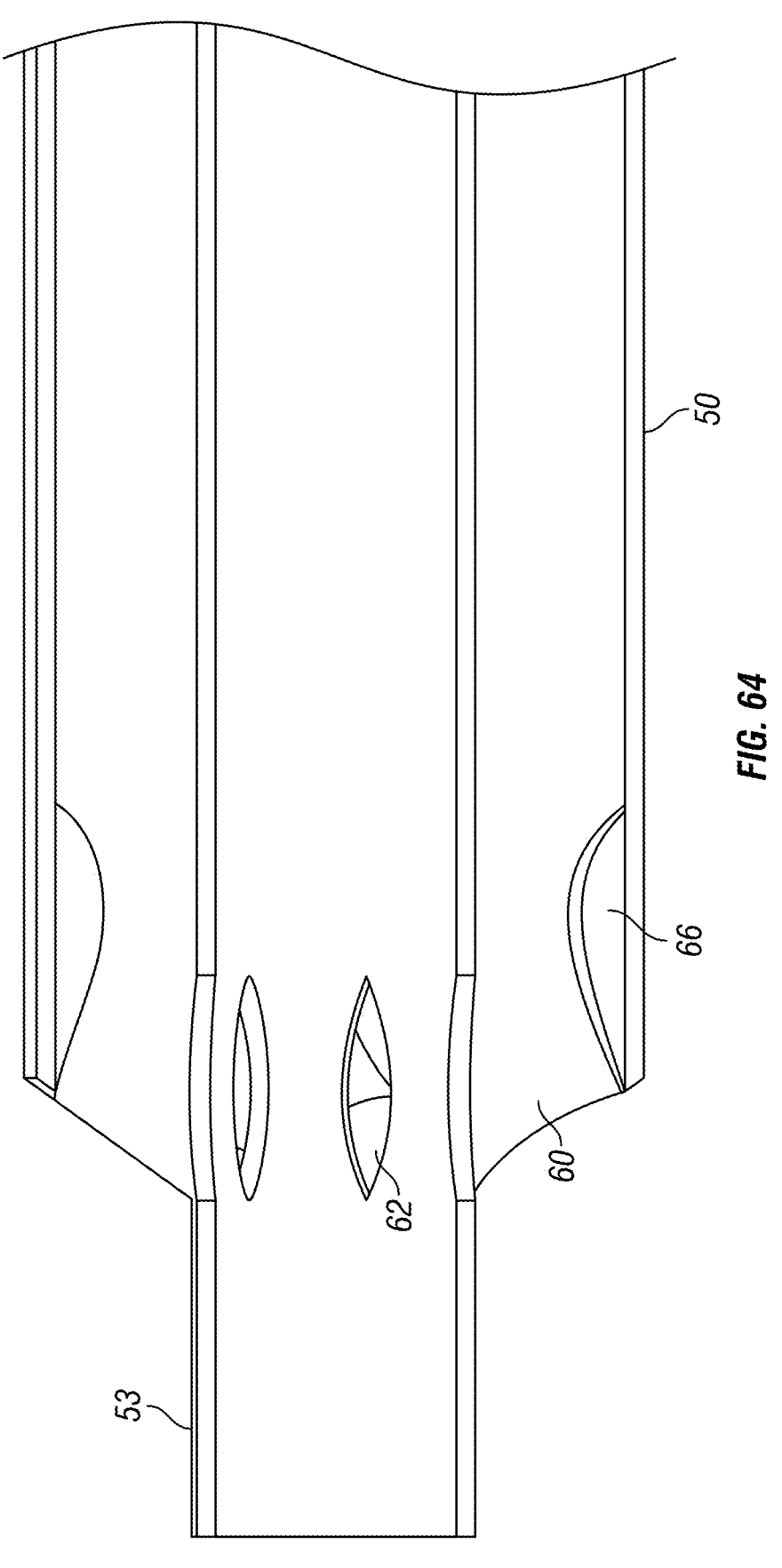
FIG. 64 is a section cutaway view of the element of FIG. 63 shown from the side revealing other internal details and shapes according to embodiments.

FIG. 64 is a sectional view of catheter 50 showing the internal chamber where shapes 66 create outwardly directed outbound flows that may include chemical agents, as well as activated physical disrupters, which following successful dislodging and dissolution of clinging materials from vessel walls, recirculate via flush, aspiration and protection cover 51 and 52 shown previously and then return for complete removal via aspiration through low pressure orifices 62 where such flow generated aspiration may be augmented by proximal vacuum sources, according to embodiments.

Figure 65:
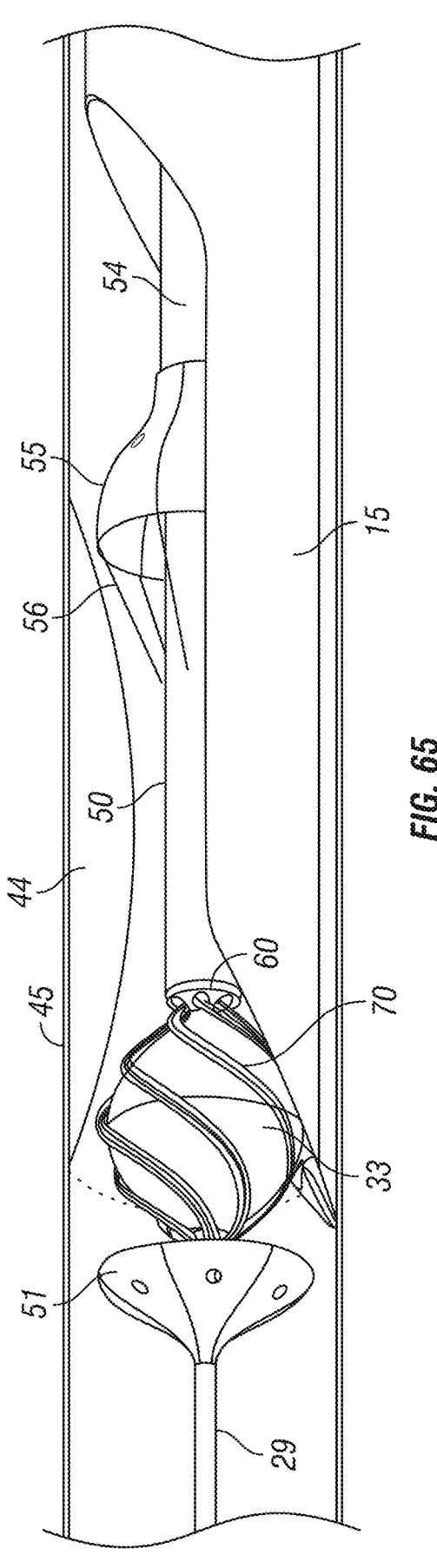
FIG. 65 is an assembly including elements of FIG. 60 as well as another excisional cutting and optionally imaging chamber supported with an expandable element inside its perimeter, supported by a scoopula and positioned beyond a partially occluding obstruction within a vessel such as a vascular structure, as well as a proximal extended element with its deploying members, similar to that shown distal to the cutting excisional, element, according to embodiments.

FIG. 65 is an illustration of an expandable, spirally deployable cutting element 70, which may function as a device introduced through the central lumen of device 10, whose function and deployment is similar to that previously fully described in U.S. Pat. No. 8,992,441, incorporated by reference in its entirety herein, as previously mentioned above, and as shown in this figure in fully deployed state within a vessel supported by an imaging, excisional assembly 10 of FIG. 1, and supported internally with an expandable inner chamber 33 that is transparent and imaging-capable, according to another embodiment. Also shown is a flush, aspiration and protection cover 51 and now also shown is an additional proximal expandable cover 55 to further isolate an area by protecting potential proximal escape of harmful materials, with its strut deploying elements 56 shown fully deploying into expanded configuration, cover 55, which itself is attached to cannula 54 according to embodiments. Upon rotation, excisional cutting device 70 may be retracted from its position distally through the area of the obstructing disease materials 44 in a vessel 45, to excise such materials. Device 70 in this way may work together with flush, aspiration and protection cover 51 and proximal expandable cover 55 to isolate, protect, capture and present for transport such obstructing and potentially embolic materials, according to embodiments.

Figure 66:
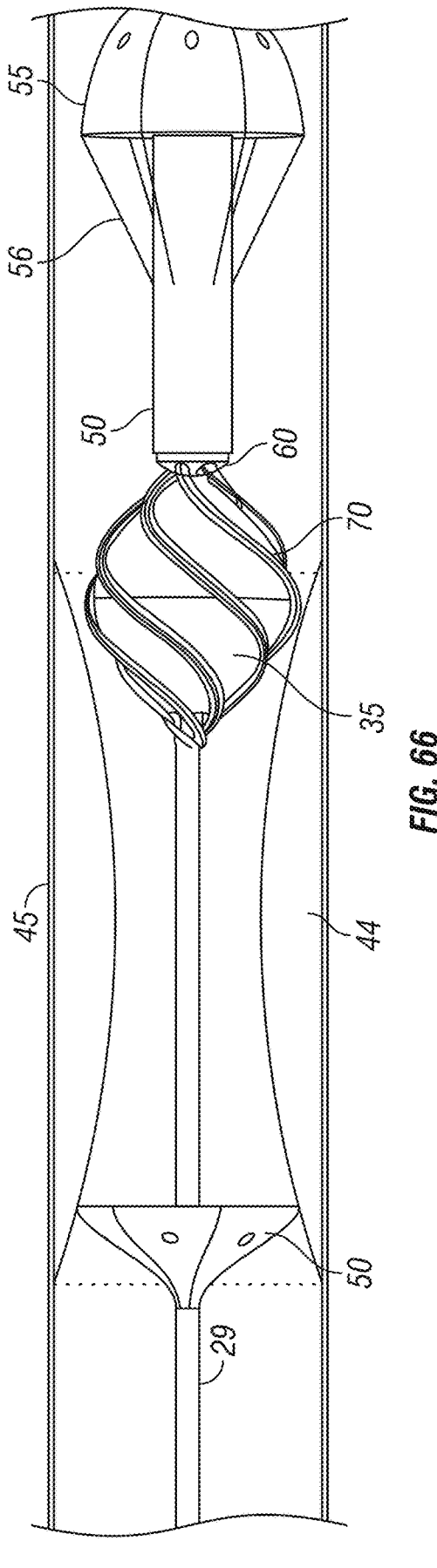
FIG. 66 is a side view of elements of FIG. 65 arranged about and within a partially occluded segment of a tubular vessel without the addition in this case of a supporting scoopula, according to embodiments.

FIG. 66 shows the above elements in a standalone configuration where they may be deployed and utilized to isolate, excise and capture by rotating ablation all obstructing materials 44 as shown in vessel 45, according to embodiments.

Figure 67:
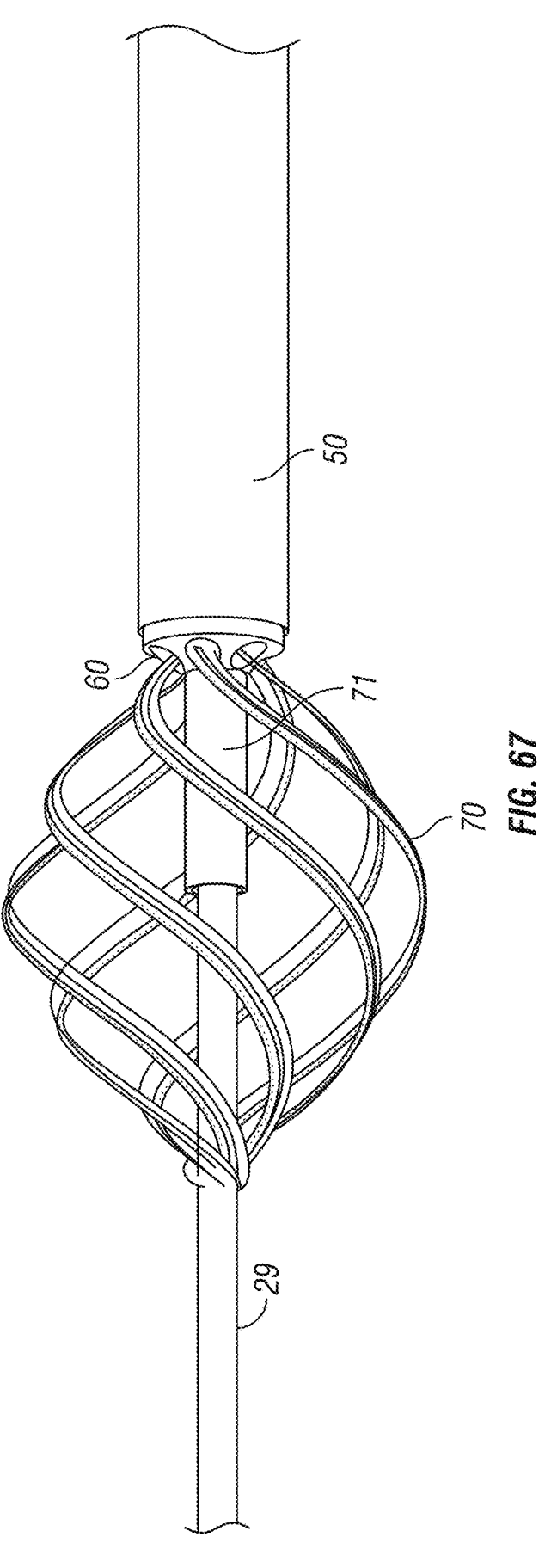
FIG. 67 is a side view of additional coaxially placed elements internal to the excisional cutting elements of FIG. 65, according to embodiments.

FIG. 67 shows, for further clarity, the way that the individual elements of device 70 may be deployed and retracted in a spiral fashion, with in this case the blade elements denoted by 67 in this figure shown somewhat more flattened in shape, due to the flexible nature of the blade elements of device 70 while a guiding wire is shown extended distally, all of which emanate from within sheath-cannula 50 according to embodiments.

Figure 68:
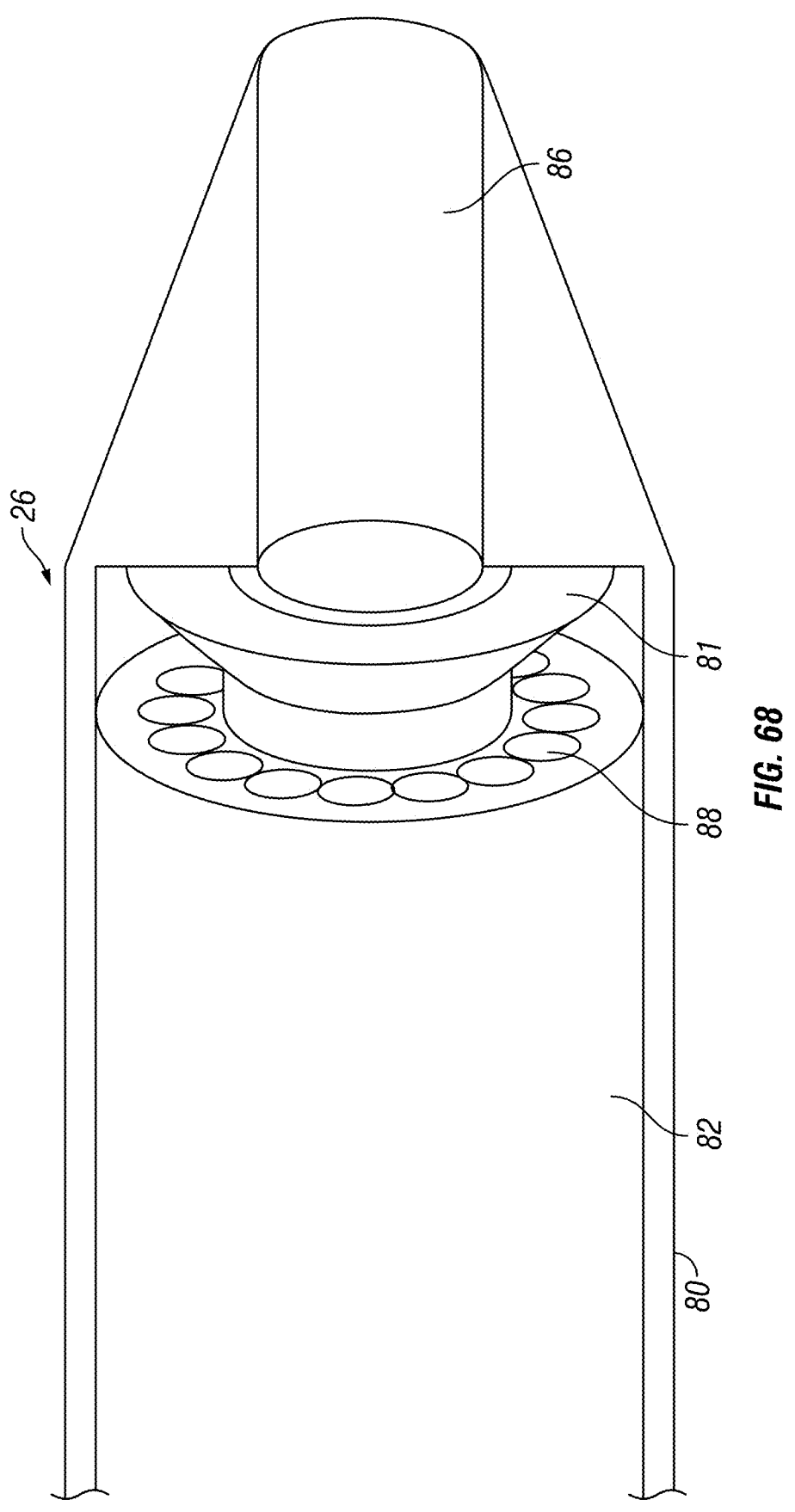
FIG. 68 is a profile view of an imaging catheter with an open internal lumen and imaging fibers arranged radially aiming towards a concentric reflecting element or elements, a central lumen terminating in a tapered nose cone according to embodiments.

FIG. 68 is an illustration of an additional configuration of an imaging element 26 that has been shown and described herein. In the configuration 80 shown in FIG. 68, however, it is optimized for coaxial imaging, simplicity of manufacture and operation. The imaging element may be configured to be independent of rotation of other elements, and may comprise an array of radially placed optical fibers 88 within a flexible covering 82 that may have an inner coating to contain any stray electromagnetic pulse-waves, with fibers 88 (which may likewise be surrounded with reflective coatings) transmitting to and receiving back from, a circular single or multiply constructed reflecting element 81, which receives optical energies from fibers 88, reflects them outwards into tissue and then receives altered (e.g., reflected and scattered) light back, and then in turn reflects these back to rearward image transmitting fibers for comparison, analysis and image generation by the actions of the generating OCT engine and the receiving and processing analytics that create useful tomographic images. In this case, conventional mechanical rotational signaling may occur with a single outbound and inbound fiber. However, pulse generation and reception may be provided digitally with fibers that need not rotate, in combination with a reflecting ring that likewise need not rotate in order to generate full 360 degrees of view while also permitting rotational elements to occupy a central open lumen according to embodiments. The integrity of multiple small imaging optical fibers, positioned within a flexible catheter, potentially spiral wound or straight for example, may be easier to protect during flexing of the assembly particularly in interventions that may require such flexibility, in the present arrangement and according to embodiments. Additionally, fibers may be arranged such that some may be dedicated to imaging alone, while others may be used to provide high energy electromagnetic particle waves to ablate, excise or dissolve materials that are causing harm by obstruction or other means, to normal structures. Another option that can be used according to embodiments includes the ability to utilize fibers for multiple rapid toggling between therapeutic and diagnostic and guidance functions. Therapeutic pulses can be quickly or in real time, guided and modulated with integrated imaging according to embodiments. Furthermore, the reflective face of reflective element 81 need not be singular, rather, the face of reflective element 81 may be constructed with multiple reflective bevels which may themselves be arranged in an arrangement of rings or individual reflective segments of element 81 may be beveled in radial sections next to one another around the circle, or there may be a combination of the two, even if the circular reflector is of a single piece with multiple grind angles, according to embodiments. Furthermore, the axial arrangement with respect to distance of such individual reflective segments may be individualized according to embodiments. Axially deposed reflective segments next to one another circumferentially for example, may be located at different levels in the axial plane, which then may be utilized to form arrays along both an axial plane (fore and aft of a reference point) and circumferentially. Images from reflective segments thus axially arranged and circumferentially arranged individually around the ring, may then be used as the basis for forming 3 dimensional images with refresh rates limited in practice only by processing speed and computing power according to embodiments. Such variations may be utilized to image and apply therapeutic pulses to and from various areas and angles with respect to the axial orientation of the catheter so equipped according to further embodiments. A full circle, partial circle, or partially circular, array may be placed on beaks 14 for example, together with their transmitting and receiving fibers in a way that maintains alignment between fibers and reflectors as well as alignment with the planes of the beak(s) element(s) as beak(s) 13 are rotated and actuated, which may make imaging and coring alignment directly linked, according to embodiments. Likewise, as a circular reflecting apparatus, reflective element 81 may be independently movable with respect to fibers proximal to it in the catheter according to embodiments, such that a variety of areas along an axis may be imaged or treated, for example, were there to be light activated agents delivered to a vessel wall, these areas could quickly be "painted" with electromagnetic energies using the freedom of movement of reflective element 81 according to embodiments. At the same time, access channel 86 could be available for simultaneous therapeutic or imaging elements that may be forward excising, delivery or forward looking and guiding according to embodiments. Fibers, whether diagnostic or for treatment, can be placed around an open central lumen, freeing up the central lumen for other working elements such as borers for a chronic total occlusion clearing, or for introducing elements distally such as other imaging or other working mechanisms (IVUS, physiologic, temperature sensing, flow measuring, debris catchers, tissue removers, wall expanders whether absorbable or permanent, among others). Furthermore, selected fibers could be utilized in a way that references virtually, the angle of the scoopula, including the position of its edges, since scoopulae may be of a variety of shapes and configurations, and whether the presence of the scoopula is in the same position or not according to embodiments. In one example, preplanning of placement, including rotation and depth of working elements such as a scoopula, could be made prior to advancement of any or all of these working elements according to embodiments.

Figure 69:
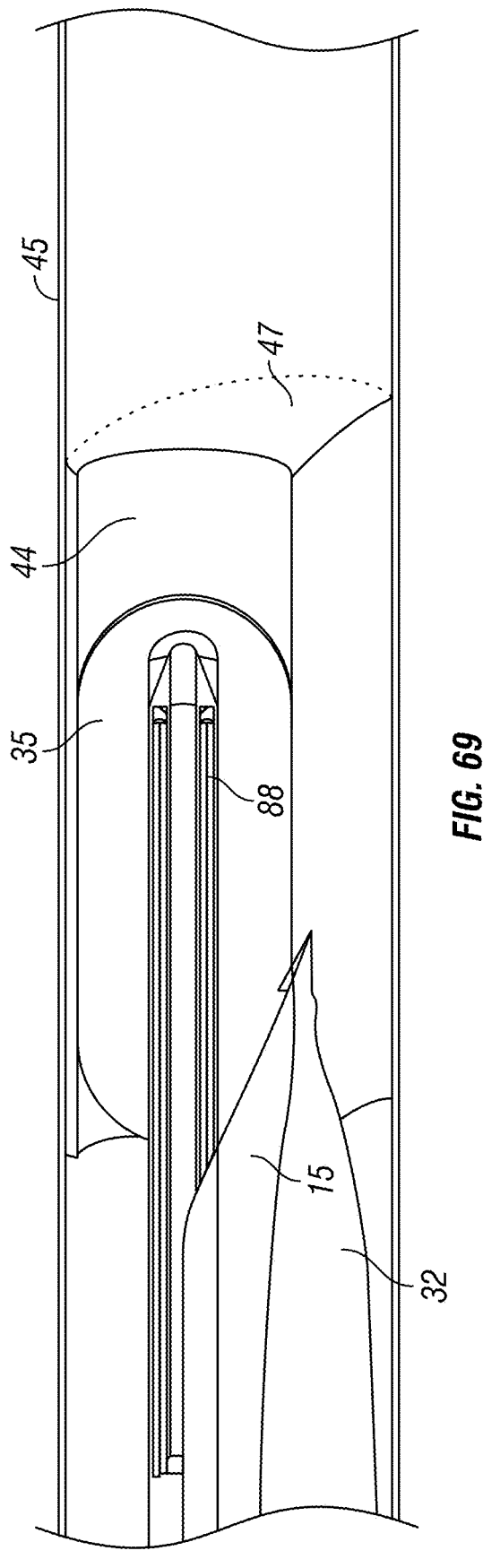
FIG. 69 is a side view in cutaway sectional illustration showing an imaging catheter of FIG. 68 positioned inside an expandable, transparent chamber within a partially occluded vessel aimed at the circumferential transmitting and receiving reflective element or plurality of elements, as well as an open central lumen for access through which other working elements such as a guidewire or other interventional elements according to embodiments and supported by a scoopula portion of an excisional imaging assembly of FIG. 49 according to embodiments.

FIG. 69 is an illustration of the above apparatus as shown in a working assembly of FIG. 1, including in this instance an expandable, transparent imaging chamber element 35 with parallel, distortion free sides that, by nature of its unobstructed, undistorted inner space, similar to that of element 33 previously described above, may extend the range of an OCT element such as element 80 with its multiple fibers 88, or an ultrasound element for another example, by creating a uniform and undistorted medium optimized for the imaging modality, between the source of energy waves of any frequency along the electromagnetic spectrum and the tissues being interrogated, according to embodiments. For example, in a pulmonary application where an air interface may obstruct ultrasound transmission, bringing an integrated chamber providing an optimal fluid medium directly to an area of interest within which a transducer may operate, may eliminate the need to continuously flush the area with fluids to create the same ultrasound pathway. In the same way, in a blood vessel and in the case of OCT modality, excluding blood between the OCT wire or catheter by allowing it to operate within a chamber of transparent medium, while positioning the chamber directly adjacent to the tissue of interest, may likewise eliminate the need for constant flushing away of blood flow to achieve the same relief of signal loss and distortion. These imaging modality working ends may be housed and utilized, shown in this example in a subtotal occlusion by materials 44 in a vessel 45, or they may be placed in any environment where it is desired to control the medium and pathway between signal outputs and inputs, such that any unwanted interfaces or intervening media can be minimized or eliminated altogether, for example, were the embodiments placed in any area of application where any non-uniform materials would normally exist in the signal pathway that would ordinarily diminish the penetration and efficiency of such an imaging modality, that limitation could be partially or even totally minimized by including at a minimum, one of the embodiments of chamber 33 (one of which is shown in this illustration and others), working together with enabling additional elements capable of positioning such a portable medium transmitting chamber remotely to any site desired, thus providing a self-contained apparatus for optimal localized imaging, according to embodiments.

Figure 70:
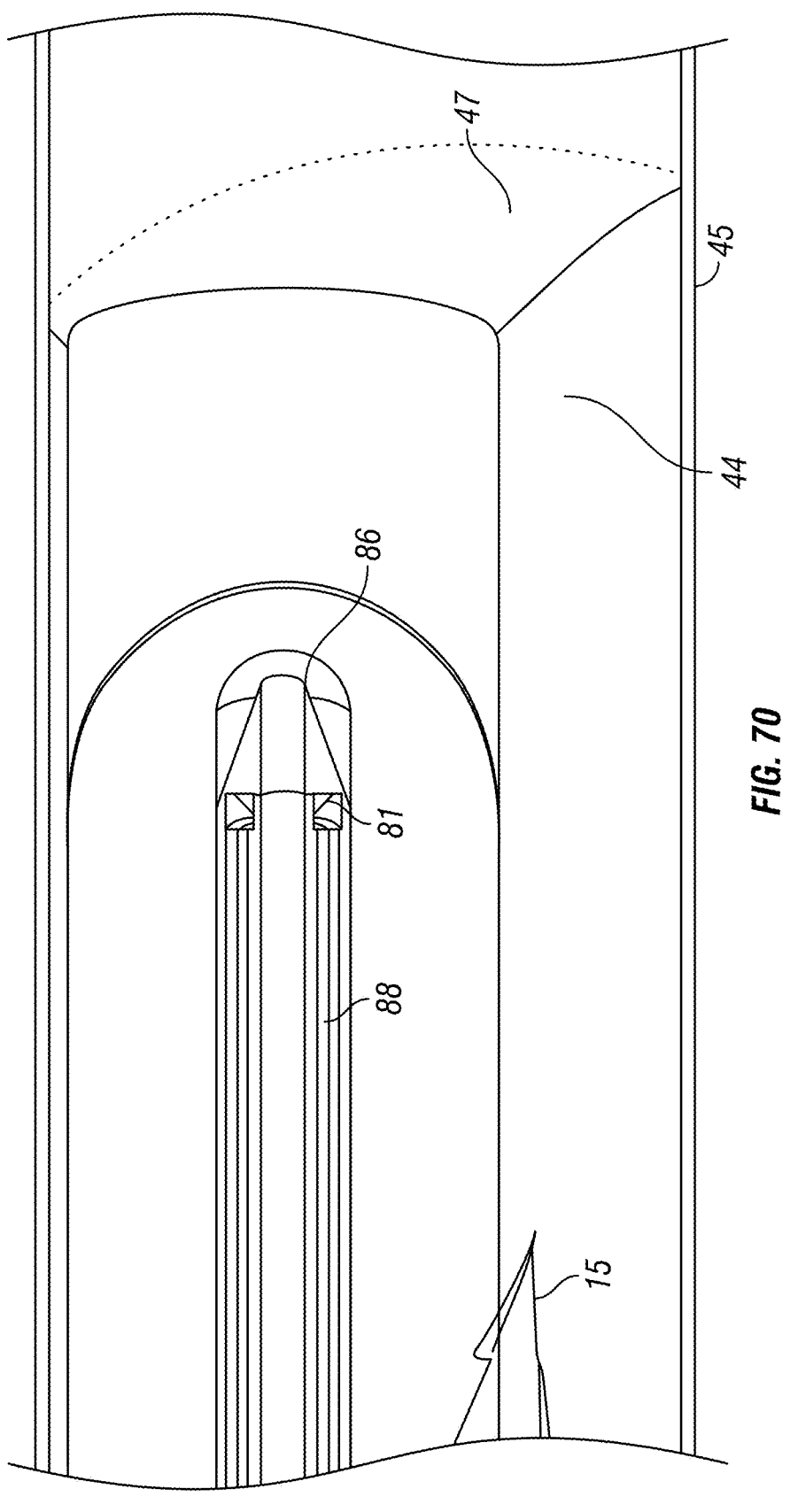
FIG. 70 is a closer view of an imaging assembly of FIG. 68 including an imaging catheter and supporting scoopula of an excisional imaging device of FIG. 49 according to embodiments.

FIG. 70 is a closer up view of element 80 of FIG. 68 with its fibers 88, circular receiving, reflecting, transmitting element 81 and its central lumen and nosecone 86 also all shown being supported and elevated by scoopula 15 according to embodiments. It should be noted that the illustrated central lumen 86 can be utilized by any of the excisional, ablative, dissolving or other physiologically altering devices that dimensionally may be introduced, directed, and supported by such a space according to embodiments.

Figure 71:
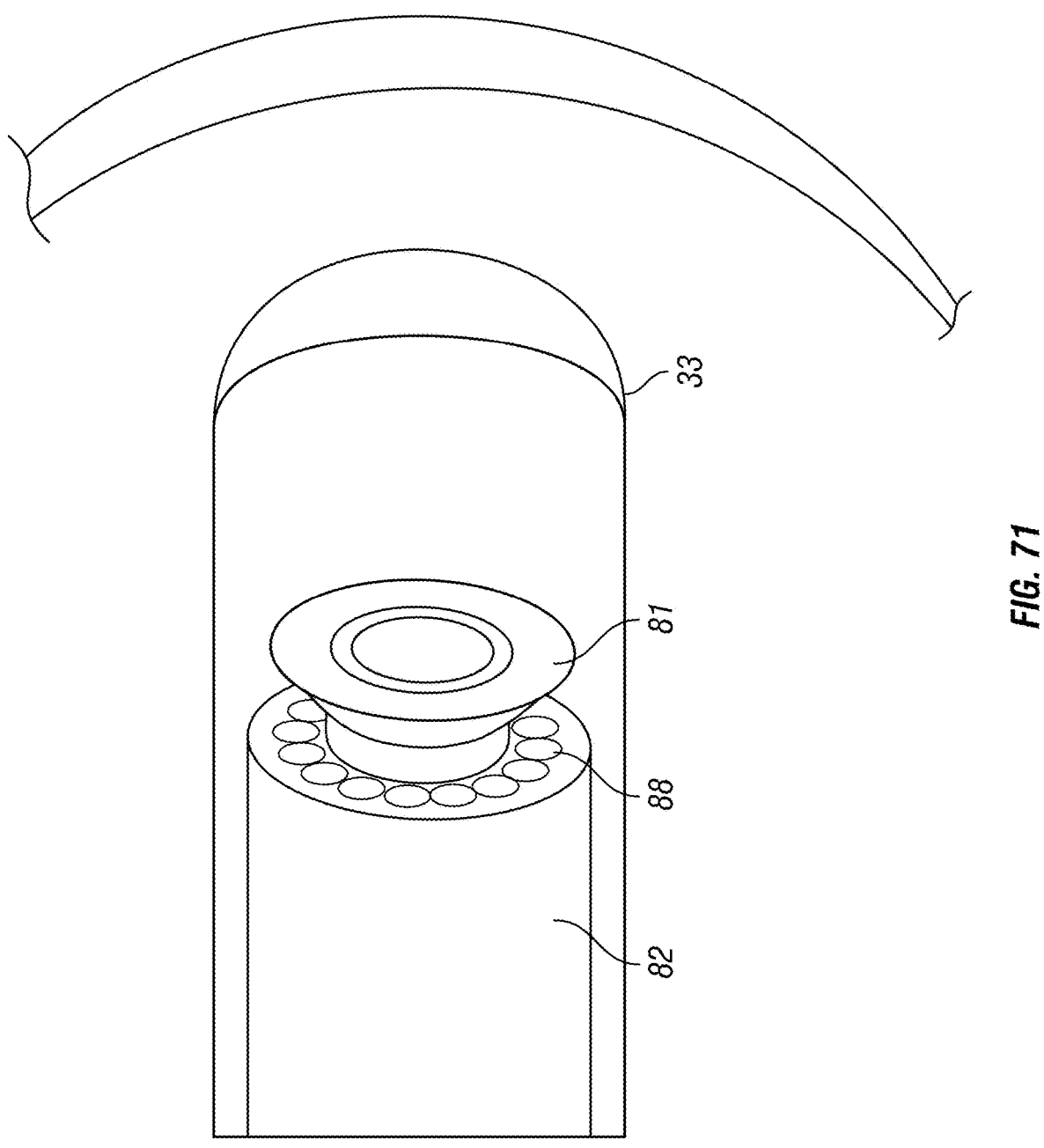
FIG. 71 is an even closer perspective view of an imaging catheter revealing its circular coaxial reflecting and transmitting fibers arranged as in FIGS. 68, 69 and 70 above, and within an outer expandable, transparent imaging chamber, according to embodiments.

FIG. 71 is another illustration of a device 80 of FIG. 68 with its outer covering 82, its optical fibers 88 and optical reception, reflection and re-transmission element or elements 81 shown within expandable, transparent imaging and extending chamber 33. In addition to imaging capabilities, laser and ultra-short wavelength modalities may be transmitted and feedback controlled utilizing multiple layers or sections of fibers to ablate materials using this configuration and in potential combination with imaging devices of a range of conventionally configured catheter and wire imaging modalities, introduced and positioned via the included open central lumen, according to embodiments.

Figure 72:
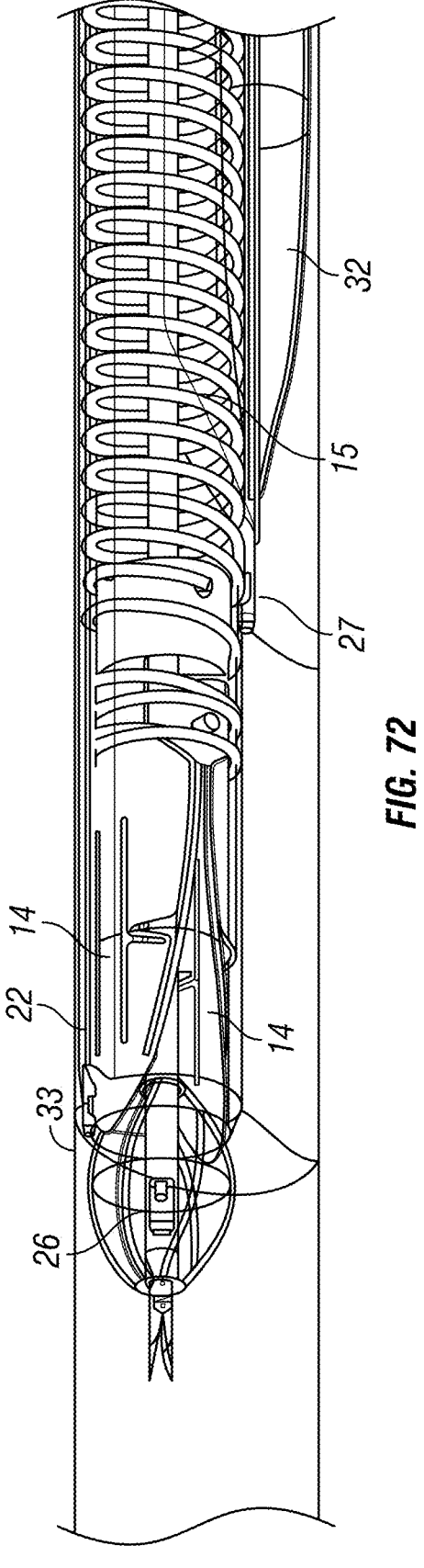
FIG. 72 is a perspective view of an imaging, excisional assembly within a new channel in a previously totally obliterated space in a tubular structure such as a vascular total occlusion according to embodiments.

FIG. 72 is an illustration of a device 10 with its stabilizing elements shown together with its guidance elements, including in this case, OCT and IVUS (26, 27), depth and elevation control elements, non-rotating sheath element 22, Scoopula 15 and expandable, flow enabling element 32 in a formerly totally occluded vessel, that is now shown as having partial restoration of original lumen diameter, at a stage where according to methods, may now continue or proceed in a remotely controlled, automated series of steps including repositioning utilizing each of the elements illustrated, followed by excising with beak(s) 14 of work element 13 as previously described, and rotational control and stability being provided by an outer sheath 25 (not shown in this illustration) alone or in combination with expandable, flow enabling element 32, to a precise depth and direction more of the material with each repetition of the logical steps with the ultimate end result being to remove as much of the remaining material as would be optimal for flow and healing, according to embodiments.

Figure 73:
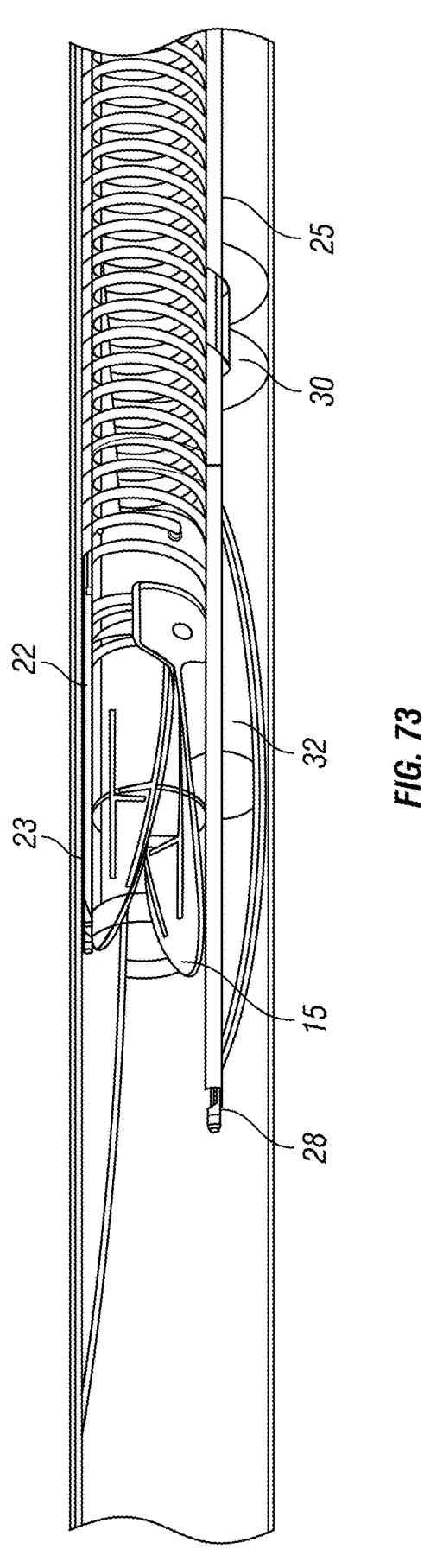
FIG. 73 is a perspective view of an imaging, excisional assembly with an additional asymmetric expansion, elevation, and control element according to embodiments.
Figures 74A, 74B, 74C, 74D:
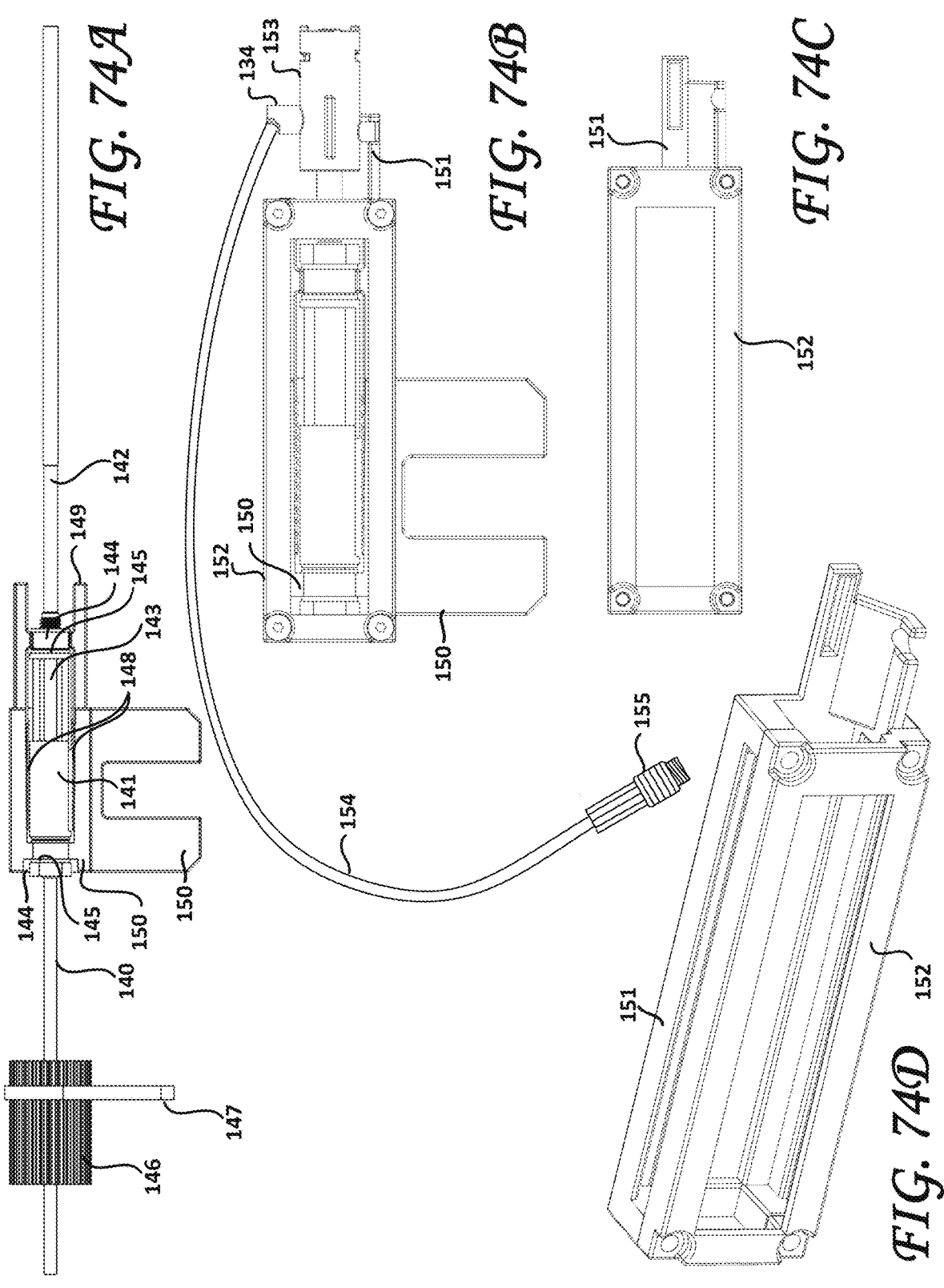
FIGS. 74A, 74B, 74C and 74D are side and perspective views of several components of a proximal control unit configured to rotate, axially drive, and actuate the beaks of the work element through by differential relative axial motions between elements, according to an embodiment.

FIG. 73 is a perspective view of a device of FIG. 1 together with elements needed for the specific purpose of clearing asymmetrically located materials encountered initially or remaining from earlier excisions, achieving maximum control of positioning in rotation, elevation, and longitudinal excursion as well as precision in depth control, the execution of which is shown by illustrating a combination of imaging represented by generic imaging element 28, elevation, stabilization and flow control with expandable element(s) 32, further elevation, flow control, local rotational stability and angle of excision manipulation by an expandable cuff 30, in this case shown proximally but which could also be duplicated distally, along with precise depth control utilizing asymmetry of the circumference of NRS 22, in this case as shown with a larger diameter area contributed by lumen 23 in the NRS 22, by rotating independently, NRS 22 to create as little or much standoff between the cutting elements and the materials to be removed as desired according to embodiments. With elevation, rotation and longitudinal positioning and flow control established and stabilized with scoopula platform 15 as provided by expandable element(s) 32, along with further stabilization in those parameters as well as angulation by element 30 acting on outer flexible tube element 25 of a device of FIG. 1, rotation of NRS 22 combined with degree of exposure of beak elements 14 can be utilized to fine tune depth control. All of these parameters may be factored in and manipulated in an automated process based on precise in-situ imaging to refine to a maximal degree, precision control of all aspects of an excision procedure, according to embodiments.

One embodiment, therefore, includes using a scoopula-based set of work elements configured to create and isolate a work area within a vascular structure, while selectively allowing or disallowing the flow of fluids in the thus isolated area.

The creation of the "work area" protects the vascular walls that we don't want to damage, and captures debris from whatever interventional work elements are introduced in any number of different stages and procedures, all of which may be introduced to the work area site thus established through the central lumen of the work element or elements that establish and maintain the work area site. This is in stark contrast to the current approach, where a single device tries to do it all, i.e., coring, shaving, capturing, expanding, re-establishing blood flow, preserving blood flow, etc. The devices and methods described and shown herein, according to embodiments, include a device, with a minimally invasive structure that first creates that protected work area, and that can be moved to successively expose additional incremental work areas, and that serves as the universal conduit for all kinds of different specialized work elements to be successively introduced through its central lumen in as many successive steps as are necessary to complete a gentle, thorough removal of blocking plaque or materials while preserving the vascular wall architecture and re-establishing or improving blood flow as quickly as possible.

Embodiments, therefore, create different types of "work area establishment" and a "isolating/debris capturing" work elements and a number of different interventional work elements configured to clear obstructive material from a first isolated and protected work area by being introduced through the work element that establishes the "work area."

One embodiment, therefore, is a device, comprising an outer flexible tube defining a longitudinal axis; a rotatable scoopula disposed within the outer flexible tube and defining an open side portion; at least one inflatable support element attached near a distal end of the rotatable scoopula; an inner sheath disposed within the rotatable scoopula and configured to move parallel to the longitudinal axis; a first pair of first and second rotatable and articulable beaks disposed within the inner sheath and partially extending into the open side portion of the scoopula, the first pair of first and second rotatable and articulable beaks being configured to cut tissue present within and beyond the open side portion of the scoopula by selectively assuming an open and a at least partially closed configuration while rotating and an expandable and collapsible cutting and imaging chamber disposed at a distal end of a central tube that is disposed coaxially between the first pair of first and second articulable beaks, the chamber being configured to enclose a removable imaging device within a volume of fluid and to move parallel to the longitudinal axis away from and back against the first pair of first and second articulable beaks.

According to further embodiments, the chamber further may include a plurality of curved blades disposed on a portion of an outer surface of the chamber that faces the first pair of first and second articulable beaks, the first and second articulable beaks being configured to engage with the plurality of curved blades when the chamber and the first and second articulable beaks are moved into contact with one another. The device may further comprise a tube defining a lumen configured to receive a guide wire. The device may also further comprise the removable imaging device disposed within the volume of fluid enclosed by the chamber. For example, the imaging device may include an optical coherence tomography imaging device including a rotating mirror or a phased array of circularly-arranged light sources disposed around a stationary reflective element. Other imaging modalities and devices are possible. For example, the imaging device may include an ultrasound imaging device disposed within the volume of fluid enclosed by the chamber. The chamber may be further configured to define a central lumen that emerges at a distal end of the chamber. The device may further comprise a second pair of first and second articulable beaks that are smaller than the first pair of first and second articulable beaks and that may be configured to be advanced within the central tube through the central lumen past the distal end of the chamber. The second pair of first and second articulable beaks may be independently articulable, movable, and rotatable to cut tissue distal to the chamber. The second pair of the first and second articulable beaks may be configured to assume an open configuration to core through tissue distal to the chamber and to assume a closed configuration to part off cored tissue. An expandable cuff may be disposed proximal of the first pair of first and second articulable beaks on the outer flexible tube. The inflatable support element(s) may include a first inflatable support element and a second inflatable support element spaced apart from the first inflatable support element to define a through channel therebetween. For example, the at least one inflatable support element may be (generally) pontoon-shaped. The chamber may be further configured to deform against one side of a passageway when the inflatable support element(s) are inflated to press against an opposing side of the passageway.

Another embodiment is a method, comprising advancing a device within a vasculature to a target region, the device comprising a scoopula comprising an open side portion, a first pair of rotatable first and second articulable beaks that partially extend into the open portion of the scoopula, at least one inflatable support element attached near a distal end of an outer surface of the scoopula and an expandable and collapsible cutting and imaging chamber disposed at a distal end of a central tube coaxially disposed between the first pair of first and second articulable beaks; inflating the chamber and at least one inflatable support element such that the chamber may be pressed against a surface of the vasculature distal to the target region; imaging the vasculature using the chamber; rotating the first pair of first and second articulable beaks; and cutting tissue that comes into contact with the rotating first pair of first and second articulable beaks within the open side portion of the scoopula to a selectable depth that may be at least partially dependent on the inflation of at least one of the chamber and of the at least one inflatable support element.

The chamber further may include a plurality of curved blades disposed on a portion of an outer surface of the chamber that faces the first pair of first and second articulable beaks, and the method may further include bringing the first pair of first and second articulable beaks into contact with the plurality of curved blades to part off tissue cut by the rotating first pair of first and second articulable beaks. Advancing may be performed over a guidewire inserted within the vasculature. The imaging may be performed using optical coherence tomography or, for example, using ultrasound.

The device further may include an independently operable second pair of first and second articulable beaks that may be smaller than the first pair of first and second articulable beaks and the chamber may be further configured to define a central lumen that emerges at a distal end of the chamber. In such a case, the method may further comprise advancing the second pair of first and second articulable beaks through the central lumen past the distal end of the chamber. The method may also comprise coring through tissue disposed distal to the chamber with the second pair of the first and second articulable beaks rotating in an open configuration and parting off the cored tissue by causing the second pair of the first and second articulable beaks to assume a closed configuration. The method may also comprise stabilizing the coring and parting off of the tissue distal to the chamber by controlling inflation of the chamber and of the inflatable support element(s). The method may also further comprise deflating the chamber and advancing the chamber within a cored path created by the second pair of the first and second articulable beaks. The method may also include re-inflating the chamber within the cored path created by the second pair of the first and second articulable beaks. Also, an expandable cuff disposed proximal of the first pair of first and second articulable beaks may also be inflated to provide additional stabilization. The inflatable support element(s) may include a first inflatable support element and a second inflatable support element spaced apart from the first inflatable support element to define a channel therebetween. The method further may include enabling fluid flow from a distal end of the device downstream past a proximal end of the device through the channel. The method may also comprise selectably deforming the chamber against one side of a passageway by inflating the at least one inflatable support element to press against an opposing side of the passageway.

*New Phoenix Material Begins Here (FIGS. 74-85)*

FIGS. 74A-D, 75 and 76 show embodiments of a proximal driving and control assembly that includes housing, driving mechanism and cassette that may be configured to control and drive the devices shown and described relative to FIGS. 1-84 and 77-85. Referring now to FIGS. 74A-74D, the proximal driving and control assembly may be partially housed in and secured to a cassette 151, 152 and functions to control and drive the operation of the devices shown and described herein. Indeed, the proximal driving and control assembly may be configured to enable collection of tissue samples and enable the other functionalities described herein by controlling the rotating, driving, and actuating elements that may be disposed at the distal tip of a stiff, flexible, or piecewise stiff and flexible catheter tipped with a work element 13 described herein. The proximal driving and control assembly may be disposed, depending upon the embodiment, within a manually controlled handle or disposed in or integrated within a robotically or other remotely controlled, mounted housing. In some embodiments, several of the control functions may be performed by a machine, which machine may be wholly manually controlled or may be controlled, to a greater or lesser degree, by an artificial intelligence or other programed machine that may be configured to respond to desired goals and inputs, whether autonomously or a hybridized autonomous/human combination. For example, some or all of the goals of the procedure may be decided and/or selected ahead of the procedure and modified by machine learning or in real time by manual inputs and/or from the output of sensors. Regardless of whether the present excisional device is controlled in whole or in part by humans or machines, its function remains the same, in that all the elements shown in FIGS. 74A-7D, 75 and 76 may perform these functions in a similar way. Therefore, the elements shown and described relative to FIGS. 74A-74D, 75 and 76 may be configured for handheld operation, stereotaxic operation, and/or robotic deployment.

As shown in FIGS. 74A-74D, 75 and 76, numeral 140 refences an inner tube that may be rotated together with outer tube 142 either synchronously or differentially, depending on whether the axial actuation of the beaks 14 is performed, according to one embodiment, by differential rotation of the inner tube 140 with respect to the outer tube 142 or simply as in this case, a simple push pull differential movement between the inner tube 140 and outer tube 142 in a direction parallel to the long axis of the tubes 140, 142. In either the differential or push-push mode of operation, the rotation of the two tubes 140, 142 is fixed together by proximal dog element 141 (fixed to inner tube 140) and by distal dog element 143 (fixed to outer tube 142). Within the present context, a dog is a device, part or tool that imparts movement or prevents movement through physical engagement. Dogs can hold objects in place, couple parts together, lock spinning components and/or transmit rotary motion. Dog elements 141 and 143 are configured to enable axial sliding of the inner tube 140 and of the outer tube 142 while keeping both tubes 140, 142 rotating together so as not to impart unwanted torsional stresses on distal work element 13 and the beaks 14 thereof. The distal dog element 143 may be configured to rotate within slidable forward outer tube actuator element (dog paddle) 149, which may flanked fore and aft by thrust washers 145 and fastened and constrained axially within forward outer tube actuator element 149 by dog fastener nut 144. Proximal dog element 141 may be similarly configured within carriage element (functioning as inner tube actuator) 150 for the same purposes. When forward outer tube actuator element 149 is drawn rearwards (i.e., in the proximal direction, away from the work element 13 and beaks 14) relative to carriage element (dog paddle) 150, beaks 14 of the work element 13 are both drawn inwardly towards the centerline of the inner tube 140 and of the outer tube 142 to close the beaks 14 against one another. In such a closed configuration, the work element 13 and the beaks 14 thereof may be configured for functions such as parting off a tissue core specimen or for rotational, non-sharp advancement through and minimally disruptive dissection of a structure such as the tissue of a bodily organ or through the lumen of a diseased vessel. Conversely, when forward outer tube actuator element 149 is drawn axially in the distal direction, (away from and within a dual track housing of carriage 150) with respect to the position of carriage 150, then the beaks 14 are caused to open widely, away from the centerline of the inner tube 140 and of the outer tube 142 back to its natural, unbiased original outer diameter or, in the case of "overdriving" the differential axial positions of inner tube 140 and of the outer tube 142, even wider than the natural outer diameters of the inner tube 140 and of the outer tube 142, as the natural diameter of the tube from which work element 13/beak set 14 was constructed as described herein elsewhere such that the distal-most tips of the beaks 13 point away from one another.

Gear 146 is a driven and "walking" gear that is affixed to inner tube 140 and rotates together both proximal dog element 141 (fixed to inner tube 140) and distal dog element 143 (fixed to outer tube 142) which in this embodiment, is driven by double bearing and tube rotation driving gear 138 (FIG. 75), which is driven by inner tube rotation driving motor 137. The rotation of the double bearing and tube rotation driving gear 138 is transmitted to the driven walking gear 146 by driving toothed belt 147. The walking function of driven walking gear 46 permits uninterrupted, unimpeded rotation of the inner tube 140 and of the outer tube 142 while tubes 140, 142 are driven fore and aft together and differentially, within cassette frames 151 and 152. In one embodiment, the entire cassette assembly 151, 152 and attached elements may be driven fore and aft to dictate the coring depth of work element 13; that is, the depth to which the work element 13 is enabled to penetrate tissue or advance within the vasculature, other natural conduit, or space.

Flush block element 513 is configured to enable the inner tube 140 and the outer tube 142 to rotate within a sealed plenum inside of element 153 such that fluids can circulate to and within the interstitial spaces between tubes 140 and 142 via passageways, while the inner tube 140 and the outer tube 142 rotate and slide axially without restriction within flush block 153. The flush block 153, according to an embodiment, may be fastened to an additional outer tube or cannula, such as imaging device 10 or NRS element 22 such that fluids may advantageously circulate within such structures in the space between device 10 and/or NRS 22. Fluids may be delivered via tube line 154, which itself may be attached to a fluid source via a suitable connector, such as commercially available diaphragm-sealed attachment connector 155 and delivered out of the distal end of the needle set, via open articulable beaks 14, for example. The assembly described above and shown in FIGS. 74A through 74C may be configured with limits and compliance members such that work element 13 (and its beak(s) 14 and/or scoopula(s)) is fully functional over the intended range of movement for the task at hand yet remains within acceptable stress ranges. Indeed, the assembly remains protected from such overstressing via cassette constraining dimensions, end play dimensions (proximal dog element 141, distal dog element 143, thrust washers 145 and forward dog retaining nut 144 aka "dog paddle" and rear thrust washer 145 "carriage" and other compliant members and helical return springs 148 located between and within proximal dog 141 and distal dog 143) in the case in which outer rotating tube element 142 and inner rotating tube 140 are themselves at least partially flexible and partially rigid, according to embodiments.

According to an embodiment, needle sets may be manufactured and delivered in sterile packaging as an integrated set of components that may comprise at least inner and outer rotating rigid, flexible or piecewise rigid and flexible tubes or needles 140, 142, proximal (rear) dog 141, distal (front) dog 143, flush block 153 and flexible NRS 22, which may be configured as transitionally flexible beginning with rigid NRS 25 and transitioning to flexible NRS 22 and then, as required, back to rigid type NRS 25. According to an embodiment, the needle sets may be configured to include at least distal work element 13 with its articulated beak sets 14. In such needle sets, the proximal dog 141 may be attached to inner rotating tube 140, the distal dog 143 may be attached to flexible outer rotating tube 142, and the flush block 153 may be attached to flexible non-rotating over-sheath NRS/RS22 (see above for optional configuration of rigid/flexible/rigid longitudinal transitioning NRS 25/22/25). In their default, unbiased position, the beaks 14 may be held open by the tension exerted by springs 148 between the proximal dog 141 and the distal dog 143. The keystone 16 (see also reference 184 in FIG. 83A—there are two keystones 184, but only one is visible in FIG. 83A) parts of work element 13 may be held back by flexible inner rotating tube 140. As the operator (human or robotic) advances the carriage 50 forward (i.e., in the distal direction) manually using, for example, a lever/trigger mechanism or with a solenoid or other linear actuator, this action first advances the proximal, rear dog 141, causing the flexible inner tube 140 to move distally forward. In certain situations the beaks 14 may be in a configuration balanced between resistance to closing and staying open. In other situations, the beak elements 14 may at least partially close and advance through tissue, biological conduit or other space, with the total forward excursion thereof being dependent on the force imparted to the input-tube set comprising flexible inner rotating tube 140, flexible outer rotating tube 142 and the aggregate compliance along the length of the flexible tube sets 140, 142. In one embodiment, depending on the length of the forward outer tube actuator/dog paddle 149, this also advances distal dog 143 and front dog paddle 149, until front dog paddle 149 posts contacts cassette frame 152, which causes the front dog paddle 149 to stop advancing. For the duration of this motion, inner and outer flexible rotating tubes 140 and 142 move together, again depending in part on the balance of resistance to relative movement counteracted by spreading helical dog return element (springs) 148. With the front (forward) dog paddle 149 stopped axially by cassette frame 152, then when the flexible outer rotatable tube 142 is held back, this action holds the keystones 16, 184) of work element 13's articulated beak sets 14 back via tendons 18. In this position, advancing the carriage 50 and in turn aft (rear, inner tube) dog 141, causes the flexible inner rotatable tube 140 and in turn backbone 17 of work element 13 to advance. In turn and according to embodiments, this combination of actions causes articulated beak sets 14 to close for rotating, non-sharp tissue dissection or for severing off a tissue cored tissue sample.

Figure 75:
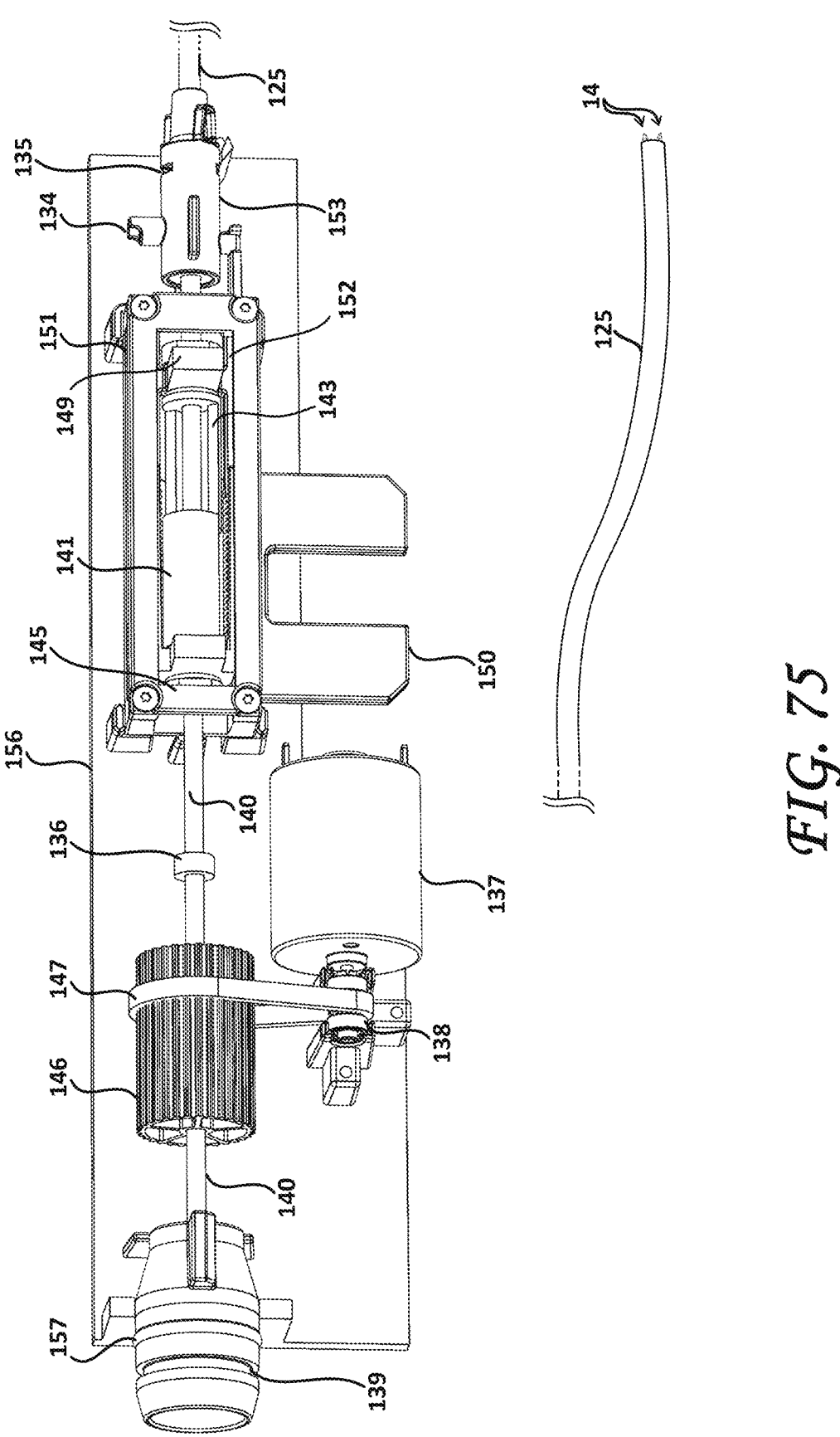
FIG. 75 is a perspective view of a control system as well as a long flexible needle assembly that the control system actuates, according to an embodiment.

FIG. 75 shows components of the proximal driving and control assembly of FIGS. 74A-74D in an assembly form, together with a tube/needle driving motor 137, driving belt gear and bearing assembly 138 and other components detailed above that may be included in a needle set, to include flush tube inlet port 134, and double luer flush-vacuum sealer 135 connecting the NRS 22/25 with flush block with an internal square shoulder O-ring. An inner tube stabilizer load bearing 136 may surround the inner rotating tube 140 between the gear 146 and the proximal end of the cassette 151, 152. The inner tube stabilizer load bearing 136 operates to counter belt forces, including minimizing belt whip and tube distortion as well as interface block 139 with its inner rotary seal and outer O-ring 157 to seal a removable tissue collection receptacle attachable to interface block 139. As shown in FIG. 75, the entire assembly may be carried on a movable platform sled 156 that serves as a machine interface and positional reference to control whole assembly excursion, thereby determining depth of penetration of the work element 13. The assembly may include inner and outer rotating tubes 140, 142 together with NRS 25 (or RS if rotating) outer over tube (sheath) as well as forward work element 13, according to embodiments. According to an embodiment, flush block 153 and attached flexible NRS/RS 125, 122 may be held in place axially in this configuration. FIG. 75 also shows the NRS/RS outer sleeve 122, 125 coupled to the flush block 153. The broken lines in FIG. 75 indicate that the NRS/RS sleeve 122, 125 is longer than shown and may be a few inches long or may be, for example, three feet long, depending upon the application and the length of the pathway from the driving and control assembly to the site of interest within the tissue. The inner and outer tubes 140, 142 and the NRS/RS 122, 125 may be flexible along at least part of their length, and may be steerable to follow torturous pathways while maintaining the ability to rotate and to transmit sufficient forces to operate the beaks 14 to carry out non-sharp rotational dissection, tissue dissection, coring through tissue and parting off of cored tissue samples, among other operations.

Figure 76:
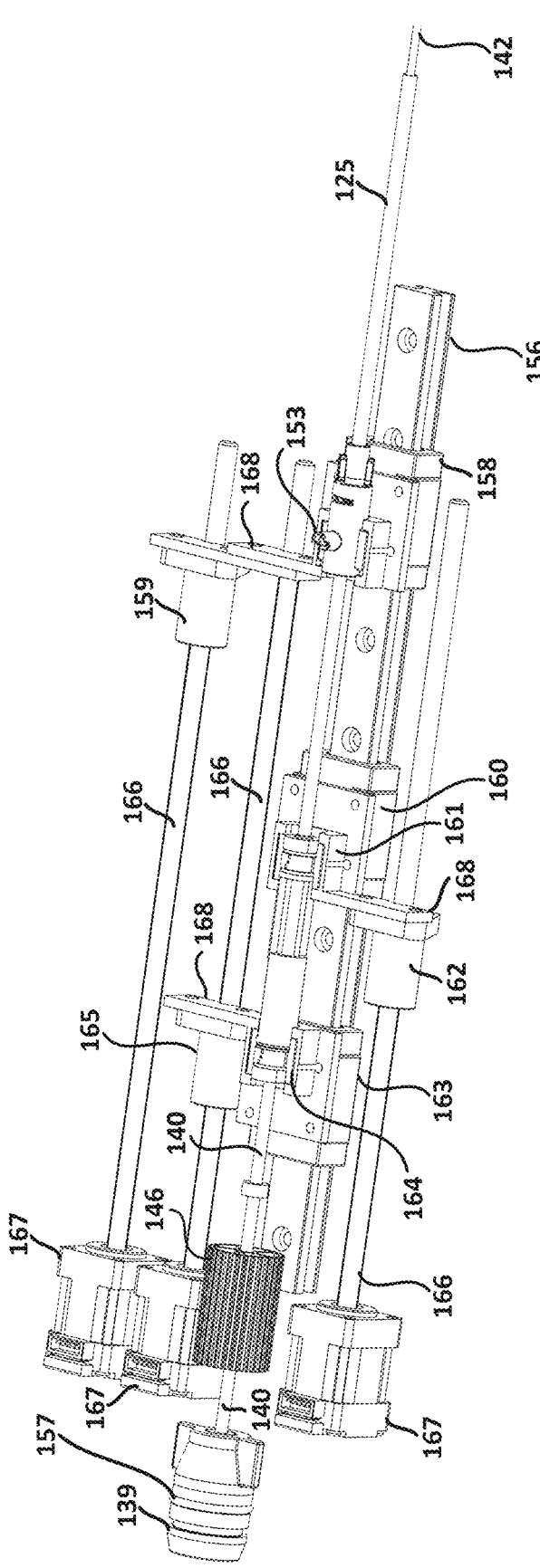
FIG. 76 is a perspective view of another control system similar in purpose to the system in FIG. 75 but with additional components according to another embodiment.

FIG. 76 shows an embodiment of the proximal driving and control assembly that enables individual control of distally-directed (forward) and proximally-directed (aft) travel of each of two, three or more components shown in FIG. 75, with additional components that enable separate and independent excursions of these elements relative to one another. Individual control of each component assembly enables separate mechanical manual or software machine determined positioning and on-the-fly (i.e., during a procedure) changes along a continuously variable axial relationship of each component or assembly attached to the control flanges, including flush block lead screw flange follower 159, outer tube lead screw flange follower 162 and inner tube lead screw follower flange 165 as driven by motors 167 positioned along lead screws 166. Similar to previous manual operation (whether "by hand" or via linear actuators), moving the proximal (aft) tube dog paddle assembly/ slide carriage assembly 141 ("aft dog paddle") and distal (forward) tube dog paddle/assembly slide carriage assembly 143 ("forward dog paddle") together causes beak sets 14 of work element 13 to close. According to embodiments, moving aft dog paddle 141 and forward dog paddle 143 apart from one another axially causes beak sets 14 to assume the open configuration. In this configuration, each component of the whole needle set (aft dog paddle 141, forward dog paddle 143, flush block slide carriage assembly ("flush block") 158 may be affixed to a slide carriage assembly that may ride along a single, common rail. Each assembly is affixed for actuation to an internally-threaded flange 159, 162, 165, via connector arms 168, and each may be driven by a separate and independent motor 167. FIG. 76 identifies flush block 153 in place on flush block slide carriage assembly, as driven by flush block lead screw follower flange 159, outer dog paddle assembly slide carriage assembly 160 shown with attached outer tube dog paddle assembly 161 installed, as driven by outer tube lead screw follower flange, inner tube dog paddle assembly slide carriage assembly 163, with its inner tube dog paddle assembly 164, installed and as driven by inner tube lead screw follower flange 165. Lead screws 166 are driven by individually controllable lead screw rotation motors and are connected to each assembly slide carriage by connector arms 168, according to embodiments.

All functions disclosed herein may be tailored and controlled according to feedback loops, whether open or closed control loops and driven individually to accommodate multiple feedback variations to optimize all functions of work element 13. These variations may include results such as total needle (rotating tubes) depth of penetration, exposure of work element beak sets 14 from beneath the forward edge of NRS 25 during non-sharp closed beak 14 dissection and penetration, during parting off of tissue specimens and during coring functions. Cored sample lengths may be individually controlled on the fly or at predetermined lengths, may be automatically controlled based on any number of feedback factors such as "visible" depth of forward travel based on desired sample length, avoidance of overpenetration into undesired locations such as nearby structures critical to avoid harm and other factors. Visualization of these modes of operation may be carried out by translating machine inputs outside of the human range to human-perceptible frequencies. These machine-generated inputs may include frequencies outside of human perception range such as, for example, ultrasonic sensations, optical coherence tomography ranges, infrared or ultraviolet frequencies, thermal, electrical conduction, impedance physical pressure including torque limits, impedance to forward excursion, among other factors encountered when activating work element 13, including optimizing rotational speeds with forward coring translation, "speeds and feeds" to borrow machining language, according to embodiments.

FIG. 76 further shows an embodiment in which the aft dog paddle 141 is affixed to a base platform sled, machine interface such as component 156 and enables the forward dog paddle 143 to translate proximally and distally with respect to the aft dog paddle 141. Other device assemblies (such as needle rotation driving motor 137, printed circuit control boards, electrical connectors, sensors and other components as required for feedback loops whether open or closed, according to embodiments) may be attached to the base platform sled 156 and may be used for dynamically controlled (and/or pre-programmed software/hardware controlled), and any number of such components may be included as needed for desired levels of control according to embodiments. The variables that may benefit from such individual, tailorable control include circumstances where flexible tube sets may be required to traverse multiple bends in order to arrive at the desired target within tissue to core a tissue sample. These variables also may include frictional losses that may vary according to the acuteness of the bends required as well as the number of twists and turns the NRS or other guidance tubes impart within the constraints of anatomical variants encountered on the pathway to a site where tissue samples are desirable to obtain for diagnosis or complete removal from the host tissue organ that is the target of a procedure. Such distances that are useful to control due to the above requirements and constraints include the distance between the aft and forward dog assemblies 141, 143 as described above (distance 1) as well as the distance between the flush block 158, aft dog paddle 141 and forward dog paddle 143 assemblies (distance 2). Distance 1 in this example is important for ensuring that beak sets 14 of work element 13 are fully closed and opened as required for the various actions required in a procedure as described above, while distance 2 defines the exposure ranges between the distal edge of NRS/RS 25, 22 during such functions as coring, which in certain tissue densities and degrees of hardness can be varied for maximum efficiency of coring, penetration and parting off actions according to embodiments. Each of these actions are desirable to control to optimal levels and include physical axial distances, degree of opening and closing of beak sets 14, rotational speeds and axial feeds (excursions) during coring, penetration, severing off, capturing, and transporting of core tissue specimens.

Such actions may be effectuated via mechanical means (helical transport, capture element encapsulated or partially encapsulated transporting with or without vacuum assistance), or fully under the action of vacuum as augmented by fluid flows whether in swirling motion or straightforward axial fluid actions or a combination thereof. Feedback examples to which dynamic variable control may be responsively applied include visual aids supplied by internal, coaxial or in tandem visual spectrum or synthetically reconstruction imaging via incorporated cameras of useful frequencies in the optical spectrum (whether perceptible directly via human optics or recreated electronically as in the case of such modalities as optical coherence tomography imaging), external imaging via x-ray, MRI, PET, tomographic, pulsed beam or radiographic, ultrasonic or other guidance modalities whether in-tissue or externally applied from the surface or remotely to the surface. Other feedback sensors may include electromagnetic positional sensors, which may be placed aft of the work element beak sets 14 for convenience and in response to physical considerations, forces required for rotation, for axial motion of any of the components as they are actuated for one or more of the desired capabilities for which they are included in the apparatus, in which case forces may be individually responded in based on which assembly or component is being monitored and also may be dynamically controlled according to algorithms devised to sense stresses or other useful relationships between components according to embodiments. As described above, a direct visualization of the actions of components may be a significant factor affecting the overall success of a procedure, such as a direct visualization of the position of beak sets 14 with respect to one another or with respect to other components, directly affect their ability to successfully complete their desired results. Such direct visualization may be used to dynamically alter forces, positions, speeds and excursion distances and directions ("aiming points/directions, speeds" in $3^{rd}$, $4^{th}$ and $5^{th}$ axes) and including optimal speeds of traverse and rotation, which can vary by tissue density, degree of hardness and other tissue factors) in any desirable individual or combination of such parameters, according to embodiments.

Figure 77:
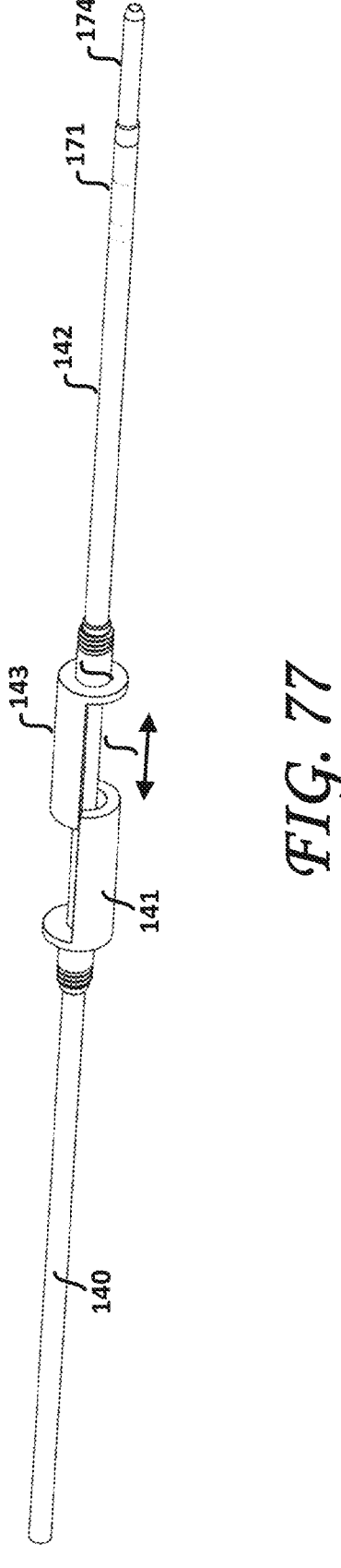
FIG. 77 is a side view of components of a long flexible needle assembly according to embodiments.

FIG. 77 is a side view of an embodiment comprising telescoping partial tube-shaped dogs 141 and 143 attached respectively to rigid proximal section of inner tube 140 and rigid proximal section of outer tube 142. These extended dogs 141 and 143 can slide past one another to telescope tubes 140 and 142 while keeping the rotations of inner long flexible tube 140 and long flexible tube 142 together to reduce and minimize torsion stresses, particularly when distal drag resistances through tissue rise.

Figures 78A, 78B, 78C, 78D:
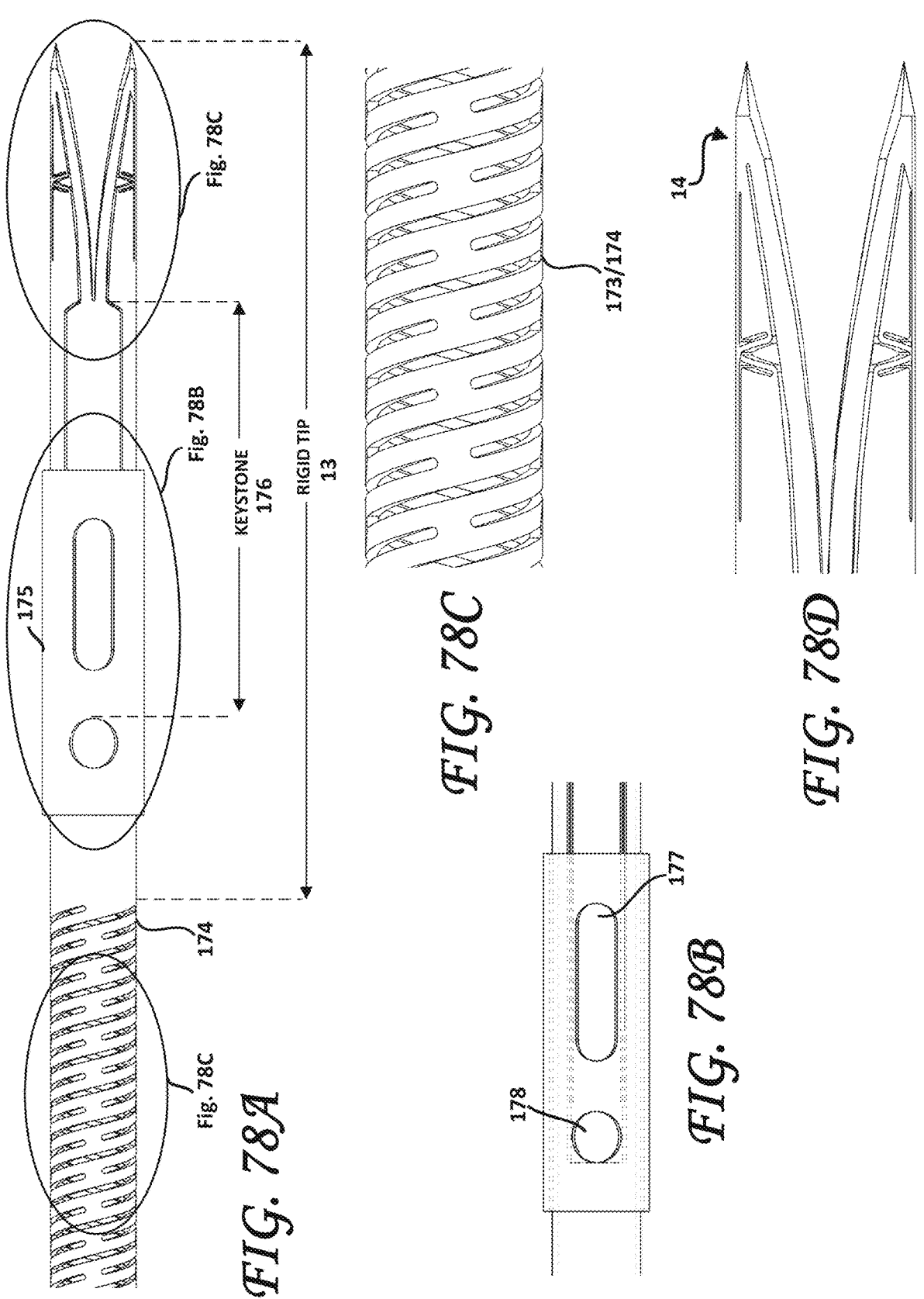
FIGS. 78A, 78B, 78C and 78D is a collection of details in side view of a telescoping set of needles with a truncated outer needle rigid section with its proximal flexible section hidden to reveal a similar construction of an inner long flexible needle with its flexible section and rigid section details shown along with construction attachment details, according to an embodiment.

FIGS. 78A, 78B, 78C and 78D show several construction details of components and assemblies of the inner and outer long flexible telescoping tubes of similar flexible section construction (173, 174), according to an embodiment. The outer tube long flexible section 173 is hidden to reveal an inner tube long flexible section 174, having a distal rigid section 176 connected at a fastening (laser welded, in one embodiment) point 178 to the backbone of work element 13. The outer tube distal rigid tip section 175 is attached to keystone elements of work element 13 at fastening (laser welded, in one embodiment) points 177 (one on each side of the work element 13). These fastening points serve to actuate beak elements 14 of distal work element 13 to and from the open and closed positions while these elements rotate via the proximal driving and control assembly detailed above in the text and shown in the drawings, according to embodiments. As shown in the detail view of FIG. 78C, a portion of the inner tube and of the outer tube may comprise changes in material thicknesses, density, treatment and/or laser cuts that form voids in a material of the tube over at least a portion of a length of the tube to vary the flexibility and/or an ability to transmit torque of that portion of the tube. In FIG. 78C, the laser cuts form discontinuous spiral patterns at a predetermined pitch, to thereby enable that portion of the tube to flex while still maintaining its ability to transmit torque. Other patterns of laser cuts are possible, as are other forms of material treatment that tend to impart greater of lesser flexibility to a selected portion of the inner and outer tubes 140, 142.

Figure 79A:
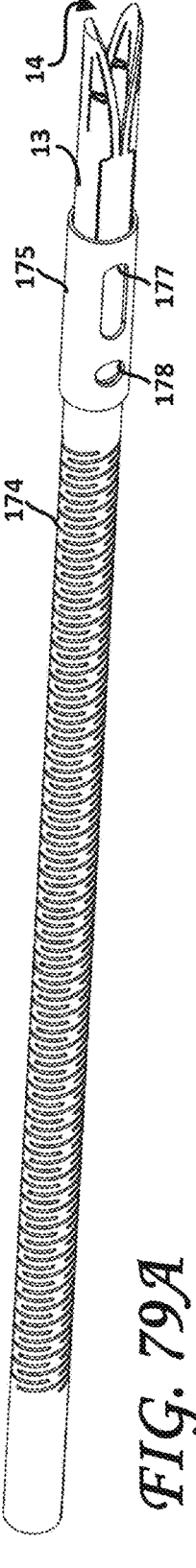
FIGS. 79A, 79B and 79C are a side perspective view and an overhead view of a long flexible inner and outer needle set with the flexible portion of an outer flexible long needle hidden to reveal an inner long flexible needle as well as rigid sections of an inner and outer needle set attached to a work element at the end, according to embodiments.

FIG. 79A is a perspective view of an embodiment of the long flexible and short rigid sections of inner rotating tube assembly comprising the inner rotating tube 140, the inner tube long flexible section 174, and the inner tube rigid tip 176 and the outer rotating tube sections assembly comprising the outer tube section 142, the outer tube flexible section 173, and the outer tube rigid tip 175 and their relationships with distal work element 13, with outer long rotating, flexible section removed for clarity. According to an embodiment, changes in material thicknesses, density and laser cuts may be made to form voids in the material that together form a pattern or patterns and define pitches (repeated axial separation of void patterns in the tube material) such that long flexible, rotating tubes 140 and 142 become more flexible distally than they are in more proximal regions. A similar effect may be imparted to NRS 125 with variations in composition and composite materials in coextrusions, including progressive changes inherent rigidity of material states, thicknesses of one or more components of a coextrusion, including any included thicknesses of materials in a continuous coextrusion. These material and manufacturing characteristics and laser cuts may be varied at will to achieve the desired flexibility over selected lengths of the outer and inner rotating tube assemblies.

Figure 79B:
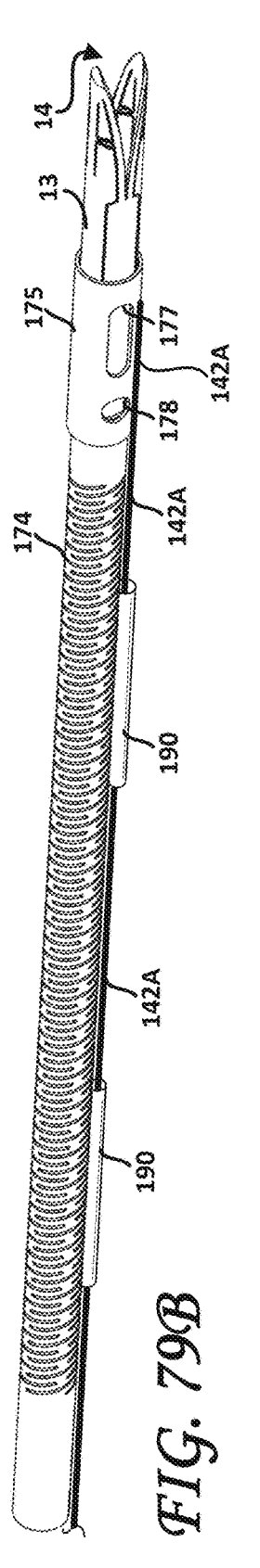

With reference now to FIG. 79B, the outer tube distal rigid tip section 175 may also serve as an attachment point for one or more elements in a coextrusion or in bare tandem arrangements with flexible elements that may have sufficient column sufficient to impart forward or rearward (or both) axial forces exerted on the outer tube distal tip section 175. Elements such as these may include microtubular structures, wires, tethers, or any combination thereof. Such elements may alternatively take the place of the inner rotating tube 140 according to embodiments. In either case, such elements would be candidates for transitional flexibility along their length to suit the tortuosity they may be expected to encounter. Any of these may be included as part of an outer sleeve or be constructed as a part of inner rotating tube 140, as a coextrusion, in a tandem enclosure, which may be continuous or discontinuous. Discontinuous enclosures could be sleeves of varying lengths and rigidity or flexibility depending on their locations and anticipated support needs, according to embodiments. An example of such sleeves is shown at 190, through which tube 142A may be disposed. The sleeve or sleeves 190 may be continuous or discontinuous (sleeve/coextrusion or tandem tube). Other external items may be attached to the outer tube distal tip section 175 and all such are included with the present scope.

Figure 79C:
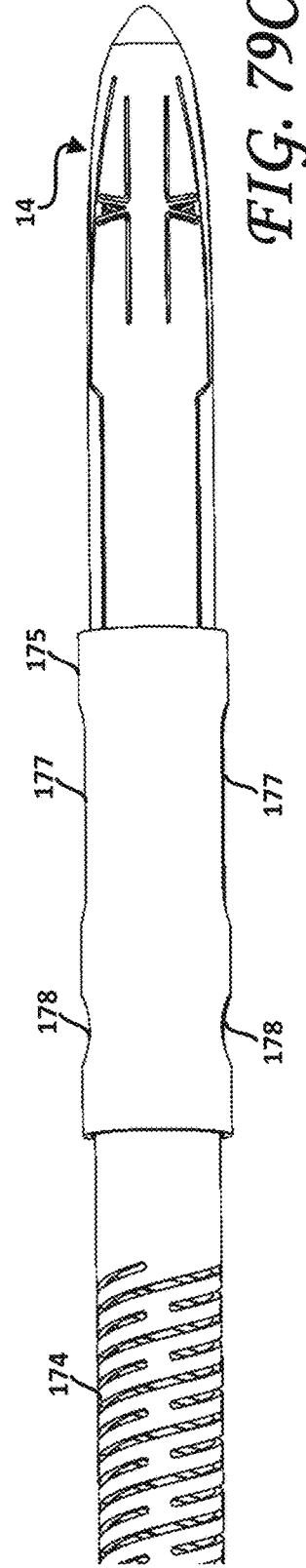

FIG. 79C is an overhead view of the long variably rigid and stiff telescoping needle set described above relative to FIG. 79A, according to an embodiment. The outer tube rigid tip 175 functions to couple the inner tube long flexible section 174 to the outer tube 174 and to the work element 13 comprising the articulable beak elements 14 by way of outer tube keystone weld points 177 and an inner tube backbone weld points 178. By way of such attachments of the inner and outer long, flexible rotating tubes 173 and 174, as well as their differential relative axial positions, rotation of the articulable beak elements 14 may be enabled. The articulable beak elements 14 may flex and straighten to enable all the functions of non-sharp, closed beak rotational dissection and traverse through potential spaces or tubular spaces whether blocked (such as Chronic Total Occlusions or CTOs), partially blocked or widely patent, open beak, rotational sharp coring as well as closed beak, rotational parting or severing off of a cored specimen of any length desired without limits, according to embodiments.

Figure 80:
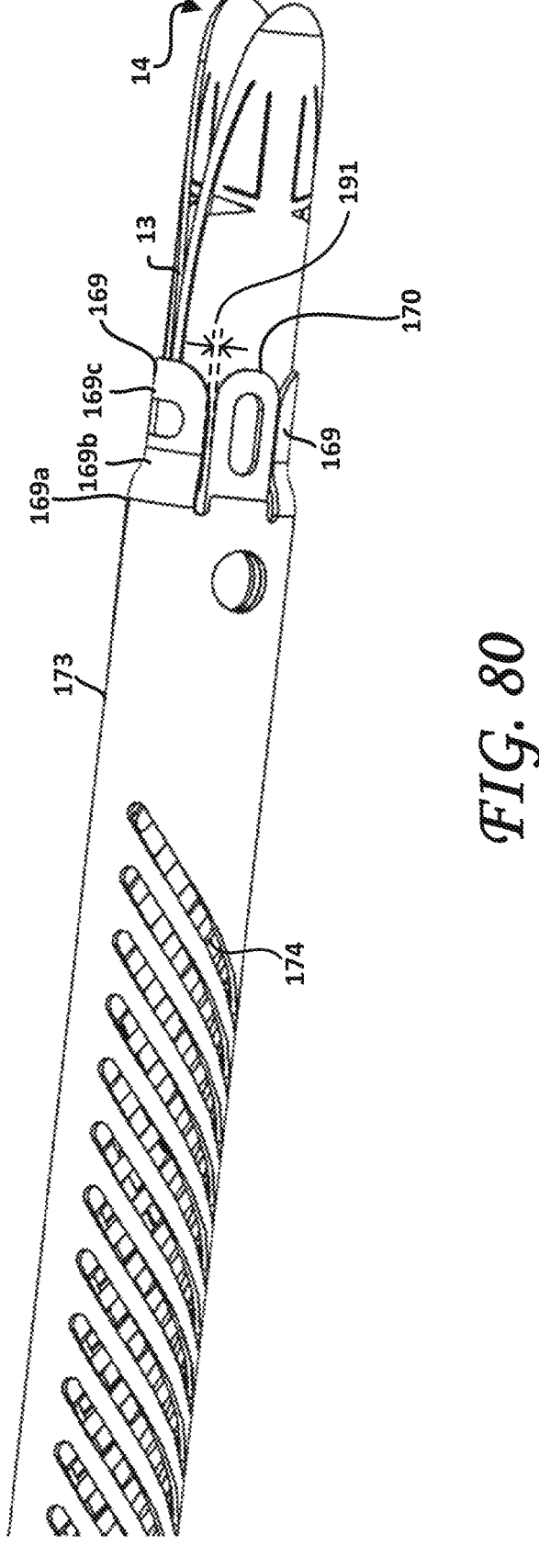
FIG. 80 is perspective and side views of a long flexible needle set with inner and outer flexible tube parts shown connecting to a distal work element according to another embodiment.

FIG. 80 is a perspective view of an alternate embodiment, showing the attachment construction of the inner tube long flexible section 174 and its attachment at inner tube flange connector 170 with the distal work element and beaks 14, shown in the wide open configuration. Shown in the perspective view of FIG. 80 is one of the inner tube flange connectors 170, coupling the inner tube long flexible section 174 to a backbone portion of a distal work element 13/beaks 14. In this embodiment, the distal-most portion of the outer tube long flexible section 174 forms an outer tube flange connector, coupling the outer tube long flexible section 173 to the keystone elements of the distal work element 13. This constructions enables axial motion of the outer tube long flexible section attached to keystone elements of distal rotating work element 13 14 via flange tab 169 relative to the inner tube long flexible section attached to a backbone portion of the work element 13 via flange tab 169, such that all functions detailed above are also enabled as a result of the relative axial positioning of the inner tube flange connector 170 and of the outer tube flange connector 169. The outer and inner tube flange connectors 169, 170 are kept aligned and substantially level with one another, thereby preventing any significant twisting stresses being imparted to the beaks 14.

Significantly, FIG. 80 demonstrates a streamlined transition between asymmetric beaks 14 when they rotate in a closed position, which closed rotational state becomes an effective and highly useful dissection tool for soft living tissues. Being substantially non-sharp or non-sharp in the closed configuration, such dissection enables tissues to maintain functionality, and also enables potential spaces through which beaks and flexible tube elements pass, to again re-appose together and more rapidly heal up, remaining unsevered by the gentle action of the rotating, non-sharp closed beaks, by virtue of their sharp edges temporarily presenting a non-sharp, covering state in the closed position. The beaks 14 may remain in the closed configuration as they are gradually advanced to a target site, or open, if coring to the target site is desired. As they reach or approach the target site, the beaks 14 may open to full diameter of the following outer sheath NRS 125, the rotating tube set may core through tissue and may accept any length of cored specimens desired, there being no predetermined and limited core length. The cored sample or samples may then be transported all the way back through the proximal-most openings of the long flexible tubes into a sample receptacle optionally attached behind any of the driving mechanisms disclosed herein. According to embodiments, once a coring operation (which need not be along a straight pathway) is finished, due to the flexible nature of the NRS 125, of the inner and of the outer rotating tubes 140, 142, then the beaks 14 may be closed again with small relative changes in axial positioning of inner rotating long, flexible tube 140, with outer, rotating, long flexible tube 142.

When the beaks 14 are in the open configuration (as shown in FIG. 80, for example), they function as two separate, thin, sharp blades, each having a cutting edge. The sharpness is a function of the thinness of the cutting edge and tip, and the outside of each beak 14 is not independently sharp without the inner part of the cutting edge being exposed. When the two beaks 14 assume the closed configuration (as shown in FIGS. 84A-84D), one against the other, the inner edges are no longer exposed and are prevented from imparting this sharpness to each edge, and the beaks act as a singular, much thicker blunt unit, as opposed to two individual thin cutting blades. This allows the device, when the beaks 14 are in the closed configuration, to carry out non-sharp dissection through tissue, to pull apart tissue non-traumatically as the distal tip of the device makes its way to the target lesion within he tissue, or other biological conduit or space. This approach is far less traumatic because bleeding, pain, and inflammatory response from the body all result from severing conduits within the tissue that carry nerves and capillaries. If these conduits can be "pushed" aside by a blunt-acting instrument (as is the present device when the beaks 14 are in the closed configuration) rather than sliced through, trauma is reduced.

The structure and configuration of the outer and inner tube flange connectors (also called tabs herein) 169, 170 according to embodiments is significant in terms of reliability, scalability, and manufacturability. The tabs 169, 170 are configured to attach the outer tube to the backbone of the work element 13 and to attach the inner tube to the keystones of the work element. In operation, the tabs 169, 170 are configured to slide next to each other with little space, which protects the beak components from twisting trauma. Surprisingly, the tabs 169, 170 were found to not only enhance operation of the device but also greatly to simplify the assembly and laser welding of these components, as well as rendering the resultant assembly far more robust, particularly in the smaller sizes, like 30 gauge needles. The tabs 169, 170 are also configured to present a streamlined profile to facing tissue, with graduated increases in diameter from the beaks 13 to the outer tubes. Indeed, each of the outer tube flange connectors (tabs 169) may comprise a first portion 169a whose radius of curvature matches the radius of curvature of the outer tube 173 and a second portion 169c having a radius of curvature that matches a radius of curvature of the rigid distal work element 13 and a transition or step up section 169b (from distal to proximal) between the first and second portions 169a and 169c, thereby presenting a tapered profile. As a result, at least a portion (169c) each of the inner tube flange connectors 170 is interdigitated with, disposed in close proximity to and substantially level with one of the outer tube flange connectors 170, such that differential tortional stresses on the rigid distal work element and on the first and second beaks are limited. This is because should the outer tube 173 undergo tortional stresses that cause it to tend to twist with respect to the inner tube 140/173, or vice versa, one side of the inner tube flange connectors 170 will abut against the facing side of the outer tube flange connectors 170 and limit the resultant twisting to the short arc distance 191 between one side of the inner tube flange connectors 170 and the facing side of the immediately adjacent outer tube flange connectors 170.

As a result, far fewer small fragment tissue hangups are observed, as the tissue does not encounter sharp transitions as the device is advanced toward the target tissue. Also surprisingly, yields and scalability were also found to have increased, by, among other factors, reducing the laser cutter's "shudder" as it does not encounter sharp level transitions, due to the gentleness of the curves it follows. The presence of the tabs 169, 170 also provide a far simpler welding pattern. Without the tabs 169, 170 the redundancy of four separate welds provided reasonable yields, about 88% overall yields but with between one to two failed welds almost 50% of the time. The failures came when two or more welds failed, which meant inevitably that two such welds must have failed on the same side. When that occurred, the entire assembly was rendered inoperable. Therefore, the presence and functionality of the tabs 169, 170 is a practical solution that led to the wholly unexpected, surprising result of the development of less costly, more readily manufacturable, and more reliable needles sets.

The presence and design of the tabs 169, 170 renders the transition from the distalmost to proximal portions of the device more continuous and inherently gentler. From a clinical standpoint, tabs 169, 170, the device tends to seek out and open the (clinically so-called) "potential spaces" that can be found all over in the structures of the body based on the developmental biology of natural tissue growth. This is the basis for the user's reports of rotational, non-sharp "like butter" dissection, enabling the devices shown and described herein to transit these spaces with minimal resistance and minimal tissue disruption along natural dissection planes. Also wholly unexpected was that the presence and design of the tabs 169, 170 enabled the stiff length of the work element 13 and beaks 13 to be significantly shortened, thereby increasing its strength and resistance to twisting. In turn, by virtue of the presence and design of the tabs 169, 170 and the shortening and strengthening of the work element 13, such design also finds broad applicability in crossing natural luminal dissection planes in vascular chronic total occlusions (CTOs).

FIGS. 81A, 81B, 81C and 81D show relevant details of how proximal driving, stabilizing and axial motion and relative motion-providing elements such as proximal dogs 141 and the distal dog 143 add telescoping forces to inner 140 and outer rotating 142 tubes at their proximal rigid sections during continuous rotation thereof. These telescoping forces are also replicated distally via the flanged attachment tabs 170 and flanged attachment tabs 169, as these are configured so as to enable them to slide past one another while their edges remain in close proximity. This configuration minimizes torsional stresses at the distal work element 13 and beaks 14 level, even under the resistances encountered during rotational operations detailed above including rotational non-sharp dissection, coring and parting off actions for efficient, minimally traumatic approaching, coring, severing off, transporting and collecting multiple core samples, which actions may be carried out without having to remove the needle assembly from within the organisms body (single insertion, multiple sample), according to embodiments.

Figures 81A, 81B, 81C, 81D:
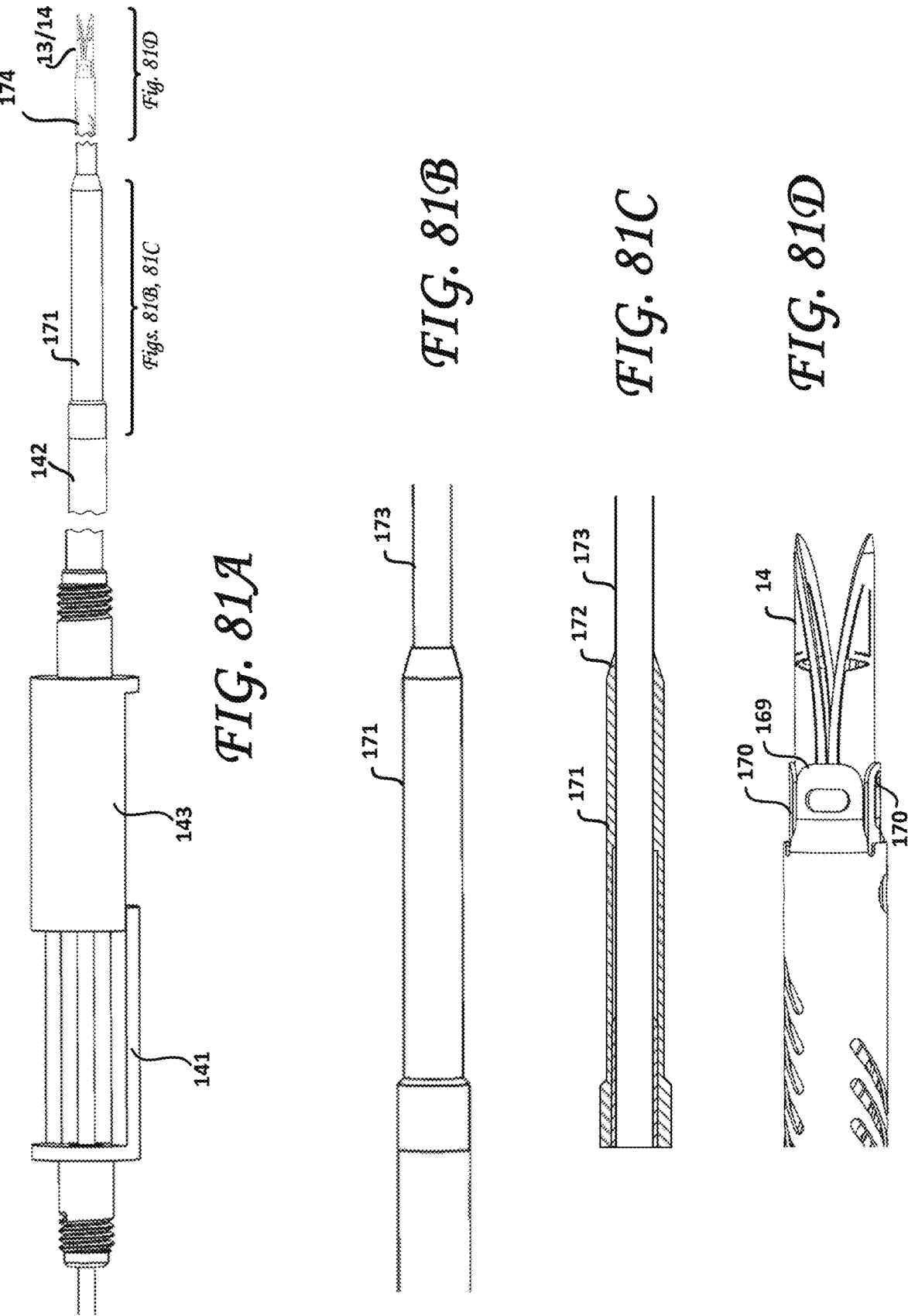
FIGS. 81A, 81B, 81C and 81D are a series of side views of various components of proximal, middle, and distal construction and connection details of rigid sections at each end of a long flexible needle set, according to an embodiment.

Also shown in FIGS. 81A, 81B and in the cross-sectional view of FIG. 81C, are step-down sections 171 transitioning from the proximal larger rigid section of a telescoping, rotating, differentially actuated outer tube 142 to a comparatively smaller diameter and then again transitioning at 172 down to the still further reduced diameter of the inner tube long flexible section 174, running from the proximal to distal directions. In the other direction, from distal to proximal, the step up to a larger diameter portions where these sections do not need to enter the living organism, provides an expansion chamber for fluids to pass, and allows a conduit for vacuum. Such interstitial spaces also enable fluids to flow therethrough to gently wash core samples as they continue on their distal to proximal transit to a tissue collection chamber.

At the collection chamber, a coaxially-disposed filter may be provided to enable fluids to pass enhancing the washing operation while capturing core samples that are fully intact and that are collected with undisturbed tissue architectures. This allows for valuable gross and microscopic pathology analysis. Other diagnostic operations may also be carried out on such intact tissue sample, such as immune-histochemistry analyses, where exposure to drying and air circulation are undesirable, according to embodiments, as the present device enables rapid fixation for preserving a pristine state of surface and deeper layers of collected core samples.

The streamlined nature of attachments tabs 169 and 170 enable smooth passage of the device through both soft and even very firm tissues, while the need for overdriving beaks (driving the beaks 13 to open wider at their distal-most tips than the diameter of the inner tube 174) during coring to gain a slightly larger outer diameter of coring opening through which the more proximal slight step up at the outer tube flange section 169 may pass is likewise a construction achievement shown here. Overdriving the beaks 13, therefore, eases the transition through tissue from a smaller diameter inner rigid tip 176 over the transition afforded by the tabs 169, 170 to the larger diameter portions of the device. Structural gains are made in the inside diameter immediately proximal to the attachment points of tabs 169 and 170, where the inner diameter of both the inner rotating flexible tube 173/174 as well as the internal diameter of the outer flexible rotating tube 142 is stepped up by approximately the same step up of the outer diameters of these tubes relative to the work element 13 outer diameter, meaning that a very short path exists for the core samples to pass before they enter an expansion chamber, which relieves compression and frictional forces almost immediately upon the sample being severed from host tissues in-situ. The practical value is less architectural compression and twisting distortion common to other conventional biopsy devices is introduced as well as minimizing resistance for transporting the core specimen tissues proximally to the collection areas. Likewise more space is available for swirling, vacuum augmented fluid flows that enter distally with the cored specimens and accompany each sample all the way proximally to the collection assembly and filter sections. According to embodiments, the simplified nature of the attachment tabs 169, 170 shortens the rigid length for attachment of a distal work element 13 to long flexible rotating telescoping tube sets 140 and 142. The larger diameter of inner and outer long flexible rotating tubes compared with the work element 13 also imparts a mechanical twisting advantage to the long flexible rotating tubes 140 and 142, making control easier to achieve, while also providing for preservation of rotational forces deliverable distally.

Figure 82:
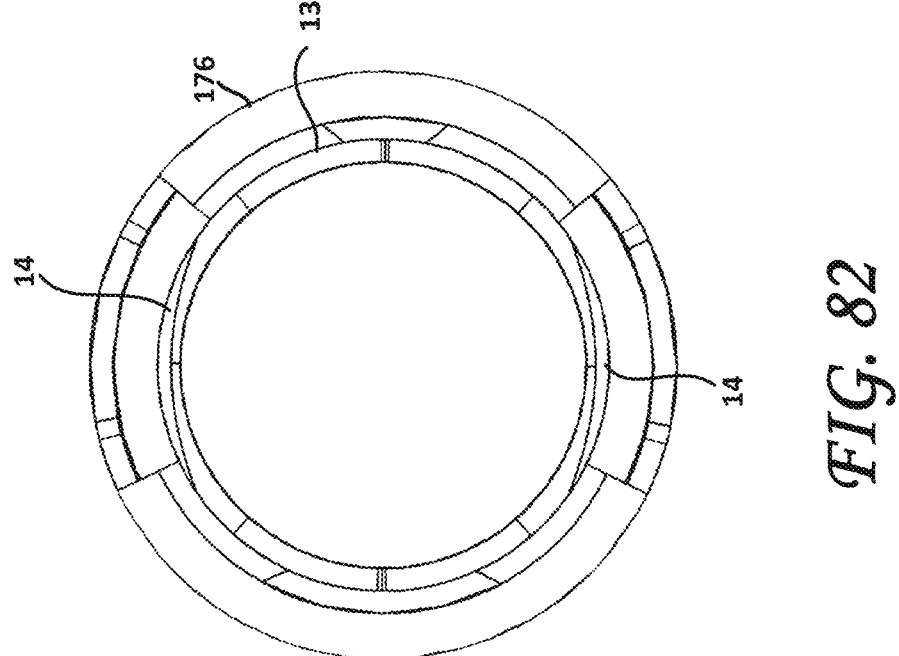
FIG. 82 is an end on view of telescoping long flexible needles coaxial with a work element shown at the innermost section, according to an embodiment.

FIG. 82 is an end-on view demonstrating diameter step-ups and tolerance views between beak elements 14 with an inner tube with its forward short rigid section (inner tube rigid tip) 176 leading to a long, flexible rotating proximal section, according to embodiments, and also shows the full diameter of widely open beaks 13 to full (or greater if overdriven) diameter of the tube from which they are constructed with simple laser cuts that enable the flexing capabilities herein. This view also demonstrates that no portion of the beaks 13 projects into the diameter of the tube from which they were cut by a laser-cutting substrative process, thereby maximizing the diameter of the tissue sample able to be collected, which is limited only by the gauge of the tube from which the beaks 13 are formed. Conversely, no structures of the beaks 13 project outside of the outer diameter of the tube from which the beaks 13 have been formed (unless the beaks 13 are purposefully over-driven). Notice also that no structures outside of the beaks 13 need act upon them to enable them to open and close (as is often necessary in conventional biopsy devices), all such structures and weld attachment points (including tabs 169, 170) being well proximal to the beaks 13.

Figures 83A, 83B, 83C, 83D:
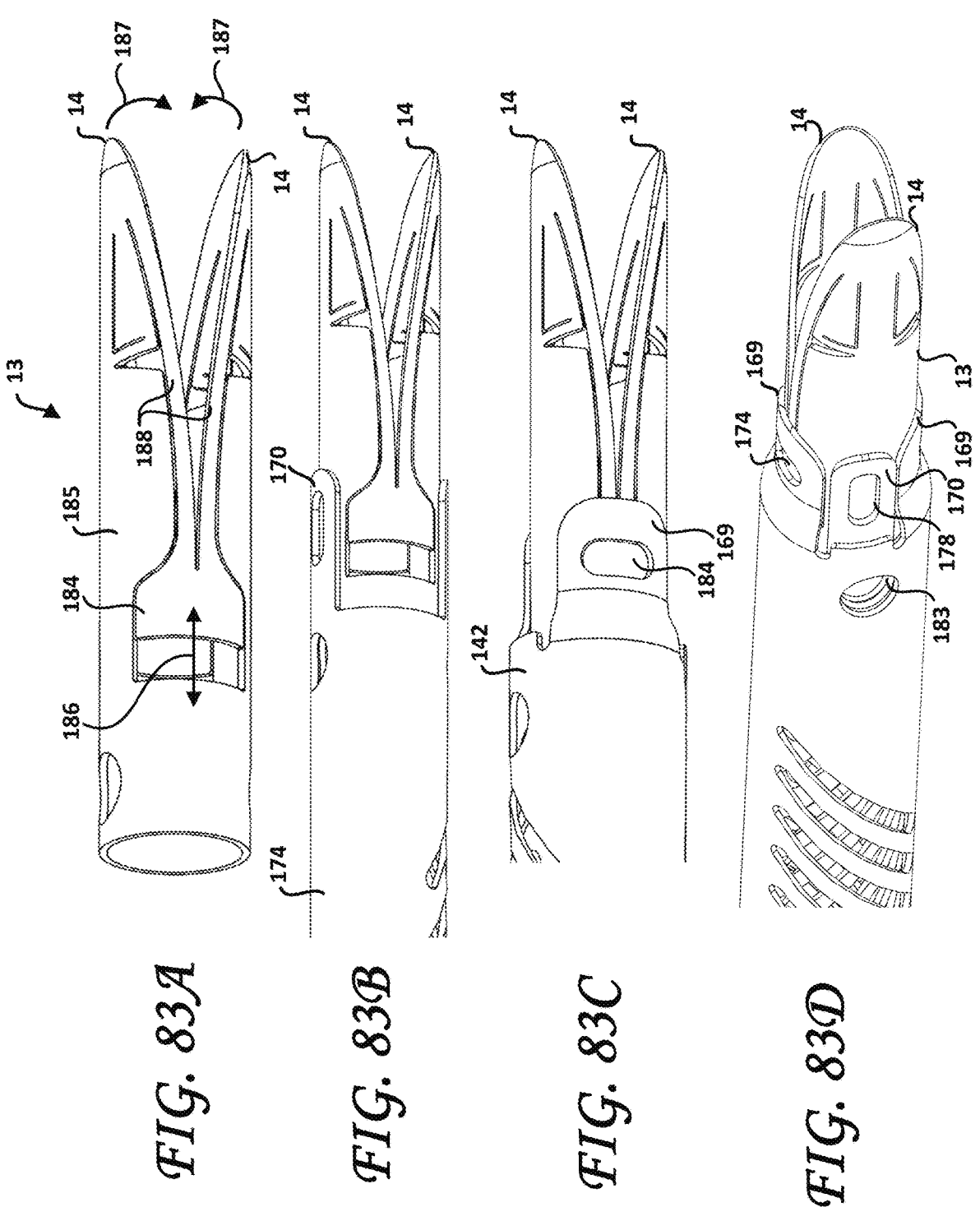
FIGS. 83A, 83B, 83C and 83D show structural constructions and attachment details of telescoping long flexible needle elements, with a work element at the distal end, according to an embodiment.

FIG. 83A shows the structure of a shortened work element 13 and the beaks 14. As shown, the work element 13 may be formed from a single homogeneous tube of material in which cuts have been made, such that the remaining tube material forms the structures shown. The shortened work element 13 may comprise a backbone portion 185 and two keystone portions 184, only one of which is visible in FIG. 83A. The other keystone portion is on the hidden side of the representation of FIG. 83A. Each of the keystone portions 184 is connected with selected ones of the tendon or tendons of both beaks 14. Imparting a proximally-directed force 186 upon the keystone portions 184 pulls on the tendons 188, which tends to move the beaks 14 in the direction of arrows 187 and them against each other. Conversely, exerting a distally-directed force upon the keystone portions 185 pushes on the tendons 188, which tends to move the beaks back to the open, unbiased configuration shown in FIG. 83A. Conversely still the distally-directed and proximally-directed forces could be exerted on the backbone portion 185, while the keystone portions 184 are maintained immobile. Moreover, differential forces exerted upon the keystone portions and the backbone portion 184, 185 will make the beaks 14 open or close or smoothly assume configurations between the two on the fly.

FIG. 83B shows the manner in which the inner tube flange connector tab 170 (in one embodiment, a distal extension of the inner tube long flexible section 174) couples to a backbone portion 185 of the work element 13 via, in one embodiment, one or more laser spot welds. FIG. 83C shows the manner in which the outer tube flange connector tab 169 (in one embodiment, a distal extension of the outer tube long flexible section 142) couples to the keystone portions 184 of the work element 13 via, in one embodiment, one or more laser spot welds. FIG. 83D shows the work element 13 coupled to both the inner tube long flexible section 174 via the inner tube flange connector tab 170 and to the outer tube long flexible section 142 via the outer tube flange connector tab 169. Also shown in FIG. 83D is the physically enlarged oval close-loop shaped, keystone welding point 177 of outer flange tab connector 169 of outer rotating tube 142 as well as the physically enlarged, closed loop ovoid welding point 178 of inner tab connector 170 of inner rotating tube 140. These welding shapes and points may be configured to enable inner circumferential welding and potting for great strength and security, which likewise enhances scalability and ease of positioning during automated welding operations, while edges of the tabs 169 and 170 being in close proximity to one another. This also stabilizes the assembly during micro-welding operations, simplifying and speeding processes while simultaneously improving production yields, according to embodiments. Also shown is an enlarged through hole 183 for positive, precise alignment of all components during weld-fastening procedures, which can be used visually or by inserting a plug gauge there-through, according to embodiments.

Figures 84A, 84B, 84C, 84D:
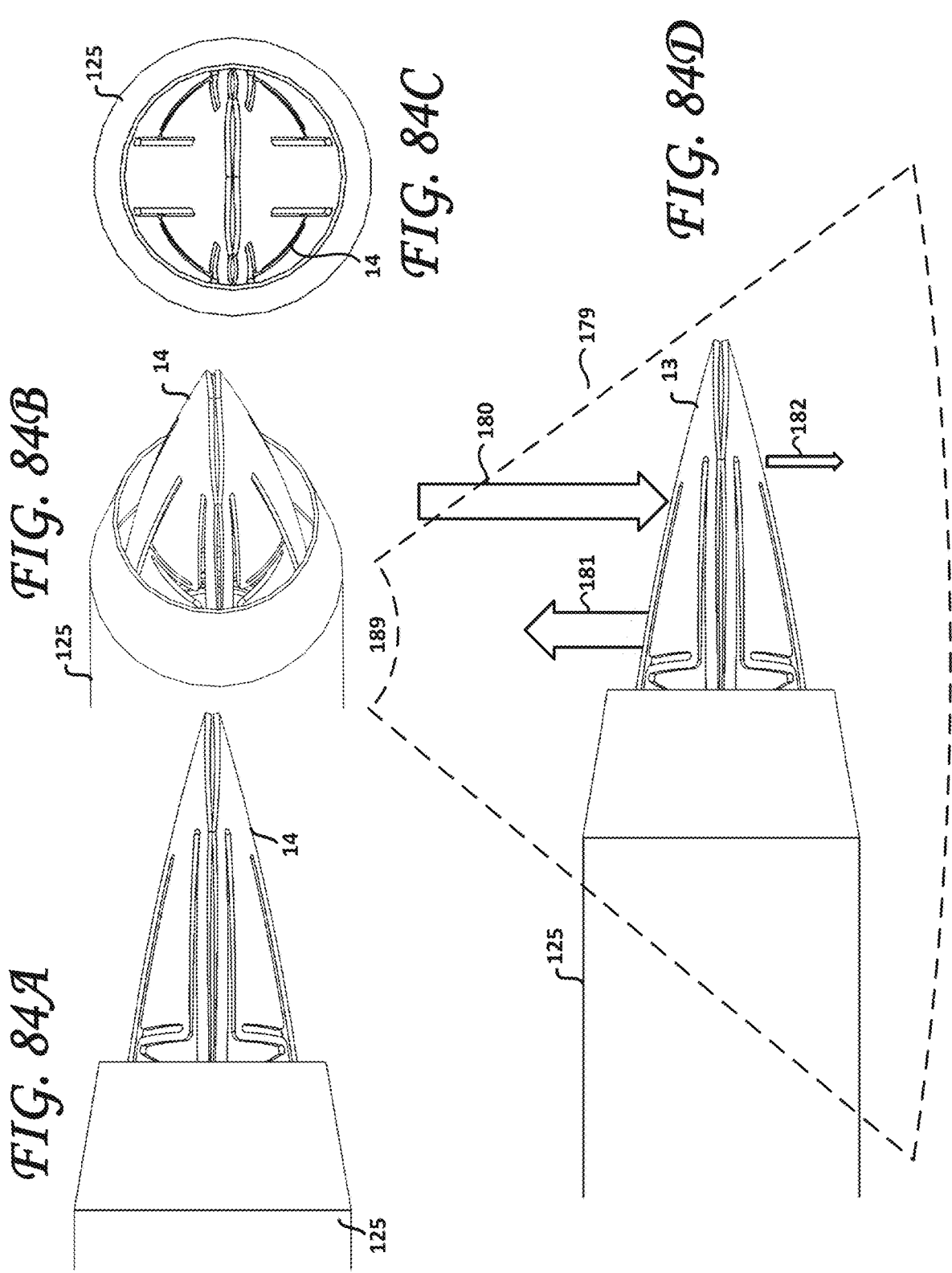
FIGS. 84A, 84B, 84C and 84D shows a work element with its over covering sheath in stop action side, perspective and end on views as well as a representation of an ultrasound sector scan with vectors showing the behaviors of ultrasound waves that encounter the present work element in this stop action horizontal position of normal rotations of the work element, according to an embodiment.

FIGS. 84A, 84B, 84C and 84D show various views of the distal end of the device of FIG. 1, with the beaks stopped in rotation, closed and in a horizontal aspect relative to a source of ultrasound radiation. FIG. 84A shows a side view, FIG. 84B shows a perspective view and FIG. 84C shows a head-on view. The profile of a surface ultrasound beam sector scan is represented by 179, with the ultrasound source and collector represented at 189 at the top vertex of the triangle 179. The ultrasound waves incident upon the work element 13 are represented by arrow 180. According to embodiments, ultrasound waves striking beak elements 14 while they pass through this rotational position are mostly reflected back upwards toward the surface and toward the ultrasound combined emitting and collector/sensing probe are shown at 181 and are visible as brightly echogenic to an operator and is enhanced on the viewing screen. The vectors are represented showing a broad arrow 180 representing the outbound ultrasound wave vector, a large reflection at 181 and a small arrow 182 showing a small fraction of ultrasound energy able to pass through the non-stealthy plate-like presentation of the beaks 14 in this position. The slightly diminished ultrasound return arrow 181 is intended to indicate that nearly all the outbound ultrasound energy 180 is reflected, as shown at 181, on a return pathway to the detector-sensor of the ultrasound probe.

FIGS. 85A, 85B, 85C and 85D show various views of the distal end of the device of FIG. 1, with the beaks stopped in rotation, closed and in a vertical, edge-on aspect relative to a source of ultrasound radiation. FIG. 85A shows a side view, FIG. 85B shows a perspective view and FIG. 85C shows a head-on view. The profile of a surface ultrasound beam sector scan is represented by 179, with the ultrasound source and collector represented at 189 at the top vertex of the triangle 179. The ultrasound waves incident upon the work element 13 are represented by arrow 180. FIG. 85D shows the same features and vectors of an ultrasound wave as it encounters rotating beaks 14 in a vertical, edge on aspect, which is minimally reflective and maximally transmissive as represented graphically by arrow 180 representing the incident ultrasound energy and very slightly smaller arrow 182 showing that the incident ultrasound energy 180 mostly passes right on past beaks 14 while they pass through this rotational position, as shown at 182. The result of the vectors depicted in FIGS. 84D and 85D is that a bright flash of reflected ultrasound is displayed to the user, flickering at about double the rate at which the work element 13 rotates, one flash each time one of the two beaks 14 is presented face-on, broadside (FIG. 84D) to the ultrasound energy, in the manner of a flashing beacon showing a real time position of the distal tip of the device during operation thereof. This flashing results in a very apparent flicker to the operator's vision via the ultrasound software and viewing screen. Furthermore, there is a dynamic tissue effect due to the asymmetric motions imparted to the living tissues, which differentiates between stiffer, firmer tissues, generally associated with diseased tissues versus the more compliant naturally less dense normal tissues within which pathological tissue can be found. This differentiation aids detection and directionality of such pathologic lesions and also enhances the edges of the limits of the abnormalities, often refining the measuring capabilities and even the shapes of the edges, all of which are important indicators of the aggressiveness of an abnormality. This differentiation also provides clues to where the most active parts of a lesion exist genetically, which is generally at the highly active margins where interactions between pathological tissue and normal bodily defense swarms of immuno-reactive elements exist in efforts to deactivate and eliminate the threats posed by such pathologies, to the entire living organism as well as effects in the region where such lesions grow, enlarge and from which they can migrate distally once a critical mass and size is achieved by the invasive lesions. Additionally, the dynamic nature of the rotating, asymmetric beaks 14 exist both in open and closed states, enhanced as the effects are in close state, nevertheless the effects are brightly visible in both states.

Surprisingly, it has also been found that another highly useful effect is that if the very thin beam of an ultrasound sector scan drifts away from a target lesion to the point where the target lesion may slide right off the ultrasound display screen, there is a vibratory tissue effect, like a Geiger counter detector, whose intensity and/or apparent frequency is perceptually greater the closer the distance between the beaks 14 and the lesion. Observing this effect leads an operator back towards the side of greater dynamic activity (vibrating tissue effect) by seeking out vibrations of higher frequencies, which is unique to the asymmetric shape in combination with rotation, of beaks 14, especially in the closed state but also useful when in the open state. These effects exist across variants of beak shapes, lengths, and diameters, as described and according to embodiments.

In another embodiment, a moving target may be stabilized by providing a mechanism to fix the tip of a catheter to the moving target in several ways individually or in combination. This has application in any area of the body where it is desirable to enable moving of the catheter tip synchronized with the movement of the target of the coring exercise, whether that target is identified by direct vision or with imaging technologies such as optical coherence topography, ultrasound, MRI or 2 or 3 dimensional X-ray technologies such as CT scanning or 3D tomosynthesis as examples.

To do so, the principles of telescopic control of flexible length combined with guiding catheters or its own scoopula, as disclosed herein, may be applied (such as disclosed in commonly-assigned U.S. Pat. Nos. 9,592,035 B2, 9,456,807 B2, 10,806,434 B2, 9,155,527 B2 and co-pending application Ser. No. 16/933,667, each of which are incorporated herein by reference in their entirety) in the case of the forward/side coring variants, as well as combining this feature with the ability to twist the tip of the variably flexible catheter by torque inputs in order to move off the tip plane.

Such off-plane movement of the tip may be necessary when it is desired to keep the guiding catheter (with or without incorporated imaging) stabilized. The term "stabilized, in this context, is not limited to immobility or near-immobility, but also is explicitly defined herein to encompass moving more or less in concert or together with the movement of structures approaching the moving target, such that relative movement between the biopsy needle and the internal structures into which the biopsy needle is inserted are minimized. For example, in the case of lung biopsy, one of the advantageous scenarios includes introducing a guiding catheter into the pulmonary tree directly. The advantage of this approach over the more direct puncture from the outside chest wall (percutaneous route), is that the intrapulmonary guiding catheter moves along with the respiratory cycle and therefore is already generally in synchronicity with the movement of a tumor target therein. In contrast, in the direct chest wall approach, there is some movement of the chest wall but not at the level nor specific movement direction of the lung elements a target lesion may be located. In other words, the lung expansion involves additional movements that are of a sliding/expanding nature that necessarily are different in extent and direction relative to chest wall movements. In some cases, the relatively immobile or differentially moving conventional biopsy needle tip, relative to the target lesion in the lung can lead to inadvertent trauma to lung tissue, especially in cases where the biopsy device includes a sharp tip distal to the side cutting trough. While this can be overcome to some extent, by asking a patient to hold their breath while reference still-images are taken, the conventional needle's sharp tip, thus introduced through the chest wall approach, is forced to move differentially from the lung tissue, by the components of the chest wall (outer skin, subcutaneous tissues, ribs, intercostal musculature and cartilage, etc.,) that constrain it. However, the intrapulmonary guiding catheter has limited ability to move with the more distal target and furthermore, the distal target may well be out of directional plane with the target. While the intrapulmonary approach can eliminate the need for breath holding and also automatically stabilizes the movement of the target in synchronicity with itself (the guiding catheter), there remains the need for more precise aiming on the part of the biopsy needle tip itself.

This problem is solved by adding the capabilities of controlling the degree of off-axis flexing as well as the ability to control the degree of twist of the flexing tip, plus adding the ability to control not just the degree of flexing but also the longitudinal length and stiffness of the distal portion of the catheter (in this case the outer sleeve NRS or RS structure 125 and all contained tubes, including at least the inner rotating tube 140, the rigid work element 13 and the outer rotating tube 142. The distal portion also includes a built-in length of rigidity (including the rigid work element 13) to enable precise control of the penetrating portion of the needle, such that denser tissue cannot deflect the needle tip off its desired target pathway. The second principle that is added to the directional flexibility that enables precision and accuracy to reach a moving target for fine tuning the needle tip, while moving in synchronicity with the target, is also to select the length of the depth of needle core-sampling within the target, by enabling an operator to choose an automatic depth setting that then automatically move the needle forward along the depth or "z" axis, thus freeing the operator from having to manually input an additional force. This adds another layer of control, which can work together with the principle of moving with the target in registry by stabilizing the needle within the natural structures already moving with the target, such as stabilizing a guiding element (catheter, scoopula, etc.,) within the natural structure that is already attached to and thus moving with, the target abnormal growth. Together these elements take advantage of the above-described common frame of reference concept, made possible by approaching within and anchoring to a natural pathway that is already moving along with a moving target, while both the target and the stabilizing structures that form the anchoring pathway are not moving substantially differentially from one another, and then moving everything needed thereafter for fine tuning in the event that the needle, while moving together with the target, may still need adjustment to precisely and repeatably hit the desired location within the target abnormality to core a sample and obtain information such as the genetic components of the abnormal growth.

According to an embodiment, elements described and shown herein, together with elements that control opening and closing of the beaks 14 may be surrounded by a non-rotating outer element such as a sheath and may be provided with a scoopula or trough. These outer elements may be configured to control several functionalities, such as length of exposure, length of exposure of the rigid and flexible lengths, provide directionality either by the direction of a side opening (in the case of the scoopula element) or by providing flexing control with their own built-in ability to flex near or at their tips, as well as by providing a controlling element that may bias the flexible segment(s) of outer sleeve 125 and contained structures as it exits the distal end (non-rotating outer element) or the distal end/side opening of a scoopula outer element. Controlling the exposure length of the rigid and flexible lengths may provide not only directionality, but also the degree of deviation off of the centerline axis of a guiding element, whether that guiding element includes a guiding outer catheter or an outer integrated sheath element. The depth control is another of the parameters that, when set by the operator or sensed by the imaging system to automatically set the 7.-depth, enables fine tuning precision and accuracy of the coring sampling motion, such that all areas of interest can be reliably and repeatably sampled with confidence. The coring sampling traverse also enables the operator to dial in a precise coring depth, in addition to being able to control sample length.

According to embodiments, depth and exposure settings may be controlled automatically when go-no go limits are determined by structures identified by imaging, either incorporated in the needle tubes themselves, as adjunct imaging catheters in-situ located coaxially or in tandem with the needle tubes, located in a guiding outer tubular element or via any location such as simple surface imaging and including modalities such as Xray, computed 3 dimensional tomography, soundwave, such as ultrasound, Magnetic Resonance, thermal, optical coherence tomography or any combination of these as well as any other imaging modality.

Artificial Intelligence guidance and control may be utilized to enhance accuracy, repeatability and precision and itself may be enhanced by imaging results, data analysis, structural limits and results of proximity of coring to such structures (such as stents, natural calcifications or other landmark structures such as layers of tubular walls or other nearby structures that lie in imaging density, elasticity, hardness or other contrast to one another whether sensed by imaging or resistance to movement or coring, including tissues being cored, penetrated, approached or referenced.

Flexed tubular elements may be disposed over the top of the needle tubes, such as an NRS-like tube, a scoopula, and a separate guiding tube element. The needles (distal region of present excisional device and length of tube structures between the work element 13 and the disclosed control and drive assembly shown in FIG. 74A through FIG. 76 may also be configured to come out of the tip of an NRS at an angle, with the farther forward it projects, the farther off axis the distal tip of the device travels. According to an embodiment, when a flexible portion (such as shown in FIG. 78C or at reference 174 in FIGS. 79A-79C) has a built-in bias, angling that curve toward the scoopula opening enables more off axis excursion, but when angling that flexible segment away from the opening, it may be held straight (er) for example. Also, a curved guiding catheter may interact with a curved needle tube, such that the curvature of the guiding catheter may be negated or enhanced by twisting the two of them, together or independently of one another to gain a precise off axis positioning of the penetration spot. One of the two could also be a simple rigid and straight tip that, once exiting the curved guiding catheter, proceeds straight ahead in the natural direction it takes upon exit.

Other embodiments include tandem lighting with simple visible lighting with a source that emanates a spectrum of frequencies, mono- or narrow band frequencies in wavelengths that may enhance identification of normal and abnormal structures and depths of such structures for example, as well as provide feedback on colors identified, such as oxygen-rich or depleted colors, which may aid guidance towards, through or away from, and also recognition of normal and abnormal structures as well as their anatomical dimensions, limits and features. Such imaging could also include onboard ultrasound and other modalities such as optical coherence tomography, or any combination thereof.

In another embodiment, a relatively robust guiding element such as a stiff wire that is located coaxially within the coring needle tube or, in a tandem arrangement running through or external to an outer non-rotating sheath or a controllably, radially oriented scoopula, which itself may be flexible enough to follow a stiff wire, whether such wire is straight, curved or modifiable once the procedure strategy is determined, based on pre- or intra-procedural imaging. When such a wire may be coaxially displaced and may be long enough to guide a flexible penetrating coring needle tube, then retracted back out of the way of coring and sampling, as well as sample transporting. If it is located in tandem (see 142A in FIG. 79B) with a coring needle tube, it may remain in place even as a tissue sample is being cored and transported, for example.

While certain embodiments of the disclosure have been described, these embodiments have been presented by way of example only and are not intended to limit the scope of the disclosure. Indeed, the novel methods, devices and systems described herein may be embodied in a variety of other forms. Furthermore, various omissions, substitutions, and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

What is claimed is:

1. A method of imaging and guiding a tissue excisional device during tissue excision, comprising:

providing an ultrasound source and an excisional device comprising a rigid distal work element formed from a single tube of material comprising cuts that define voids, the voids and remaining tube material first and second beaks that are articulable between an open configuration and a closed configuration, the first and second beaks being configured to rotate and configured to alternatively present, along an ultrasound monitoring plane that intersects a target lesion within the tissue, a broad surface to the ultrasound source and a narrow, edge-on surface to the ultrasound source;

inserting at least the rigid distal work element into tissue while rotating and activating the ultrasound source to generate the ultrasound monitoring plane;

responsive to the activation of the ultrasound source, detecting a tissue vibration whose frequency varies depending upon a distance away from the target lesion, and when the monitoring plane drifts away from the target lesion, re-positioning the ultrasound source until a highest tissue vibration frequency is detected and the target lesion re-acquired within the ultrasound monitoring plane.

2. The method of claim 1, further comprising:

observing echogenic flashes on a display as the broad surface of each of the first and second beaks face the ultrasound source and reflect ultrasonic energy incident upon them, the flashes being interrupted by an interval during which the narrow, edge-on surface of each of the first and second beaks face the ultrasound source, during which interval less ultrasonic energy is reflected, and guiding the rigid distal work element relative to the target lesion according to the observed echogenic flashes on the display.

3. The method of claim 2, a rate of the echogenic flashes is about twice a rate of rotation of the rigid distal work element.

\*  \*  \*  \*  \*